US011167028B2

(12) United States Patent
Brito et al.

(10) Patent No.: US 11,167,028 B2
**(45) Date of Patent: *Nov. 9, 2021**

(54) CATIONIC OIL-IN-WATER EMULSIONS

(71) Applicant: GLAXOSMITHKLINE BIOLOGICALS, S.A., Rixensart (BE)

(72) Inventors: Luis Brito, Concord, MA (US); Michelle Chan, Florence, MA (US); Andrew Geall, Littleton, MA (US); Derek O'Hagan, Winchester, MA (US)

(73) Assignee: GlaxoSmithKline Biologicals SA

(*) Notice: Subject to any disclaimer, the term of this patent is extended or adjusted under 35 U.S.C. 154(b) by 375 days.

This patent is subject to a terminal disclaimer.

(21) Appl. No.: 16/212,245

(22) Filed: Dec. 6, 2018

(65) Prior Publication Data

US 2019/0091329 A1 Mar. 28, 2019

Related U.S. Application Data

(60) Continuation of application No. 15/467,660, filed on Mar. 23, 2017, now Pat. No. 10,183,074, which is a division of application No. 14/130,886, filed on Apr. 14, 2014, now Pat. No. 9,636,410.

(60) Provisional application No. 61/585,641, filed on Jan. 11, 2012, provisional application No. 61/545,936, filed on Oct. 11, 2011, provisional application No. 61/505,109, filed on Jul. 6, 2011.

(51) Int. Cl.

| | |
|---|---|
| ***A61K 39/39*** | (2006.01) |
| ***A61K 9/107*** | (2006.01) |
| ***A61K 47/06*** | (2006.01) |
| ***A61K 47/24*** | (2006.01) |
| ***A61K 39/12*** | (2006.01) |
| ***A61K 39/155*** | (2006.01) |
| ***A61K 39/245*** | (2006.01) |
| ***A61K 47/02*** | (2006.01) |
| ***A61K 47/12*** | (2006.01) |
| ***A61K 47/22*** | (2006.01) |
| ***A61K 47/26*** | (2006.01) |
| ***A61K 47/34*** | (2017.01) |
| ***C12N 7/00*** | (2006.01) |
| ***A61K 39/00*** | (2006.01) |

(52) U.S. Cl.

CPC ............ *A61K 39/39* (2013.01); *A61K 9/1075* (2013.01); *A61K 39/12* (2013.01); *A61K 39/155* (2013.01); *A61K 39/245* (2013.01); *A61K 47/02* (2013.01); *A61K 47/06* (2013.01); *A61K 47/12* (2013.01); *A61K 47/22* (2013.01); *A61K 47/24* (2013.01); *A61K 47/26* (2013.01); *A61K 47/34* (2013.01); *C12N 7/00* (2013.01); *A61K 2039/5256* (2013.01); *A61K 2039/53* (2013.01); *A61K 2039/55555* (2013.01); *A61K 2039/55566* (2013.01); *A61K 2039/575* (2013.01); *C12N 2710/16134* (2013.01); *C12N 2710/16171* (2013.01); *C12N 2710/16734* (2013.01); *C12N 2710/16771* (2013.01); *C12N 2760/18534* (2013.01); *C12N 2760/18571* (2013.01); *C12N 2770/36134* (2013.01); *C12N 2770/36143* (2013.01); *C12N 2840/203* (2013.01); *Y02A 50/30* (2018.01)

(58) Field of Classification Search

CPC ........ A61K 39/12; A61K 39/39; A61K 47/06; A61K 47/24; A61K 47/48046; A61K 2039/5256; A61K 39/155; A61K 39/245; A61K 47/02; A61K 47/12; A61K 47/22; A61K 47/26; A61K 47/34; A61K 9/0019; A61K 9/113; A61K 31/7105; A61K 9/1075; A61K 2039/575; A61K 2039/55555; A61K 2039/53; A61K 2039/55566; Y02A 50/30; C12N 2770/36134; C12N 7/00; C12N 2710/16171; C12N 2710/16771; C12N 2760/18571; C12N 2840/203; C12N 2710/16134; C12N 2710/16734; C12N 2760/18534; C12N 2770/36143; A61P 43/00; A61P 37/04

USPC ........................ 424/193.1, 196.11, 400, 450

See application file for complete search history.

(56) References Cited

U.S. PATENT DOCUMENTS

| | | | |
|---|---|---|---|
| 3,906,092 | A | 9/1975 | Hilleman et al. |
| 5,264,618 | A | 11/1993 | Felgner et al. |
| 5,384,133 | A | 1/1995 | Boyes et al. |
| 5,670,152 | A | 9/1997 | Weiner et al. |
| 5,712,257 | A | 1/1998 | Carter |

(Continued)

FOREIGN PATENT DOCUMENTS

| | | | |
|---|---|---|---|
| EP | 1723972 | A1 | 11/2006 |
| WO | 199014837 | A1 | 12/1990 |

(Continued)

OTHER PUBLICATIONS

Pizza et al., Identification of vaccine candidates against serogroup B meningococcus by whole-genome sequencing. Science. Mar. 10, 2000; 287(5459):1816-20.

(Continued)

*Primary Examiner* — Janet L Epps-Smith

(74) *Attorney, Agent, or Firm* — Dana L. Broughton

(57) ABSTRACT

This invention generally relates to cationic oil-in-water emulsions that contain high concentrations of cationic lipids and have a defined oil:lipid ratio. The cationic lipid can interact with the negatively charged molecule thereby anchoring the molecule to the emulsion particles. The cationic emulsions described herein are useful for delivering negatively charged molecules, such as nucleic acid molecules to cells, and for formulating nucleic acid-based vaccines.

20 Claims, 4 Drawing Sheets

Specification includes a Sequence Listing.

(56) References Cited

U.S. PATENT DOCUMENTS

| | | | | |
|---|---|---|---|---|
| 5,739,118 | A | 4/1998 | Carrano et al. | |
| 5,795,587 | A | 8/1998 | Gao et al. | |
| 5,906,980 | A | 5/1999 | Carter | |
| 6,040,295 | A | 3/2000 | Rolland et al. | |
| 6,086,901 | A | 7/2000 | O'Hagan et al. | |
| 6,150,087 | A | 11/2000 | Chien | |
| 6,171,586 | B1 | 1/2001 | Lam et al. | |
| 6,218,371 | B1 | 4/2001 | Krieg et al. | |
| 6,239,116 | B1 | 5/2001 | Krieg et al. | |
| 6,299,884 | B1 | 10/2001 | Van Nest et al. | |
| 6,306,405 | B1 | 10/2001 | O'Hagan et al. | |
| 6,451,325 | B1 | 9/2002 | Van Nest et al. | |
| 6,458,370 | B1 | 10/2002 | O'Hagan et al. | |
| 6,610,321 | B2 | 8/2003 | Huang et al. | |
| 6,855,492 | B2 | 2/2005 | O'Hagan et al. | |
| 6,861,410 | B1 | 3/2005 | Ott et al. | |
| 6,884,435 | B1 | 4/2005 | O'Hagan et al. | |
| 6,890,554 | B2 | 5/2005 | Jessee et al. | |
| 7,303,881 | B2 | 12/2007 | Huang et al. | |
| 7,314,627 | B2 | 1/2008 | Haynes et al. | |
| 7,550,145 | B2 | 6/2009 | O'Hagan et al. | |
| 7,641,911 | B2 | 1/2010 | Ott et al. | |
| 7,749,520 | B2 | 7/2010 | Davidsen et al. | |
| 7,790,696 | B2 | 9/2010 | Gregoriadis | |
| 9,295,646 | B2 | 3/2016 | Brito et al. | |
| 9,636,410 | B2 * | 5/2017 | Brito | A61K 47/26 |
| 2003/0170273 | A1 * | 9/2003 | O'Hagan | A61P 31/18 424/225.1 |
| 2006/0084617 | A1 | 4/2006 | Satishchandran | |
| 2009/0017057 | A1 | 1/2009 | Chen et al. | |
| 2011/0110972 | A1 | 5/2011 | Vasievich et al. | |
| 2012/0156251 | A1 | 6/2012 | Brito et al. | |
| 2013/0195968 | A1 | 8/2013 | Geall et al. | |
| 2014/0220083 | A1 | 8/2014 | Brito et al. | |

FOREIGN PATENT DOCUMENTS

| | | | |
|---|---|---|---|
| WO | 199622765 | A1 | 8/1996 |
| WO | 199711682 | A2 | 4/1997 |
| WO | 199833487 | A1 | 8/1998 |
| WO | 199902132 | A2 | 1/1999 |
| WO | 199930737 | | 6/1999 |
| WO | 200006123 | A1 | 2/2000 |
| WO | 200015768 | A1 | 3/2000 |
| WO | 200050006 | A2 | 8/2000 |
| WO | 200067787 | A2 | 11/2000 |
| WO | 200136599 | A1 | 5/2001 |
| WO | 200226209 | A2 | 4/2002 |
| WO | 2003028656 | A2 | 4/2003 |
| WO | 2004053056 | A2 | 6/2004 |
| WO | 2007001423 | A2 | 1/2007 |
| WO | 2007121947 | A1 | 11/2007 |
| WO | 2008029276 | A2 | 3/2008 |
| WO | 2008116078 | A2 | 9/2008 |
| WO | 2009129227 | A1 | 10/2009 |
| WO | 2010009277 | A2 | 1/2010 |
| WO | 2011005799 | A2 | 1/2011 |
| WO | 20152006380 | A2 | 1/2012 |
| WO | 2013006834 | A1 | 1/2013 |

OTHER PUBLICATIONS

Semple et al., Rational design of cationic lipids for siRNA delivery. Nat Biotechnol. Feb. 2010; 28(2): 172-6.

She et al., TLR4 links innate immunity and fatty acid-induced insulin resistance, J Clin Invest. Nov. 2006; 116(11): 3015-25.

Simberg et al., DOTAP (and other cationic lipids): chemistry, biophysics, and transfection. Crit Rev Ther Drug Carrier Syst. 2004; 21(4): 257-317.

Singh et al., Advances in vaccine adjuvants. Nat Biotechnol. Nov. 1999; 17(11): 1075-81.

Singh et al., Cationic microparticles: A potent delivery system for DNA vaccines, Proc Natl Acad Sci U S A. Jan. 18, 2000; 97(2): 811-6.

Tabatt et al., Effect of cationic lipid and matrix lipid composition on solid lipid nanoparticle-mediated gene transfer. Eur J Pharm Biopharm. Mar. 2004; 57(2): 155-62.

Tamilvanan et al., Manufacturing techniques and excipients used during the formulation of oil-in-water type nanosized emulsions for medical applications. J Excipients and Food Chem. 2010; 1(1): 11-29.

Tamilvanan et al., Stability assessment of injectable castor oil-based nano-sized emulsion containing cationic droplets stabilized by poloxamer-chitosan emulsifier films. AAPS PharmSciTech. Jun. 2010; 11(2): 904-9.

Tazulakhova et al., Russian experience in screening, analysis, and clinical application of novel interferon inducers. J Interferon Cytokine Res. Feb. 2001; 21(2): 65-73.

Vajdy et al., Mucosal adjuvants and delivery systems for protein-, DNA- and RNA-based vaccines, Immunol Cell Biol, Dec. 2004, 82(6): 617-27.

Walker et al., Cationic lipids direct a viral glycoprotein into the class I major histocompatibility complex antigen-presentation pathway. Proc Natl Acad Sci U S A. Sep. 1, 1992; 89(17): 7915-8.

Weide et al., Plasmid DNA- and messenger RNA-based anti-cancer vaccination, Immunol Lett. Jan. 15, 2008; 115(1): 33-42.

Wikipedia, Phosphate-buffered saline. retrieved online at: https://en.wikipedia.org/wiki/Phosphate-buffered_saline. Wikipedia, San Francisco, CA, Jun. 24, 2015.

Yew et al., Toxicity of cationic lipid-DNA complexes, Adv Genet. 2005; 53: 189-214.

Yi et al., A cationic lipid emulsion/DNA complex as a physically stable and serum-resistant gene delivery system. Pharm Res. Mar. 2000; 17(3): 314-20.

Ying et al., Cancer therapy using a self-replicated RNA vaccine. Nat Med. Jul. 1999; 5(7): 823-7.

Yoo et al., In vivo gene therapy of type I diabetic mellitus using a cationic emulsion containing an Epstein Barr Virus (EBV) based plasmid vector. J Control Release. May 1, 2006; 112(1): 139-44.

Zur Mühlen et al., Solid lipid nanoparticles (SLN) for controlled drug delivery—drug release and release mechanism. Eur J Pharm Biopharm. Mar. 1998; 45(2): 149-55.

Benita et al., Submicron emulsions as colloidal drug carriers for intravenous administration: comprehensive physiochemical characterization. J Pharm Sci., Nov. 1993; 82(11): 1069-79.

Bramson et al., Activation of hosts antitumoral responses by cationic lipid/DNA complexes. Cancer Gene Ther. Mar. 2000; 7(3): 353-9.

Brgles et al., Liposime fusogenicity and entrapment efficiency of antigen determine the Th1/Th2 bias of antigen-specific immune response. Vaccine. Sep. 4, 2000; 27(40): 5435-42.

Brito et al., A cationic nanoemulstion for the delivery of next-generation RNA vaccines. Mol Ther. Dec. 2014; 22(12): 2118-29.

Cella et al., Maturation, activation, and protection of dendritic cells induced by double-stranded RNA. J Exp Med. Mar. 1, 1999; 189(5): 821-9.

Choi et al., Low toxicity of cationic lipid-based emulstion for gene transfer. Biomaterials. Dec. 2004; 25(27): 5893-903.

Chung et al., Oil components modulate physical characteristics and function of the natural oil emulsions as drug or gene delivery system. J Control Release. Apr. 2, 20018;71 (3):339-50.

Dow et al., Lipid-DNA complexes Induce potent activation of innate immune responses and antitumor activity when administered intravenously. J Immunol. Aug. 1, 1999; 163(3):1552-61.

Dupuis et al., Dendritic cells internalize vaccine adjuvant after intramuscular injection. Cell Immunol. May 2, 1998; 186(1):18-27.

Elbashir et al., Duplexes of 21-nucleotide RNAs mediate RNA interference in cultured mammalian cells. Nature. May 24, 2001; 411(6836):494-8.

Even-Chen et al., DOTAP cationic liposomes prefer relaxed over supercoiled plasmids. Biochim Biophys Acta. Dec. 20, 2000; 1509(1-2): 176-88.

Fire, RNA-triggered gene silencing. Trends Genet. Sep. 1999;15(9): 358-63.

Fox, Squalene emulsions for parenteral vaccine and drug delivery. Molecules. Sep. 1, 2009; 14(9): 3286-312.

(56) References Cited

OTHER PUBLICATIONS

Geall et al., Nonviral delivery of self-amplifying RNA vaccines. Proc Natl Acad Sci U S A. Sep. 4, 2012 ; 109(36): 14604-9.
Gregoriadis et al., Liposome-mediated DNA vaccination. FEBS Lett. Feb. 3, 1997, 402(2-3): 107-10.
Guy, The perfect mix: recent progress in adjuvant research. Nat Rev Microbiol. Jul. 2007; 5(7): 505-17.
Hagigit et al., The influence of cationic lipid type on in-vitro release kinetic profiles of antisense oligonucleotide from cationic nanoemulsions. Eur J Pharm Biopharm. Sep. 2008; 70(1): 248-59.
Heyes et al., Cationic lipid saturation influences intracellular delviery of encapsulated nucleic acids. J Control Release. Oct. 3, 2005; 107(2): 276-87.
Hoerr et al., In vivo application of RNA leads to induction of specific cytotoxic T lymphocytes and antibodies. Eur J Immunol. Jan. 2000; 30(1): 1-7.
Hung et al., Physicological characterization and gene transfection efficiency of lipid emulsions with various co-emulsifiers. Int J Pharm. Jan. 31, 2005; 289(1-2): 197-208.
Jeffs et al., A scalable, extrusion-free method of efficient liposomal encapsulation of plasmid DNA. Pharm Res. Mar. 2005; 22(3): 362-72.
Kang et al., ery of interleukin-18 gene to lung cancer cells using cationic emulsion. J Drug Target. Jan. 2009; 17(1): 19-28.
Kim et al., Airway gene transfer using cationic emulsion as a mucosal gene carrier, J Gene Med. Jun. 2005; 7(6): 749-58.
Kim et al., Optimization of lipid compisistion in cationic emulstion as in vitro and in vivo transfection agents. Pharm Res. Jan. 2001; 18(1): 54-60.
Kim et al., Polycations enhance emulsion-mediated in vitro and in vivo transfections. Int J Pharm. May 13, 2005; 295(1-2): 35-45.
Kwon et al., In vivo time-dependent gene expression of cationic lipid-based emulstion as a stable and biocompatible non-viral gene carrier. J Control Release. May 22, 2008; 128(1): 89-97.
Le Bon et al., Type I interferons potently enhance humoral immunity and can promote isotype switching by stimulating dendritic cells in vivo. Immunity. Apr. 2001; 14(4): 461-70.
Lee et al., Novel molecular approaches to cystic fibrosis gene therapy, Biochem J. Apr. 1, 2005; 387 (Pt 1): 1-15.
Liu et al., Effect of non-lonic surfactants on the formation of DNA/erulsion complexes and emulsion-mediated gene transfer. Pharm Res. Nov. 1996; 13(11): 1642-6.
Majde, Viral double-stranded RNA, cytokines, and the flu. J Interferon Cytokine Res. Mar. 2000;20(3):259-72.
Malone et al., Cationic liposome-mediated RNA transfection. Proc Natl Acad Sci U S A. Aug. 1989; 86(16): 6077-81.
Martinon et al., Induction of virus-specific cytotoxic T lymphocytes in vivo by liposome-entrapped mRNA. Eur J Immunol. Jul. 1993; 23(7): 1719-22.
McCluskie et al., CpG DNA is an effective oral adjuvant to protein antigens in mice. Vaccine. Nov. 22, 2000; 19(7-8): 950-7.
Min et al., Improved gene expression pattern using Epstein-Barr virus (EBV)-based plasmid and cationic emulsion. Biomaterials. Mar. 2005;26(9):1063-70.
Montana et al., Cloning, expression, and localization of a new member of a Paracentrotus lividus cell surface multigene family. Mol Reprod Dev. May 1996; 44(1): 36-43,.
Montana et al., Employment of cationic solid-iipid nanoparticles as RNA carriers. Bioconjug Chem. Mar.-Apr. 2007; 18(2):302-8.
Moret et al., Stability of PEI-DNA and DOTAP-DNA complexes: effect of alkaline pH, heparin and serum. J Control Release. Sep. 11, 2001; 76(1-2): 169-81.
Moss et al., Human immunodeficiency virus (HIV)-specific immune responses are generated with the simultaneous vaccination of a gp120-depleted, whole-killed HIV-1 immunogen with cytosine-phosphorothioate-guanine dinucleotide immunostimulatory sequences of DNA. J Hum Virol. Jan.-Feb. 2001; 4(1): 39-43.
Moss et al., In vitro immune function after vaccination with an inactivated, gp120-depleted HIV-1 antigen with immunostimulatory oligodeoxynucleotides. Vaccine. Jan. 6, 2000; 18(11-12): 1081-7.
Nam et al., Lipid-based emulsion system as non-viral gene carriers. Arch Pharm Res. May 2009; 32(5): 639-46.
O'Hagan et al., Induction of potent immune responses by cationic microparticles with adsorbed human immunodeficiency virus DNA vaccines. J Virol. Oct. 2001; 75(19): 9037-43.
O'Hagan et al., Microparticles in MF59, a potent adjuvant combination fora recombinant protein vaccine against HIV-1. Vaccine. Mar. 6, 2000; 18(17): 1793-801.
O'Hagan et al., Synergistic adjuvant activity of immunostimulatory DNA and oil/water emulsions for immunization with HIV p55 gag antigen. Vaccine. Sep. 10, 2020; 20(27-28): 3389-98.
Opawale et al., Influence of interfacial rheological properties of mixed emulsifier films on the stability of water-in-oil-in-water emulsions. J Pharm Pharmacol. Sep. 1998; 50(9): 965-73.
Ott et al., A cationic sub-micron emulsion (MF59/DOTAP) is an effective delivery system for DNA vaccines. J Controi Release. Feb. 19, 2002; 79(1-3): 1-5.
Ott et al., MF59. Design and evaluation of a safe and potent adjuvant for human vaccines.Pharm Biotechnol. 1995;6: 277-96.
Parkin et al., An overview of the immune system. Lancet. Jun. 2, 2001; 357(9270): 1777-89.
Pascolo, Vaccination with messenger RNA (mRNA). Handb Exp Pharmacol, 2008;(183): 221-35.
Pascolo, Vaccination with messenger RNA. Methods Mol Med. 2006; 127: 23-40.
Perrie et al., Liposome-mediated DNA vaccination: the effect of vesicle composition. Vaccine. Apr. 30, 2001; 19(23-24): 3301-10.

* cited by examiner

Figure 4

SEQUENCE LISTING

<160> NUMBER OF SEQ ID NOS: 28

<210> SEQ ID NO 1
<211> LENGTH: 12463
<212> TYPE: DNA
<213> ORGANISM: Respiratory syncytial virus

<400> SEQUENCE: 1

```
ataggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagct cgccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tagacttgat gttacaagag gctggggccg gctcagtgga gacacctcgt ggcttgataa   1680
```

```
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct ggagagaccc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg actttcttc attcgtcagc aaattgaagg    3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
```

-continued

```
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
```

```
ttaaagaaaa ccccatcagg cttactgaag aaaacgtggt aaattacatt accaaattaa   6480

aaggaccaaa agctgctgct ctttttgcga agacacataa tttgaatatg ttgcaggaca   6540

taccaatgga caggtttgta atggacttaa agagagacgt gaaagtgact ccaggaacaa   6600

aacatactga agaacggccc aaggtacagg tgatccaggc tgccgatccg ctagcaacag   6660

cgtatctgtg cggaatccac cgagagctgg ttaggagatt aaatgcggtc ctgcttccga   6720

acattcatac actgtttgat atgtcggctg aagactttga cgctattata gccgagcact   6780

tccagcctgg ggattgtgtt ctggaaactg acatcgcgtc gtttgataaa agtgaggacg   6840

acgccatggc tctgaccgcg ttaatgattc tggaagactt aggtgtggac gcagagctgt   6900

tgacgctgat tgaggcggct ttcggcgaaa tttcatcaat acatttgccc actaaaacta   6960

aatttaaatt cggagccatg atgaaatctg gaatgttcct cacactgttt gtgaacacag   7020

tcattaacat tgtaatcgca agcagagtgt tgagagaacg gctaaccgga tcaccatgtg   7080

cagcattcat tggagatgac aatatcgtga aaggagtcaa atcggacaaa ttaatggcag   7140

acaggtgcgc cacctggttg aatatggaag tcaagattat agatgctgtg gtgggcgaga   7200

aagcgcctta tttctgtgga gggtttattt tgtgtgactc cgtgaccggc acagcgtgcc   7260

gtgtggcaga cccccctaaaa aggctgttta agcttggcaa acctctggca gcagacgatg   7320

aacatgatga tgacaggaga agggcattgc atgaagagtc aacacgctgg aaccgagtgg   7380

gtattctttc agagctgtgc aaggcagtag aatcaaggta tgaaaccgta ggaacttcca   7440

tcatagttat ggccatgact actctagcta gcagtgttaa atcattcagc tacctgagag   7500

gggcccctat aactctctac ggctaacctg aatggactac gacatagtct agtcgacgcc   7560

accatggaac tgctgatcct gaaggccaac gccatcacca ccatcctgac cgccgtgacc   7620

ttctgcttcg ccagcggcca gaacatcacc gaggaattct accagagcac ctgcagcgcc   7680

gtgagcaagg gctacctgag cgccctgcgg accggctggt acaccagcgt gatcaccatc   7740

gagctgtcca acatcaaaga aaacaagtgc aacggcaccg acgccaaggt gaaactgatc   7800

aagcaggaac tggacaagta caagaacgcc gtgaccgagc tgcagctgct gatgcagagc   7860

acccccgcca ccaacaaccg ggccagaaga gagctgcccc ggttcatgaa ctacaccctg   7920

aacaacgcca agaaaaccaa cgtgaccctg agcaagaagc ggaagcggcg gttcctgggc   7980

ttcctgctgg gcgtgggcag cgccatcgcc agcggggtgg ccgtgtccaa ggtgctgcac   8040

ctggaaggcg aggtgaacaa gatcaagtcc gccctgctgt ccaccaacaa ggccgtggtg   8100

tccctgagca acggcgtgag cgtgctgacc agcaaggtgc tggatctgaa gaactacatc   8160

gacaagcagc tgctgcccat cgtgaacaag cagagctgca gcatcagcaa catcgagacc   8220

gtgatcgagt tccagcagaa gaacaaccgg ctgctggaaa tcacccggga gttcagcgtg   8280

aacgccggcg tgaccacccc cgtgagcacc tacatgctga ccaacagcga gctgctgtcc   8340

ctgatcaatg acatgcccat caccaacgac cagaaaaagc tgatgagcaa caacgtgcag   8400

atcgtgcggc agcagagcta ctccatcatg agcatcatca aagaagaggt gctggcctac   8460

gtggtgcagc tgcccctgta cggcgtgatc gacacccccct gctggaagct gcacaccagc   8520

cccctgtgca ccaccaacac caaagagggc agcaacatct gcctgacccg gaccgaccgg   8580

ggctggtact gcgacaacgc cggcagcgtg agcttcttcc cccaagccga gacctgcaag   8640

gtgcagagca accgggtgtt ctgcgacacc atgaacagcc tgaccctgcc ctccgaggtg   8700

aacctgtgca acgtggacat cttcaacccc aagtacgact gcaagatcat gacctccaag   8760
```

```
accgacgtga gcagctccgt gatcacctcc ctgggcgcca tcgtgagctg ctacggcaag   8820
accaagtgca ccgccagcaa caagaaccgg ggcatcatca agaccttcag caacggctgc   8880
gactacgtga gcaacaaggg cgtggacacc gtgagcgtgg gcaacacact gtactacgtg   8940
aataagcagg aaggcaagag cctgtacgtg aagggcgagc ccatcatcaa cttctacgac   9000
cccctggtgt tccccagcga cgagttcgac gccagcatca gccaggtcaa cgagaagatc   9060
aaccagagcc tggccttcat ccggaagagc gacgagctgc tgcacaatgt gaatgccggc   9120
aagagcacca ccaatatcat gatcaccaca atcatcatcg tgatcattgt gatcctgctg   9180
tctctgattg ccgtgggcct gctgctgtac tgcaaggccc gcagcacccc tgtgaccctg   9240
tccaaggacc agctgtccgg catcaacaat atcgccttct ccaactgaag tctagacggc   9300
gcgcccaccc agcggccgca tacagcagca attggcaagc tgcttacata gaactcgcgg   9360
cgattggcat gccgccttaa aatttttatt ttattttttct tttcttttcc gaatcggatt   9420
ttgtttttaa tatttcaaaa aaaaaaaaaa aaaaaaaaaa aaaaaaaaaa agggtcggca   9480
tggcatctcc acctcctcgc ggtccgacct gggcatccga aggaggacgc acgtccactc   9540
ggatggctaa gggagagcca cgtttaaacc agctccaatt cgccctatag tgagtcgtat   9600
tacgcgcgct cactggccgt cgttttacaa cgtcgtgact gggaaaaccc tggcgttacc   9660
caacttaatc gccttgcagc acatccccct ttcgccagct ggcgtaatag cgaagaggcc   9720
cgcaccgatc gcccttccca acagttgcgc agcctgaatg gcgaatggga cgcgccctgt   9780
agcggcgcat taagcgcggc gggtgtggtg gttacgcgca gcgtgaccgc tacacttgcc   9840
agcgccctag cgcccgctcc tttcgctttc ttcccttcct ttctcgccac gttcgccggc   9900
tttccccgtc aagctctaaa tcgggggctc cctttagggt tccgatttag tgctttacgg   9960
cacctcgacc ccaaaaaact tgattagggt gatggttcac gtagtgggcc atcgccctga  10020
tagacggttt ttcgcccttt gacgttggag tccacgttct ttaatagtgg actcttgttc  10080
caaactggaa caacactcaa ccctatctcg gtctattctt ttgatttata agggattttg  10140
ccgatttcgg cctattggtt aaaaaatgag ctgatttaac aaaaatttaa cgcgaatttt  10200
aacaaaatat taacgcttac aatttaggtg gcacttttcg gggaaatgtg cgcggaaccc  10260
ctatttgttt atttttctaa atacattcaa atatgtatcc gctcatgaga caataaccct  10320
gataaatgct tcaataatat tgaaaaagga agagtatgag tattcaacat ttccgtgtcg  10380
cccttattcc cttttttgcg gcattttgcc ttcctgtttt tgctcaccca gaaacgctgg  10440
tgaaagtaaa agatgctgaa gatcagttgg gtgcacgagt gggttacatc gaactggatc  10500
tcaacagcgg taagatcctt gagagttttc gccccgaaga acgttttcca atgatgagca  10560
cttttaaagt tctgctatgt ggcgcggtat tatcccgtat tgacgccggg caagagcaac  10620
tcggtcgccg catacactat tctcagaatg acttggttga gtactcacca gtcacagaaa  10680
agcatcttac ggatggcatg acagtaagag aattatgcag tgctgccata accatgagtg  10740
ataacactgc ggccaactta cttctgacaa cgatcggagg accgaaggag ctaaccgctt  10800
ttttgcacaa catgggggat catgtaactc gccttgatcg ttgggaaccg gagctgaatg  10860
aagccatacc aaacgacgag cgtgacacca cgatgcctgt agcaatggca acaacgttgc  10920
gcaaactatt aactggcgaa ctacttactc tagcttcccg gcaacaatta atagactgga  10980
tggaggcgga taaagttgca ggaccacttc tgcgctcggc ccttccggct ggctggttta  11040
ttgctgataa atctggagcc ggtgagcgtg ggtctcgcgg tatcattgca gcactggggc  11100
cagatggtaa gccctcccgt atcgtagtta tctacacgac ggggagtcag gcaactatgg  11160
```

```
atgaacgaaa tagacagatc gctgagatag gtgcctcact gattaagcat tggtaactgt  11220
cagaccaagt ttactcatat atactttaga ttgatttaaa acttcatttt taatttaaaa  11280
ggatctaggt gaagatcctt tttgataatc tcatgaccaa aatcccttaa cgtgagtttt  11340
cgttccactg agcgtcagac cccgtagaaa agatcaaagg atcttcttga gatccttttt  11400
ttctgcgcgt aatctgctgc ttgcaaacaa aaaaaccacc gctaccagcg gtggtttgtt  11460
tgccggatca agagctacca actctttttc cgaaggtaac tggcttcagc agagcgcaga  11520
taccaaatac tgttcttcta gtgtagccgt agttaggcca ccacttcaag aactctgtag  11580
caccgcctac atacctcgct ctgctaatcc tgttaccagt ggctgctgcc agtggcgata  11640
agtcgtgtct taccgggttg gactcaagac gatagttacc ggataaggcg cagcggtcgg  11700
gctgaacggg gggttcgtgc acacagccca gcttggagcg aacgacctac accgaactga  11760
gatacctaca gcgtgagcta tgagaaagcg ccacgcttcc cgaagggaga aaggcggaca  11820
ggtatccggt aagcggcagg gtcggaacag gagagcgcac gagggagctt ccagggggaa  11880
acgcctggta tctttatagt cctgtcgggt ttcgccacct ctgacttgag cgtcgatttt  11940
tgtgatgctc gtcagggggg cggagcctat ggaaaaacgc cagcaacgcg gcctttttac  12000
ggttcctggc cttttgctgg ccttttgctc acatgttctt tcctgcgtta tcccctgatt  12060
ctgtggataa ccgtattacc gcctttgagt gagctgatac cgctcgccgc agccgaacga  12120
ccgagcgcag cgagtcagtg agcgaggaag cggaagagcg cccaatacgc aaaccgcctc  12180
tccccgcgcg ttggccgatt cattaatgca gctggcacga caggtttccc gactggaaag  12240
cgggcagtga gcgcaacgca attaatgtga gttagctcac tcattaggca ccccaggctt  12300
tacactttat gctcccggct cgtatgttgt gtggaattgt gagcggataa caatttcaca  12360
caggaaacag ctatgaccat gattacgcca agcgcgcaat taaccctcac taaagggaac  12420
aaaagctggg taccgggccc acgcgtaata cgactcacta tag                    12463
```

```
<210> SEQ ID NO 2
<211> LENGTH: 12436
<212> TYPE: DNA
<213> ORGANISM: Respiratory syncytial virus

<400> SEQUENCE: 2

ataggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagct cgccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
```

-continued

```
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tagacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
```

```
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
```

-continued

```
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtcgacgcc   7560
accatggaac tgctgatcct gaaggccaac gccatcacca ccatcctgac cgccgtgacc   7620
ttctgcttcg ccagcggcca gaacatcacc gaggaattct accagagcac ctgcagcgcc   7680
gtgagcaagg gctacctgag cgccctgcgg accggctggt acaccagcgt gatcaccatc   7740
gagctgtcca acatcaaaga aaacaagtgc aacggcaccg acgccaaggt gaaactgatc   7800
aagcaggaac tggacaagta caagaacgcc gtgaccgagc tgcagctgct gatgcagagc   7860
acccccgcca ccaacaaccg ggccagaaga gagctgcccc ggttcatgaa ctacaccctg   7920
```

```
aacaacgcca agaaaaccaa cgtgaccctg agcaagaagc ggaagcggcg gagcgccatc   7980
gccagcgggg tggccgtgtc caaggtgctg cacctggaag gcgaggtgaa caagatcaag   8040
tccgccctgc tgtccaccaa caaggccgtg gtgtccctga gcaacggcgt gagcgtgctg   8100
accagcaagg tgctggatct gaagaactac atcgacaagc agctgctgcc catcgtgaac   8160
aagcagagct gcagcatcag caacatcgag accgtgatcg agttccagca gaagaacaac   8220
cggctgctgg aaatcacccg ggagttcagc gtgaacgccg gcgtgaccac ccccgtgagc   8280
acctacatgc tgaccaacag cgagctgctg tccctgatca atgacatgcc catcaccaac   8340
gaccagaaaa agctgatgag caacaacgtg cagatcgtgc ggcagcagag ctactccatc   8400
atgagcatca tcaaagaaga ggtgctggcc tacgtggtgc agctgcccct gtacggcgtg   8460
atcgacaccc cctgctggaa gctgcacacc agcccccctgt gcaccaccaa caccaaagag   8520
ggcagcaaca tctgcctgac ccggaccgac cggggctggt actgcgacaa cgccggcagc   8580
gtgagcttct tcccccaagc cgagacctgc aaggtgcaga gcaaccgggt gttctgcgac   8640
accatgaaca gcctgaccct gccctccgag gtgaacctgt gcaacgtgga catcttcaac   8700
cccaagtacg actgcaagat catgacctcc aagaccgacg tgagcagctc cgtgatcacc   8760
tccctgggcg ccatcgtgag ctgctacggc aagaccaagt gcaccgccag caacaagaac   8820
cggggcatca tcaagacctt cagcaacggc tgcgactacg tgagcaacaa gggcgtggac   8880
accgtgagcg tgggcaacac actgtactac gtgaataagc aggaaggcaa gagcctgtac   8940
gtgaagggcg agcccatcat caacttctac gacccccctgg tgttccccag cgacgagttc   9000
gacgccagca tcagccaggt caacgagaag atcaaccaga gcctggcctt catccggaag   9060
agcgacgagc tgctgcacaa tgtgaatgcc ggcaagagca ccaccaatat catgatcacc   9120
acaatcatca tcgtgatcat tgtgatcctg ctgtctctga ttgccgtggg cctgctgctg   9180
tactgcaagg cccgcagcac ccctgtgacc ctgtccaagg accagctgtc cggcatcaac   9240
aatatcgcct tctccaactg aagtctagac ggcgcgccca cccagcggcc gcatacagca   9300
gcaattggca agctgcttac atagaactcg cggcgattgg catgccgcct taaaattttt   9360
attttatttt tcttttcttt tccgaatcgg attttgtttt taatatttca aaaaaaaaaa   9420
aaaaaaaaaa aaaaaaaaaa aaaagggtcg gcatggcatc tccacctcct cgcggtccga   9480
cctgggcatc cgaaggagga cgcacgtcca ctcggatggc taagggagag ccacgtttaa   9540
accagctcca attcgcccta tagtgagtcg tattacgcgc gctcactggc cgtcgtttta   9600
caacgtcgtg actgggaaaa ccctggcgtt acccaactta atcgccttgc agcacatccc   9660
cctttcgcca gctggcgtaa tagcgaagag gcccgcaccg atcgcccttc ccaacagttg   9720
cgcagcctga atggcgaatg ggacgcgccc tgtagcggcg cattaagcgc ggcgggtgtg   9780
gtggttacgc gcagcgtgac cgctacactt gccagcgccc tagcgcccgc tcctttcgct   9840
ttcttccctt cctttctcgc cacgttcgcc ggctttcccc gtcaagctct aaatcggggg   9900
ctccctttag ggttccgatt tagtgcttta cggcacctcg accccaaaaa acttgattag   9960
ggtgatggtt cacgtagtgg gccatcgccc tgatagacgg tttttcgccc tttgacgttg  10020
gagtccacgt tctttaatag tggactcttg ttccaaactg gaacaacact caaccctatc  10080
tcggtctatt cttttgattt ataagggatt ttgccgattt cggcctattg gttaaaaaat  10140
gagctgattt aacaaaaatt taacgcgaat tttaacaaaa tattaacgct tacaatttag  10200
gtggcacttt tcggggaaat gtgcgcggaa cccctatttg tttatttttc taaatacatt  10260
```

```
caaatatgta tccgctcatg agacaataac cctgataaat gcttcaataa tattgaaaaa  10320
ggaagagtat gagtattcaa catttccgtg tcgcccttat tccctttttt gcggcatttt  10380
gccttcctgt ttttgctcac ccagaaacgc tggtgaaagt aaaagatgct gaagatcagt  10440
tgggtgcacg agtgggttac atcgaactgg atctcaacag cggtaagatc cttgagagtt  10500
ttcgccccga agaacgtttt ccaatgatga gcacttttaa agttctgcta tgtggcgcgg  10560
tattatcccg tattgacgcc gggcaagagc aactcggtcg ccgcatacac tattctcaga  10620
atgacttggt tgagtactca ccagtcacag aaaagcatct tacggatggc atgacagtaa  10680
gagaattatg cagtgctgcc ataaccatga gtgataacac tgcggccaac ttacttctga  10740
caacgatcgg aggaccgaag gagctaaccg cttttttgca caacatgggg gatcatgtaa  10800
ctcgccttga tcgttgggaa ccggagctga atgaagccat accaaacgac gagcgtgaca  10860
ccacgatgcc tgtagcaatg gcaacaacgt tgcgcaaact attaactggc gaactactta  10920
ctctagcttc ccggcaacaa ttaatagact ggatggaggc ggataaagtt gcaggaccac  10980
ttctgcgctc ggcccttccg gctggctggt ttattgctga taaatctgga gccggtgagc  11040
gtgggtctcg cggtatcatt gcagcactgg ggccagatgg taagccctcc cgtatcgtag  11100
ttatctacac gacggggagt caggcaacta tggatgaacg aaatagacag atcgctgaga  11160
taggtgcctc actgattaag cattggtaac tgtcagacca agtttactca tatatacttt  11220
agattgattt aaaacttcat ttttaattta aaaggatcta ggtgaagatc ctttttgata  11280
atctcatgac caaaatccct taacgtgagt tttcgttcca ctgagcgtca gaccccgtag  11340
aaaagatcaa aggatcttct tgagatcctt tttttctgcg cgtaatctgc tgcttgcaaa  11400
caaaaaaacc accgctacca gcggtggttt gtttgccgga tcaagagcta ccaactcttt  11460
ttccgaaggt aactggcttc agcagagcgc agataccaaa tactgttctt ctagtgtagc  11520
cgtagttagg ccaccacttc aagaactctg tagcaccgcc tacatacctc gctctgctaa  11580
tcctgttacc agtggctgct gccagtggcg ataagtcgtg tcttaccggg ttggactcaa  11640
gacgatagtt accggataag gcgcagcggt cgggctgaac ggggggttcg tgcacacagc  11700
ccagcttgga gcgaacgacc tacaccgaac tgagatacct acagcgtgag ctatgagaaa  11760
gcgccacgct tcccgaaggg agaaaggcgg acaggtatcc ggtaagcggc agggtcggaa  11820
caggagagcg cacgagggag cttccagggg gaaacgcctg gtatctttat agtcctgtcg  11880
ggtttcgcca cctctgactt gagcgtcgat ttttgtgatg ctcgtcaggg gggcggagcc  11940
tatggaaaaa cgccagcaac gcggcctttt tacggttcct ggccttttgc tggccttttg  12000
ctcacatgtt ctttcctgcg ttatcccctg attctgtgga taaccgtatt accgcctttg  12060
agtgagctga taccgctcgc cgcagccgaa cgaccgagcg cagcgagtca gtgagcgagg  12120
aagcggaaga gcgcccaata cgcaaaccgc ctctccccgc gcgttggccg attcattaat  12180
gcagctggca cgacaggttt cccgactgga aagcgggcag tgagcgcaac gcaattaatg  12240
tgagttagct cactcattag gcaccccagg ctttacactt tatgctcccg gctcgtatgt  12300
tgtgtggaat tgtgagcgga taacaatttc acacaggaaa cagctatgac catgattacg  12360
ccaagcgcgc aattaaccct cactaaaggg aacaaaagct gggtaccggg cccacgcgta  12420
atacgactca ctatag                                                  12436
```

<210> SEQ ID NO 3
<211> LENGTH: 11702
<212> TYPE: DNA
<213> ORGANISM: Respiratory syncytial virus

<400> SEQUENCE: 3

```
gcagtcacca aaaaagatct agtggtgagc gccaagaaag aaaactgtgc agaaattata     60
agggacgtca agaaaatgaa agggctggac gtcaatgcca gaactgtgga ctcagtgctc    120
ttgaatggat gcaaacaccc cgtagagacc ctgtatattg acgaagcttt tgcttgtcat    180
gcaggtactc tcagagcgct catagccatt ataagaccta aaaaggcagt gctctgcggg    240
gatcccaaac agtgcggttt ttttaacatg atgtgcctga aagtgcattt taaccacgag    300
atttgcacac aagtcttcca caaaagcatc tctcgccgtt gcactaaatc tgtgacttcg    360
gtcgtctcaa ccttgtttta cgacaaaaaa atgagaacga cgaatccgaa agagactaag    420
attgtgattg acactaccgg cagtaccaaa cctaagcagg acgatctcat tctcacttgt    480
ttcagagggt gggtgaagca gttgcaaata gattacaaag gcaacgaaat aatgacggca    540
gctgcctctc aagggctgac ccgtaaaggt gtgtatgccg ttcggtacaa ggtgaatgaa    600
aatcctctgt acgcacccac ctcagaacat gtgaacgtcc tactgacccg cacggaggac    660
cgcatcgtgt ggaaaacact agccggcgac ccatggataa aaacactgac tgccaagtac    720
cctgggaatt tcactgccac gatagaggag tggcaagcag agcatgatgc catcatgagg    780
cacatcttgg agagaccgga ccctaccgac gtcttccaga ataaggcaaa cgtgtgttgg    840
gccaaggctt tagtgccggt gctgaagacc gctggcatag acatgaccac tgaacaatgg    900
aacactgtgg attattttga aacggacaaa gctcactcag cagagatagt attgaaccaa    960
ctatgcgtga ggttctttgg actcgatctg gactccggtc tattttctgc acccactgtt   1020
ccgttatcca ttaggaataa tcactgggat aactccccgt cgcctaacat gtacgggctg   1080
aataaagaag tggtccgtca gctctctcgc aggtacccac aactgcctcg ggcagttgcc   1140
actggaagag tctatgacat gaacactggt acactgcgca attatgatcc gcgcataaac   1200
ctagtacctg taaacagaag actgcctcat gctttagtcc tccaccataa tgaacaccca   1260
cagagtgact tttcttcatt cgtcagcaaa ttgaagggca gaactgtcct ggtggtcggg   1320
gaaaagttgt ccgtcccagg caaaatggtt gactggttgt cagaccggcc tgaggctacc   1380
ttcagagctc ggctggattt aggcatccca ggtgatgtgc ccaaatatga cataaatattt  1440
gttaatgtga ggacccccata taaataccat cactatcagc agtgtgaaga ccatgccatt   1500
aagcttagca tgttgaccaa gaaagcttgt ctgcatctga atcccggcgg aacctgtgtc   1560
agcataggtt atggttacgc tgacagggcc agcgaaagca tcattggtgc tatagcgcgg   1620
cagttcaagt tttcccgggt atgcaaaccg aaatcctcac ttgaagagac ggaagttctg   1680
tttgtattca ttgggtacga tcgcaaggcc cgtacgcaca atccttacaa gctttcatca   1740
accttgacca acatttatac aggttccaga ctccacgaag ccggatgtgc accctcatat   1800
catgtggtgc gaggggatat tgccacggcc accgaaggag tgattataaa tgctgctaac   1860
agcaaaggac aacctggcgg aggggtgtgc ggagcgctgt ataagaaatt cccggaaagc   1920
ttcgatttac agccgatcga agtaggaaaa gcgcgactgg tcaaaggtgc agctaaacat   1980
atcattcatg ccgtaggacc aaacttcaac aaagtttcgg aggttgaagg tgacaaacag   2040
ttggcagagg cttatgagtc catcgctaag attgtcaacg ataacaatta caagtcagta   2100
gcgattccac tgttgtccac cggcatcttt tccgggaaca aagatcgact aacccaatca   2160
ttgaaccatt tgctgacagc tttagacacc actgatgcag atgtagccat atactgcagg   2220
gacaagaaat gggaaatgac tctcaaggaa gcagtggcta ggagagaagc agtggaggag   2280
```

```
atatgcatat ccgacgactc ttcagtgaca gaacctgatg cagagctggt gagggtgcat   2340
ccgaagagtt ctttggctgg aaggaagggc tacagcacaa gcgatggcaa aactttctca   2400
tatttggaag ggaccaagtt tcaccaggcg gccaaggata tagcagaaat taatgccatg   2460
tggcccgttg caacggaggc caatgagcag gtatgcatgt atatcctcgg agaaagcatg   2520
agcagtatta ggtcgaaatg ccccgtcgaa gagtcggaag cctccacacc acctagcacg   2580
ctgccttgct tgtgcatcca tgccatgact ccagaaagag tacagcgcct aaaagcctca   2640
cgtccagaac aaattactgt gtgctcatcc tttccattgc cgaagtatag aatcactggt   2700
gtgcagaaga tccaatgctc ccagcctata ttgttctcac cgaaagtgcc tgcgtatatt   2760
catccaagga agtatctcgt ggaaacacca ccggtagacg agactccgga gccatcggca   2820
gagaaccaat ccacagaggg gacacctgaa caaccaccac ttataaccga ggatgagacc   2880
aggactagaa cgcctgagcc gatcatcatc gaagaggaag aagaggatag cataagtttg   2940
ctgtcagatg gcccgaccca ccaggtgctg caagtcgagg cagacattca cgggccgccc   3000
tctgtatcta gctcatcctg gtccattcct catgcatccg actttgatgt ggacagttta   3060
tccatacttg acaccctgga gggagctagc gtgaccagcg gggcaacgtc agccgagact   3120
aactcttact tcgcaaagag tatggagttt ctggcgcgac cggtgcctgc gcctcgaaca   3180
gtattcagga accctccaca tcccgctccg cgcacaagaa caccgtcact tgcacccagc   3240
agggcctgct cgagaaccag cctagtttcc accccgccag gcgtgaatag ggtgatcact   3300
agagaggagc tcgaggcgct taccccgtca cgcactccta gcaggtcggt ctcgagaacc   3360
agcctggtct ccaacccgcc aggcgtaaat agggtgatta caagagagga gtttgaggcg   3420
ttcgtagcac aacaacaatg acggtttgat gcgggtgcat acatcttttc ctccgacacc   3480
ggtcaagggc atttacaaca aaaatcagta aggcaaacgg tgctatccga agtggtgttg   3540
gagaggaccg aattggagat ttcgtatgcc ccgcgcctcg accaagaaaa agaagaatta   3600
ctacgcaaga aattacagtt aaatcccaca cctgctaaca gaagcagata ccagtccagg   3660
aaggtggaga acatgaaagc cataacagct agacgtattc tgcaaggcct agggcattat   3720
ttgaaggcag aaggaaaagt ggagtgctac cgaaccctgc atcctgttcc tttgtattca   3780
tctagtgtga accgtgcctt ttcaagcccc aaggtcgcag tggaagcctg taacgccatg   3840
ttgaaagaga actttccgac tgtggcttct tactgtatta ttccagagta cgatgcctat   3900
ttggacatgg ttgacggagc ttcatgctgc ttagacactg ccagtttttg ccctgcaaag   3960
ctgcgcagct ttccaaagaa acactcctat ttggaaccca caatacgatc ggcagtgcct   4020
tcagcgatcc agaacacgct ccagaacgtc ctggcagctg ccacaaaaag aaattgcaat   4080
gtcacgcaaa tgagagaatt gcccgtattg gattcggcgg cctttaatgt ggaatgcttc   4140
aagaaatatg cgtgtaataa tgaatattgg gaaacgttta aagaaaaccc catcaggctt   4200
actgaagaaa acgtggtaaa ttacattacc aaattaaaag gaccaaaagc tgctgctctt   4260
tttgcgaaga cacataattt gaatatgttg caggacatac caatggacag gtttgtaatg   4320
gacttaaaga gagacgtgaa agtgactcca ggaacaaaac atactgaaga acggcccaag   4380
gtacaggtga tccaggctgc cgatccgcta gcaacagcgt atctgtgcgg aatccaccga   4440
gagctggtta ggagattaaa tgcggtcctg cttccgaaca ttcatacact gtttgatatg   4500
tcggctgaag actttgacgc tattatagcc gagcacttcc agcctgggga ttgtgttctg   4560
gaaactgaca tcgcgtcgtt tgataaaagt gaggacgacg ccatggctct gaccgcgtta   4620
atgattctgg aagacttagg tgtggacgca gagctgttga cgctgattga ggcggctttc   4680
```

-continued ggcgaaattt catcaataca tttgcccact aaaactaaat ttaaattcgg agccatgatg 4740
aaatctggaa tgttcctcac actgtttgtg aacacagtca ttaacattgt aatcgcaagc 4800
agagtgttga gagaacggct aaccggatca ccatgtgcag cattcattgg agatgacaat 4860
atcgtgaaag gagtcaaatc ggacaaatta atggcagaca ggtgcgccac ctggttgaat 4920
atggaagtca agattataga tgctgtggtg ggcgagaaag cgccttattt ctgtggaggg 4980
tttattttgt gtgactccgt gaccggcaca gcgtgccgtg tggcagaccc cctaaaaagg 5040
ctgtttaagc ttggcaaacc tctggcagca gacgatgaac atgatgatga caggagaagg 5100
gcattgcatg aagagtcaac acgctggaac cgagtgggta ttctttcaga gctgtgcaag 5160
gcagtagaat caaggtatga aaccgtagga acttccatca tagttatggc catgactact 5220
ctagctagca gtgttaaatc attcagctac ctgagagggg cccctataac tctctacggc 5280
taacctgaat ggactacgac atagtctagt cgacgccacc atggaactgc tgatcctgaa 5340
ggccaacgcc atcaccacca tcctgaccgc cgtgaccttc tgcttcgcca gcggccagaa 5400
catcaccgag gaattctacc agagcacctg cagcgccgtg agcaagggct acctgagcgc 5460
cctgcggacc ggctggtaca ccagcgtgat caccatcgag ctgtccaaca tcaaagaaaa 5520
caagtgcaac ggcaccgacg ccaaggtgaa actgatcaag caggaactgg acaagtacaa 5580
gaacgccgtg accgagctgc agctgctgat gcagagcacc cccgccacca acaaccgggc 5640
cagaagagag ctgccccggt tcatgaacta caccctgaac aacgccaaga aaaccaacgt 5700
gaccctgagc aagaagcgga agcggcggag cgccatcgcc agcggggtgg ccgtgtccaa 5760
ggtgctgcac ctggaaggcg aggtgaacaa gatcaagtcc gccctgctgt ccaccaacaa 5820
ggccgtggtg tccctgagca acggcgtgag cgtgctgacc agcaaggtgc tggatctgaa 5880
gaactacatc gacaagcagc tgctgcccat cgtgaacaag cagagctgca gcatcagcaa 5940
catcgagacc gtgatcgagt tccagcagaa gaacaaccgg ctgctggaaa tcacccggga 6000
gttcagcgtg aacgccggcg tgaccacccc cgtgagcacc tacatgctga ccaacagcga 6060
gctgctgtcc ctgatcaatg acatgcccat caccaacgac cagaaaaagc tgatgagcaa 6120
caacgtgcag atcgtgcggc agcagagcta ctccatcatg agcatcatca aagaagaggt 6180
gctggcctac gtggtgcagc tgcccctgta cggcgtgatc gacacccccct gctggaagct 6240
gcacaccagc cccctgtgca ccaccaacac caaagagggc agcaacatct gcctgacccg 6300
gaccgaccgg ggctggtact gcgacaacgc cggcagcgtg agcttcttcc cccaagccga 6360
gacctgcaag gtgcagagca accgggtgtt ctgcgacacc atgaacagcc tgaccctgcc 6420
ctccgaggtg aacctgtgca acgtggacat cttcaacccc aagtacgact gcaagatcat 6480
gacctccaag accgacgtga gcagctccgt gatcacctcc ctgggcgcca tcgtgagctg 6540
ctacggcaag accaagtgca ccgccagcaa caagaaccgg ggcatcatca agaccttcag 6600
caacggctgc gactacgtga gcaacaaggg cgtggacacc gtgagcgtgg gcaacacact 6660
gtactacgtg aataagcagg aaggcaagag cctgtacgtg aagggcgagc ccatcatcaa 6720
cttctacgac cccctggtgt tccccagcga cgagttcgac gccagcatca gccaggtcaa 6780
cgagaagatc aaccagagcc tggccttcat ccggaagtcc gacgagctgc tgcacaatgt 6840
gaatgccggc aagagcacca ccaatatcat gatcaccaca atcatcatcg tgatcattgt 6900
gatcctgctg tctctgattg ccgtgggcct gctgctgtac tgcaaggccc gcagcacccc 6960
tgtgaccctg tccaaggacc agctgtccgg catcaacaat atcgccttct ccaactgaag 7020

-continued

```
tctagacggc gcgcccaccc agcggccgca tacagcagca attggcaagc tgcttacata   7080
gaactcgcgg cgattggcat gccgccttaa aatttttatt ttattttttct tttcttttcc   7140
gaatcggatt ttgtttttaa tatttcaaaa aaaaaaaaaa aaaaaaaaaa aaaaaaaaaa   7200
aaaaaagaag agcgtttaaa cacgtgatat ctggcctcat gggccttcct ttcactgccc   7260
gctttccagt cgggaaacct gtcgtgccag ctgcattaac atggtcatag ctgtttcctt   7320
gcgtattggg cgctctccgc ttcctcgctc actgactcgc tgcgctcggt cgttcgggta   7380
aagcctgggg tgcctaatga gcaaaaggcc agcaaaaggc caggaaccgt aaaaaggccg   7440
cgttgctggc gtttttccat aggctccgcc cccctgacga gcatcacaaa aatcgacgct   7500
caagtcagag gtggcgaaac ccgacaggac tataaagata ccaggcgttt ccccctggaa   7560
gctccctcgt gcgctctcct gttccgaccc tgccgcttac cggatacctg tccgcctttc   7620
tcccttcggg aagcgtggcg ctttctcata gctcacgctg taggtatctc agttcggtgt   7680
aggtcgttcg ctccaagctg ggctgtgtgc acgaaccccc cgttcagccc gaccgctgcg   7740
ccttatccgg taactatcgt cttgagtcca acccggtaag acacgactta tcgccactgg   7800
cagcagccac tggtaacagg attagcagag cgaggtatgt aggcggtgct acagagttct   7860
tgaagtggtg gcctaactac ggctacacta gaagaacagt atttggtatc tgcgctctgc   7920
tgaagccagt taccttcgga aaaagagttg gtagctcttg atccggcaaa caaaccaccg   7980
ctggtagcgg tggttttttt gtttgcaagc agcagattac gcgcagaaaa aaaggatctc   8040
aagaagatcc tttgatcttt tctacggggt ctgacgctca gtggaacgaa aactcacgtt   8100
aagggatttt ggtcatgaat acacggtgcc tgactgcgtt agcaatttaa ctgtgataaa   8160
ctaccgcatt aaagcttatc gatgataagc tgtcaaacat gagaattctt agaaaaactc   8220
atcgagcatc aaatgaaact gcaatttatt catatcagga ttatcaatac catatttttg   8280
aaaaagccgt ttctgtaatg aaggagaaaa ctcaccgagg cagttccata ggatggcaag   8340
atcctggtat cggtctgcga ttccgactcg tccaacatca atacaaccta ttaatttccc   8400
ctcgtcaaaa ataaggttat caagtgagaa atcaccatga gtgacgactg aatccggtga   8460
gaatggcaaa agcttatgca tttctttcca gacttgttca acaggccagc cattacgctc   8520
gtcatcaaaa tcactcgcat caaccaaacc gttattcatt cgtgattgcg cctgagcgag   8580
acgaaatacg cgatcgctgt taaaaggaca attacaaaca ggaatcgaat gcaaccggcg   8640
caggaacact gccagcgcat caacaatatt ttcacctgaa tcaggatatt cttctaatac   8700
ctggaatgct gttttcccgg ggatcgcagt ggtgagtaac catgcatcat caggagtacg   8760
gataaaatgc ttgatggtcg gaagaggcat aaattccgtc agccagttta gtctgaccat   8820
ctcatctgta acatcattgg caacgctacc tttgccatgt ttcagaaaca actctggcgc   8880
atcgggcttc ccatacaatc gatagattgt cgcacctgat tgcccgacat tatcgcgagc   8940
ccatttatac ccatataaat cagcatccat gttggaattt aatcgcggcc tcgagcaaga   9000
cgtttcccgt tgaatatggc tcataacacc ccttgtatta ctgtttatgt aagcagacag   9060
ttttattgtt catgagcgga tacatatttg aatgtattta gaaaaataaa caaatagggg   9120
ttccgcgcac atttccccga aaagtgccac ctaaattgta agcgttaata ttttgttaaa   9180
attcgcgtta aatttttgtt aaatcagctc attttttaac caataggccg aaatcggcaa   9240
aatcccttat aaatcaaaag aatagaccga gatagggttg agtggccgct acagggcgct   9300
cccattcgcc attcaggctg cgcaactgtt gggaagggcg tttcggtgcg ggcctcttcg   9360
ctattacgcc agctggcgaa agggggatgt gctgcaaggc gattaagttg ggtaacgcca   9420
```

```
gggttttccc agtcacacgc gtaatacgac tcactataga taggcggcgc atgagagaag   9480
cccagaccaa ttacctaccc aaaatggaga aagttcacgt tgacatcgag gaagacagcc   9540
cattcctcag agctttgcag cggagcttcc cgcagtttga ggtagaagcc aagcaggtca   9600
ctgataatga ccatgctaat gccagagcgt tttcgcatct ggcttcaaaa ctgatcgaaa   9660
cggaggtgga cccatccgac acgatccttg acattggaag tgcgcccgcc cgcagaatgt   9720
attctaagca caagtatcat tgtatctgtc cgatgagatg tgcggaagat ccggacagat   9780
tgtataagta tgcaactaag ctgaagaaaa actgtaagga aataactgat aaggaattgg   9840
acaagaaaat gaaggagctc gccgccgtca tgagcgaccc tgacctggaa actgagacta   9900
tgtgcctcca cgacgacgag tcgtgtcgct acgaagggca agtcgctgtt taccaggatg   9960
tatacgcggt tgacggaccg acaagtctct atcaccaagc caataaggga gttagagtcg  10020
cctactggat aggctttgac accacccctt ttatgtttaa gaacttggct ggagcatatc  10080
catcatactc taccaactgg gccgacgaaa ccgtgttaac ggctcgtaac ataggcctat  10140
gcagctctga cgttatggag cggtcacgta gagggatgtc cattcttaga aagaagtatt  10200
tgaaaccatc caacaatgtt ctattctctg ttggctcgac catctaccac gagaagaggg  10260
acttactgag gagctggcac ctgccgtctg tatttcactt acgtggcaag caaaattaca  10320
catgtcggtg tgagactata gttagttgcg acgggtacgt cgttaaaaga atagctatca  10380
gtccaggcct gtatgggaag ccttcaggct atgctgctac gatgcaccgc gagggattct  10440
tgtgctgcaa agtgacagac acattgaacg gggagagggt ctcttttccc gtgtgcacgt  10500
atgtgccagc tacattgtgt gaccaaatga ctggcatact ggcaacagat gtcagtgcgg  10560
acgacgcgca aaaactgctg gttgggctca accagcgtat agtcgtcaac ggtcgcaccc  10620
agagaaacac caataccatg aaaaattacc ttttgcccgt agtggcccag gcatttgcta  10680
ggtgggcaaa ggaatataag gaagatcaag aagatgaaag gccactagga ctacgagata  10740
gacagttagt catggggtgt tgttgggctt ttagaaggca caagataaca tctatttata  10800
agcgcccgga tacccaaacc atcatcaaag tgaacagcga tttccactca ttcgtgctgc  10860
ccaggatagg cagtaacaca ttggagatcg ggctgagaac aagaatcagg aaaatgttag  10920
aggagcacaa ggagccgtca cctctcatta ccgccgagga cgtacaagaa gctaagtgcg  10980
cagccgatga ggctaaggag gtgcgtgaag ccgaggagtt gcgcgcagct ctaccacctt  11040
tggcagctga tgttgaggag cccactctgg aagccgatgt agacttgatg ttacaagagg  11100
ctggggccgg ctcagtggag acacctcgtg gcttgataaa ggttaccagc tacgatggcg  11160
aggacaagat cggctcttac gctgtgcttt ctccgcaggc tgtactcaag agtgaaaaat  11220
tatcttgcat ccaccctctc gctgaacaag tcatagtgat aacacactct ggccgaaaag  11280
ggcgttatgc cgtggaacca taccatggta aagtagtggt gccagaggga catgcaatac  11340
ccgtccagga ctttcaagct ctgagtgaaa gtgccaccat tgtgtacaac gaacgtgagt  11400
tcgtaaacag gtacctgcac catattgcca cacatggagg agcgctgaac actgatgaag  11460
aatattacaa aactgtcaag cccagcgagc acgacggcga atacctgtac gacatcgaca  11520
ggaaacagtg cgtcaagaaa gaactagtca ctgggctagg gctcacaggc gagctggtgg  11580
atcctccctt ccatgaattc gcctacgaga gtctgagaac acgaccagcc gctccttacc  11640
aagtaccaac catagggggtg tatggcgtgc caggatcagg caagtctggc atcattaaaa  11700
gc                                                                 11702
```

<210> SEQ ID NO 4
<211> LENGTH: 15271
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 4
ataggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct cgccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600
agaacttggc tggagcatat ccatcatact ctaccaactg ggccgacgaa accgtgttaa 660
cggctcgtaa cataggccta tgcagctctg acgttatgga gcggtcacgt agagggatgt 720
ccattcttag aaagaagtat ttgaaaccat ccaacaatgt tctattctct gttggctcga 780
ccatctacca cgagaagagg gacttactga ggagctggca cctgccgtct gtatttcact 840
tacgtggcaa gcaaaattac acatgtcggt gtgagactat agttagttgc gacgggtacg 900
tcgttaaaag aatagctatc agtccaggcc tgtatgggaa gccttcaggc tatgctgcta 960
cgatgcaccg cgagggattc ttgtgctgca aagtgacaga cacattgaac ggggagaggg 1020
tctcttttcc cgtgtgcacg tatgtgccag ctacattgtg tgaccaaatg actggcatac 1080
tggcaacaga tgtcagtgcg gacgacgcgc aaaaactgct ggttgggctc aaccagcgta 1140
tagtcgtcaa cggtcgcacc cagagaaaca ccaataccat gaaaaattac cttttgcccg 1200
tagtggccca ggcatttgct aggtgggcaa aggaatataa ggaagatcaa gaagatgaaa 1260
ggccactagg actacgagat agacagttag tcatggggtg ttgttgggct tttagaaggc 1320
acaagataac atctatttat aagcgcccgg atacccaaac catcatcaaa gtgaacagcg 1380
atttccactc attcgtgctg cccaggatag gcagtaacac attggagatc gggctgagaa 1440
caagaatcag gaaaatgtta gaggagcaca aggagccgtc acctctcatt accgccgagg 1500
acgtacaaga agctaagtgc gcagccgatg aggctaagga ggtgcgtgaa gccgaggagt 1560
tgcgcgcagc tctaccacct ttggcagctg atgttgagga gcccactctg gaagccgatg 1620
tagacttgat gttacaagag gctggggccg gctcagtgga gacacctcgt ggcttgataa 1680
aggttaccag ctacgatggc gaggacaaga tcggctctta cgctgtgctt tctccgcagg 1740
ctgtactcaa gagtgaaaaa ttatcttgca tccaccctct cgctgaacaa gtcatagtga 1800
taacacactc tggccgaaaa gggcgttatg ccgtggaacc ataccatggt aaagtagtgg 1860
tgccagaggg acatgcaata cccgtccagg actttcaagc tctgagtgaa agtgccacca 1920
ttgtgtacaa cgaacgtgag ttcgtaaaca ggtacctgca ccatattgcc acacatggag 1980
gagcgctgaa cactgatgaa gaatattaca aaactgtcaa gcccagcgag cacgacggcg 2040

```
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgaggggga tattgccacg gccaccgaag   4080
gagtgattat aaatgctgct aacagcaaag gacaacctgg cggagggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
```

-continued

```
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
```

```
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gatgaggcct ggcctgccct cctacctgat catcctggcc gtgtgcctgt tcagccacct   7620
gctgtccagc agatacggcg ccgaggccgt gagcgagccc ctggacaagg ctttccacct   7680
gctgctgaac acctacggca gacccatccg gtttctgcgg gagaacacca cccagtgcac   7740
ctacaacagc agcctgcgga acagcaccgt cgtgagagag aacgccatca gcttcaactt   7800
tttccagagc tacaaccagt actacgtgtt ccacatgccc agatgcctgt ttgccggccc   7860
tctggccgag cagttcctga accaggtgga cctgaccgag acactggaaa gataccagca   7920
gcggctgaat acctacgccc tggtgtccaa ggacctggcc agctaccggt cctttagcca   7980
gcagctcaag gctcaggata gcctcggcga gcagcctacc accgtgcccc ctcccatcga   8040
cctgagcatc ccccacgtgt ggatgcctcc ccagaccacc cctcacggct ggaccgagag   8100
ccacaccacc tccggcctgc acagacccca cttcaaccag acctgcatcc tgttcgacgg   8160
ccacgacctg ctgtttagca ccgtgacccc ctgcctgcac cagggcttct acctgatcga   8220
cgagctgaga tacgtgaaga tcaccctgac cgaggatttc ttcgtggtca ccgtgtccat   8280
cgacgacgac acccccatgc tgctgatctt cggccacctg cccagagtgc tgttcaaggc   8340
cccctaccag cgggacaact tcatcctgcg gcagaccgag aagcacgagc tgctggtgct   8400
ggtcaagaag gaccagctga accggcactc ctacctgaag gaccccgact tcctggacgc   8460
cgccctggac ttcaactacc tggacctgag cgccctgctg agaaacagct tccacagata   8520
cgccgtggac gtgctgaagt ccggacggtg ccagatgctc gatcggcgga ccgtggagat   8580
ggccttcgcc tatgccctcg ccctgttcgc cgctgccaga caggaagagg ctggcgccca   8640
ggtgtcagtg cccagagccc tggatagaca ggccgccctg ctgcagatcc aggaattcat   8700
gatcacctgc ctgagccaga cccccccctag aaccaccctg ctgctgtacc ccacagccgt   8760
ggatctggcc aagagggccc tgtggacccc caaccagatc accgacatca caagcctcgt   8820
gcggctcgtg tacatcctga gcaagcagaa ccagcagcac ctgatccccc agtgggccct   8880
gagacagatc gccgacttcg ccctgaagct gcacaagacc catctggcca gctttctgag   8940
cgccttcgcc aggcaggaac tgtacctgat gggcagcctg gtccacagca tgctggtgca   9000
taccaccgag cggcgggaga tcttcatcgt ggagacaggc ctgtgtagcc tggccgagct   9060
gtcccacttt acccagctgc tggcccaccc tcaccacgag tacctgagcg acctgtacac   9120
```

```
cccctgcagc agcagcggca gacgggacca cagcctggaa cggctgacca gactgttccc   9180

cgatgccacc gtgcctgcta cagtgcctgc cgccctgtcc atcctgtcca ccatgcagcc   9240

cagcaccctg gaaaccttcc ccgacctgtt ctgcctgccc ctgggcgaga gctttagcgc   9300

cctgaccgtg tccgagcacg tgtcctacat cgtgaccaat cagtacctga tcaagggcat   9360

cagctacccc gtgtccacca cagtcgtggg ccagagcctg atcatcaccc agaccgacag   9420

ccagaccaag tgcgagctga cccggaacat gcacaccaca cacagcatca ccgtggccct   9480

gaacatcagc ctggaaaact gcgctttctg tcagtctgcc ctgctggaat acgacgatac   9540

ccagggcgtg atcaacatca tgtacatgca cgacagcgac gacgtgctgt tcgccctgga   9600

cccctacaac gaggtggtgg tgtccagccc ccggacccac tacctgatgc tgctgaagaa   9660

cggcaccgtg ctggaagtga ccgacgtggt ggtggacgcc accgacagca gactgctgat   9720

gatgagcgtg tacgccctga gcgccatcat cggcatctac ctgctgtacc ggatgctgaa   9780

aacctgctga taatctagag gcccctataa ctctctacgg ctaacctgaa tggactacga   9840

catagtctag tccgccaaga tgtgcagaag gcccgactgc ggcttcagct tcagccctgg   9900

acccgtgatc ctgctgtggt gctgcctgct gctgcctatc gtgtcctctg ccgccgtgtc   9960

tgtggcccct acagccgccg agaaggtgcc agccgagtgc cccgagctga ccagaagatg  10020

cctgctgggc gaggtgttcg agggcgacaa gtacgagagc tggctgcggc ccctggtcaa  10080

cgtgaccggc agagatggcc ccctgagcca gctgatccgg tacagacccg tgacccccga  10140

ggccgccaat agcgtgctgc tggacgaggc cttcctggat accctggccc tgctgtacaa  10200

caaccccgac cagctgagag ccctgctgac cctgctgtcc agcgacaccg cccccagatg  10260

gatgaccgtg atgcggggct acagcgagtg tggagatggc agccctgccg tgtacacctg  10320

cgtggacgac ctgtgcagag gctacgacct gaccagactg agctacggcc ggtccatctt  10380

cacagagcac gtgctgggct tcgagctggt gccccccagc ctgttcaacg tggtggtggc  10440

catccggaac gaggccacca gaaccaacag agccgtgcgg ctgcctgtgt ctacagccgc  10500

tgcacctgag ggcatcacac tgttctacgg cctgtacaac gccgtgaaag agttctgcct  10560

ccggcaccag ctggatcccc ccctgctgag acacctggac aagtactacg ccggcctgcc  10620

cccagagctg aagcagacca gagtgaacct gcccgcccac agcagatatg gccctcaggc  10680

cgtggacgcc agatgataac gccggcggcc cctataactc tctacggcta acctgaatgg  10740

actacgacat agtctagtcc gccaagatga gccccaagga cctgaccccc ttcctgacaa  10800

ccctgtggct gctcctgggc catagcagag tgcctagagt gcgggccgag gaatgctgcg  10860

agttcatcaa cgtgaaccac ccccccgagc ggtgctacga cttcaagatg tgcaaccggt  10920

tcaccgtggc cctgagatgc cccgacggcg aagtgtgcta cagccccgag aaaaccgccg  10980

agatccgggg catcgtgacc accatgaccc acagcctgac ccggcaggtg gtgcacaaca  11040

agctgaccag ctgcaactac aacccccctgt acctggaagc cgacggccgg atcagatgcg  11100

gcaaagtgaa cgacaaggcc cagtacctgc tgggagccgc cggaagcgtg ccctaccggt  11160

ggatcaacct ggaatacgac aagatcaccc ggatcgtggg cctggaccag tacctggaaa  11220

gcgtgaagaa gcacaagcgg ctggacgtgt gcagagccaa gatgggctac atgctgcagc  11280

tgttgaattt tgaccttctt aagcttgcgg gagacgtcga gtccaacccc gggcccatgc  11340

tgcggctgct gctgagacac cacttccact gcctgctgct gtgtgccgtg tgggccaccc  11400

cttgtctggc cagcccttgg agcaccctga ccgccaacca gaaccctagc ccccccttggt  11460

ccaagctgac ctacagcaag ccccacgacg ccgccacctt ctactgcccc tttctgtacc  11520
```

```
ccagccctcc cagaagcccc ctgcagttca gcggcttcca gagagtgtcc accggccctg  11580

agtgccggaa cgagacactg tacctgctgt acaaccggga gggccagaca ctggtggagc  11640

ggagcagcac ctgggtgaaa aaagtgatct ggtatctgag cggccggaac cagaccatcc  11700

tgcagcggat gcccagaacc gccagcaagc ccagcgacgg caacgtgcag atcagcgtgg  11760

aggacgccaa aatcttcggc gcccacatgg tgcccaagca gaccaagctg ctgagattcg  11820

tggtcaacga cggcaccaga tatcagatgt gcgtgatgaa gctggaaagc tgggcccacg  11880

tgttccggga ctactccgtg agcttccagg tccggctgac cttcaccgag gccaacaacc  11940

agacctacac cttctgcacc caccccaacc tgatcgtgct gctgaacttc gacctgctga  12000

agctggccgg cgacgtggag agcaaccccg gcccccatat gcggctgtgc agagtgtggc  12060

tgtccgtgtg cctgtgtgcc gtggtgctgg gccagtgcca gagagagaca gccgagaaga  12120

acgactacta ccgggtgccc cactactggg atgcctgcag cagagccctg cccgaccaga  12180

cccggtacaa atacgtggag cagctcgtgg acctgaccct gaactaccac tacgacgcca  12240

gccacggcct ggacaacttc gacgtgctga agcggatcaa cgtgaccgag gtgtccctgc  12300

tgatcagcga cttccggcgg cagaacagaa gaggcggcac caacaagcgg accaccttca  12360

acgccgctgg ctctctggcc cctcacgcca gatccctgga attcagcgtg cggctgttcg  12420

ccaactgata acgttgcatc ctgcaggata cagcagcaat tggcaagctg cttacataga  12480

actcgcggcg attggcatgc cgccttaaaa tttttatttt atttttcttt tcttttccga  12540

atcggatttt gtttttaata tttcaaaaaa aaaaaaaaaa aaaaaaaaaa aaaaaaaaag  12600

ggtcggcatg gcatctccac ctcctcgcgg tccgacctgg gcatccgaag gaggacgcac  12660

gtccactcgg atggctaagg gagagccacg tttaaacgct agagcaagac gtttcccgtt  12720

gaatatggct cataacaccc cttgtattac tgtttatgta agcagacagt tttattgttc  12780

atgatgatat atttttatct tgtgcaatgt aacatcagag attttgagac acaacgtggc  12840

tttgttgaat aaatcgaact tttgctgagt tgaaggatca gatcacgcat cttcccgaca  12900

acgcagaccg ttccgtggca aagcaaaagt tcaaaatcac caactggtcc acctacaaca  12960

aagctctcat caaccgtggc tccctcactt tctggctgga tgatggggcg attcaggcct  13020

ggtatgagtc agcaacacct tcttcacgag gcagacctca gcgctagcgg agtgtatact  13080

ggcttactat gttggcactg atgagggtgt cagtgaagtg cttcatgtgg caggagaaaa  13140

aaggctgcac cggtgcgtca gcagaatatg tgatacagga tatattccgc ttcctcgctc  13200

actgactcgc tacgctcggt cgttcgactg cggcgagcgg aaatggctta cgaacggggc  13260

ggagatttcc tggaagatgc caggaagata cttaacaggg aagtgagagg gccgcggcaa  13320

agccgttttt ccataggctc cgcccccctg acaagcatca cgaaatctga cgctcaaatc  13380

agtggtggcg aaacccgaca ggactataaa gataccaggc gtttccccctg gcggctccct  13440

cgtgcgctct cctgttcctg cctttcggtt taccggtgtc attccgctgt tatggccgcg  13500

tttgtctcat tccacgcctg acactcagtt ccgggtaggc agttcgctcc aagctggact  13560

gtatgcacga accccccgtt cagtccgacc gctgcgcctt atccggtaac tatcgtcttg  13620

agtccaaccc ggaaagacat gcaaaagcac cactggcagc agccactggt aattgattta  13680

gaggagttag tcttgaagtc atgcgccggt taaggctaaa ctgaaaggac aagttttggt  13740

gactgcgctc ctccaagcca gttacctcgg ttcaaagagt tggtagctca gagaaccttc  13800

gaaaaaccgc cctgcaaggc ggtttttcg ttttcagagc aagagattac gcgcagacca  13860
```

aaacgatctc aagaagatca tcttattaag ggtctgacg ctcagtggaa cgaaaactca 13920
cgttaaggga ttttggtcat gagattatca aaaaggatct tcacctagat ccttttaaat 13980
taaaaatgaa gttttaaatc aatctaaagt atatatgagt aaacttggtc tgacagttat 14040
tagaaaaatt catccagcag acgataaaac gcaatacgct ggctatccgg tgccgcaatg 14100
ccatacagca ccagaaaacg atccgcccat tcgccgccca gttcttccgc aatatcacgg 14160
gtggccagcg caatatcctg ataacgatcc gccacgccca gacggccgca atcaataaag 14220
ccgctaaaac ggccattttc caccataatg ttcggcaggc acgcatcacc atgggtcacc 14280
accagatctt cgccatccgg catgctcgct ttcagacgcg caaacagctc tgccggtgcc 14340
aggccctgat gttcttcatc cagatcatcc tgatccacca ggcccgcttc catacgggta 14400
cgcgcacgtt caatacgatg tttcgcctga tgatcaaacg gacaggtcgc cgggtccagg 14460
gtatgcagac gacgcatggc atccgccata atgctcactt tttctgccgg cgccagatgg 14520
ctagacagca gatcctgacc cggcacttcg cccagcagca gccaatcacg gcccgcttcg 14580
gtcaccacat ccagcaccgc cgcacacgga acaccggtgg tggccagcca gctcagacgc 14640
gccgcttcat cctgcagctc gttcagcgca ccgctcagat cggttttcac aaacagcacc 14700
ggacgaccct gcgcgctcag acgaaacacc gccgcatcag agcagccaat ggtctgctgc 14760
gcccaatcat agccaaacag acgttccacc cacgctgccg ggctacccgc atgcaggcca 14820
tcctgttcaa tcatactctt cctttttcaa tattattgaa gcatttatca gggttattgt 14880
ctcatgagcg gatacatatt tgaatgtatt tagaaaaata aacaaatagg ggttccgcgc 14940
acatttcccc gaaaagtgcc acctaaattg taagcgttaa tattttgtta aaattcgcgt 15000
taaatttttg ttaaatcagc tcatttttta accaataggc cgaaatcggc aaaatccctt 15060
ataaatcaaa agaatagacc gagatagggt tgagtggccg ctacagggcg ctcccattcg 15120
ccattcaggc tgcgcaactg ttgggaaggg cgtttcggtg cgggcctctt cgctattacg 15180
ccagctggcg aaagggggat gtgctgcaag gcgattaagt tgggtaacgc cagggttttc 15240
ccagtcacac gcgtaatacg actcactata g 15271

<210> SEQ ID NO 5
<211> LENGTH: 16405
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 5
ataggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct cgccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600

```
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tagacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
```

-continued taaaaacact gactgccaag taccctggga atttcactgc cacgatagag gagtggcaag 3000
cagagcatga tgccatcatg aggcacatct tggagagacc ggaccctacc gacgtcttcc 3060
agaataaggc aaacgtgtgt tgggccaagg ctttagtgcc ggtgctgaag accgctggca 3120
tagacatgac cactgaacaa tggaacactg tggattattt tgaaacggac aaagctcact 3180
cagcagagat agtattgaac caactatgcg tgaggttctt tggactcgat ctggactccg 3240
gtctattttc tgcacccact gttccgttat ccattaggaa taatcactgg gataactccc 3300
cgtcgcctaa catgtacggg ctgaataaag aagtggtccg tcagctctct cgcaggtacc 3360
cacaactgcc tcgggcagtt gccactggaa gagtctatga catgaacact ggtacactgc 3420
gcaattatga tccgcgcata aacctagtac ctgtaaacag aagactgcct catgctttag 3480
tcctccacca taatgaacac ccacagagtg acttttcttc attcgtcagc aaattgaagg 3540
gcagaactgt cctggtggtc ggggaaaagt tgtccgtccc aggcaaaatg gttgactggt 3600
tgtcagaccg gcctgaggct accttcagag ctcggctgga tttaggcatc ccaggtgatg 3660
tgcccaaata tgacataata tttgttaatg tgaggacccc atataaatac catcactatc 3720
agcagtgtga agaccatgcc attaagctta gcatgttgac caagaaagct tgtctgcatc 3780
tgaatcccgg cggaacctgt gtcagcatag gttatggtta cgctgacagg gccagcgaaa 3840
gcatcattgg tgctatagcg cggcagttca agttttcccg ggtatgcaaa ccgaaatcct 3900
cacttgaaga gacggaagtt ctgtttgtat tcattgggta cgatcgcaag gcccgtacgc 3960
acaatcctta caagctttca tcaaccttga ccaacattta tacaggttcc agactccacg 4020
aagccggatg tgcaccctca tatcatgtgg tgcgagggga tattgccacg gccaccgaag 4080
gagtgattat aaatgctgct aacagcaaag gacaacctgg cggaggggtg tgcggagcgc 4140
tgtataagaa attcccggaa agcttcgatt tacagccgat cgaagtagga aaagcgcgac 4200
tggtcaaagg tgcagctaaa catatcattc atgccgtagg accaaacttc aacaaagttt 4260
cggaggttga aggtgacaaa cagttggcag aggcttatga gtccatcgct aagattgtca 4320
acgataacaa ttacaagtca gtagcgattc cactgttgtc caccggcatc ttttccggga 4380
acaaagatcg actaacccaa tcattgaacc atttgctgac agctttagac accactgatg 4440
cagatgtagc catatactgc agggacaaga aatgggaaat gactctcaag gaagcagtgg 4500
ctaggagaga agcagtggag gagatatgca tatccgacga ctcttcagtg acagaacctg 4560
atgcagagct ggtgagggtg catccgaaga gttctttggc tggaaggaag ggctacagca 4620
caagcgatgg caaaactttc tcatatttgg aagggaccaa gtttcaccag gcggccaagg 4680
atatagcaga aattaatgcc atgtggcccg ttgcaacgga ggccaatgag caggtatgca 4740
tgtatatcct cggagaaagc atgagcagta ttaggtcgaa atgccccgtc gaagagtcgg 4800
aagcctccac accacctagc acgctgcctt gcttgtgcat ccatgccatg actccagaaa 4860
gagtacagcg cctaaaagcc tcacgtccag aacaaattac tgtgtgctca tcctttccat 4920
tgccgaagta tagaatcact ggtgtgcaga agatccaatg ctcccagcct atattgttct 4980
caccgaaagt gcctgcgtat attcatccaa ggaagtatct cgtggaaaca ccaccggtag 5040
acgagactcc ggagccatcg gcagagaacc aatccacaga ggggacacct gaacaaccac 5100
cacttataac cgaggatgag accaggacta gaacgcctga gccgatcatc atcgaagagg 5160
aagaagagga tagcataagt ttgctgtcag atggcccgac ccaccaggtg ctgcaagtcg 5220
aggcagacat tcacgggccg ccctctgtat ctagctcatc ctggtccatt cctcatgcat 5280
ccgactttga tgtggacagt ttatccatac ttgacaccct ggagggagct agcgtgacca 5340

```
gcggggcaac gtcagccgag actaactctt acttcgcaaa gagtatggag tttctggcgc   5400

gaccggtgcc tgcgcctcga acagtattca ggaaccctcc acatcccgct ccgcgcacaa   5460

gaacaccgtc acttgcaccc agcagggcct gctcgagaac cagcctagtt tccaccccgc   5520

caggcgtgaa tagggtgatc actagagagg agctcgaggc gcttaccccg tcacgcactc   5580

ctagcaggtc ggtctcgaga accagcctgg tctccaaccc gccaggcgta aatagggtga   5640

ttacaagaga ggagtttgag gcgttcgtag cacaacaaca atgacggttt gatgcgggtg   5700

catacatctt ttcctccgac accggtcaag ggcatttaca acaaaaatca gtaaggcaaa   5760

cggtgctatc cgaagtggtg ttggagagga ccgaattgga gatttcgtat gccccgcgcc   5820

tcgaccaaga aaaagaagaa ttactacgca agaaattaca gttaaatccc acacctgcta   5880

acagaagcag ataccagtcc aggaaggtgg agaacatgaa agccataaca gctagacgta   5940

ttctgcaagg cctagggcat tatttgaagg cagaaggaaa agtggagtgc taccgaaccc   6000

tgcatcctgt tcctttgtat tcatctagtg tgaaccgtgc cttttcaagc cccaaggtcg   6060

cagtggaagc ctgtaacgcc atgttgaaag agaactttcc gactgtggct tcttactgta   6120

ttattccaga gtacgatgcc tatttggaca tggttgacgg agcttcatgc tgcttagaca   6180

ctgccagttt ttgccctgca aagctgcgca gctttccaaa gaaacactcc tatttggaac   6240

ccacaatacg atcggcagtg ccttcagcga tccagaacac gctccagaac gtcctggcag   6300

ctgccacaaa aagaaattgc aatgtcacgc aaatgagaga attgcccgta ttggattcgg   6360

cggcctttaa tgtggaatgc ttcaagaaat atgcgtgtaa taatgaatat tgggaaacgt   6420

ttaaagaaaa ccccatcagg cttactgaag aaaacgtggt aaattacatt accaaattaa   6480

aaggaccaaa agctgctgct ctttttgcga agacacataa tttgaatatg ttgcaggaca   6540

taccaatgga caggtttgta atggacttaa agagagacgt gaaagtgact ccaggaacaa   6600

aacatactga agaacggccc aaggtacagg tgatccaggc tgccgatccg ctagcaacag   6660

cgtatctgtg cggaatccac cgagagctgg ttaggagatt aaatgcggtc ctgcttccga   6720

acattcatac actgtttgat atgtcggctg aagactttga cgctattata gccgagcact   6780

tccagcctgg ggattgtgtt ctggaaactg acatcgcgtc gtttgataaa agtgaggacg   6840

acgccatggc tctgaccgcg ttaatgattc tggaagactt aggtgtggac gcagagctgt   6900

tgacgctgat tgaggcggct ttcggcgaaa tttcatcaat acatttgccc actaaaacta   6960

aatttaaatt cggagccatg atgaaatctg gaatgttcct cacactgttt gtgaacacag   7020

tcattaacat tgtaatcgca agcagagtgt tgagagaacg gctaaccgga tcaccatgtg   7080

cagcattcat tggagatgac aatatcgtga aaggagtcaa atcggacaaa ttaatggcag   7140

acaggtgcgc cacctggttg aatatggaag tcaagattat agatgctgtg gtgggcgaga   7200

aagcgcctta tttctgtgga gggtttattt tgtgtgactc cgtgaccggc acagcgtgcc   7260

gtgtggcaga ccccctaaaa aggctgttta agcttggcaa acctctggca gcagacgatg   7320

aacatgatga tgacaggaga agggcattgc atgaagagtc aacacgctgg aaccgagtgg   7380

gtattctttc agagctgtgc aaggcagtag aatcaaggta tgaaaccgta ggaacttcca   7440

tcatagttat ggccatgact actctagcta gcagtgttaa atcattcagc tacctgagag   7500

gggcccctat aactctctac ggctaacctg aatggactac gacatagtct agtccgccaa   7560

gatgaggcct ggcctgccct cctacctgat catcctggcc gtgtgcctgt tcagccacct   7620

gctgtccagc agatacggcg ccgaggccgt gagcgagccc ctggacaagg ctttccacct   7680
```

```
gctgctgaac acctacggca gacccatccg gtttctgcgg gagaacacca cccagtgcac   7740
ctacaacagc agcctgcgga acagcaccgt cgtgagagag aacgccatca gcttcaactt   7800
tttccagagc tacaaccagt actacgtgtt ccacatgccc agatgcctgt ttgccggccc   7860
tctggccgag cagttcctga accaggtgga cctgaccgag acactggaaa gataccagca   7920
gcggctgaat acctacgccc tggtgtccaa ggacctggcc agctaccggt cctttagcca   7980
gcagctcaag gctcaggata gcctcggcga gcagcctacc accgtgcccc ctcccatcga   8040
cctgagcatc ccccacgtgt ggatgcctcc ccagaccacc cctcacggct ggaccgagag   8100
ccacaccacc tccggcctgc acagacccca cttcaaccag acctgcatcc tgttcgacgg   8160
ccacgacctg ctgtttagca ccgtgacccc ctgcctgcac cagggcttct acctgatcga   8220
cgagctgaga tacgtgaaga tcaccctgac cgaggatttc ttcgtggtca ccgtgtccat   8280
cgacgacgac acccccatgc tgctgatctt cggccacctg cccagagtgc tgttcaaggc   8340
cccctaccag cgggacaact tcatcctgcg gcagaccgag aagcacgagc tgctggtgct   8400
ggtcaagaag gaccagctga accggcactc ctacctgaag gaccccgact tcctggacgc   8460
cgccctggac ttcaactacc tggacctgag cgccctgctg agaaacagct tccacagata   8520
cgccgtggac gtgctgaagt ccggacggtg ccagatgctc gatcggcgga ccgtggagat   8580
ggccttcgcc tatgccctcg ccctgttcgc cgctgccaga caggaagagg ctggcgccca   8640
ggtgtcagtg cccagagccc tggatagaca ggccgccctg ctgcagatcc aggaattcat   8700
gatcacctgc ctgagccaga ccccccctag aaccaccctg ctgctgtacc ccacagccgt   8760
ggatctggcc aagagggccc tgtggacccc caaccagatc accgacatca caagcctcgt   8820
gcggctcgtg tacatcctga gcaagcagaa ccagcagcac ctgatccccc agtgggccct   8880
gagacagatc gccgacttcg ccctgaagct gcacaagacc catctggcca gctttctgag   8940
cgccttcgcc aggcaggaac tgtacctgat gggcagcctg gtccacagca tgctggtgca   9000
taccaccgag cggcgggaga tcttcatcgt ggagacaggc ctgtgtagcc tggccgagct   9060
gtcccacttt acccagctgc tggcccaccc tcaccacgag tacctgagcg acctgtacac   9120
cccctgcagc agcagcggca gacgggacca cagcctggaa cggctgacca gactgttccc   9180
cgatgccacc gtgcctgcta cagtgcctgc cgccctgtcc atcctgtcca ccatgcagcc   9240
cagcaccctg gaaaccttcc ccgacctgtt ctgcctgccc ctgggcgaga gctttagcgc   9300
cctgaccgtg tccgagcacg tgtcctacat cgtgaccaat cagtacctga tcaagggcat   9360
cagctacccc gtgtccacca cagtcgtggg ccagagcctg atcatcaccc agaccgacag   9420
ccagaccaag tgcgagctga cccggaacat gcacaccaca cacagcatca ccgtggccct   9480
gaacatcagc ctggaaaact gcgctttctg tcagtctgcc ctgctggaat acgacgatac   9540
ccagggcgtg atcaacatca tgtacatgca cgacagcgac gacgtgctgt tcgccctgga   9600
cccctacaac gaggtggtgg tgtccagccc ccggacccac tacctgatgc tgctgaagaa   9660
cggcaccgtg ctggaagtga ccgacgtggt ggtggacgcc accgacagca gactgctgat   9720
gatgagcgtg tacgccctga gcgccatcat cggcatctac ctgctgtacc ggatgctgaa   9780
aacctgctga taatctagag gcccctataa ctctctacgg ctaacctgaa tggactacga   9840
catagtctag tccgccaaga tgtgcagaag gcccgactgc ggcttcagct tcagccctgg   9900
acccgtgatc ctgctgtggt gctgcctgct gctgcctatc gtgtcctctg ccgccgtgtc   9960
tgtggcccct acagccgccg agaaggtgcc agccgagtgc cccgagctga ccagaagatg  10020
cctgctgggc gaggtgttcg agggcgacaa gtacgagagc tggctgcggc cctggtcaa  10080
```

```
cgtgaccggc agagatggcc ccctgagcca gctgatccgg tacagacccg tgaccccga  10140
ggccgccaat agcgtgctgc tggacgaggc cttcctggat accctggccc tgctgtacaa  10200
caaccccgac cagctgagag ccctgctgac cctgctgtcc agcgacaccg cccccagatg  10260
gatgaccgtg atgcggggct acagcgagtg tggagatggc agccctgccg tgtacacctg  10320
cgtggacgac ctgtgcagag gctacgacct gaccagactg agctacggcc ggtccatctt  10380
cacagagcac gtgctgggct tcgagctggt gccccccagc ctgttcaacg tggtggtggc  10440
catccggaac gaggccacca gaaccaacag agccgtgcgg ctgcctgtgt ctacagccgc  10500
tgcacctgag ggcatcacac tgttctacgg cctgtacaac gccgtgaaag agttctgcct  10560
ccggcaccag ctggatcccc ccctgctgag acacctggac aagtactacg ccggcctgcc  10620
cccagagctg aagcagacca gagtgaacct gcccgcccac agcagatatg gccctcaggc  10680
cgtggacgcc agatgataac gccggcggcc cctataactc tctacggcta acctgaatgg  10740
actacgacat agtctagtcc gccaagatga gccccaagga cctgaccccc ttcctgacaa  10800
ccctgtggct gctcctgggc catagcagag tgcctagagt gcgggccgag gaatgctgcg  10860
agttcatcaa cgtgaaccac ccccccgagc ggtgctacga cttcaagatg tgcaaccggt  10920
tcaccgtggc cctgagatgc cccgacggcg aagtgtgcta cagccccgag aaaaccgccg  10980
agatccgggg catcgtgacc accatgaccc acagcctgac ccggcaggtg gtgcacaaca  11040
agctgaccag ctgcaactac aaccccctgt acctggaagc cgacggccgg atcagatgcg  11100
gcaaagtgaa cgacaaggcc cagtacctgc tgggagccgc cggaagcgtg ccctaccggt  11160
ggatcaacct ggaatacgac aagatcaccc ggatcgtggg cctggaccag tacctggaaa  11220
gcgtgaagaa gcacaagcgg ctggacgtgt gcagagccaa gatgggctac atgctgcagt  11280
gataaggcgc gccaacgtta ctggccgaag ccgcttggaa taaggccggt gtgcgtttgt  11340
ctatatgtta ttttccacca tattgccgtc ttttggcaat gtgagggccc ggaaacctgg  11400
ccctgtcttc ttgacgagca ttcctagggg tctttcccct ctcgccaaag gaatgcaagg  11460
tctgttgaat gtcgtgaagg aagcagttcc tctggaagct tcttgaagac aaacaacgtc  11520
tgtagcgacc ctttgcaggc agcggaaccc cccacctggc gacaggtgcc tctgcggcca  11580
aaagccacgt gtataagata cacctgcaaa ggcggcacaa ccccagtgcc acgttgtgag  11640
ttggatagtt gtggaaagag tcaaatggct ctcctcaagc gtattcaaca aggggctgaa  11700
ggatgcccag aaggtacccc attgtatggg atctgatctg gggcctcggt gcacatgctt  11760
tacatgtgtt tagtcgaggt taaaaaaacg tctaggcccc ccgaaccacg gggacgtggt  11820
tttcctttga aaaacacgat aatatgctgc ggctgctgct gagacaccac ttccactgcc  11880
tgctgctgtg tgccgtgtgg gccacccctt gtctggccag cccttggagc accctgaccg  11940
ccaaccagaa ccctagcccc ccttggtcca agctgaccta cagcaagccc cacgacgccg  12000
ccaccttcta ctgccccttt ctgtacccca gccctcccag aagccccctg cagttcagcg  12060
gcttccagag agtgtccacc ggccctgagt gccggaacga gacactgtac ctgctgtaca  12120
accgggaggg ccagacactg gtggagcgga gcagcacctg ggtgaaaaaa gtgatctggt  12180
atctgagcgg ccggaaccag accatcctgc agcggatgcc cagaaccgcc agcaagccca  12240
gcgacggcaa cgtgcagatc agcgtggagg acgccaaaat cttcggagcc cacatggtgc  12300
ccaagcagac caagctgctg agattcgtgg tcaacgacgg caccagatat cagatgtgcg  12360
tgatgaagct ggaaagctgg gcccacgtgt tccgggacta ctccgtgagc ttccaggtcc  12420
```

```
ggctgacctt caccgaggcc aacaaccaga cctacacctt ctgcacccac cccaacctga  12480
tcgtgtgata agtacctttg tacgcctgtt ttataccccc tccctgattt gcaacttaga  12540
agcaacgcaa accagatcaa tagtaggtgt gacataccag tcgcatcttg atcaagcact  12600
tctgtatccc cggaccgagt atcaatagac tgtgcacacg gttgaaggag aaaacgtccg  12660
ttacccggct aactacttcg agaagcctag taacgccatt gaagttgcag agtgtttcgc  12720
tcagcactcc ccccgtgtag atcaggtcga tgagtcaccg cattccccac gggcgaccgt  12780
ggcggtggct gcgttggcgg cctgcctatg gggtaaccca taggacgctc taatacggac  12840
atggcgtgaa gagtctattg agctagttag tagtcctccg gcccctgaat gcggctaatc  12900
ctaactgcgg agcacatacc cttaatccaa agggcagtgt gtcgtaacgg gcaactctgc  12960
agcggaaccg actactttgg gtgtccgtgt ttctttttat tcttgtattg gctgcttatg  13020
gtgacaatta aagaattgtt accatatagc tattggattg gccatccagt gtcaaacaga  13080
gctattgtat atctctttgt tggattcaca cctctcactc ttgaaacgtt acacaccctc  13140
aattacatta tactgctgaa cacgaagcgc atatgcggct gtgcagagtg tggctgtccg  13200
tgtgcctgtg tgccgtggtg ctgggccagt gccagagaga gacagccgag aagaacgact  13260
actaccgggt gccccactac tgggatgcct gcagcagagc cctgcccgac cagacccggt  13320
acaaatacgt ggagcagctc gtggacctga ccctgaacta ccactacgac gccagccacg  13380
gcctggacaa cttcgacgtg ctgaagcgga tcaacgtgac cgaggtgtcc ctgctgatca  13440
gcgacttccg gcggcagaac agaagaggcg gcaccaacaa gcggaccacc ttcaacgccg  13500
ctggctctct ggcccctcac gccagatccc tggaattcag cgtgcggctg ttcgccaact  13560
gataacgttg catcctgcag gatacagcag caattggcaa gctgcttaca tagaactcgc  13620
ggcgattggc atgccgcctt aaaattttta ttttattttt cttttctttt ccgaatcgga  13680
ttttgttttt aatatttcaa aaaaaaaaaa aaaaaaaaaa aaaaaaaaaa aaagggtcgg  13740
catggcatct ccacctcctc gcggtccgac ctgggcatcc gaaggaggac gcacgtccac  13800
tcggatggct aagggagagc cacgtttaaa cgctagagca agacgtttcc cgttgaatat  13860
ggctcataac accccttgta ttactgttta tgtaagcaga cagttttatt gttcatgatg  13920
atatattttt atcttgtgca atgtaacatc agagattttg agacacaacg tggctttgtt  13980
gaataaatcg aacttttgct gagttgaagg atcagatcac gcatcttccc gacaacgcag  14040
accgttccgt ggcaaagcaa aagttcaaaa tcaccaactg gtccacctac aacaaagctc  14100
tcatcaaccg tggctccctc actttctggc tggatgatgg ggcgattcag gcctggtatg  14160
agtcagcaac accttcttca cgaggcagac ctcagcgcta gcggagtgta tactggctta  14220
ctatgttggc actgatgagg gtgtcagtga agtgcttcat gtggcaggag aaaaaaggct  14280
gcaccggtgc gtcagcagaa tatgtgatac aggatatatt ccgcttcctc gctcactgac  14340
tcgctacgct cggtcgttcg actgcggcga gcggaaatgg cttacgaacg gggcggagat  14400
ttcctggaag atgccaggaa gatacttaac agggaagtga gagggccgcg gcaaagccgt  14460
ttttccatag gctccgcccc cctgacaagc atcacgaaat ctgacgctca aatcagtggt  14520
ggcgaaaccc gacaggacta taaagatacc aggcgtttcc cctggcggct ccctcgtgcg  14580
ctctcctgtt cctgcctttc ggtttaccgg tgtcattccg ctgttatggc cgcgtttgtc  14640
tcattccacg cctgacactc agttccgggt aggcagttcg ctccaagctg gactgtatgc  14700
acgaaccccc cgttcagtcc gaccgctgcg ccttatccgg taactatcgt cttgagtcca  14760
acccggaaag acatgcaaaa gcaccactgg cagcagccac tggtaattga tttagaggag  14820
```

```
ttagtcttga agtcatgcgc cggttaaggc taaactgaaa ggacaagttt tggtgactgc  14880

gctcctccaa gccagttacc tcggttcaaa gagttggtag ctcagagaac cttcgaaaaa  14940

ccgccctgca aggcggtttt ttcgttttca gagcaagaga ttacgcgcag accaaaacga  15000

tctcaagaag atcatcttat taaggggtct gacgctcagt ggaacgaaaa ctcacgttaa  15060

gggattttgg tcatgagatt atcaaaaagg atcttcacct agatcctttt aaattaaaaa  15120

tgaagtttta aatcaatcta aagtatatat gagtaaactt ggtctgacag ttattagaaa  15180

aattcatcca gcagacgata aaacgcaata cgctggctat ccggtgccgc aatgccatac  15240

agcaccagaa aacgatccgc ccattcgccg cccagttctt ccgcaatatc acgggtggcc  15300

agcgcaatat cctgataacg atccgccacg cccagacggc cgcaatcaat aaagccgcta  15360

aaacggccat tttccaccat aatgttcggc aggcacgcat caccatgggt caccaccaga  15420

tcttcgccat ccggcatgct cgctttcaga cgcgcaaaca gctctgccgg tgccaggccc  15480

tgatgttctt catccagatc atcctgatcc accaggcccg cttccatacg ggtacgcgca  15540

cgttcaatac gatgtttcgc ctgatgatca aacggacagg tcgccgggtc cagggtatgc  15600

agacgacgca tggcatccgc cataatgctc actttttctg ccggcgccag atggctagac  15660

agcagatcct gacccggcac ttcgcccagc agcagccaat cacggcccgc ttcggtcacc  15720

acatccagca ccgccgcaca cggaacaccg gtggtggcca gccagctcag acgcgccgct  15780

tcatcctgca gctcgttcag cgcaccgctc agatcggttt tcacaaacag caccggacga  15840

ccctgcgcgc tcagacgaaa caccgccgca tcagagcagc caatggtctg ctgcgcccaa  15900

tcatagccaa acagacgttc cacccacgct gccgggctac ccgcatgcag gccatcctgt  15960

tcaatcatac tcttcctttt tcaatattat tgaagcattt atcagggtta ttgtctcatg  16020

agcggataca tatttgaatg tatttagaaa aataaacaaa taggggttcc gcgcacattt  16080

ccccgaaaag tgccacctaa attgtaagcg ttaatatttt gttaaaattc gcgttaaatt  16140

tttgttaaat cagctcattt tttaaccaat aggccgaaat cggcaaaatc ccttataaat  16200

caaaagaata gaccgagata gggttgagtg gccgctacag ggcgctccca ttcgccattc  16260

aggctgcgca actgttggga agggcgtttc ggtgcgggcc tcttcgctat tacgccagct  16320

ggcgaaaggg ggatgtgctg caaggcgatt aagttgggta acgccagggt tttcccagtc  16380

acacgcgtaa tacgactcac tatag                                        16405
```

```
<210> SEQ ID NO 6
<211> LENGTH: 13102
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 6

ataggcggcg catgagagaa gcccagacca attacctacc caaaatggag aaagttcacg     60

ttgacatcga ggaagacagc ccattcctca gagctttgca gcggagcttc ccgcagtttg    120

aggtagaagc caagcaggtc actgataatg accatgctaa tgccagagcg ttttcgcatc    180

tggcttcaaa actgatcgaa acggaggtgg acccatccga cacgatcctt gacattggaa    240

gtgcgcccgc ccgcagaatg tattctaagc acaagtatca ttgtatctgt ccgatgagat    300

gtgcggaaga tccggacaga ttgtataagt atgcaactaa gctgaagaaa aactgtaagg    360
```

-continued

```
aaataactga taaggaattg gacaagaaaa tgaaggagct cgccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
```

```
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
```

-continued

```
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
```

```
gggcccctat aactctctac ggctaacctg aatggactac gacatagtct agtccgccaa   7560

gatgaggcct ggcctgccct cctacctgat catcctggcc gtgtgcctgt tcagccacct   7620

gctgtccagc agatacggcg ccgaggccgt gagcgagccc ctggacaagg ctttccacct   7680

gctgctgaac acctacggca gacccatccg gtttctgcgg gagaacacca cccagtgcac   7740

ctacaacagc agcctgcgga acagcaccgt cgtgagagag aacgccatca gcttcaactt   7800

tttccagagc tacaaccagt actacgtgtt ccacatgccc agatgcctgt ttgccggccc   7860

tctggccgag cagttcctga accaggtgga cctgaccgag acactggaaa gataccagca   7920

gcggctgaat acctacgccc tggtgtccaa ggacctggcc agctaccggt cctttagcca   7980

gcagctcaag gctcaggata gcctcggcga gcagcctacc accgtgcccc ctcccatcga   8040

cctgagcatc ccccacgtgt ggatgcctcc ccagaccacc cctcacggct ggaccgagag   8100

ccacaccacc tccggcctgc acagacccca cttcaaccag acctgcatcc tgttcgacgg   8160

ccacgacctg ctgtttagca ccgtgacccc ctgcctgcac cagggcttct acctgatcga   8220

cgagctgaga tacgtgaaga tcaccctgac cgaggatttc ttcgtggtca ccgtgtccat   8280

cgacgacgac acccccatgc tgctgatctt cggccacctg cccagagtgc tgttcaaggc   8340

cccctaccag cgggacaact tcatcctgcg gcagaccgag aagcacgagc tgctggtgct   8400

ggtcaagaag gaccagctga accggcactc ctacctgaag gaccccgact tcctggacgc   8460

cgccctggac ttcaactacc tggacctgag cgccctgctg agaaacagct tccacagata   8520

cgccgtggac gtgctgaagt ccggacggtg ccagatgctc gatcggcgga ccgtggagat   8580

ggccttcgcc tatgccctcg ccctgttcgc cgctgccaga caggaagagg ctggcgccca   8640

ggtgtcagtg cccagagccc tggatagaca ggccgccctg ctgcagatcc aggaattcat   8700

gatcacctgc ctgagccaga cccccccctag aaccaccctg ctgctgtacc ccacagccgt   8760

ggatctggcc aagagggccc tgtggacccc caaccagatc accgacatca caagcctcgt   8820

gcggctcgtg tacatcctga gcaagcagaa ccagcagcac ctgatccccc agtgggccct   8880

gagacagatc gccgacttcg ccctgaagct gcacaagacc catctggcca gctttctgag   8940

cgccttcgcc aggcaggaac tgtacctgat gggcagcctg gtccacagca tgctggtgca   9000

taccaccgag cggcgggaga tcttcatcgt ggagacaggc ctgtgtagcc tggccgagct   9060

gtcccacttt acccagctgc tggcccaccc tcaccacgag tacctgagcg acctgtacac   9120

cccctgcagc agcagcggca gacgggacca cagcctggaa cggctgacca gactgttccc   9180

cgatgccacc gtgcctgcta cagtgcctgc cgccctgtcc atcctgtcca ccatgcagcc   9240

cagcaccctg gaaaccttcc ccgacctgtt ctgcctgccc ctgggcgaga gctttagcgc   9300

cctgaccgtg tccgagcacg tgtcctacat cgtgaccaat cagtacctga tcaagggcat   9360

cagctacccc gtgtccacca cagtcgtggg ccagagcctg atcatcaccc agaccgacag   9420

ccagaccaag tgcgagctga cccggaacat gcacaccaca cacagcatca ccgtggccct   9480

gaacatcagc ctggaaaact gcgctttctg tcagtctgcc ctgctggaat acgacgatac   9540

ccagggcgtg atcaacatca tgtacatgca cgacagcgac gacgtgctgt tcgccctgga   9600

cccctacaac gaggtggtgg tgtccagccc ccggacccac tacctgatgc tgctgaagaa   9660

cggcaccgtg ctggaagtga ccgacgtggt ggtggacgcc accgactgat aatctagagg   9720

cccctataac tctctacggc taacctgaat ggactacgac atagtctagt ccgccaagat   9780

gtgcagaagg cccgactgcg gcttcagctt cagccctgga cccgtgatcc tgctgtggtg   9840
```

```
ctgcctgctg ctgcctatcg tgtcctctgc cgccgtgtct gtggccccta cagccgccga   9900
gaaggtgcca gccgagtgcc ccgagctgac cagaagatgc ctgctgggcg aggtgttcga   9960
gggcgacaag tacgagagct ggctgcggcc cctggtcaac gtgaccggca gagatggccc  10020
cctgagccag ctgatccggt acagacccgt gacccccgag gccgccaata gcgtgctgct  10080
ggacgaggcc ttcctggata ccctggccct gctgtacaac aaccccgacc agctgagagc  10140
cctgctgacc ctgctgtcca gcgacaccgc ccccagatgg atgaccgtga tgcggggcta  10200
cagcgagtgt ggagatggca gccctgccgt gtacacctgc gtggacgacc tgtgcagagg  10260
ctacgacctg accagactga gctacggccg gtccatcttc acagagcacg tgctgggctt  10320
cgagctggtg ccccccagcc tgttcaacgt ggtggtggcc atccggaacg aggccaccag  10380
aaccaacaga gccgtgcggc tgcctgtgtc tacagccgct gcacctgagg gcatcacact  10440
gttctacggc ctgtacaacg ccgtgaaaga gttctgcctc cggcaccagc tggatccccc  10500
cctgctgaga cacctggaca agtactacgc cggcctgccc ccagagctga agcagaccag  10560
agtgaacctg cccgcccaca gcagatatgg ccctcaggcc gtggacgcca gatgataagc  10620
ggccgcatac agcagcaatt ggcaagctgc ttacatagaa ctcgcggcga ttggcatgcc  10680
gccttaaaat ttttatttta tttttctttt cttttccgaa tcggattttg tttttaatat  10740
ttcaaaaaaa aaaaaaaaaa aaaaaaaaaa aaaaaaaagg gtcggcatgg catctccacc  10800
tcctcgcggt ccgacctggg catccgaagg aggacgcacg tccactcgga tggctaaggg  10860
agagccacgt ttaaacacgt gatatctggc ctcatgggcc ttcctttcac tgcccgcttt  10920
ccagtcggga aacctgtcgt gccagctgca ttaacatggt catagctgtt tccttgcgta  10980
ttgggcgctc tccgcttcct cgctcactga ctcgctgcgc tcggtcgttc gggtaaagcc  11040
tggggtgcct aatgagcaaa aggccagcaa aaggccagga accgtaaaaa ggccgcgttg  11100
ctggcgtttt tccataggct ccgcccccct gacgagcatc acaaaaatcg acgctcaagt  11160
cagaggtggc gaaacccgac aggactataa agataccagg cgtttccccc tggaagctcc  11220
ctcgtgcgct ctcctgttcc gaccctgccg cttaccggat acctgtccgc ctttctccct  11280
tcgggaagcg tggcgctttc tcatagctca cgctgtaggt atctcagttc ggtgtaggtc  11340
gttcgctcca agctgggctg tgtgcacgaa ccccccgttc agcccgaccg ctgcgcctta  11400
tccggtaact atcgtcttga gtccaacccg gtaagacacg acttatcgcc actggcagca  11460
gccactggta acaggattag cagagcgagg tatgtaggcg gtgctacaga gttcttgaag  11520
tggtggccta actacggcta cactagaaga acagtatttg gtatctgcgc tctgctgaag  11580
ccagttacct tcggaaaaag agttggtagc tcttgatccg gcaaacaaac caccgctggt  11640
agcggtggtt tttttgtttg caagcagcag attacgcgca gaaaaaaagg atctcaagaa  11700
gatcctttga tcttttctac ggggtctgac gctcagtgga acgaaaactc acgttaaggg  11760
attttggtca tgagattatc aaaaaggatc ttcacctaga tccttttaaa ttaaaaatga  11820
agttttaaat caatctaaag tatatatgag taaacttggt ctgacagtta ttagaaaaat  11880
tcatccagca gacgataaaa cgcaatacgc tggctatccg gtgccgcaat gccatacagc  11940
accagaaaac gatccgccca ttcgccgccc agttcttccg caatatcacg ggtggccagc  12000
gcaatatcct gataacgatc cgccacgccc agacggccgc aatcaataaa gccgctaaaa  12060
cggccatttt ccaccataat gttcggcagg cacgcatcac catgggtcac caccagatct  12120
tcgccatccg gcatgctcgc tttcagacgc gcaaacagct ctgccggtgc caggccctga  12180
tgttcttcat ccagatcatc ctgatccacc aggcccgctt ccatacgggt acgcgcacgt  12240
```

tcaatacgat gtttcgcctg atgatcaaac ggacaggtcg ccgggtccag ggtatgcaga 12300
cgacgcatgg catccgccat aatgctcact ttttctgccg gcgccagatg gctagacagc 12360
agatcctgac ccggcacttc gcccagcagc agccaatcac ggcccgcttc ggtcaccaca 12420
tccagcaccg ccgcacacgg aacaccggtg gtggccagcc agctcagacg cgccgcttca 12480
tcctgcagct cgttcagcgc accgctcaga tcggttttca caaacagcac cggacgaccc 12540
tgcgcgctca gacgaaacac cgccgcatca gagcagccaa tggtctgctg cgcccaatca 12600
tagccaaaca gacgttccac ccacgctgcc gggctacccg catgcaggcc atcctgttca 12660
atcatactct tcctttttca atattattga agcatttatc agggttattg tctcatgagc 12720
ggatacatat ttgaatgtat ttagaaaaat aaacaaatag gggttccgcg cacatttccc 12780
cgaaaagtgc cacctaaatt gtaagcgtta atattttgtt aaaattcgcg ttaaattttt 12840
gttaaatcag ctcatttttt aaccaatagg ccgaaatcgg caaaatccct tataaatcaa 12900
aagaatagac cgagataggg ttgagtggcc gctacagggc gctcccattc gccattcagg 12960
ctgcgcaact gttgggaagg gcgtttcggt gcgggcctct tcgctattac gccagctggc 13020
gaaaggggga tgtgctgcaa ggcgattaag ttgggtaacg ccagggtttt cccagtcaca 13080
cgcgtaatac gactcactat ag 13102

<210> SEQ ID NO 7
<211> LENGTH: 13087
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 7
ataggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct cgccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600
agaacttggc tggagcatat ccatcatact ctaccaactg ggccgacgaa accgtgttaa 660
cggctcgtaa cataggccta tgcagctctg acgttatgga gcggtcacgt agagggatgt 720
ccattcttag aaagaagtat ttgaaaccat ccaacaatgt tctattctct gttggctcga 780
ccatctacca cgagaagagg gacttactga ggagctggca cctgccgtct gtatttcact 840
tacgtggcaa gcaaaattac acatgtcggt gtgagactat agttagttgc gacgggtacg 900
tcgttaaaag aatagctatc agtccaggcc tgtatgggaa gccttcaggc tatgctgcta 960
cgatgcaccg cgagggattc ttgtgctgca aagtgacaga cacattgaac ggggagaggg 1020
tctcttttcc cgtgtgcacg tatgtgccag ctacattgtg tgaccaaatg actggcatac 1080

```
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataaggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
```

```
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggagggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaaatca gtaaggcaaa   5760
cggtgctatc cgaagtggtg ttggagagga ccgaattgga gatttcgtat gccccgcgcc   5820
```

```
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gatgaggcct ggcctgccct cctacctgat catcctggcc gtgtgcctgt tcagccacct   7620
gctgtccagc agatacggcg ccgaggccgt gagcgagccc ctggacaagg ctttccacct   7680
gctgctgaac acctacggca gacccatccg gtttctgcgg gagaacacca cccagtgcac   7740
ctacaacagc agcctgcgga acagcaccgt cgtgagagag aacgccatca gcttcaactt   7800
tttccagagc tacaaccagt actacgtgtt ccacatgccc agatgcctgt ttgccggccc   7860
tctggccgag cagttcctga accaggtgga cctgaccgag acactggaaa gataccagca   7920
gcggctgaat acctacgccc tggtgtccaa ggacctggcc agctaccggt cctttagcca   7980
gcagctcaag gctcaggata gcctcggcga gcagcctacc accgtgcccc ctcccatcga   8040
cctgagcatc ccccacgtgt ggatgcctcc ccagaccacc cctcacggct ggaccgagag   8100
ccacaccacc tccggcctgc acagacccca cttcaaccag acctgcatcc tgttcgacgg   8160
ccacgacctg ctgtttagca ccgtgacccc ctgcctgcac cagggcttct acctgatcga   8220
```

```
cgagctgaga tacgtgaaga tcaccctgac cgaggatttc ttcgtggtca ccgtgtccat   8280
cgacgacgac acccccatgc tgctgatctt cggccacctg cccagagtgc tgttcaaggc   8340
cccctaccag cgggacaact tcatcctgcg gcagaccgag aagcacgagc tgctggtgct   8400
ggtcaagaag gaccagctga accggcactc ctacctgaag gaccccgact tcctggacgc   8460
cgccctggac ttcaactacc tggacctgag cgccctgctg agaaacagct tccacagata   8520
cgccgtggac gtgctgaagt ccggacggtg ccagatgctc gatcggcgga ccgtggagat   8580
ggccttcgcc tatgccctcg ccctgttcgc cgctgccaga caggaagagg ctggcgccca   8640
ggtgtcagtg cccagagccc tggatagaca ggccgccctg ctgcagatcc aggaattcat   8700
gatcacctgc ctgagccaga cccccccctag aaccaccctg ctgctgtacc ccacagccgt   8760
ggatctggcc aagagggccc tgtggacccc caaccagatc accgacatca caagcctcgt   8820
gcggctcgtg tacatcctga gcaagcagaa ccagcagcac ctgatccccc agtgggccct   8880
gagacagatc gccgacttcg ccctgaagct gcacaagacc catctggcca gctttctgag   8940
cgccttcgcc aggcaggaac tgtacctgat gggcagcctg gtccacagca tgctggtgca   9000
taccaccgag cggcgggaga tcttcatcgt ggagacaggc ctgtgtagcc tggccgagct   9060
gtcccacttt acccagctgc tggcccaccc tcaccacgag tacctgagcg acctgtacac   9120
cccctgcagc agcagcggca gacgggacca cagcctggaa cggctgacca gactgttccc   9180
cgatgccacc gtgcctgcta cagtgcctgc cgccctgtcc atcctgtcca ccatgcagcc   9240
cagcaccctg gaaaccttcc ccgacctgtt ctgcctgccc ctgggcgaga gctttagcgc   9300
cctgaccgtg tccgagcacg tgtcctacat cgtgaccaat cagtacctga tcaagggcat   9360
cagctacccc gtgtccacca cagtcgtggg ccagagcctg atcatcaccc agaccgacag   9420
ccagaccaag tgcgagctga cccggaacat gcacaccaca cacagcatca ccgtggccct   9480
gaacatcagc ctggaaaact gcgctttctg tcagtctgcc ctgctggaat acgacgatac   9540
ccagggcgtg atcaacatca tgtacatgca cgacagcgac gacgtgctgt tcgccctgga   9600
cccctacaac gaggtggtgg tgtccagccc ccggacccac tacctgatgc tgctgaagaa   9660
cggcaccgtg ctggaagtga ccgacgtggt ggtggacgcc accgacctgt tgaattttga   9720
ccttcttaag cttgcgggag acgtcgagtc caaccccggg cccatgtgca gaaggcccga   9780
ctgcggcttc agcttcagcc ctggacccgt gatcctgctg tggtgctgcc tgctgctgcc   9840
tatcgtgtcc tctgccgccg tgtctgtggc ccctacagcc gccgagaagg tgccagccga   9900
gtgccccgag ctgaccagaa gatgcctgct gggcgaggtg ttcgagggcg acaagtacga   9960
gagctggctg cggcccctgg tcaacgtgac cggcagagat ggcccccctga gccagctgat  10020
ccggtacaga cccgtgaccc ccgaggccgc caatagcgtg ctgctggacg aggccttcct  10080
ggataccctg gccctgctgt acaacaaccc cgaccagctg agagccctgc tgaccctgct  10140
gtccagcgac accgcccccca gatggatgac cgtgatgcgg ggctacagcg agtgtggaga  10200
tggcagccct gccgtgtaca cctgcgtgga cgacctgtgc agaggctacg acctgaccag  10260
actgagctac ggccggtcca tcttcacaga gcacgtgctg ggcttcgagc tggtgccccc  10320
cagcctgttc aacgtggtgg tggccatccg gaacgaggcc accagaacca acagagccgt  10380
gcggctgcct gtgtctacag ccgctgcacc tgagggcatc acactgttct acggcctgta  10440
caacgccgtg aaagagttct gcctccggca ccagctggat cccccccctgc tgagacacct  10500
ggacaagtac tacgccggcc tgcccccaga gctgaagcag accagagtga acctgcccgc  10560
```

```
ccacagcaga tatggccctc aggccgtgga cgccagatga taagcggccg catacagcag  10620
caattggcaa gctgcttaca tagaactcgc ggcgattggc atgccgcctt aaaattttta  10680
ttttattttt cttttctttt ccgaatcgga ttttgttttt aatatttcaa aaaaaaaaaa  10740
aaaaaaaaaa aaaaaaaaaa aaagggtcgg catggcatct ccacctcctc gcggtccgac  10800
ctgggcatcc gaaggaggac gcacgtccac tcggatggct aagggagagc cacgtttaaa  10860
cacgtgatat ctggcctcat gggccttcct ttcactgccc gctttccagt cgggaaacct  10920
gtcgtgccag ctgcattaac atggtcatag ctgtttcctt gcgtattggg cgctctccgc  10980
ttcctcgctc actgactcgc tgcgctcggt cgttcgggta aagcctgggg tgcctaatga  11040
gcaaaaggcc agcaaaaggc caggaaccgt aaaaaggccg cgttgctggc gtttttccat  11100
aggctccgcc cccctgacga gcatcacaaa aatcgacgct caagtcagag gtggcgaaac  11160
ccgacaggac tataaagata ccaggcgttt ccccctggaa gctccctcgt gcgctctcct  11220
gttccgaccc tgccgcttac cggatacctg tccgcctttc tcccttcggg aagcgtggcg  11280
ctttctcata gctcacgctg taggtatctc agttcggtgt aggtcgttcg ctccaagctg  11340
ggctgtgtgc acgaaccccc cgttcagccc gaccgctgcg ccttatccgg taactatcgt  11400
cttgagtcca acccggtaag acacgactta tcgccactgg cagcagccac tggtaacagg  11460
attagcagag cgaggtatgt aggcggtgct acagagttct tgaagtggtg gcctaactac  11520
ggctacacta gaagaacagt atttggtatc tgcgctctgc tgaagccagt taccttcgga  11580
aaaagagttg gtagctcttg atccggcaaa caaaccaccg ctggtagcgg tggttttttt  11640
gtttgcaagc agcagattac gcgcagaaaa aaaggatctc aagaagatcc tttgatcttt  11700
tctacggggt ctgacgctca gtggaacgaa aactcacgtt aagggatttt ggtcatgaga  11760
ttatcaaaaa ggatcttcac ctagatcctt ttaaattaaa aatgaagttt taaatcaatc  11820
taaagtatat atgagtaaac ttggtctgac agttattaga aaaattcatc cagcagacga  11880
taaaacgcaa tacgctggct atccggtgcc gcaatgccat acagcaccag aaaacgatcc  11940
gcccattcgc cgcccagttc ttccgcaata tcacgggtgg ccagcgcaat atcctgataa  12000
cgatccgcca cgcccagacg gccgcaatca ataaagccgc taaaacggcc attttccacc  12060
ataatgttcg gcaggcacgc atcaccatgg gtcaccacca gatcttcgcc atccggcatg  12120
ctcgctttca gacgcgcaaa cagctctgcc ggtgccaggc cctgatgttc ttcatccaga  12180
tcatcctgat ccaccaggcc cgcttccata cgggtacgcg cacgttcaat acgatgtttc  12240
gcctgatgat caaacggaca ggtcgccggg tccagggtat gcagacgacg catggcatcc  12300
gccataatgc tcactttttc tgccggcgcc agatggctag acagcagatc ctgacccggc  12360
acttcgccca gcagcagcca atcacggccc gcttcggtca ccacatccag caccgccgca  12420
cacggaacac cggtggtggc cagccagctc agacgcgccg cttcatcctg cagctcgttc  12480
agcgcaccgc tcagatcggt tttcacaaac agcaccggac gaccctgcgc gctcagacga  12540
aacaccgccg catcagagca gccaatggtc tgctgcgccc aatcatagcc aaacagacgt  12600
tccacccacg ctgccgggct acccgcatgc aggccatcct gttcaatcat actcttcctt  12660
tttcaatatt attgaagcat ttatcagggt tattgtctca tgagcggata catatttgaa  12720
tgtatttaga aaaataaaca aataggggtt ccgcgcacat ttccccgaaa agtgccacct  12780
aaattgtaag cgttaatatt ttgttaaaat tcgcgttaaa tttttgttaa atcagctcat  12840
tttttaacca ataggccgaa atcggcaaaa tcccttataa atcaaaagaa tagaccgaga  12900
tagggttgag tggccgctac agggcgctcc cattcgccat tcaggctgcg caactgttgg  12960
```

gaagggcgtt tcggtgcggg cctcttcgct attacgccag ctggcgaaag ggggatgtgc 13020
tgcaaggcga ttaagttggg taacgccagg gttttcccag tcacacgcgt aatacgactc 13080
actatag 13087

<210> SEQ ID NO 8
<211> LENGTH: 13788
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 8
ataggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct cgccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600
agaacttggc tggagcatat ccatcatact ctaccaactg ggccgacgaa accgtgttaa 660
cggctcgtaa cataggccta tgcagctctg acgttatgga gcggtcacgt agagggatgt 720
ccattcttag aaagaagtat ttgaaaccat ccaacaatgt tctattctct gttggctcga 780
ccatctacca cgagaagagg gacttactga ggagctggca cctgccgtct gtatttcact 840
tacgtggcaa gcaaaattac acatgtcggt gtgagactat agttagttgc gacgggtacg 900
tcgttaaaag aatagctatc agtccaggcc tgtatgggaa gccttcaggc tatgctgcta 960
cgatgcaccg cgagggattc ttgtgctgca aagtgacaga cacattgaac ggggagaggg 1020
tctcttttcc cgtgtgcacg tatgtgccag ctacattgtg tgaccaaatg actggcatac 1080
tggcaacaga tgtcagtgcg gacgacgcgc aaaaactgct ggttgggctc aaccagcgta 1140
tagtcgtcaa cggtcgcacc cagagaaaca ccaataccat gaaaaattac cttttgcccg 1200
tagtggccca ggcatttgct aggtgggcaa aggaatataa ggaagatcaa gaagatgaaa 1260
ggccactagg actacgagat agacagttag tcatggggtg ttgttgggct tttagaaggc 1320
acaagataac atctatttat aagcgcccgg atacccaaac catcatcaaa gtgaacagcg 1380
atttccactc attcgtgctg cccaggatag gcagtaacac attggagatc gggctgagaa 1440
caagaatcag gaaaatgtta gaggagcaca aggagccgtc acctctcatt accgccgagg 1500
acgtacaaga agctaagtgc gcagccgatg aggctaagga ggtgcgtgaa gccgaggagt 1560
tgcgcgcagc tctaccacct ttggcagctg atgttgagga gcccactctg gaagccgatg 1620
tcgacttgat gttacaagag gctggggccg gctcagtgga gacacctcgt ggcttgataa 1680
aggttaccag ctacgatggc gaggacaaga tcggctctta cgctgtgctt tctccgcagg 1740
ctgtactcaa gagtgaaaaa ttatcttgca tccaccctct cgctgaacaa gtcatagtga 1800

```
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
```

```
tggtcaaagg tgcagctaaa catatcattc atgccgtagg accaaacttc aacaaagttt   4260

cggaggttga aggtgacaaa cagttggcag aggcttatga gtccatcgct aagattgtca   4320

acgataacaa ttacaagtca gtagcgattc cactgttgtc caccggcatc ttttccggga   4380

acaaagatcg actaacccaa tcattgaacc atttgctgac agctttagac accactgatg   4440

cagatgtagc catatactgc agggacaaga aatgggaaat gactctcaag gaagcagtgg   4500

ctaggagaga agcagtggag gagatatgca tatccgacga ctcttcagtg acagaacctg   4560

atgcagagct ggtgagggtg catccgaaga gttctttggc tggaaggaag ggctacagca   4620

caagcgatgg caaaactttc tcatatttgg aagggaccaa gtttcaccag gcggccaagg   4680

atatagcaga aattaatgcc atgtggcccg ttgcaacgga ggccaatgag caggtatgca   4740

tgtatatcct cggagaaagc atgagcagta ttaggtcgaa atgccccgtc gaagagtcgg   4800

aagcctccac accacctagc acgctgcctt gcttgtgcat ccatgccatg actccagaaa   4860

gagtacagcg cctaaaagcc tcacgtccag aacaaattac tgtgtgctca tcctttccat   4920

tgccgaagta tagaatcact ggtgtgcaga agatccaatg ctcccagcct atattgttct   4980

caccgaaagt gcctgcgtat attcatccaa ggaagtatct cgtggaaaca ccaccggtag   5040

acgagactcc ggagccatcg gcagagaacc aatccacaga ggggacacct gaacaaccac   5100

cacttataac cgaggatgag accaggacta gaacgcctga gccgatcatc atcgaagagg   5160

aagaagagga tagcataagt ttgctgtcag atggcccgac ccaccaggtg ctgcaagtcg   5220

aggcagacat tcacgggccg ccctctgtat ctagctcatc ctggtccatt cctcatgcat   5280

ccgactttga tgtggacagt ttatccatac ttgacaccct ggagggagct agcgtgacca   5340

gcggggcaac gtcagccgag actaactctt acttcgcaaa gagtatggag tttctggcgc   5400

gaccggtgcc tgcgcctcga acagtattca ggaaccctcc acatcccgct ccgcgcacaa   5460

gaacaccgtc acttgcaccc agcagggcct gctcgagaac cagcctagtt tccaccccgc   5520

caggcgtgaa tagggtgatc actagagagg agctcgaggc gcttaccccg tcacgcactc   5580

ctagcaggtc ggtctcgaga accagcctgg tctccaaccc gccaggcgta aatagggtga   5640

ttacaagaga ggagtttgag gcgttcgtag cacaacaaca atgacggttt gatgcgggtg   5700

catacatctt ttcctccgac accggtcaag ggcatttaca acaaaaatca gtaaggcaaa   5760

cggtgctatc cgaagtggtg ttggagagga ccgaattgga gatttcgtat gccccgcgcc   5820

tcgaccaaga aaaagaagaa ttactacgca agaaattaca gttaaatccc acacctgcta   5880

acagaagcag ataccagtcc aggaaggtgg agaacatgaa agccataaca gctagacgta   5940

ttctgcaagg cctagggcat tatttgaagg cagaaggaaa agtggagtgc taccgaaccc   6000

tgcatcctgt tcctttgtat tcatctagtg tgaaccgtgc cttttcaagc cccaaggtcg   6060

cagtggaagc ctgtaacgcc atgttgaaag agaactttcc gactgtggct tcttactgta   6120

ttattccaga gtacgatgcc tatttggaca tggttgacgg agcttcatgc tgcttagaca   6180

ctgccagttt ttgccctgca aagctgcgca gctttccaaa gaaacactcc tatttggaac   6240

ccacaatacg atcggcagtg ccttcagcga tccagaacac gctccagaac gtcctggcag   6300

ctgccacaaa aagaaattgc aatgtcacgc aaatgagaga attgcccgta ttggattcgg   6360

cggcctttaa tgtggaatgc ttcaagaaat atgcgtgtaa taatgaatat tgggaaacgt   6420

ttaaagaaaa ccccatcagg cttactgaag aaaacgtggt aaattacatt accaaattaa   6480

aaggaccaaa agctgctgct ctttttgcga agacacataa tttgaatatg ttgcaggaca   6540
```

-continued

```
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gatgaggcct ggcctgccct cctacctgat catcctggcc gtgtgcctgt tcagccacct   7620
gctgtccagc agatacggcg ccgaggccgt gagcgagccc ctggacaagg ctttccacct   7680
gctgctgaac acctacggca gacccatccg gtttctgcgg gagaacacca cccagtgcac   7740
ctacaacagc agcctgcgga acagcaccgt cgtgagagag aacgccatca gcttcaactt   7800
tttccagagc tacaaccagt actacgtgtt ccacatgccc agatgcctgt ttgccggccc   7860
tctggccgag cagttcctga accaggtgga cctgaccgag acactggaaa gataccagca   7920
gcggctgaat acctacgccc tggtgtccaa ggacctggcc agctaccggt cctttagcca   7980
gcagctcaag gctcaggata gcctcggcga gcagcctacc accgtgcccc ctcccatcga   8040
cctgagcatc ccccacgtgt ggatgcctcc ccagaccacc cctcacggct ggaccgagag   8100
ccacaccacc tccggcctgc acagacccca cttcaaccag acctgcatcc tgttcgacgg   8160
ccacgacctg ctgtttagca ccgtgacccc ctgcctgcac cagggcttct acctgatcga   8220
cgagctgaga tacgtgaaga tcaccctgac cgaggatttc ttcgtggtca ccgtgtccat   8280
cgacgacgac acccccatgc tgctgatctt cggccacctg cccagagtgc tgttcaaggc   8340
cccctaccag cgggacaact tcatcctgcg gcagaccgag aagcacgagc tgctggtgct   8400
ggtcaagaag gaccagctga accggcactc ctacctgaag gaccccgact tcctggacgc   8460
cgccctggac ttcaactacc tggacctgag cgccctgctg agaaacagct tccacagata   8520
cgccgtggac gtgctgaagt ccggacggtg ccagatgctc gatcggcgga ccgtggagat   8580
ggccttcgcc tatgccctcg ccctgttcgc cgctgccaga caggaagagg ctggcgccca   8640
ggtgtcagtg cccagagccc tggatagaca ggccgccctg ctgcagatcc aggaattcat   8700
gatcacctgc ctgagccaga cccccccctag aaccaccctg ctgctgtacc ccacagccgt   8760
ggatctggcc aagagggccc tgtggacccc caaccagatc accgacatca caagcctcgt   8820
gcggctcgtg tacatcctga gcaagcagaa ccagcagcac ctgatccccc agtgggccct   8880
gagacagatc gccgacttcg ccctgaagct gcacaagacc catctggcca gctttctgag   8940
```

```
cgccttcgcc aggcaggaac tgtacctgat gggcagcctg gtccacagca tgctggtgca   9000
taccaccgag cggcgggaga tcttcatcgt ggagacaggc ctgtgtagcc tggccgagct   9060
gtcccacttt acccagctgc tggcccaccc tcaccacgag tacctgagcg acctgtacac   9120
cccctgcagc agcagcggca gacgggacca cagcctggaa cggctgacca gactgttccc   9180
cgatgccacc gtgcctgcta cagtgcctgc cgccctgtcc atcctgtcca ccatgcagcc   9240
cagcaccctg gaaaccttcc ccgacctgtt ctgcctgccc ctgggcgaga gctttagcgc   9300
cctgaccgtg tccgagcacg tgtcctacat cgtgaccaat cagtacctga tcaagggcat   9360
cagctacccc gtgtccacca cagtcgtggg ccagagcctg atcatcaccc agaccgacag   9420
ccagaccaag tgcgagctga cccggaacat gcacaccaca cacagcatca ccgtggccct   9480
gaacatcagc ctggaaaact gcgctttctg tcagtctgcc ctgctggaat acgacgatac   9540
ccagggcgtg atcaacatca tgtacatgca cgacagcgac gacgtgctgt tcgccctgga   9600
cccctacaac gaggtggtgg tgtccagccc ccggacccac tacctgatgc tgctgaagaa   9660
cggcaccgtg ctggaagtga ccgacgtggt ggtggacgcc accgactgat aatctagatt   9720
aaaacagctg tgggttgttc ccacccacag ggcccactgg gcgctagcac tctgatttta   9780
cgaaatcctt gtgcgcctgt tttatatccc ttccctaatt cgaaacgtag aagcaatgcg   9840
caccactgat caatagtagg cgtaacgcgc cagttacgtc atgatcaagc atatctgttc   9900
ccccggactg agtatcaata gactgcttac gcggttgaag gagaaaacgt tcgttatccg   9960
gctaactact tcgagaagcc cagtaacacc atggaagctg cagggtgttt cgctcagcac  10020
ttcccccgtg tagatcaggt cgatgagcca ctgcaatccc cacaggtgac tgtggcagtg  10080
gctgcgttgg cggcctgcct atggggagac ccataggacg ctctaatgtg gacatggtgc  10140
gaagagccta ttgagctagt tagtagtcct ccggcccctg aatgcggcta atcctaactg  10200
cggagcacat gccttcaacc cagagggtag tgtgtcgtaa tgggcaactc tgcagcggaa  10260
ccgactactt tgggtgtccg tgtttctttt tattcttata ttggctgctt atggtgacaa  10320
ttacagaatt gttaccatat agctattgga ttggccatcc ggtgtgtaat agagctgtta  10380
tatacctatt tgttggcttt gtaccactaa ctttaaaatc tataactacc ctcaacttta  10440
tattaaccct caatacagtt gaacatgtgc agaaggcccg actgcggctt cagcttcagc  10500
cctggacccg tgatcctgct gtggtgctgc ctgctgctgc ctatcgtgtc ctctgccgcc  10560
gtgtctgtgg cccctacagc cgccgagaag gtgccagccg agtgccccga gctgaccaga  10620
agatgcctgc tgggcgaggt gttcgagggc gacaagtacg agagctggct gcggcccctg  10680
gtcaacgtga ccggcagaga tggcccccctg agccagctga tccggtacag acccgtgacc  10740
cccgaggccg ccaatagcgt gctgctggac gaggccttcc tggataccct ggccctgctg  10800
tacaacaacc ccgaccagct gagagccctg ctgaccctgc tgtccagcga caccgccccc  10860
agatggatga ccgtgatgcg gggctacagc gagtgtggag atggcagccc tgccgtgtac  10920
acctgcgtgg acgacctgtg cagaggctac gacctgacca gactgagcta cggccggtcc  10980
atcttcacag agcacgtgct gggcttcgag ctggtgcccc ccagcctgtt caacgtggtg  11040
gtggccatcc ggaacgaggc caccagaacc aacagagccg tgcggctgcc tgtgtctaca  11100
gccgctgcac ctgagggcat cacactgttc tacggcctgt acaacgccgt gaaagagttc  11160
tgcctccggc accagctgga tcccccccctg ctgagacacc tggacaagta ctacgccggc  11220
ctgcccccag agctgaagca gaccagagtg aacctgcccg cccacagcag atatggccct  11280
```

caggccgtgg acgccagatg ataagcggcc gcatacagca gcaattggca agctgcttac 11340
atagaactcg cggcgattgg catgccgcct taaaattttt attttatttt tcttttcttt 11400
tccgaatcgg attttgtttt taatatttca aaaaaaaaaa aaaaaaaaaa aaaaaaaaaa 11460
aaaagggtcg gcatggcatc tccacctcct cgcggtccga cctgggcatc cgaaggagga 11520
cgcacgtcca ctcggatggc taagggagag ccacgtttaa acacgtgata tctggcctca 11580
tgggccttcc tttcactgcc cgctttccag tcgggaaacc tgtcgtgcca gctgcattaa 11640
catggtcata gctgtttcct tgcgtattgg gcgctctccg cttcctcgct cactgactcg 11700
ctgcgctcgg tcgttcgggt aaagcctggg gtgcctaatg agcaaaaggc cagcaaaagg 11760
ccaggaaccg taaaaaggcc gcgttgctgg cgtttttcca taggctccgc ccccctgacg 11820
agcatcacaa aaatcgacgc tcaagtcaga ggtggcgaaa cccgacagga ctataaagat 11880
accaggcgtt tccccctgga agctccctcg tgcgctctcc tgttccgacc ctgccgctta 11940
ccggatacct gtccgccttt ctcccttcgg gaagcgtggc gctttctcat agctcacgct 12000
gtaggtatct cagttcggtg taggtcgttc gctccaagct gggctgtgtg cacgaacccc 12060
ccgttcagcc cgaccgctgc gccttatccg gtaactatcg tcttgagtcc aacccggtaa 12120
gacacgactt atcgccactg gcagcagcca ctggtaacag gattagcaga gcgaggtatg 12180
taggcggtgc tacagagttc ttgaagtggt ggcctaacta cggctacact agaagaacag 12240
tatttggtat ctgcgctctg ctgaagccag ttaccttcgg aaaaagagtt ggtagctctt 12300
gatccggcaa acaaaccacc gctggtagcg gtggtttttt tgtttgcaag cagcagatta 12360
cgcgcagaaa aaaaggatct caagaagatc ctttgatctt ttctacgggg tctgacgctc 12420
agtggaacga aaactcacgt taagggattt tggtcatgag attatcaaaa aggatcttca 12480
cctagatcct tttaaattaa aaatgaagtt ttaaatcaat ctaaagtata tatgagtaaa 12540
cttggtctga cagttattag aaaaattcat ccagcagacg ataaaacgca atacgctggc 12600
tatccggtgc cgcaatgcca tacagcacca gaaaacgatc cgcccattcg ccgcccagtt 12660
cttccgcaat atcacgggtg gccagcgcaa tatcctgata acgatccgcc acgcccagac 12720
ggccgcaatc aataaagccg ctaaaacggc cattttccac cataatgttc ggcaggcacg 12780
catcaccatg ggtcaccacc agatcttcgc catccggcat gctcgctttc agacgcgcaa 12840
acagctctgc cggtgccagg ccctgatgtt cttcatccag atcatcctga tccaccaggc 12900
ccgcttccat acgggtacgc gcacgttcaa tacgatgttt cgcctgatga tcaaacggac 12960
aggtcgccgg gtccagggta tgcagacgac gcatggcatc cgccataatg ctcacttttt 13020
ctgccggcgc cagatggcta gacagcagat cctgacccgg cacttcgccc agcagcagcc 13080
aatcacggcc cgcttcggtc accacatcca gcaccgccgc acacggaaca ccggtggtgg 13140
ccagccagct cagacgcgcc gcttcatcct gcagctcgtt cagcgcaccg ctcagatcgg 13200
ttttcacaaa cagcaccgga cgaccctgcg cgctcagacg aaacaccgcc gcatcagagc 13260
agccaatggt ctgctgcgcc caatcatagc caaacagacg ttccacccac gctgccgggc 13320
tacccgcatg caggccatcc tgttcaatca tactcttcct ttttcaatat tattgaagca 13380
tttatcaggg ttattgtctc atgagcggat acatatttga atgtatttag aaaaataaac 13440
aaataggggt tccgcgcaca tttccccgaa aagtgccacc taaattgtaa gcgttaatat 13500
tttgttaaaa ttcgcgttaa atttttgtta aatcagctca ttttttaacc aataggccga 13560
aatcggcaaa atcccttata aatcaaaaga atagaccgag atagggttga gtggccgcta 13620
cagggcgctc ccattcgcca ttcaggctgc gcaactgttg ggaagggcgt ttcggtgcgg 13680
gcctcttcgc tattacgcca gctggcgaaa gggggatgtg ctgcaaggcg attaagttgg 13740
gtaacgccag ggttttccca gtcacacgcg taatacgact cactatag 13788

<210> SEQ ID NO 9
<211> LENGTH: 13788
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 9
ataggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct cgccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600
agaacttggc tggagcatat ccatcatact ctaccaactg ggccgacgaa accgtgttaa 660
cggctcgtaa cataggccta tgcagctctg acgttatgga gcggtcacgt agagggatgt 720
ccattcttag aaagaagtat ttgaaaccat ccaacaatgt tctattctct gttggctcga 780
ccatctacca cgagaagagg gacttactga ggagctggca cctgccgtct gtatttcact 840
tacgtggcaa gcaaaattac acatgtcggt gtgagactat agttagttgc gacgggtacg 900
tcgttaaaag aatagctatc agtccaggcc tgtatgggaa gccttcaggc tatgctgcta 960
cgatgcaccg cgagggattc ttgtgctgca aagtgacaga cacattgaac ggggagaggg 1020
tctcttttcc cgtgtgcacg tatgtgccag ctacattgtg tgaccaaatg actggcatac 1080
tggcaacaga tgtcagtgcg gacgacgcgc aaaaactgct ggttgggctc aaccagcgta 1140
tagtcgtcaa cggtcgcacc cagagaaaca ccaataccat gaaaaattac cttttgcccg 1200
tagtggccca ggcatttgct aggtgggcaa aggaatataa ggaagatcaa gaagatgaaa 1260
ggccactagg actacgagat agacagttag tcatggggtg ttgttgggct tttagaaggc 1320
acaagataac atctatttat aagcgcccgg atacccaaac catcatcaaa gtgaacagcg 1380
atttccactc attcgtgctg cccaggatag gcagtaacac attggagatc gggctgagaa 1440
caagaatcag gaaaatgtta gaggagcaca aggagccgtc acctctcatt accgccgagg 1500
acgtacaaga agctaagtgc gcagccgatg aggctaagga ggtgcgtgaa gccgaggagt 1560
tgcgcgcagc tctaccacct ttggcagctg atgttgagga gcccactctg gaagccgatg 1620
tcgacttgat gttacaagag gctggggccg gctcagtgga gacacctcgt ggcttgataa 1680
aggttaccag ctacgatggc gaggacaaga tcggctctta cgctgtgctt tctccgcagg 1740
ctgtactcaa gagtgaaaaa ttatcttgca tccaccctct cgctgaacaa gtcatagtga 1800
taacacactc tggccgaaaa gggcgttatg ccgtggaacc ataccatggt aaagtagtgg 1860

-continued

```
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgaggggga tattgccacg gccaccgaag   4080
gagtgattat aaatgctgct aacagcaaag gacaacctgg cggagggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
```

```
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
```

-continued

```
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gatgtgcaga aggcccgact gcggcttcag cttcagccct ggacccgtga tcctgctgtg   7620
gtgctgcctg ctgctgccta tcgtgtcctc tgccgccgtg tctgtggccc ctacagccgc   7680
cgagaaggtg ccagccgagt gccccgagct gaccagaaga tgcctgctgg gcgaggtgtt   7740
cgagggcgac aagtacgaga gctggctgcg gcccctggtc aacgtgaccg gcagagatgg   7800
cccccctgagc cagctgatcc ggtacagacc cgtgaccccc gaggccgcca atagcgtgct   7860
gctggacgag gccttcctgg ataccctggc cctgctgtac aacaaccccg accagctgag   7920
agccctgctg accctgctgt ccagcgacac cgcccccaga tggatgaccg tgatgcgggg   7980
ctacagcgag tgtggagatg gcagccctgc cgtgtacacc tgcgtggacg acctgtgcag   8040
aggctacgac ctgaccagac tgagctacgg ccggtccatc ttcacagagc acgtgctggg   8100
cttcgagctg gtgcccccca gcctgttcaa cgtggtggtg gccatccgga acgaggccac   8160
cagaaccaac agagccgtgc ggctgcctgt gtctacagcc gctgcacctg agggcatcac   8220
actgttctac ggcctgtaca acgccgtgaa agagttctgc ctccggcacc agctggatcc   8280
ccccctgctg agacacctgg acaagtacta cgccggcctg cccccagagc tgaagcagac   8340
cagagtgaac ctgcccgccc acagcagata tggccctcag gccgtggacg ccagatgata   8400
atctagatta aaacagctgt gggttgttcc cacccacagg gcccactggg cgctagcact   8460
ctgattttac gaaatccttg tgcgcctgtt ttatatccct tccctaattc gaaacgtaga   8520
agcaatgcgc accactgatc aatagtaggc gtaacgcgcc agttacgtca tgatcaagca   8580
tatctgttcc cccggactga gtatcaatag actgcttacg cggttgaagg agaaaacgtt   8640
cgttatccgg ctaactactt cgagaagccc agtaacacca tggaagctgc agggtgtttc   8700
gctcagcact tccccgtgt agatcaggtc gatgagccac tgcaatcccc acaggtgact   8760
gtggcagtgg ctgcgttggc ggcctgccta tggggagacc cataggacgc tctaatgtgg   8820
acatggtgcg aagagcctat tgagctagtt agtagtcctc cggcccctga atgcggctaa   8880
tcctaactgc ggagcacatg ccttcaaccc agagggtagt gtgtcgtaat gggcaactct   8940
gcagcggaac cgactacttt gggtgtccgt gtttcctttt attcttatat tggctgctta   9000
```

```
tggtgacaat tacagaattg ttaccatata gctattggat tggccatccg gtgtgtaata   9060
gagctgttat atacctattt gttggctttg taccactaac tttaaaatct ataactaccc   9120
tcaactttat attaaccctc aatacagttg aacatgaggc ctggcctgcc ctcctacctg   9180
atcatcctgg ccgtgtgcct gttcagccac ctgctgtcca gcagatacgg cgccgaggcc   9240
gtgagcgagc cctggacaa ggctttccac ctgctgctga acacctacgg cagacccatc   9300
cggtttctgc gggagaacac cacccagtgc acctacaaca gcagcctgcg gaacagcacc   9360
gtcgtgagag agaacgccat cagcttcaac tttttccaga gctacaacca gtactacgtg   9420
ttccacatgc ccagatgcct gtttgccggc cctctggccg agcagttcct gaaccaggtg   9480
gacctgaccg agacactgga aagataccag cagcggctga atacctacgc cctggtgtcc   9540
aaggacctgg ccagctaccg gtcctttagc cagcagctca aggctcagga tagcctcggc   9600
gagcagccta ccaccgtgcc ccctcccatc gacctgagca tcccccacgt gtggatgcct   9660
ccccagacca cccctcacgg ctggaccgag agccacacca cctccggcct gcacagaccc   9720
cacttcaacc agacctgcat cctgttcgac ggccacgacc tgctgtttag caccgtgacc   9780
ccctgcctgc accagggctt ctacctgatc gacgagctga gatacgtgaa gatcaccctg   9840
accgaggatt tcttcgtggt caccgtgtcc atcgacgacg acacccccat gctgctgatc   9900
ttcggccacc tgcccagagt gctgttcaag gccccctacc agcgggacaa cttcatcctg   9960
cggcagaccg agaagcacga gctgctggtg ctggtcaaga aggaccagct gaaccggcac  10020
tcctacctga aggaccccga cttcctggac gccgccctgg acttcaacta cctggacctg  10080
agcgccctgc tgagaaacag cttccacaga tacgccgtgg acgtgctgaa gtccggacgg  10140
tgccagatgc tcgatcggcg gaccgtggag atggccttcg cctatgccct cgccctgttc  10200
gccgctgcca gacaggaaga ggctggcgcc caggtgtcag tgcccagagc cctggataga  10260
caggccgccc tgctgcagat ccaggaattc atgatcacct gcctgagcca gacccccccct  10320
agaaccaccc tgctgctgta ccccacagcc gtggatctgg ccaagagggc cctgtggacc  10380
cccaaccaga tcaccgacat cacaagcctc gtgcggctcg tgtacatcct gagcaagcag  10440
aaccagcagc acctgatccc ccagtgggcc ctgagacaga tcgccgactt cgccctgaag  10500
ctgcacaaga cccatctggc cagctttctg agcgccttcg ccaggcagga actgtacctg  10560
atgggcagcc tggtccacag catgctggtg cataccaccg agcggcggga gatcttcatc  10620
gtggagacag gcctgtgtag cctggccgag ctgtcccact ttacccagct gctggcccac  10680
cctcaccacg agtacctgag cgacctgtac accccctgca gcagcagcgg cagacgggac  10740
cacagcctgg aacggctgac cagactgttc cccgatgcca ccgtgcctgc tacagtgcct  10800
gccgccctgt ccatcctgtc caccatgcag cccagcaccc tggaaacctt ccccgacctg  10860
ttctgcctgc ccctgggcga gagctttagc gccctgaccg tgtccgagca cgtgtcctac  10920
atcgtgacca atcagtacct gatcaagggc atcagctacc ccgtgtccac cacagtcgtg  10980
ggccagagcc tgatcatcac ccagaccgac agccagacca agtgcgagct gacccggaac  11040
atgcacacca cacacagcat caccgtggcc ctgaacatca gcctggaaaa ctgcgctttc  11100
tgtcagtctg ccctgctgga atacgacgat acccagggcg tgatcaacat catgtacatg  11160
cacgacagcg acgacgtgct gttcgccctg gacccctaca acgaggtggt ggtgtccagc  11220
ccccggaccc actacctgat gctgctgaag aacggcaccg tgctggaagt gaccgacgtg  11280
gtggtggacg ccaccgactg ataagcggcc gcatacagca gcaattggca agctgcttac  11340
```

```
atagaactcg cggcgattgg catgccgcct taaaattttt attttatttt tcttttcttt  11400
tccgaatcgg attttgtttt taatatttca aaaaaaaaaa aaaaaaaaaa aaaaaaaaaa  11460
aaaagggtcg gcatggcatc tccacctcct cgcggtccga cctgggcatc cgaaggagga  11520
cgcacgtcca ctcggatggc taagggagag ccacgtttaa acacgtgata tctggcctca  11580
tgggccttcc tttcactgcc cgctttccag tcgggaaacc tgtcgtgcca gctgcattaa  11640
catggtcata gctgtttcct tgcgtattgg gcgctctccg cttcctcgct cactgactcg  11700
ctgcgctcgg tcgttcgggt aaagcctggg gtgcctaatg agcaaaaggc cagcaaaagg  11760
ccaggaaccg taaaaaggcc gcgttgctgg cgtttttcca taggctccgc ccccctgacg  11820
agcatcacaa aaatcgacgc tcaagtcaga ggtggcgaaa cccgacagga ctataaagat  11880
accaggcgtt tccccctgga agctccctcg tgcgctctcc tgttccgacc ctgccgctta  11940
ccggatacct gtccgccttt ctcccttcgg gaagcgtggc gctttctcat agctcacgct  12000
gtaggtatct cagttcggtg taggtcgttc gctccaagct gggctgtgtg cacgaacccc  12060
ccgttcagcc cgaccgctgc gccttatccg gtaactatcg tcttgagtcc aacccggtaa  12120
gacacgactt atcgccactg gcagcagcca ctggtaacag gattagcaga gcgaggtatg  12180
taggcggtgc tacagagttc ttgaagtggt ggcctaacta cggctacact agaagaacag  12240
tatttggtat ctgcgctctg ctgaagccag ttaccttcgg aaaaagagtt ggtagctctt  12300
gatccggcaa acaaaccacc gctggtagcg gtggtttttt tgtttgcaag cagcagatta  12360
cgcgcagaaa aaaaggatct caagaagatc ctttgatctt ttctacgggg tctgacgctc  12420
agtggaacga aaactcacgt taagggattt tggtcatgag attatcaaaa aggatcttca  12480
cctagatcct tttaaattaa aaatgaagtt ttaaatcaat ctaaagtata tatgagtaaa  12540
cttggtctga cagttattag aaaaattcat ccagcagacg ataaaacgca atacgctggc  12600
tatccggtgc cgcaatgcca tacagcacca gaaaacgatc cgcccattcg ccgcccagtt  12660
cttccgcaat atcacgggtg gccagcgcaa tatcctgata acgatccgcc acgcccagac  12720
ggccgcaatc aataaagccg ctaaaacggc cattttccac cataatgttc ggcaggcacg  12780
catcaccatg ggtcaccacc agatcttcgc catccggcat gctcgctttc agacgcgcaa  12840
acagctctgc cggtgccagg ccctgatgtt cttcatccag atcatcctga tccaccaggc  12900
ccgcttccat acgggtacgc gcacgttcaa tacgatgttt cgcctgatga tcaaacggac  12960
aggtcgccgg gtccagggta tgcagacgac gcatggcatc cgccataatg ctcacttttt  13020
ctgccggcgc cagatggcta gacagcagat cctgacccgg cacttcgccc agcagcagcc  13080
aatcacggcc cgcttcggtc accacatcca gcaccgccgc acacggaaca ccggtggtgg  13140
ccagccagct cagacgcgcc gcttcatcct gcagctcgtt cagcgcaccg ctcagatcgg  13200
ttttcacaaa cagcaccgga cgaccctgcg cgctcagacg aaacaccgcc gcatcagagc  13260
agccaatggt ctgctgcgcc caatcatagc caaacagacg ttccacccac gctgccgggc  13320
tacccgcatg caggccatcc tgttcaatca tactcttcct tttcaatat tattgaagca  13380
tttatcaggg ttattgtctc atgagcggat acatatttga atgtatttag aaaaataaac  13440
aaataggggt tccgcgcaca tttccccgaa aagtgccacc taaattgtaa gcgttaatat  13500
tttgttaaaa ttcgcgttaa atttttgtta aatcagctca ttttttaacc aataggccga  13560
aatcggcaaa atcccttata aatcaaaaga atagaccgag atagggttga gtggccgcta  13620
cagggcgctc ccattcgcca ttcaggctgc gcaactgttg ggaagggcgt ttcggtgcgg  13680
gcctcttcgc tattacgcca gctggcgaaa gggggatgtg ctgcaaggcg attaagttgg  13740
```

gtaacgccag ggttttccca gtcacacgcg taatacgact cactatag 13788

<210> SEQ ID NO 10
<211> LENGTH: 14202
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 10
ataggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct cgccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600
agaacttggc tggagcatat ccatcatact ctaccaactg ggccgacgaa accgtgttaa 660
cggctcgtaa cataggccta tgcagctctg acgttatgga gcggtcacgt agagggatgt 720
ccattcttag aaagaagtat ttgaaaccat ccaacaatgt tctattctct gttggctcga 780
ccatctacca cgagaagagg gacttactga ggagctggca cctgccgtct gtatttcact 840
tacgtggcaa gcaaaattac acatgtcggt gtgagactat agttagttgc gacgggtacg 900
tcgttaaaag aatagctatc agtccaggcc tgtatgggaa gccttcaggc tatgctgcta 960
cgatgcaccg cgagggattc ttgtgctgca aagtgacaga cacattgaac ggggagaggg 1020
tctcttttcc cgtgtgcacg tatgtgccag ctacattgtg tgaccaaatg actggcatac 1080
tggcaacaga tgtcagtgcg gacgacgcgc aaaaactgct ggttgggctc aaccagcgta 1140
tagtcgtcaa cggtcgcacc cagagaaaca ccaataccat gaaaaattac cttttgcccg 1200
tagtggccca ggcatttgct aggtgggcaa aggaatataa ggaagatcaa gaagatgaaa 1260
ggccactagg actacgagat agacagttag tcatggggtg ttgttgggct tttagaaggc 1320
acaagataac atctatttat aagcgcccgg atacccaaac catcatcaaa gtgaacagcg 1380
atttccactc attcgtgctg cccaggatag gcagtaacac attggagatc gggctgagaa 1440
caagaatcag gaaaatgtta gaggagcaca aggagccgtc acctctcatt accgccgagg 1500
acgtacaaga agctaagtgc gcagccgatg aggctaagga ggtgcgtgaa gccgaggagt 1560
tgcgcgcagc tctaccacct ttggcagctg atgttgagga gcccactctg gaagccgatg 1620
tcgacttgat gttacaagag gctggggccg gctcagtgga gacacctcgt ggcttgataa 1680
aggttaccag ctacgatggc gaggacaaga tcggctctta cgctgtgctt tctccgcagg 1740
ctgtactcaa gagtgaaaaa ttatcttgca tccaccctct cgctgaacaa gtcatagtga 1800
taacacactc tggccgaaaa gggcgttatg ccgtggaacc ataccatggt aaagtagtgg 1860
tgccagaggg acatgcaata cccgtccagg actttcaagc tctgagtgaa agtgccacca 1920

```
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg actttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
```

```
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
```

```
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gctattccag aagtagtgag gaggcttttt tggaggccta ggcttttgca aaaagcttgt   7620
atatccattt tcggatctga tcaagagaca ggatgaggat cgtttcgcat gattgaataa   7680
gatggattgc acgtaggttc tccggccgct tgggtggaga ggctattcgg ctatgactgg   7740
gcacaactga caatcggctg ctctgatgcc gccgtgatcc ggttgtcagc gcaggggcgc   7800
ccggttcttt ttgtcaagac cgacctgtcc ggtgccctga atgaactgaa ggacgaggca   7860
gcgcggctat cgtggctggc cacgacgggc gttccttgcg cagtctagac tggcgcgcca   7920
aacctgcagg ttaaaacagc tgtgggttgt tcccacccac agggcccact gggcgctagc   7980
actctgattt tacgaaatcc ttgtgcgcct gttttatatc ccttccctaa ttcgaaacgt   8040
agaagcaatg cgcaccactg atcaatagta ggcgtaacgc gccagttacg tcatgatcaa   8100
gcatatctgt tcccccggac tgagtatcaa tagactgctt acgcggttga aggagaaaac   8160
gttcgttatc cggctaacta cttcgagaag cccagtaaca ccatggaagc tgcagggtgt   8220
ttcgctcagc acttcccccg tgtagatcag gtcgatgagc cactgcaatc cccacaggtg   8280
actgtggcag tggctgcgtt ggcggcctgc ctatggggag acccatagga cgctctaatg   8340
tggacatggt gcgaagagcc tattgagcta gttagtagtc ctccggcccc tgaatgcggc   8400
taatcctaac tgcggagcac atgccttcaa cccagagggt agtgtgtcgt aatgggcaac   8460
tctgcagcgg aaccgactac tttgggtgtc cgtgtttctt tttattctta tattggctgc   8520
ttatggtgac aattacagaa ttgttaccat atagctattg gattggccat ccggtgtgta   8580
atagagctgt tatataccta tttgttggct ttgtaccact aactttaaaa tctataacta   8640
ccctcaactt tatattaacc ctcaatacag ttgaacatga ggcctggcct gccctcctac   8700
ctgatcatcc tggccgtgtg cctgttcagc cacctgctgt ccagcagata cggcgccgag   8760
gccgtgagcg agcccctgga caaggctttc cacctgctgc tgaacaccta cggcagaccc   8820
atccggtttc tgcgggagaa caccacccag tgcacctaca acagcagcct gcggaacagc   8880
accgtcgtga gagagaacgc catcagcttc aactttttcc agagctacaa ccagtactac   8940
gtgttccaca tgcccagatg cctgtttgcc ggccctctgg ccgagcagtt cctgaaccag   9000
gtggacctga ccgagacact ggaaagatac cagcagcggc tgaataccta cgccctggtg   9060
```

```
tccaaggacc tggccagcta ccggtccttt agccagcagc tcaaggctca ggatagcctc   9120
ggcgagcagc ctaccaccgt gccccctccc atcgacctga gcatccccca cgtgtggatg   9180
cctccccaga ccacccctca cggctggacc gagagccaca ccacctccgg cctgcacaga   9240
ccccacttca accagacctg catcctgttc gacggccacg acctgctgtt tagcaccgtg   9300
acccccctgcc tgcaccaggg cttctacctg atcgacgagc tgagatacgt gaagatcacc   9360
ctgaccgagg atttcttcgt ggtcaccgtg tccatcgacg acgacacccc catgctgctg   9420
atcttcggcc acctgcccag agtgctgttc aaggcccccct accagcggga caacttcatc   9480
ctgcggcaga ccgagaagca cgagctgctg gtgctggtca agaaggacca gctgaaccgg   9540
cactcctacc tgaaggaccc cgacttcctg gacgccgccc tggacttcaa ctacctggac   9600
ctgagcgccc tgctgagaaa cagcttccac agatacgccg tggacgtgct gaagtccgga   9660
cggtgccaga tgctcgatcg gcggaccgtg gagatggcct tcgcctatgc cctcgccctg   9720
ttcgccgctg ccagacagga agaggctggc gcccaggtgt cagtgcccag agccctggat   9780
agacaggccg ccctgctgca gatccaggaa ttcatgatca cctgcctgag ccagaccccc   9840
cctagaacca ccctgctgct gtaccccaca gccgtggatc tggccaagag ggccctgtgg   9900
acccccaacc agatcaccga catcacaagc ctcgtgcggc tcgtgtacat cctgagcaag   9960
cagaaccagc agcacctgat cccccagtgg gccctgagac agatcgccga cttcgccctg  10020
aagctgcaca agacccatct ggccagcttt ctgagcgcct tcgccaggca ggaactgtac  10080
ctgatgggca gcctggtcca cagcatgctg gtgcatacca ccgagcggcg ggagatcttc  10140
atcgtggaga caggcctgtg tagcctggcc gagctgtccc actttaccca gctgctggcc  10200
caccctcacc acgagtacct gagcgacctg tacaccccct gcagcagcag cggcagacgg  10260
gaccacagcc tggaacggct gaccagactg ttccccgatg ccaccgtgcc tgctacagtg  10320
cctgccgccc tgtccatcct gtccaccatg cagcccagca ccctggaaac cttccccgac  10380
ctgttctgcc tgcccctggg cgagagcttt agcgccctga ccgtgtccga gcacgtgtcc  10440
tacatcgtga ccaatcagta cctgatcaag ggcatcagct accccgtgtc caccacagtc  10500
gtgggccaga gcctgatcat cacccagacc gacagccaga ccaagtgcga gctgacccgg  10560
aacatgcaca ccacacacag catcaccgtg gccctgaaca tcagcctgga aaactgcgct  10620
ttctgtcagt ctgccctgct ggaatacgac gatacccagg gcgtgatcaa catcatgtac  10680
atgcacgaca gcgacgacgt gctgttcgcc ctggacccct acaacgaggt ggtggtgtcc  10740
agcccccgga cccactacct gatgctgctg aagaacggca ccgtgctgga agtgaccgac  10800
gtggtggtgg acgccaccga cctgttgaat tttgaccttc ttaagcttgc gggagacgtc  10860
gagtccaacc ccgggcccat gtgcagaagg cccgactgcg gcttcagctt cagccctgga  10920
cccgtgatcc tgctgtggtg ctgcctgctg ctgcctatcg tgtcctctgc cgccgtgtct  10980
gtggccccta cagccgccga gaaggtgcca gccgagtgcc ccgagctgac cagaagatgc  11040
ctgctgggcg aggtgttcga gggcgacaag tacgagagct ggctgcggcc cctggtcaac  11100
gtgaccggca gagatggccc cctgagccag ctgatccggt acagacccgt gacccccgag  11160
gccgccaata gcgtgctgct ggacgaggcc ttcctggata ccctggccct gctgtacaac  11220
aaccccgacc agctgagagc cctgctgacc ctgctgtcca gcgacaccgc ccccagatgg  11280
atgaccgtga tgcggggcta cagcgagtgt ggagatggca gccctgccgt gtacacctgc  11340
gtggacgacc tgtgcagagg ctacgacctg accagactga gctacggccg gtccatcttc  11400
```

```
acagagcacg tgctgggctt cgagctggtg ccccccagcc tgttcaacgt ggtggtggcc  11460
atccggaacg aggccaccag aaccaacaga gccgtgcggc tgcctgtgtc tacagccgct  11520
gcacctgagg gcatcacact gttctacggc ctgtacaacg ccgtgaaaga gttctgcctc  11580
cggcaccagc tggatccccc cctgctgaga cacctggaca agtactacgc cggcctgccc  11640
ccagagctga agcagaccag agtgaacctg cccgcccaca gcagatatgg ccctcaggcc  11700
gtggacgcca gatgataagc ggccgcatac agcagcaatt ggcaagctgc ttacatagaa  11760
ctcgcggcga ttggcatgcc gccttaaaat ttttatttta tttttctttt cttttccgaa  11820
tcggattttg tttttaatat ttcaaaaaaa aaaaaaaaaa aaaaaaaaaa aaaaaaaagg  11880
gtcggcatgg catctccacc tcctcgcggt ccgacctggg catccgaagg aggacgcacg  11940
tccactcgga tggctaaggg agagccacgt ttaaacacgt gatatctggc ctcatgggcc  12000
ttcctttcac tgcccgcttt ccagtcggga aacctgtcgt gccagctgca ttaacatggt  12060
catagctgtt tccttgcgta ttgggcgctc tccgcttcct cgctcactga ctcgctgcgc  12120
tcggtcgttc gggtaaagcc tggggtgcct aatgagcaaa aggccagcaa aaggccagga  12180
accgtaaaaa ggccgcgttg ctggcgtttt tccataggct ccgcccccct gacgagcatc  12240
acaaaaatcg acgctcaagt cagaggtggc gaaacccgac aggactataa agataccagg  12300
cgtttccccc tggaagctcc ctcgtgcgct ctcctgttcc gaccctgccg cttaccggat  12360
acctgtccgc ctttctccct tcgggaagcg tggcgctttc tcatagctca cgctgtaggt  12420
atctcagttc ggtgtaggtc gttcgctcca agctgggctg tgtgcacgaa ccccccgttc  12480
agcccgaccg ctgcgcctta tccggtaact atcgtcttga gtccaacccg gtaagacacg  12540
acttatcgcc actggcagca gccactggta acaggattag cagagcgagg tatgtaggcg  12600
gtgctacaga gttcttgaag tggtggccta actacggcta cactagaaga acagtatttg  12660
gtatctgcgc tctgctgaag ccagttacct tcggaaaaag agttggtagc tcttgatccg  12720
gcaaacaaac caccgctggt agcggtggtt tttttgtttg caagcagcag attacgcgca  12780
gaaaaaaagg atctcaagaa gatcctttga tcttttctac ggggtctgac gctcagtgga  12840
acgaaaactc acgttaaggg attttggtca tgagattatc aaaaaggatc ttcacctaga  12900
tccttttaaa ttaaaaatga agttttaaat caatctaaag tatatatgag taaacttggt  12960
ctgacagtta ttagaaaaat tcatccagca gacgataaaa cgcaatacgc tggctatccg  13020
gtgccgcaat gccatacagc accagaaaac gatccgccca ttcgccgccc agttcttccg  13080
caatatcacg ggtggccagc gcaatatcct gataacgatc cgccacgccc agacggccgc  13140
aatcaataaa gccgctaaaa cggccatttt ccaccataat gttcggcagg cacgcatcac  13200
catgggtcac caccagatct tcgccatccg gcatgctcgc tttcagacgc gcaaacagct  13260
ctgccggtgc caggccctga tgttcttcat ccagatcatc ctgatccacc aggcccgctt  13320
ccatacgggt acgcgcacgt tcaatacgat gtttcgcctg atgatcaaac ggacaggtcg  13380
ccgggtccag ggtatgcaga cgacgcatgg catccgccat aatgctcact ttttctgccg  13440
gcgccagatg gctagacagc agatcctgac ccggcacttc gcccagcagc agccaatcac  13500
ggcccgcttc ggtcaccaca tccagcaccg ccgcacacgg aacaccggtg gtggccagcc  13560
agctcagacg cgccgcttca tcctgcagct cgttcagcgc accgctcaga tcggttttca  13620
caaacagcac cggacgaccc tgcgcgctca gacgaaacac cgccgcatca gagcagccaa  13680
tggtctgctg cgcccaatca tagccaaaca gacgttccac ccacgctgcc gggctacccg  13740
catgcaggcc atcctgttca atcatactct tcctttttca atattattga agcatttatc  13800
```

agggttattg tctcatgagc ggatacatat ttgaatgtat ttagaaaaat aaacaaatag 13860
gggttccgcg cacatttccc cgaaaagtgc cacctaaatt gtaagcgtta atattttgtt 13920
aaaattcgcg ttaaattttt gttaaatcag ctcatttttt aaccaatagg ccgaaatcgg 13980
caaaatccct tataaatcaa aagaatagac cgagataggg ttgagtggcc gctacagggc 14040
gctcccattc gccattcagg ctgcgcaact gttgggaagg gcgtttcggt gcgggcctct 14100
tcgctattac gccagctggc gaaaggggga tgtgctgcaa ggcgattaag ttgggtaacg 14160
ccagggtttt cccagtcaca cgcgtaatac gactcactat ag 14202

<210> SEQ ID NO 11
<211> LENGTH: 14721
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 11
ataggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct cgccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600
agaacttggc tggagcatat ccatcatact ctaccaactg ggccgacgaa accgtgttaa 660
cggctcgtaa cataggccta tgcagctctg acgttatgga gcggtcacgt agagggatgt 720
ccattcttag aaagaagtat ttgaaaccat ccaacaatgt tctattctct gttggctcga 780
ccatctacca cgagaagagg gacttactga ggagctggca cctgccgtct gtatttcact 840
tacgtggcaa gcaaaattac acatgtcggt gtgagactat agttagttgc gacgggtacg 900
tcgttaaaag aatagctatc agtccaggcc tgtatgggaa gccttcaggc tatgctgcta 960
cgatgcaccg cgagggattc ttgtgctgca aagtgacaga cacattgaac ggggagaggg 1020
tctcttttcc cgtgtgcacg tatgtgccag ctacattgtg tgaccaaatg actggcatac 1080
tggcaacaga tgtcagtgcg gacgacgcgc aaaaactgct ggttgggctc aaccagcgta 1140
tagtcgtcaa cggtcgcacc cagagaaaca ccaataccat gaaaaattac cttttgcccg 1200
tagtggccca ggcatttgct aggtgggcaa aggaatataa ggaagatcaa gaagatgaaa 1260
ggccactagg actacgagat agacagttag tcatggggtg ttgttgggct tttagaaggc 1320
acaagataac atctatttat aagcgcccgg atacccaaac catcatcaaa gtgaacagcg 1380
atttccactc attcgtgctg cccaggatag gcagtaacac attggagatc gggctgagaa 1440
caagaatcag gaaaatgtta gaggagcaca aggagccgtc acctctcatt accgccgagg 1500
acgtacaaga agctaagtgc gcagccgatg aggctaagga ggtgcgtgaa gccgaggagt 1560

```
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
```

```
acaatcctta caagctttca tcaaccttga ccaacattta tacaggttcc agactccacg   4020

aagccggatg tgcaccctca tatcatgtgg tgcgagggga tattgccacg gccaccgaag   4080

gagtgattat aaatgctgct aacagcaaag gacaacctgg cggaggggtg tgcggagcgc   4140

tgtataagaa attcccggaa agcttcgatt tacagccgat cgaagtagga aaagcgcgac   4200

tggtcaaagg tgcagctaaa catatcattc atgccgtagg accaaacttc aacaaagttt   4260

cggaggttga aggtgacaaa cagttggcag aggcttatga gtccatcgct aagattgtca   4320

acgataacaa ttacaagtca gtagcgattc cactgttgtc caccggcatc ttttccggga   4380

acaaagatcg actaacccaa tcattgaacc atttgctgac agctttagac accactgatg   4440

cagatgtagc catatactgc agggacaaga aatgggaaat gactctcaag gaagcagtgg   4500

ctaggagaga agcagtggag gagatatgca tatccgacga ctcttcagtg acagaacctg   4560

atgcagagct ggtgagggtg catccgaaga gttctttggc tggaaggaag ggctacagca   4620

caagcgatgg caaaactttc tcatatttgg aagggaccaa gtttcaccag gcggccaagg   4680

atatagcaga aattaatgcc atgtggcccg ttgcaacgga ggccaatgag caggtatgca   4740

tgtatatcct cggagaaagc atgagcagta ttaggtcgaa atgccccgtc gaagagtcgg   4800

aagcctccac accacctagc acgctgcctt gcttgtgcat ccatgccatg actccagaaa   4860

gagtacagcg cctaaaagcc tcacgtccag aacaaattac tgtgtgctca tcctttccat   4920

tgccgaagta tagaatcact ggtgtgcaga agatccaatg ctcccagcct atattgttct   4980

caccgaaagt gcctgcgtat attcatccaa ggaagtatct cgtggaaaca ccaccggtag   5040

acgagactcc ggagccatcg gcagagaacc aatccacaga ggggacacct gaacaaccac   5100

cacttataac cgaggatgag accaggacta gaacgcctga gccgatcatc atcgaagagg   5160

aagaagagga tagcataagt ttgctgtcag atggcccgac ccaccaggtg ctgcaagtcg   5220

aggcagacat tcacgggccg ccctctgtat ctagctcatc ctggtccatt cctcatgcat   5280

ccgactttga tgtggacagt ttatccatac ttgacaccct ggagggagct agcgtgacca   5340

gcggggcaac gtcagccgag actaactctt acttcgcaaa gagtatggag tttctggcgc   5400

gaccggtgcc tgcgcctcga acagtattca ggaaccctcc acatcccgct ccgcgcacaa   5460

gaacaccgtc acttgcaccc agcagggcct gctcgagaac cagcctagtt tccaccccgc   5520

caggcgtgaa tagggtgatc actagagagg agctcgaggc gcttaccccg tcacgcactc   5580

ctagcaggtc ggtctcgaga accagcctgg tctccaaccc gccaggcgta aatagggtga   5640

ttacaagaga ggagtttgag gcgttcgtag cacaacaaca atgacggttt gatgcgggtg   5700

catacatctt ttcctccgac accggtcaag ggcatttaca acaaaaatca gtaaggcaaa   5760

cggtgctatc cgaagtggtg ttggagagga ccgaattgga gatttcgtat gccccgcgcc   5820

tcgaccaaga aaaagaagaa ttactacgca agaaattaca gttaaatccc acacctgcta   5880

acagaagcag ataccagtcc aggaaggtgg agaacatgaa agccataaca gctagacgta   5940

ttctgcaagg cctagggcat tatttgaagg cagaaggaaa agtggagtgc taccgaaccc   6000

tgcatcctgt tcctttgtat tcatctagtg tgaaccgtgc cttttcaagc cccaaggtcg   6060

cagtggaagc ctgtaacgcc atgttgaaag agaactttcc gactgtggct tcttactgta   6120

ttattccaga gtacgatgcc tatttggaca tggttgacgg agcttcatgc tgcttagaca   6180

ctgccagttt ttgccctgca aagctgcgca gctttccaaa gaaacactcc tatttggaac   6240

ccacaatacg atcggcagtg ccttcagcga tccagaacac gctccagaac gtcctggcag   6300
```

```
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gctattccag aagtagtgag gaggcttttt tggaggccta ggcttttgca aaaagcttgt   7620
atatccattt tcggatctga tcaagagaca ggatgaggat cgtttcgcat gattgaataa   7680
gatggattgc acgtaggttc tccggccgct tgggtggaga ggctattcgg ctatgactgg   7740
gcacaactga caatcggctg ctctgatgcc gccgtgatcc ggttgtcagc gcaggggcgc   7800
ccggttcttt ttgtcaagac cgacctgtcc ggtgccctga atgaactgaa ggacgaggca   7860
gcgcggctat cgtggctggc cacgacgggc gttccttgcg cagtctagac tggcgcgcca   7920
aacctgcagg ttaaaacagc tgtgggttgt tcccacccac agggcccact gggcgctagc   7980
actctgattt tacgaaatcc ttgtgcgcct gttttatatc ccttccctaa ttcgaaacgt   8040
agaagcaatg cgcaccactg atcaatagta ggcgtaacgc gccagttacg tcatgatcaa   8100
gcatatctgt tcccccggac tgagtatcaa tagactgctt acgcggttga aggagaaaac   8160
gttcgttatc cggctaacta cttcgagaag cccagtaaca ccatggaagc tgcagggtgt   8220
ttcgctcagc acttcccccg tgtagatcag gtcgatgagc cactgcaatc cccacaggtg   8280
actgtggcag tggctgcgtt ggcggcctgc ctatggggag acccatagga cgctctaatg   8340
tggacatggt gcgaagagcc tattgagcta gttagtagtc ctccggcccc tgaatgcggc   8400
taatcctaac tgcggagcac atgccttcaa cccagagggt agtgtgtcgt aatgggcaac   8460
tctgcagcgg aaccgactac tttgggtgtc cgtgtttctt tttattctta tattggctgc   8520
ttatggtgac aattacagaa ttgttaccat atagctattg gattggccat ccggtgtgta   8580
atagagctgt tatataccta tttgttggct ttgtaccact aactttaaaa tctataacta   8640
ccctcaactt tatattaacc ctcaatacag ttgaacatga ggcctggcct gccctcctac   8700
```

```
ctgatcatcc tggccgtgtg cctgttcagc cacctgctgt ccagcagata cggcgccgag   8760
gccgtgagcg agcccctgga caaggctttc cacctgctgc tgaacaccta cggcagaccc   8820
atccggtttc tgcgggagaa caccacccag tgcacctaca acagcagcct gcggaacagc   8880
accgtcgtga gagagaacgc catcagcttc aactttttcc agagctacaa ccagtactac   8940
gtgttccaca tgcccagatg cctgtttgcc ggccctctgg ccgagcagtt cctgaaccag   9000
gtggacctga ccgagacact ggaaagatac cagcagcggc tgaataccta cgccctggtg   9060
tccaaggacc tggccagcta ccggtccttt agccagcagc tcaaggctca ggatagcctc   9120
ggcgagcagc ctaccaccgt gccccctccc atcgacctga gcatccccca cgtgtggatg   9180
cctccccaga ccacccctca cggctggacc gagagccaca ccacctccgg cctgcacaga   9240
ccccacttca accagacctg catcctgttc gacggccacg acctgctgtt tagcaccgtg   9300
accccctgcc tgcaccaggg cttctacctg atcgacgagc tgagatacgt gaagatcacc   9360
ctgaccgagg atttcttcgt ggtcaccgtg tccatcgacg acgacacccc catgctgctg   9420
atcttcggcc acctgcccag agtgctgttc aaggccccct accagcggga caacttcatc   9480
ctgcggcaga ccgagaagca cgagctgctg gtgctggtca agaaggacca gctgaaccgg   9540
cactcctacc tgaaggaccc cgacttcctg gacgccgccc tggacttcaa ctacctggac   9600
ctgagcgccc tgctgagaaa cagcttccac agatacgccg tggacgtgct gaagtccgga   9660
cggtgccaga tgctcgatcg gcggaccgtg gagatggcct tcgcctatgc cctcgccctg   9720
ttcgccgctg ccagacagga agaggctggc gcccaggtgt cagtgcccag agccctggat   9780
agacaggccg ccctgctgca gatccaggaa ttcatgatca cctgcctgag ccagaccccc   9840
cctagaacca ccctgctgct gtaccccaca gccgtggatc tggccaagag ggccctgtgg   9900
acccccaacc agatcaccga catcacaagc ctcgtgcggc tcgtgtacat cctgagcaag   9960
cagaaccagc agcacctgat cccccagtgg gccctgagac agatcgccga cttcgccctg  10020
aagctgcaca agacccatct ggccagcttt ctgagcgcct tcgccaggca ggaactgtac  10080
ctgatgggca gcctggtcca cagcatgctg gtgcatacca ccgagcggcg ggagatcttc  10140
atcgtggaga caggcctgtg tagcctggcc gagctgtccc actttaccca gctgctggcc  10200
caccctcacc acgagtacct gagcgacctg tacacccccct gcagcagcag cggcagacgg  10260
gaccacagcc tggaacggct gaccagactg ttccccgatg ccaccgtgcc tgctacagtg  10320
cctgccgccc tgtccatcct gtccaccatg cagcccagca ccctggaaac cttccccgac  10380
ctgttctgcc tgccccctggg cgagagcttt agcgccctga ccgtgtccga gcacgtgtcc  10440
tacatcgtga ccaatcagta cctgatcaag ggcatcagct accccgtgtc caccacagtc  10500
gtgggccaga gcctgatcat cacccagacc gacagccaga ccaagtgcga gctgacccgg  10560
aacatgcaca ccacacacag catcaccgtg gccctgaaca tcagcctgga aaactgcgct  10620
ttctgtcagt ctgccctgct ggaatacgac gatacccagg gcgtgatcaa catcatgtac  10680
atgcacgaca gcgacgacgt gctgttcgcc ctggacccct acaacgaggt ggtggtgtcc  10740
agcccccgga cccactacct gatgctgctg aagaacggca ccgtgctgga agtgaccgac  10800
gtggtggtgg acgccaccga ctgataacgc cggcgccccc ccctaacgtt actggccgaa  10860
gccgcttgga ataaggccgg tgtgcgtttg tctatatgtt attttccacc atattgccgt  10920
cttttggcaa tgtgagggcc cggaaacctg gccctgtctt cttgacgagc attcctaggg  10980
gtctttcccc tctcgccaaa ggaatgcaag gtctgttgaa tgtcgtgaag gaagcagttc  11040
```

```
ctctggaagc ttcttgaaga caaacaacgt ctgtagcgac cctttgcagg cagcggaacc  11100
ccccacctgg cgacaggtgc ctctgcggcc aaaagccacg tgtataagat acacctgcaa  11160
aggcggcaca accccagtgc cacgttgtga gttggatagt tgtggaaaga gtcaaatggc  11220
tctcctcaag cgtattcaac aaggggctga aggatgccca gaaggtaccc cattgtatgg  11280
gatctgatct ggggcctcgg tgcacatgct ttacatgtgt ttagtcgagg ttaaaaaaac  11340
gtctaggccc cccgaaccac ggggacgtgg ttttcctttg aaaaacacga taataatatg  11400
tgcagaaggc ccgactgcgg cttcagcttc agccctggac ccgtgatcct gctgtggtgc  11460
tgcctgctgc tgcctatcgt gtcctctgcc gccgtgtctg tggcccctac agccgccgag  11520
aaggtgccag ccgagtgccc cgagctgacc agaagatgcc tgctgggcga ggtgttcgag  11580
ggcgacaagt acgagagctg gctgcggccc ctggtcaacg tgaccggcag agatggcccc  11640
ctgagccagc tgatccggta cagacccgtg acccccgagg ccgccaatag cgtgctgctg  11700
gacgaggcct tcctggatac cctggccctg ctgtacaaca accccgacca gctgagagcc  11760
ctgctgaccc tgctgtccag cgacaccgcc cccagatgga tgaccgtgat gcggggctac  11820
agcgagtgtg gagatggcag ccctgccgtg tacacctgcg tggacgacct gtgcagaggc  11880
tacgacctga ccagactgag ctacggccgg tccatcttca cagagcacgt gctgggcttc  11940
gagctggtgc cccccagcct gttcaacgtg gtggtggcca tccggaacga ggccaccaga  12000
accaacagag ccgtgcggct gcctgtgtct acagccgctg cacctgaggg catcacactg  12060
ttctacggcc tgtacaacgc cgtgaaagag ttctgcctcc ggcaccagct ggatcccccc  12120
ctgctgagac acctggacaa gtactacgcc ggcctgcccc cagagctgaa gcagaccaga  12180
gtgaacctgc ccgcccacag cagatatggc cctcaggccg tggacgccag atgataagcg  12240
gccgcataca gcagcaattg gcaagctgct tacatagaac tcgcggcgat tggcatgccg  12300
ccttaaaatt tttattttat ttttcttttc ttttccgaat cggattttgt ttttaatatt  12360
tcaaaaaaaa aaaaaaaaaa aaaaaaaaaa aaaaaaaggg tcggcatggc atctccacct  12420
cctcgcggtc cgacctgggc atccgaagga ggacgcacgt ccactcggat ggctaaggga  12480
gagccacgtt taaacacgtg atatctggcc tcatgggcct tcctttcact gcccgctttc  12540
cagtcgggaa acctgtcgtg ccagctgcat taacatggtc atagctgttt ccttgcgtat  12600
tgggcgctct ccgcttcctc gctcactgac tcgctgcgct cggtcgttcg ggtaaagcct  12660
ggggtgccta atgagcaaaa ggccagcaaa aggccaggaa ccgtaaaaag gccgcgttgc  12720
tggcgttttt ccataggctc cgcccccctg acgagcatca caaaaatcga cgctcaagtc  12780
agaggtggcg aaacccgaca ggactataaa gataccaggc gtttccccct ggaagctccc  12840
tcgtgcgctc tcctgttccg accctgccgc ttaccggata cctgtccgcc tttctccctt  12900
cgggaagcgt ggcgctttct catagctcac gctgtaggta tctcagttcg gtgtaggtcg  12960
ttcgctccaa gctgggctgt gtgcacgaac cccccgttca gcccgaccgc tgcgccttat  13020
ccggtaacta tcgtcttgag tccaacccgg taagacacga cttatcgcca ctggcagcag  13080
ccactggtaa caggattagc agagcgaggt atgtaggcgg tgctacagag ttcttgaagt  13140
ggtggcctaa ctacggctac actagaagaa cagtatttgg tatctgcgct ctgctgaagc  13200
cagttacctt cggaaaaaga gttggtagct cttgatccgg caaacaaacc accgctggta  13260
gcggtggttt ttttgtttgc aagcagcaga ttacgcgcag aaaaaaagga tctcaagaag  13320
atcctttgat cttttctacg gggtctgacg ctcagtggaa cgaaaactca cgttaaggga  13380
ttttggtcat gagattatca aaaaggatct tcacctagat ccttttaaat taaaaatgaa  13440
```

```
gttttaaatc aatctaaagt atatatgagt aaacttggtc tgacagttat tagaaaaatt  13500

catccagcag acgataaaac gcaatacgct ggctatccgg tgccgcaatg ccatacagca  13560

ccagaaaacg atccgcccat tcgccgccca gttcttccgc aatatcacgg gtggccagcg  13620

caatatcctg ataacgatcc gccacgccca gacggccgca atcaataaag ccgctaaaac  13680

ggccattttc caccataatg ttcggcaggc acgcatcacc atgggtcacc accagatctt  13740

cgccatccgg catgctcgct ttcagacgcg caaacagctc tgccggtgcc aggccctgat  13800

gttcttcatc cagatcatcc tgatccacca ggcccgcttc catacgggta cgcgcacgtt  13860

caatacgatg tttcgcctga tgatcaaacg gacaggtcgc cgggtccagg gtatgcagac  13920

gacgcatggc atccgccata atgctcactt tttctgccgg cgccagatgg ctagacagca  13980

gatcctgacc cggcacttcg cccagcagca gccaatcacg gcccgcttcg gtcaccacat  14040

ccagcaccgc cgcacacgga acaccggtgg tggccagcca gctcagacgc gccgcttcat  14100

cctgcagctc gttcagcgca ccgctcagat cggttttcac aaacagcacc ggacgaccct  14160

gcgcgctcag acgaaacacc gccgcatcag agcagccaat ggtctgctgc gcccaatcat  14220

agccaaacag acgttccacc cacgctgccg ggctacccgc atgcaggcca tcctgttcaa  14280

tcatactctt cctttttcaa tattattgaa gcatttatca gggttattgt ctcatgagcg  14340

gatacatatt tgaatgtatt tagaaaaata aacaaatagg ggttccgcgc acatttcccc  14400

gaaaagtgcc acctaaattg taagcgttaa tattttgtta aaattcgcgt taaatttttg  14460

ttaaatcagc tcatttttta accaataggc cgaaatcggc aaaatccctt ataaatcaaa  14520

agaatagacc gagatagggt tgagtggccg ctacagggcg ctcccattcg ccattcaggc  14580

tgcgcaactg ttgggaaggg cgtttcggtg cgggcctctt cgctattacg ccagctggcg  14640

aaagggggat gtgctgcaag gcgattaagt tgggtaacgc cagggttttc ccagtcacac  14700

gcgtaatacg actcactata g                                             14721
```

```
<210> SEQ ID NO 12
<211> LENGTH: 14721
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 12
```

```
ataggcggcg catgagagaa gcccagacca attacctacc caaaatggag aaagttcacg     60

ttgacatcga ggaagacagc ccattcctca gagctttgca gcggagcttc ccgcagtttg    120

aggtagaagc caagcaggtc actgataatg accatgctaa tgccagagcg ttttcgcatc    180

tggcttcaaa actgatcgaa acggaggtgg acccatccga cacgatcctt gacattggaa    240

gtgcgcccgc ccgcagaatg tattctaagc acaagtatca ttgtatctgt ccgatgagat    300

gtgcggaaga tccggacaga ttgtataagt atgcaactaa gctgaagaaa aactgtaagg    360

aaataactga taaggaattg gacaagaaaa tgaaggagct cgccgccgtc atgagcgacc    420

ctgacctgga aactgagact atgtgcctcc acgacgacga gtcgtgtcgc tacgaagggc    480

aagtcgctgt ttaccaggat gtatacgcgg ttgacggacc gacaagtctc tatcaccaag    540

ccaataaggg agttagagtc gcctactgga taggctttga caccacccct tttatgttta    600

agaacttggc tggagcatat ccatcatact ctaccaactg ggccgacgaa accgtgttaa    660
```

```
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
```

```
agaataaggc aaacgtgtgt tgggccaagg ctttagtgcc ggtgctgaag accgctggca   3120

tagacatgac cactgaacaa tggaacactg tggattattt tgaaacggac aaagctcact   3180

cagcagagat agtattgaac caactatgcg tgaggttctt tggactcgat ctggactccg   3240

gtctattttc tgcacccact gttccgttat ccattaggaa taatcactgg gataactccc   3300

cgtcgcctaa catgtacggg ctgaataaag aagtggtccg tcagctctct cgcaggtacc   3360

cacaactgcc tcgggcagtt gccactggaa gagtctatga catgaacact ggtacactgc   3420

gcaattatga tccgcgcata aacctagtac ctgtaaacag aagactgcct catgctttag   3480

tcctccacca taatgaacac ccacagagtg acttttcttc attcgtcagc aaattgaagg   3540

gcagaactgt cctggtggtc ggggaaaagt tgtccgtccc aggcaaaatg gttgactggt   3600

tgtcagaccg gcctgaggct accttcagag ctcggctgga tttaggcatc ccaggtgatg   3660

tgcccaaata tgacataata tttgttaatg tgaggacccc atataaatac catcactatc   3720

agcagtgtga agaccatgcc attaagctta gcatgttgac caagaaagct tgtctgcatc   3780

tgaatcccgg cggaacctgt gtcagcatag gttatggtta cgctgacagg gccagcgaaa   3840

gcatcattgg tgctatagcg cggcagttca agttttcccg ggtatgcaaa ccgaaatcct   3900

cacttgaaga gacggaagtt ctgtttgtat tcattgggta cgatcgcaag gcccgtacgc   3960

acaatcctta caagctttca tcaaccttga ccaacattta tacaggttcc agactccacg   4020

aagccggatg tgcaccctca tatcatgtgg tgcgagggga tattgccacg gccaccgaag   4080

gagtgattat aaatgctgct aacagcaaag gacaacctgg cggaggggtg tgcggagcgc   4140

tgtataagaa attcccggaa agcttcgatt tacagccgat cgaagtagga aaagcgcgac   4200

tggtcaaagg tgcagctaaa catatcattc atgccgtagg accaaacttc aacaaagttt   4260

cggaggttga aggtgacaaa cagttggcag aggcttatga gtccatcgct aagattgtca   4320

acgataacaa ttacaagtca gtagcgattc cactgttgtc caccggcatc ttttccggga   4380

acaaagatcg actaacccaa tcattgaacc atttgctgac agctttagac accactgatg   4440

cagatgtagc catatactgc agggacaaga aatgggaaat gactctcaag gaagcagtgg   4500

ctaggagaga agcagtggag gagatatgca tatccgacga ctcttcagtg acagaacctg   4560

atgcagagct ggtgagggtg catccgaaga gttctttggc tggaaggaag ggctacagca   4620

caagcgatgg caaaactttc tcatatttgg aagggaccaa gtttcaccag gcggccaagg   4680

atatagcaga aattaatgcc atgtggcccg ttgcaacgga ggccaatgag caggtatgca   4740

tgtatatcct cggagaaagc atgagcagta ttaggtcgaa atgccccgtc gaagagtcgg   4800

aagcctccac accacctagc acgctgcctt gcttgtgcat ccatgccatg actccagaaa   4860

gagtacagcg cctaaaagcc tcacgtccag aacaaattac tgtgtgctca tcctttccat   4920

tgccgaagta tagaatcact ggtgtgcaga agatccaatg ctcccagcct atattgttct   4980

caccgaaagt gcctgcgtat attcatccaa ggaagtatct cgtggaaaca ccaccggtag   5040

acgagactcc ggagccatcg gcagagaacc aatccacaga ggggacacct gaacaaccac   5100

cacttataac cgaggatgag accaggacta gaacgcctga gccgatcatc atcgaagagg   5160

aagaagagga tagcataagt ttgctgtcag atggcccgac ccaccaggtg ctgcaagtcg   5220

aggcagacat tcacgggccg ccctctgtat ctagctcatc ctggtccatt cctcatgcat   5280

ccgactttga tgtggacagt ttatccatac ttgacaccct ggagggagct agcgtgacca   5340

gcggggcaac gtcagccgag actaactctt acttcgcaaa gagtatggag tttctggcgc   5400
```

```
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gctattccag aagtagtgag gaggcttttt tggaggccta ggcttttgca aaaagcttgt   7620
atatccattt tcggatctga tcaagagaca ggatgaggat cgtttcgcat gattgaataa   7680
gatggattgc acgtaggttc tccggccgct tgggtggaga ggctattcgg ctatgactgg   7740
gcacaactga caatcggctg ctctgatgcc gccgtgatcc ggttgtcagc gcaggggcgc   7800
```

```
ccggttcttt ttgtcaagac cgacctgtcc ggtgccctga atgaactgaa ggacgaggca   7860
gcgcggctat cgtggctggc cacgacgggc gttccttgcg cagtctagac tggcgcgcca   7920
aacctgcagg ttaaaacagc tgtgggttgt tcccacccac agggcccact gggcgctagc   7980
actctgattt tacgaaatcc ttgtgcgcct gttttatatc ccttccctaa ttcgaaacgt   8040
agaagcaatg cgcaccactg atcaatagta ggcgtaacgc gccagttacg tcatgatcaa   8100
gcatatctgt tcccccggac tgagtatcaa tagactgctt acgcggttga aggagaaaac   8160
gttcgttatc cggctaacta cttcgagaag cccagtaaca ccatggaagc tgcagggtgt   8220
ttcgctcagc acttcccccg tgtagatcag gtcgatgagc cactgcaatc cccacaggtg   8280
actgtggcag tggctgcgtt ggcggcctgc ctatggggag acccatagga cgctctaatg   8340
tggacatggt gcgaagagcc tattgagcta gttagtagtc ctccggcccc tgaatgcggc   8400
taatcctaac tgcggagcac atgccttcaa cccagagggt agtgtgtcgt aatgggcaac   8460
tctgcagcgg aaccgactac tttgggtgtc cgtgtttctt tttattctta tattggctgc   8520
ttatggtgac aattacagaa ttgttaccat atagctattg gattggccat ccggtgtgta   8580
atagagctgt tatataccta tttgttggct ttgtaccact aactttaaaa tctataacta   8640
ccctcaactt tatattaacc ctcaatacag ttgaacatgt gcagaaggcc cgactgcggc   8700
ttcagcttca gccctggacc cgtgatcctg ctgtggtgct gcctgctgct gcctatcgtg   8760
tcctctgccg ccgtgtctgt ggcccctaca gccgccgaga aggtgccagc cgagtgcccc   8820
gagctgacca gaagatgcct gctgggcgag gtgttcgagg gcgacaagta cgagagctgg   8880
ctgcggcccc tggtcaacgt gaccggcaga gatggccccc tgagccagct gatccggtac   8940
agacccgtga cccccgaggc cgccaatagc gtgctgctgg acgaggcctt cctggatacc   9000
ctggccctgc tgtacaacaa ccccgaccag ctgagagccc tgctgaccct gctgtccagc   9060
gacaccgccc ccagatggat gaccgtgatg cggggctaca gcgagtgtgg agatggcagc   9120
cctgccgtgt acacctgcgt ggacgacctg tgcagaggct acgacctgac cagactgagc   9180
tacggccggt ccatcttcac agagcacgtg ctgggcttcg agctggtgcc ccccagcctg   9240
ttcaacgtgg tggtggccat ccggaacgag gccaccagaa ccaacagagc cgtgcggctg   9300
cctgtgtcta cagccgctgc acctgagggc atcacactgt tctacggcct gtacaacgcc   9360
gtgaaagagt tctgcctccg gcaccagctg gatccccccc tgctgagaca cctggacaag   9420
tactacgccg gcctgccccc agagctgaag cagaccagag tgaacctgcc cgcccacagc   9480
agatatggcc ctcaggccgt ggacgccaga tgataacgcc ggcgcccccc cctaacgtta   9540
ctggccgaag ccgcttggaa taaggccggt gtgcgtttgt ctatatgtta ttttccacca   9600
tattgccgtc ttttggcaat gtgagggccc ggaaacctgg ccctgtcttc ttgacgagca   9660
ttcctagggg tctttcccct ctcgccaaag gaatgcaagg tctgttgaat gtcgtgaagg   9720
aagcagttcc tctggaagct tcttgaagac aaacaacgtc tgtagcgacc ctttgcaggc   9780
agcggaaccc cccacctggc gacaggtgcc tctgcggcca aaagccacgt gtataagata   9840
cacctgcaaa ggcggcacaa ccccagtgcc acgttgtgag ttggatagtt gtggaaagag   9900
tcaaatggct ctcctcaagc gtattcaaca aggggctgaa ggatgcccag aaggtacccc   9960
attgtatggg atctgatctg gggcctcggt gcacatgctt tacatgtgtt tagtcgaggt  10020
taaaaaaacg tctaggcccc ccgaaccacg ggacgtggt tttcctttga aaaacacgat  10080
aataatatga ggcctggcct gccctcctac ctgatcatcc tggccgtgtg cctgttcagc  10140
```

cacctgctgt ccagcagata cggcgccgag gccgtgagcg agcccctgga caaggctttc 10200
cacctgctgc tgaacaccta cggcagaccc atccggtttc tgcgggagaa caccacccag 10260
tgcacctaca acagcagcct gcggaacagc accgtcgtga gagagaacgc catcagcttc 10320
aactttttcc agagctacaa ccagtactac gtgttccaca tgcccagatg cctgtttgcc 10380
ggccctctgg ccgagcagtt cctgaaccag gtggacctga ccgagacact ggaaagatac 10440
cagcagcggc tgaataccta cgccctggtg tccaaggacc tggccagcta ccggtccttt 10500
agccagcagc tcaaggctca ggatagcctc ggcgagcagc ctaccaccgt gccccctccc 10560
atcgacctga gcatccccca cgtgtggatg cctccccaga ccacccctca cggctggacc 10620
gagagccaca ccacctccgg cctgcacaga ccccacttca accagacctg catcctgttc 10680
gacggccacg acctgctgtt tagcaccgtg accccctgcc tgcaccaggg cttctacctg 10740
atcgacgagc tgagatacgt gaagatcacc ctgaccgagg atttcttcgt ggtcaccgtg 10800
tccatcgacg acgacacccc catgctgctg atcttcggcc acctgcccag agtgctgttc 10860 aaggcccccct accagcggga caacttcatc ctgcggcaga ccgagaagca cgagctgctg 10920
gtgctggtca agaaggacca gctgaaccgg cactcctacc tgaaggaccc cgacttcctg 10980
gacgccgccc tggacttcaa ctacctggac ctgagcgccc tgctgagaaa cagcttccac 11040
agatacgccg tggacgtgct gaagtccgga cggtgccaga tgctcgatcg gcggaccgtg 11100
gagatggcct tcgcctatgc cctcgccctg ttcgccgctg ccagacagga agaggctggc 11160
gcccaggtgt cagtgcccag agccctggat agacaggccg ccctgctgca gatccaggaa 11220
ttcatgatca cctgcctgag ccagaccccc cctagaacca ccctgctgct gtaccccaca 11280
gccgtggatc tggccaagag ggccctgtgg acccccaacc agatcaccga catcacaagc 11340
ctcgtgcggc tcgtgtacat cctgagcaag cagaaccagc agcacctgat cccccagtgg 11400
gccctgagac agatcgccga cttcgccctg aagctgcaca agacccatct ggccagcttt 11460
ctgagcgcct tcgccaggca ggaactgtac ctgatgggca gcctggtcca cagcatgctg 11520
gtgcatacca ccgagcggcg ggagatcttc atcgtggaga caggcctgtg tagcctggcc 11580
gagctgtccc actttaccca gctgctggcc caccctcacc acgagtacct gagcgacctg 11640 tacacccccct gcagcagcag cggcagacgg gaccacagcc tggaacggct gaccagactg 11700
ttccccgatg ccaccgtgcc tgctacagtg cctgccgccc tgtccatcct gtccaccatg 11760
cagcccagca ccctggaaac cttccccgac ctgttctgcc tgcccctggg cgagagcttt 11820
agcgccctga ccgtgtccga gcacgtgtcc tacatcgtga ccaatcagta cctgatcaag 11880
ggcatcagct accccgtgtc caccacagtc gtgggccaga gcctgatcat cacccagacc 11940
gacagccaga ccaagtgcga gctgacccgg aacatgcaca ccacacacag catcaccgtg 12000
gccctgaaca tcagcctgga aaactgcgct ttctgtcagt ctgccctgct ggaatacgac 12060
gatacccagg gcgtgatcaa catcatgtac atgcacgaca gcgacgacgt gctgttcgcc 12120
ctggacccct acaacgaggt ggtggtgtcc agcccccgga cccactacct gatgctgctg 12180
aagaacggca ccgtgctgga agtgaccgac gtggtggtgg acgccaccga ctgataagcg 12240
gccgcataca gcagcaattg gcaagctgct tacatagaac tcgcggcgat tggcatgccg 12300
ccttaaaatt tttattttat ttttcttttc ttttccgaat cggattttgt ttttaatatt 12360
tcaaaaaaaa aaaaaaaaaa aaaaaaaaaa aaaaaaaggg tcggcatggc atctccacct 12420
cctcgcggtc cgacctgggc atccgaagga ggacgcacgt ccactcggat ggctaaggga 12480
gagccacgtt taaacacgtg atatctggcc tcatgggcct tcctttcact gcccgctttc 12540

```
cagtcgggaa acctgtcgtg ccagctgcat taacatggtc atagctgttt ccttgcgtat  12600
tgggcgctct ccgcttcctc gctcactgac tcgctgcgct cggtcgttcg ggtaaagcct  12660
ggggtgccta atgagcaaaa ggccagcaaa aggccaggaa ccgtaaaaag gccgcgttgc  12720
tggcgttttt ccataggctc cgcccccctg acgagcatca caaaaatcga cgctcaagtc  12780
agaggtggcg aaacccgaca ggactataaa gataccaggc gtttccccct ggaagctccc  12840
tcgtgcgctc tcctgttccg accctgccgc ttaccggata cctgtccgcc tttctccctt  12900
cgggaagcgt ggcgctttct catagctcac gctgtaggta tctcagttcg gtgtaggtcg  12960
ttcgctccaa gctgggctgt gtgcacgaac cccccgttca gcccgaccgc tgcgccttat  13020
ccggtaacta tcgtcttgag tccaacccgg taagacacga cttatcgcca ctggcagcag  13080
ccactggtaa caggattagc agagcgaggt atgtaggcgg tgctacagag ttcttgaagt  13140
ggtggcctaa ctacggctac actagaagaa cagtatttgg tatctgcgct ctgctgaagc  13200
cagttacctt cggaaaaaga gttggtagct cttgatccgg caaacaaacc accgctggta  13260
gcggtggttt ttttgtttgc aagcagcaga ttacgcgcag aaaaaaagga tctcaagaag  13320
atcctttgat cttttctacg gggtctgacg ctcagtggaa cgaaaactca cgttaaggga  13380
ttttggtcat gagattatca aaaaggatct tcacctagat ccttttaaat taaaaatgaa  13440
gttttaaatc aatctaaagt atatatgagt aaacttggtc tgacagttat tagaaaaatt  13500
catccagcag acgataaaac gcaatacgct ggctatccgg tgccgcaatg ccatacagca  13560
ccagaaaacg atccgcccat tcgccgccca gttcttccgc aatatcacgg gtggccagcg  13620
caatatcctg ataacgatcc gccacgccca gacggccgca atcaataaag ccgctaaaac  13680
ggccattttc caccataatg ttcggcaggc acgcatcacc atgggtcacc accagatctt  13740
cgccatccgg catgctcgct ttcagacgcg caaacagctc tgccggtgcc aggccctgat  13800
gttcttcatc cagatcatcc tgatccacca ggcccgcttc catacgggta cgcgcacgtt  13860
caatacgatg tttcgcctga tgatcaaacg gacaggtcgc cgggtccagg gtatgcagac  13920
gacgcatggc atccgccata atgctcactt tttctgccgg cgccagatgg ctagacagca  13980
gatcctgacc cggcacttcg cccagcagca gccaatcacg gcccgcttcg gtcaccacat  14040
ccagcaccgc cgcacacgga acaccggtgg tggccagcca gctcagacgc gccgcttcat  14100
cctgcagctc gttcagcgca ccgctcagat cggttttcac aaacagcacc ggacgaccct  14160
gcgcgctcag acgaaacacc gccgcatcag agcagccaat ggtctgctgc gcccaatcat  14220
agccaaacag acgttccacc cacgctgccg ggctacccgc atgcaggcca tcctgttcaa  14280
tcatactctt cctttttcaa tattattgaa gcatttatca gggttattgt ctcatgagcg  14340
gatacatatt tgaatgtatt tagaaaaata aacaaatagg ggttccgcgc acatttcccc  14400
gaaaagtgcc acctaaattg taagcgttaa tattttgtta aaattcgcgt taaatttttg  14460
ttaaatcagc tcatttttta accaataggc cgaaatcggc aaaatccctt ataaatcaaa  14520
agaatagacc gagatagggt tgagtggccg ctacagggcg ctcccattcg ccattcaggc  14580
tgcgcaactg ttgggaaggg cgtttcggtg cgggcctctt cgctattacg ccagctggcg  14640
aaagggggat gtgctgcaag gcgattaagt tgggtaacgc cagggttttc ccagtcacac  14700
gcgtaatacg actcactata g                                            14721
```

<210> SEQ ID NO 13
<211> LENGTH: 15300
<212> TYPE: DNA

<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 13

```
ataggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagct cgccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tagacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
```

```
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
```

-continued

```
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
```

```
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gatgaggcct ggcctgccct cctacctgat catcctggcc gtgtgcctgt tcagccacct   7620
gctgtccagc agatacggcg ccgaggccgt gagcgagccc ctggacaagg ctttccacct   7680
gctgctgaac acctacggca gacccatccg gtttctgcgg gagaacacca cccagtgcac   7740
ctacaacagc agcctgcgga acagcaccgt cgtgagagag aacgccatca gcttcaactt   7800
tttccagagc tacaaccagt actacgtgtt ccacatgccc agatgcctgt ttgccggccc   7860
tctggccgag cagttcctga accaggtgga cctgaccgag acactggaaa gataccagca   7920
gcggctgaat acctacgccc tggtgtccaa ggacctggcc agctaccggt cctttagcca   7980
gcagctcaag gctcaggata gcctcggcga gcagcctacc accgtgcccc ctcccatcga   8040
cctgagcatc ccccacgtgt ggatgcctcc ccagaccacc cctcacggct ggaccgagag   8100
ccacaccacc tccggcctgc acagacccca cttcaaccag acctgcatcc tgttcgacgg   8160
ccacgacctg ctgtttagca ccgtgacccc ctgcctgcac cagggcttct acctgatcga   8220
cgagctgaga tacgtgaaga tcaccctgac cgaggatttc ttcgtggtca ccgtgtccat   8280
cgacgacgac acccccatgc tgctgatctt cggccacctg cccagagtgc tgttcaaggc   8340
cccctaccag cgggacaact tcatcctgcg gcagaccgag aagcacgagc tgctggtgct   8400
ggtcaagaag gaccagctga accggcactc ctacctgaag gaccccgact tcctggacgc   8460
cgccctggac ttcaactacc tggacctgag cgccctgctg agaaacagct tccacagata   8520
cgccgtggac gtgctgaagt ccggacggtg ccagatgctc gatcggcgga ccgtggagat   8580
ggccttcgcc tatgccctcg ccctgttcgc cgctgccaga caggaagagg ctggcgccca   8640
ggtgtcagtg cccagagccc tggatagaca ggccgccctg ctgcagatcc aggaattcat   8700
gatcacctgc ctgagccaga cccccctag aaccaccctg ctgctgtacc ccacagccgt   8760
ggatctggcc aagagggccc tgtggacccc caaccagatc accgacatca caagcctcgt   8820
gcggctcgtg tacatcctga gcaagcagaa ccagcagcac ctgatccccc agtgggccct   8880
gagacagatc gccgacttcg ccctgaagct gcacaagacc catctggcca gctttctgag   8940
cgccttcgcc aggcaggaac tgtacctgat gggcagcctg gtccacagca tgctggtgca   9000
taccaccgag cggcgggaga tcttcatcgt ggagacaggc ctgtgtagcc tggccgagct   9060
gtcccacttt acccagctgc tggcccaccc tcaccacgag tacctgagcg acctgtacac   9120
cccctgcagc agcagcggca gacgggacca cagcctggaa cggctgacca gactgttccc   9180
cgatgccacc gtgcctgcta cagtgcctgc cgccctgtcc atcctgtcca ccatgcagcc   9240
```

```
cagcaccctg gaaaccttcc ccgacctgtt ctgcctgccc ctgggcgaga gctttagcgc   9300
cctgaccgtg tccgagcacg tgtcctacat cgtgaccaat cagtacctga tcaagggcat   9360
cagctacccc gtgtccacca cagtcgtggg ccagagcctg atcatcaccc agaccgacag   9420
ccagaccaag tgcgagctga cccggaacat gcacaccaca cacagcatca ccgtggccct   9480
gaacatcagc ctggaaaact gcgctttctg tcagtctgcc ctgctggaat acgacgatac   9540
ccagggcgtg atcaacatca tgtacatgca cgacagcgac gacgtgctgt tcgccctgga   9600
cccctacaac gaggtggtgg tgtccagccc ccggacccac tacctgatgc tgctgaagaa   9660
cggcaccgtg ctggaagtga ccgacgtggt ggtggacgcc accgacagca gactgctgat   9720
gatgagcgtg tacgccctga gcgccatcat cggcatctac ctgctgtacc ggatgctgaa   9780
aacctgctga taatctagag gcccctataa ctctctacgg ctaacctgaa tggactacga   9840
catagtctag tccgccaaga tgtgcagaag gcccgactgc ggcttcagct tcagccctgg   9900
acccgtgatc ctgctgtggt gctgcctgct gctgcctatc gtgtcctctg ccgccgtgtc   9960
tgtggcccct acagccgccg agaaggtgcc agccgagtgc cccgagctga ccagaagatg  10020
cctgctgggc gaggtgttcg agggcgacaa gtacgagagc tggctgcggc ccctggtcaa  10080
cgtgaccggc agagatggcc ccctgagcca gctgatccgg tacagacccg tgacccccga  10140
ggccgccaat agcgtgctgc tggacgaggc cttcctggat accctggccc tgctgtacaa  10200
caaccccgac cagctgagag ccctgctgac cctgctgtcc agcgacaccg cccccagatg  10260
gatgaccgtg atgcggggct acagcgagtg tggagatggc agccctgccg tgtacacctg  10320
cgtggacgac ctgtgcagag gctacgacct gaccagactg agctacggcc ggtccatctt  10380
cacagagcac gtgctgggct tcgagctggt gccccccagc ctgttcaacg tggtggtggc  10440
catccggaac gaggccacca gaaccaacag agccgtgcgg ctgcctgtgt ctacagccgc  10500
tgcacctgag ggcatcacac tgttctacgg cctgtacaac gccgtgaaag agttctgcct  10560
ccggcaccag ctggatcccc ccctgctgag acacctggac aagtactacg ccggcctgcc  10620
cccagagctg aagcagacca gagtgaacct gcccgcccac agcagatatg gccctcaggc  10680
cgtggacgcc agatgataac gccggcggcc cctataactc tctacggcta acctgaatgg  10740
actacgacat agtctagtcc gccaagatga gccccaagga cctgaccccc ttcctgacaa  10800
ccctgtggct gctcctgggc catagcagag tgcctagagt gcgggccgag gaatgctgcg  10860
agttcatcaa cgtgaaccac ccccccgagc ggtgctacga cttcaagatg tgcaaccggt  10920
tcaccgtggc cctgagatgc cccgacggcg aagtgtgcta cagccccgag aaaaccgccg  10980
agatccgggg catcgtgacc accatgaccc acagcctgac ccggcaggtg gtgcacaaca  11040
agctgaccag ctgcaactac aaccccctgt acctggaagc cgacggccgg atcagatgcg  11100
gcaaagtgaa cgacaaggcc cagtacctgc tgggagccgc cggaagcgtg ccctaccggt  11160
ggatcaacct ggaatacgac aagatcaccc ggatcgtggg cctggaccag tacctggaaa  11220
gcgtgaagaa gcacaagcgg ctggacgtgt gcagagccaa gatgggctac atgctgcagt  11280
gataaggcgc gccgccccta taactctcta cggctaacct gaatggacta cgacatagtc  11340
tagtccgcca agatgctgcg gctgctgctg agacaccact tccactgcct gctgctgtgt  11400
gccgtgtggg ccacccccttg tctggccagc ccttggagca ccctgaccgc caaccagaac  11460
cctagccccc cttggtccaa gctgacctac agcaagcccc acgacgccgc caccttctac  11520
tgccccttttc tgtaccccag ccctcccaga agcccccctgc agttcagcgg cttccagaga  11580
gtgtccaccg gccctgagtg ccggaacgag acactgtacc tgctgtacaa ccgggagggc  11640
```

cagacactgg tggagcggag cagcacctgg gtgaaaaaag tgatctggta tctgagcggc 11700
cggaaccaga ccatcctgca gcggatgccc agaaccgcca gcaagcccag cgacggcaac 11760
gtgcagatca gcgtggagga cgccaaaatc ttcggagccc acatggtgcc caagcagacc 11820
aagctgctga gattcgtggt caacgacggc accagatatc agatgtgcgt gatgaagctg 11880
gaaagctggg cccacgtgtt ccgggactac tccgtgagct tccaggtccg gctgaccttc 11940
accgaggcca acaaccagac ctacaccttc tgcacccacc ccaacctgat cgtgtgataa 12000
gcggccgcgc ccctataact ctctacggct aacctgaatg gactacgaca tagtctagtc 12060
cgccaagatg cggctgtgca gagtgtggct gtccgtgtgc ctgtgtgccg tggtgctggg 12120
ccagtgccag agagagacag ccgagaagaa cgactactac cgggtgcccc actactggga 12180
tgcctgcagc agagccctgc ccgaccagac ccggtacaaa tacgtggagc agctcgtgga 12240
cctgaccctg aactaccact acgacgccag ccacggcctg gacaacttcg acgtgctgaa 12300
gcggatcaac gtgaccgagg tgtccctgct gatcagcgac ttccggcggc agaacagaag 12360
aggcggcacc aacaagcgga ccaccttcaa cgccgctggc tctctggccc ctcacgccag 12420
atccctggaa ttcagcgtgc ggctgttcgc caactgataa cgttgcatcc tgcaggatac 12480
agcagcaatt ggcaagctgc ttacatagaa ctcgcggcga ttggcatgcc gccttaaaat 12540
ttttatttta tttttctttt cttttccgaa tcggattttg tttttaatat ttcaaaaaaa 12600
aaaaaaaaaa aaaaaaaaaa aaaaaaaagg gtcggcatgg catctccacc tcctcgcggt 12660
ccgacctggg catccgaagg aggacgcacg tccactcgga tggctaaggg agagccacgt 12720
ttaaacgcta gagcaagacg tttcccgttg aatatggctc ataacacccc ttgtattact 12780
gtttatgtaa gcagacagtt ttattgttca tgatgatata tttttatctt gtgcaatgta 12840
acatcagaga ttttgagaca caacgtggct ttgttgaata aatcgaactt ttgctgagtt 12900
gaaggatcag atcacgcatc ttcccgacaa cgcagaccgt tccgtggcaa agcaaaagtt 12960
caaaatcacc aactggtcca cctacaacaa agctctcatc aaccgtggct ccctcacttt 13020
ctggctggat gatggggcga ttcaggcctg gtatgagtca gcaacacctt cttcacgagg 13080
cagacctcag cgctagcgga gtgtatactg gcttactatg ttggcactga tgagggtgtc 13140
agtgaagtgc ttcatgtggc aggagaaaaa aggctgcacc ggtgcgtcag cagaatatgt 13200
gatacaggat atattccgct tcctcgctca ctgactcgct acgctcggtc gttcgactgc 13260
ggcgagcgga aatggcttac gaacggggcg gagatttcct ggaagatgcc aggaagatac 13320
ttaacaggga agtgagaggg ccgcggcaaa gccgtttttc cataggctcc gcccccctga 13380
caagcatcac gaaatctgac gctcaaatca gtggtggcga aacccgacag gactataaag 13440
ataccaggcg tttccccctgg cggctccctc gtgcgctctc ctgttcctgc ctttcggttt 13500
accggtgtca ttccgctgtt atggccgcgt ttgtctcatt ccacgcctga cactcagttc 13560
cgggtaggca gttcgctcca agctggactg tatgcacgaa ccccccgttc agtccgaccg 13620
ctgcgcctta tccggtaact atcgtcttga gtccaacccg gaaagacatg caaaagcacc 13680
actggcagca gccactggta attgatttag aggagttagt cttgaagtca tgcgccggtt 13740
aaggctaaac tgaaaggaca agttttggtg actgcgctcc tccaagccag ttacctcggt 13800
tcaaagagtt ggtagctcag agaaccttcg aaaaaccgcc ctgcaaggcg gttttttcgt 13860
tttcagagca agagattacg cgcagaccaa aacgatctca agaagatcat cttattaagg 13920
ggtctgacgc tcagtggaac gaaaactcac gttaagggat tttggtcatg agattatcaa 13980
aaaggatctt cacctagatc cttttaaatt aaaaatgaag ttttaaatca atctaaagta 14040
tatatgagta aacttggtct gacagttatt agaaaaattc atccagcaga cgataaaacg 14100
caatacgctg gctatccggt gccgcaatgc catacagcac cagaaaacga tccgcccatt 14160
cgccgcccag ttcttccgca atatcacggg tggccagcgc aatatcctga taacgatccg 14220
ccacgcccag acggccgcaa tcaataaagc cgctaaaacg gccattttcc accataatgt 14280
tcggcaggca cgcatcacca tgggtcacca ccagatcttc gccatccggc atgctcgctt 14340
tcagacgcgc aaacagctct gccggtgcca ggccctgatg ttcttcatcc agatcatcct 14400
gatccaccag gcccgcttcc atacgggtac gcgcacgttc aatacgatgt ttcgcctgat 14460
gatcaaacgg acaggtcgcc gggtccaggg tatgcagacg acgcatggca tccgccataa 14520
tgctcacttt ttctgccggc gccagatggc tagacagcag atcctgaccc ggcacttcgc 14580
ccagcagcag ccaatcacgg cccgcttcgg tcaccacatc cagcaccgcc gcacacggaa 14640
caccggtggt ggccagccag ctcagacgcg ccgcttcatc ctgcagctcg ttcagcgcac 14700
cgctcagatc ggttttcaca aacagcaccg gacgaccctg cgcgctcaga cgaaacaccg 14760
ccgcatcaga gcagccaatg gtctgctgcg cccaatcata gccaaacaga cgttccaccc 14820
acgctgccgg gctacccgca tgcaggccat cctgttcaat catactcttc ctttttcaat 14880
attattgaag catttatcag ggttattgtc tcatgagcgg atacatattt gaatgtattt 14940
agaaaaataa acaaataggg gttccgcgca catttccccg aaaagtgcca cctaaattgt 15000
aagcgttaat attttgttaa aattcgcgtt aaatttttgt taaatcagct cattttttaa 15060
ccaataggcc gaaatcggca aaatccctta taaatcaaaa gaatagaccg agatagggtt 15120
gagtggccgc tacagggcgc tcccattcgc cattcaggct gcgcaactgt tgggaagggc 15180
gtttcggtgc gggcctcttc gctattacgc cagctggcga aagggggatg tgctgcaagg 15240
cgattaagtt gggtaacgcc agggttttcc cagtcacacg cgtaatacga ctcactatag 15300

<210> SEQ ID NO 14
<211> LENGTH: 16324
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 14
ataggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct cgccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600
agaacttggc tggagcatat ccatcatact ctaccaactg ggccgacgaa accgtgttaa 660
cggctcgtaa cataggccta tgcagctctg acgttatgga gcggtcacgt agagggatgt 720

```
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tagacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataaggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
```

```
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
```

gaacaccgtc acttgcaccc agcagggcct gctcgagaac cagcctagtt tccaccccgc 5520
caggcgtgaa tagggtgatc actagagagg agctcgaggc gcttaccccg tcacgcactc 5580
ctagcaggtc ggtctcgaga accagcctgg tctccaaccc gccaggcgta aatagggtga 5640
ttacaagaga ggagtttgag gcgttcgtag cacaacaaca atgacggttt gatgcgggtg 5700
catacatctt ttcctccgac accggtcaag ggcatttaca acaaaaatca gtaaggcaaa 5760
cggtgctatc cgaagtggtg ttggagagga ccgaattgga gatttcgtat gccccgcgcc 5820
tcgaccaaga aaaagaagaa ttactacgca agaaattaca gttaaatccc acacctgcta 5880
acagaagcag ataccagtcc aggaaggtgg agaacatgaa agccataaca gctagacgta 5940
ttctgcaagg cctagggcat tatttgaagg cagaaggaaa agtggagtgc taccgaaccc 6000
tgcatcctgt tcctttgtat tcatctagtg tgaaccgtgc cttttcaagc cccaaggtcg 6060
cagtggaagc ctgtaacgcc atgttgaaag agaactttcc gactgtggct tcttactgta 6120
ttattccaga gtacgatgcc tatttggaca tggttgacgg agcttcatgc tgcttagaca 6180
ctgccagttt ttgccctgca aagctgcgca gctttccaaa gaaacactcc tatttggaac 6240
ccacaatacg atcggcagtg ccttcagcga tccagaacac gctccagaac gtcctggcag 6300
ctgccacaaa aagaaattgc aatgtcacgc aaatgagaga attgcccgta ttggattcgg 6360
cggcctttaa tgtggaatgc ttcaagaaat atgcgtgtaa taatgaatat tgggaaacgt 6420
ttaaagaaaa ccccatcagg cttactgaag aaaacgtggt aaattacatt accaaattaa 6480
aaggaccaaa agctgctgct ctttttgcga agacacataa tttgaatatg ttgcaggaca 6540
taccaatgga caggtttgta atggacttaa agagagacgt gaaagtgact ccaggaacaa 6600
aacatactga agaacggccc aaggtacagg tgatccaggc tgccgatccg ctagcaacag 6660
cgtatctgtg cggaatccac cgagagctgg ttaggagatt aaatgcggtc ctgcttccga 6720
acattcatac actgtttgat atgtcggctg aagactttga cgctattata gccgagcact 6780
tccagcctgg ggattgtgtt ctggaaactg acatcgcgtc gtttgataaa agtgaggacg 6840
acgccatggc tctgaccgcg ttaatgattc tggaagactt aggtgtggac gcagagctgt 6900
tgacgctgat tgaggcggct ttcggcgaaa tttcatcaat acatttgccc actaaaacta 6960
aatttaaatt cggagccatg atgaaatctg gaatgttcct cacactgttt gtgaacacag 7020
tcattaacat tgtaatcgca agcagagtgt tgagagaacg gctaaccgga tcaccatgtg 7080
cagcattcat tggagatgac aatatcgtga aaggagtcaa atcggacaaa ttaatggcag 7140
acaggtgcgc cacctggttg aatatggaag tcaagattat agatgctgtg gtgggcgaga 7200
aagcgcctta tttctgtgga gggtttattt tgtgtgactc cgtgaccggc acagcgtgcc 7260
gtgtggcaga cccccctaaaa aggctgttta agcttggcaa acctctggca gcagacgatg 7320
aacatgatga tgacaggaga agggcattgc atgaagagtc aacacgctgg aaccgagtgg 7380
gtattctttc agagctgtgc aaggcagtag aatcaaggta tgaaaccgta ggaacttcca 7440
tcatagttat ggccatgact actctagcta gcagtgttaa atcattcagc tacctgagag 7500
gggcccctat aactctctac ggctaacctg aatggactac gacatagtct agtccgccaa 7560
gatgaggcct ggcctgccct cctacctgat catcctggcc gtgtgcctgt tcagccacct 7620
gctgtccagc agatacggcg ccgaggccgt gagcgagccc ctggacaagg ctttccacct 7680
gctgctgaac acctacggca gacccatccg gtttctgcgg gagaacacca cccagtgcac 7740
ctacaacagc agcctgcgga acagcaccgt cgtgagagag aacgccatca gcttcaactt 7800

```
tttccagagc tacaaccagt actacgtgtt ccacatgccc agatgcctgt ttgccggccc   7860
tctggccgag cagttcctga accaggtgga cctgaccgag acactggaaa gataccagca   7920
gcggctgaat acctacgccc tggtgtccaa ggacctggcc agctaccggt cctttagcca   7980
gcagctcaag gctcaggata gcctcggcga gcagcctacc accgtgcccc ctcccatcga   8040
cctgagcatc ccccacgtgt ggatgcctcc ccagaccacc cctcacggct ggaccgagag   8100
ccacaccacc tccggcctgc acagacccca cttcaaccag acctgcatcc tgttcgacgg   8160
ccacgacctg ctgtttagca ccgtgacccc ctgcctgcac cagggcttct acctgatcga   8220
cgagctgaga tacgtgaaga tcaccctgac cgaggatttc ttcgtggtca ccgtgtccat   8280
cgacgacgac acccccatgc tgctgatctt cggccacctg cccagagtgc tgttcaaggc   8340
cccctaccag cgggacaact tcatcctgcg gcagaccgag aagcacgagc tgctggtgct   8400
ggtcaagaag gaccagctga accggcactc ctacctgaag gaccccgact tcctggacgc   8460
cgccctggac ttcaactacc tggacctgag cgccctgctg agaaacagct tccacagata   8520
cgccgtggac gtgctgaagt ccggacggtg ccagatgctc gatcggcgga ccgtggagat   8580
ggccttcgcc tatgccctcg ccctgttcgc cgctgccaga caggaagagg ctggcgccca   8640
ggtgtcagtg cccagagccc tggatagaca ggccgccctg ctgcagatcc aggaattcat   8700
gatcacctgc ctgagccaga cccccccctag aaccaccctg ctgctgtacc ccacagccgt   8760
ggatctggcc aagagggccc tgtggacccc caaccagatc accgacatca caagcctcgt   8820
gcggctcgtg tacatcctga gcaagcagaa ccagcagcac ctgatccccc agtgggccct   8880
gagacagatc gccgacttcg ccctgaagct gcacaagacc catctggcca gctttctgag   8940
cgccttcgcc aggcaggaac tgtacctgat gggcagcctg gtccacagca tgctggtgca   9000
taccaccgag cggcgggaga tcttcatcgt ggagacaggc ctgtgtagcc tggccgagct   9060
gtcccacttt acccagctgc tggcccaccc tcaccacgag tacctgagcg acctgtacac   9120
cccctgcagc agcagcggca gacgggacca cagcctggaa cggctgacca gactgttccc   9180
cgatgccacc gtgcctgcta cagtgcctgc cgccctgtcc atcctgtcca ccatgcagcc   9240
cagcaccctg gaaaccttcc ccgacctgtt ctgcctgccc ctgggcgaga gctttagcgc   9300
cctgaccgtg tccgagcacg tgtcctacat cgtgaccaat cagtacctga tcaagggcat   9360
cagctacccc gtgtccacca cagtcgtggg ccagagcctg atcatcaccc agaccgacag   9420
ccagaccaag tgcgagctga cccggaacat gcacaccaca cacagcatca ccgtggccct   9480
gaacatcagc ctggaaaact gcgctttctg tcagtctgcc ctgctggaat acgacgatac   9540
ccagggcgtg atcaacatca tgtacatgca cgacagcgac gacgtgctgt tcgccctgga   9600
cccctacaac gaggtggtgg tgtccagccc ccggacccac tacctgatgc tgctgaagaa   9660
cggcaccgtg ctggaagtga ccgacgtggt ggtggacgcc accgactgat aatctagagg   9720
cccctataac tctctacggc taacctgaat ggactacgac atagtctagt ccgccaagat   9780
gtgcagaagg cccgactgcg gcttcagctt cagccctgga cccgtgatcc tgctgtggtg   9840
ctgcctgctg ctgcctatcg tgtcctctgc cgccgtgtct gtggccccta cagccgccga   9900
gaaggtgcca gccgagtgcc ccgagctgac cagaagatgc ctgctgggcg aggtgttcga   9960
gggcgacaag tacgagagct ggctgcggcc cctggtcaac gtgaccggca gagatggccc  10020
cctgagccag ctgatccggt acagacccgt gacccccgag gccgccaata gcgtgctgct  10080
ggacgaggcc ttcctggata ccctggccct gctgtacaac aaccccgacc agctgagagc  10140
cctgctgacc ctgctgtcca gcgacaccgc ccccagatgg atgaccgtga tgcggggcta  10200
```

```
cagcgagtgt ggagatggca gccctgccgt gtacacctgc gtggacgacc tgtgcagagg  10260
ctacgacctg accagactga gctacggccg gtccatcttc acagagcacg tgctgggctt  10320
cgagctggtg ccccccagcc tgttcaacgt ggtggtggcc atccggaacg aggccaccag  10380
aaccaacaga gccgtgcggc tgcctgtgtc tacagccgct gcacctgagg gcatcacact  10440
gttctacggc ctgtacaacg ccgtgaaaga gttctgcctc cggcaccagc tggatccccc  10500
cctgctgaga cacctggaca agtactacgc cggcctgccc ccagagctga agcagaccag  10560
agtgaacctg cccgcccaca gcagatatgg ccctcaggcc gtggacgcca gatgataacg  10620
ccggcggccc ctataactct ctacggctaa cctgaatgga ctacgacata gtctagtccg  10680
ccaagatgag ccccaaggac ctgaccccct tcctgacaac cctgtggctg ctcctgggcc  10740
atagcagagt gcctagagtg cgggccgagg aatgctgcga gttcatcaac gtgaaccacc  10800
cccccgagcg gtgctacgac ttcaagatgt gcaaccggtt caccgtggcc ctgagatgcc  10860
ccgacggcga agtgtgctac agccccgaga aaaccgccga gatccggggc atcgtgacca  10920
ccatgaccca cagcctgacc cggcaggtgg tgcacaacaa gctgaccagc tgcaactaca  10980
acccccctgta cctggaagcc gacggccgga tcagatgcgg caaagtgaac gacaaggccc  11040
agtacctgct gggagccgcc ggaagcgtgc cctaccggtg gatcaacctg gaatacgaca  11100
agatcacccg gatcgtgggc ctggaccagt acctggaaag cgtgaagaag cacaagcggc  11160
tggacgtgtg cagagccaag atgggctaca tgctgcagtg ataaggcgcg ccaacgttac  11220
tggccgaagc cgcttggaat aaggccggtg tgcgtttgtc tatatgttat tttccaccat  11280
attgccgtct tttggcaatg tgagggcccg gaaacctggc cctgtcttct tgacgagcat  11340
tcctaggggt ctttcccctc tcgccaaagg aatgcaaggt ctgttgaatg tcgtgaagga  11400
agcagttcct ctggaagctt cttgaagaca aacaacgtct gtagcgaccc tttgcaggca  11460
gcggaacccc ccacctggcg acaggtgcct ctgcggccaa aagccacgtg tataagatac  11520
acctgcaaag gcggcacaac cccagtgcca cgttgtgagt tggatagttg tggaaagagt  11580
caaatggctc tcctcaagcg tattcaacaa ggggctgaag gatgcccaga aggtacccca  11640
ttgtatggga tctgatctgg ggcctcggtg cacatgcttt acatgtgttt agtcgaggtt  11700
aaaaaaacgt ctaggccccc cgaaccacgg ggacgtggtt ttcctttgaa aaacacgata  11760
atatgctgcg gctgctgctg agacaccact tccactgcct gctgctgtgt gccgtgtggg  11820
ccacccccttg tctggccagc ccttggagca ccctgaccgc caaccagaac cctagccccc  11880
cttggtccaa gctgacctac agcaagcccc acgacgccgc caccttctac tgcccctttc  11940
tgtaccccag ccctcccaga agccccctgc agttcagcgg cttccagaga gtgtccaccg  12000
gccctgagtg ccggaacgag acactgtacc tgctgtacaa ccgggagggc cagacactgg  12060
tggagcggag cagcacctgg gtgaaaaaag tgatctggta tctgagcggc cggaaccaga  12120
ccatcctgca gcggatgccc agaaccgcca gcaagcccag cgacggcaac gtgcagatca  12180
gcgtggagga cgccaaaatc ttcggagccc acatggtgcc caagcagacc aagctgctga  12240
gattcgtggt caacgacggc accagatatc agatgtgcgt gatgaagctg gaaagctggg  12300
cccacgtgtt ccgggactac tccgtgagct tccaggtccg gctgaccttc accgaggcca  12360
acaaccagac ctacaccttc tgcacccacc ccaacctgat cgtgtgataa gtacctttgt  12420
acgcctgttt tatacccccct ccctgatttg caacttagaa gcaacgcaaa ccagatcaat  12480
agtaggtgtg acataccagt cgcatcttga tcaagcactt ctgtatcccc ggaccgagta  12540
```

```
tcaatagact gtgcacacgg ttgaaggaga aaacgtccgt tacccggcta actacttcga  12600
gaagcctagt aacgccattg aagttgcaga gtgtttcgct cagcactccc cccgtgtaga  12660
tcaggtcgat gagtcaccgc attccccacg ggcgaccgtg gcggtggctg cgttggcggc  12720
ctgcctatgg ggtaacccat aggacgctct aatacggaca tggcgtgaag agtctattga  12780
gctagttagt agtcctccgg cccctgaatg cggctaatcc taactgcgga gcacataccc  12840
ttaatccaaa gggcagtgtg tcgtaacggg caactctgca gcggaaccga ctactttggg  12900
tgtccgtgtt tctttttatt cttgtattgg ctgcttatgg tgacaattaa agaattgtta  12960
ccatatagct attggattgg ccatccagtg tcaaacagag ctattgtata tctctttgtt  13020
ggattcacac ctctcactct tgaaacgtta cacaccctca attacattat actgctgaac  13080
acgaagcgca tatgcggctg tgcagagtgt ggctgtccgt gtgcctgtgt gccgtggtgc  13140
tgggccagtg ccagagagag acagccgaga agaacgacta ctaccgggtg ccccactact  13200
gggatgcctg cagcagagcc ctgcccgacc agacccggta caaatacgtg gagcagctcg  13260
tggacctgac cctgaactac cactacgacg ccagccacgg cctggacaac ttcgacgtgc  13320
tgaagcggat caacgtgacc gaggtgtccc tgctgatcag cgacttccgg cggcagaaca  13380
gaagaggcgg caccaacaag cggaccacct tcaacgccgc tggctctctg gcccctcacg  13440
ccagatccct ggaattcagc gtgcggctgt tcgccaactg ataacgttgc atcctgcagg  13500
atacagcagc aattggcaag ctgcttacat agaactcgcg gcgattggca tgccgcctta  13560
aaatttttat tttatttttc ttttcttttc cgaatcggat tttgttttta atatttcaaa  13620
aaaaaaaaaa aaaaaaaaaa aaaaaaaaaa aagggtcggc atggcatctc cacctcctcg  13680
cggtccgacc tgggcatccg aaggaggacg cacgtccact cggatggcta agggagagcc  13740
acgtttaaac gctagagcaa gacgtttccc gttgaatatg gctcataaca ccccttgtat  13800
tactgtttat gtaagcagac agttttattg ttcatgatga tatattttta tcttgtgcaa  13860
tgtaacatca gagattttga gacacaacgt ggctttgttg aataaatcga acttttgctg  13920
agttgaagga tcagatcacg catcttcccg acaacgcaga ccgttccgtg gcaaagcaaa  13980
agttcaaaat caccaactgg tccacctaca acaaagctct catcaaccgt ggctccctca  14040
ctttctggct ggatgatggg gcgattcagg cctggtatga gtcagcaaca ccttcttcac  14100
gaggcagacc tcagcgctag cggagtgtat actggcttac tatgttggca ctgatgaggg  14160
tgtcagtgaa gtgcttcatg tggcaggaga aaaaaggctg caccggtgcg tcagcagaat  14220
atgtgataca ggatatattc cgcttcctcg ctcactgact cgctacgctc ggtcgttcga  14280
ctgcggcgag cggaaatggc ttacgaacgg ggcggagatt tcctggaaga tgccaggaag  14340
atacttaaca gggaagtgag agggccgcgg caaagccgtt tttccatagg ctccgccccc  14400
ctgacaagca tcacgaaatc tgacgctcaa atcagtggtg gcgaaacccg acaggactat  14460
aaagatacca ggcgtttccc ctggcggctc cctcgtgcgc tctcctgttc ctgcctttcg  14520
gtttaccggt gtcattccgc tgttatggcc gcgtttgtct cattccacgc ctgacactca  14580
gttccgggta ggcagttcgc tccaagctgg actgtatgca cgaacccccc gttcagtccg  14640
accgctgcgc cttatccggt aactatcgtc ttgagtccaa cccggaaaga catgcaaaag  14700
caccactggc agcagccact ggtaattgat ttagaggagt tagtcttgaa gtcatgcgcc  14760
ggttaaggct aaactgaaag gacaagtttt ggtgactgcg ctcctccaag ccagttacct  14820
cggttcaaag agttggtagc tcagagaacc ttcgaaaaac cgccctgcaa ggcggttttt  14880
tcgttttcag agcaagagat tacgcgcaga ccaaaacgat ctcaagaaga tcatcttatt  14940
```

```
aaggggtctg acgctcagtg gaacgaaaac tcacgttaag ggattttggt catgagatta  15000

tcaaaaagga tcttcaccta gatcctttta aattaaaaat gaagttttaa atcaatctaa  15060

agtatatatg agtaaacttg gtctgacagt tattagaaaa attcatccag cagacgataa  15120

aacgcaatac gctggctatc cggtgccgca atgccataca gcaccagaaa acgatccgcc  15180

cattcgccgc ccagttcttc cgcaatatca cgggtggcca gcgcaatatc ctgataacga  15240

tccgccacgc ccagacggcc gcaatcaata aagccgctaa aacggccatt ttccaccata  15300

atgttcggca ggcacgcatc accatgggtc accaccagat cttcgccatc cggcatgctc  15360

gctttcagac gcgcaaacag ctctgccggt gccaggccct gatgttcttc atccagatca  15420

tcctgatcca ccaggcccgc ttccatacgg gtacgcgcac gttcaatacg atgtttcgcc  15480

tgatgatcaa acggacaggt cgccgggtcc agggtatgca gacgacgcat ggcatccgcc  15540

ataatgctca ctttttctgc cggcgccaga tggctagaca gcagatcctg acccggcact  15600

tcgcccagca gcagccaatc acggcccgct tcggtcacca catccagcac cgccgcacac  15660

ggaacaccgg tggtggccag ccagctcaga cgcgccgctt catcctgcag ctcgttcagc  15720

gcaccgctca gatcggtttt cacaaacagc accggacgac cctgcgcgct cagacgaaac  15780

accgccgcat cagagcagcc aatggtctgc tgcgcccaat catagccaaa cagacgttcc  15840

acccacgctg ccgggctacc cgcatgcagg ccatcctgtt caatcatact cttccttttt  15900

caatattatt gaagcattta tcagggttat tgtctcatga gcggatacat atttgaatgt  15960

atttagaaaa ataaacaaat aggggttccg cgcacatttc cccgaaaagt gccacctaaa  16020

ttgtaagcgt taatattttg ttaaaattcg cgttaaattt ttgttaaatc agctcatttt  16080

ttaaccaata ggccgaaatc ggcaaaatcc cttataaatc aaaagaatag accgagatag  16140

ggttgagtgg ccgctacagg gcgctcccat tcgccattca ggctgcgcaa ctgttgggaa  16200

gggcgtttcg gtgcgggcct cttcgctatt acgccagctg gcgaaagggg gatgtgctgc  16260

aaggcgatta agttgggtaa cgccagggtt ttcccagtca cacgcgtaat acgactcact  16320

atag                                                               16324
```

<210> SEQ ID NO 15
<211> LENGTH: 16360
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 15

```
ataggcggcg catgagagaa gcccagacca attacctacc caaaatggag aaagttcacg     60

ttgacatcga ggaagacagc ccattcctca gagctttgca gcggagcttc ccgcagtttg    120

aggtagaagc caagcaggtc actgataatg accatgctaa tgccagagcg ttttcgcatc    180

tggcttcaaa actgatcgaa acggaggtgg acccatccga cacgatcctt gacattggaa    240

gtgcgcccgc ccgcagaatg tattctaagc acaagtatca ttgtatctgt ccgatgagat    300

gtgcggaaga tccggacaga ttgtataagt atgcaactaa gctgaagaaa aactgtaagg    360

aaataactga taaggaattg gacaagaaaa tgaaggagct cgccgccgtc atgagcgacc    420

ctgacctgga aactgagact atgtgcctcc acgacgacga gtcgtgtcgc tacgaagggc    480

aagtcgctgt ttaccaggat gtatacgcgg ttgacggacc gacaagtctc tatcaccaag    540
```

ccaataaggg agttagagtc gcctactgga taggctttga caccacccct tttatgttta 600
agaacttggc tggagcatat ccatcatact ctaccaactg ggccgacgaa accgtgttaa 660
cggctcgtaa cataggccta tgcagctctg acgttatgga gcggtcacgt agagggatgt 720
ccattcttag aaagaagtat ttgaaaccat ccaacaatgt tctattctct gttggctcga 780
ccatctacca cgagaagagg gacttactga ggagctggca cctgccgtct gtatttcact 840
tacgtggcaa gcaaaattac acatgtcggt gtgagactat agttagttgc gacgggtacg 900
tcgttaaaag aatagctatc agtccaggcc tgtatgggaa gccttcaggc tatgctgcta 960
cgatgcaccg cgagggattc ttgtgctgca aagtgacaga cacattgaac ggggagaggg 1020
tctcttttcc cgtgtgcacg tatgtgccag ctacattgtg tgaccaaatg actggcatac 1080
tggcaacaga tgtcagtgcg gacgacgcgc aaaaactgct ggttgggctc aaccagcgta 1140
tagtcgtcaa cggtcgcacc cagagaaaca ccaataccat gaaaaattac cttttgcccg 1200
tagtggccca ggcatttgct aggtgggcaa aggaatataa ggaagatcaa gaagatgaaa 1260
ggccactagg actacgagat agacagttag tcatggggtg ttgttgggct tttagaaggc 1320
acaagataac atctatttat aagcgcccgg atacccaaac catcatcaaa gtgaacagcg 1380
atttccactc attcgtgctg cccaggatag gcagtaacac attggagatc gggctgagaa 1440
caagaatcag gaaaatgtta gaggagcaca aggagccgtc acctctcatt accgccgagg 1500
acgtacaaga agctaagtgc gcagccgatg aggctaagga ggtgcgtgaa gccgaggagt 1560
tgcgcgcagc tctaccacct ttggcagctg atgttgagga gcccactctg gaagccgatg 1620
tagacttgat gttacaagag gctggggccg gctcagtgga gacacctcgt ggcttgataa 1680
aggttaccag ctacgatggc gaggacaaga tcggctctta cgctgtgctt tctccgcagg 1740
ctgtactcaa gagtgaaaaa ttatcttgca tccaccctct cgctgaacaa gtcatagtga 1800
taacacactc tggccgaaaa gggcgttatg ccgtggaacc ataccatggt aaagtagtgg 1860
tgccagaggg acatgcaata cccgtccagg actttcaagc tctgagtgaa agtgccacca 1920
ttgtgtacaa cgaacgtgag ttcgtaaaca ggtacctgca ccatattgcc acacatggag 1980
gagcgctgaa cactgatgaa gaatattaca aaactgtcaa gcccagcgag cacgacggcg 2040
aatacctgta cgacatcgac aggaaacagt gcgtcaagaa agaactagtc actgggctag 2100
ggctcacagg cgagctggtg gatcctccct tccatgaatt cgcctacgag agtctgagaa 2160
cacgaccagc cgctccttac caagtaccaa ccataggggt gtatggcgtg ccaggatcag 2220
gcaagtctgg catcattaaa agcgcagtca ccaaaaaaga tctagtggtg agcgccaaga 2280
aagaaaactg tgcagaaatt ataaggacg tcaagaaaat gaaagggctg gacgtcaatg 2340
ccagaactgt ggactcagtg ctcttgaatg gatgcaaaca ccccgtagag accctgtata 2400
ttgacgaagc ttttgcttgt catgcaggta ctctcagagc gctcatagcc attataagac 2460
ctaaaaaggc agtgctctgc ggggatccca aacagtgcgg ttttttaac atgatgtgcc 2520 tgaaagtgca ttttaaccac gagatttgca cacaagtctt ccacaaaagc atctctcgcc 2580
gttgcactaa atctgtgact tcggtcgtct caaccttgtt ttacgacaaa aaaatgagaa 2640
cgacgaatcc gaaagagact aagattgtga ttgacactac cggcagtacc aaacctaagc 2700
aggacgatct cattctcact tgtttcagag ggtgggtgaa gcagttgcaa atagattaca 2760
aaggcaacga aataatgacg gcagctgcct ctcaagggct gacccgtaaa ggtgtgtatg 2820
ccgttcggta caaggtgaat gaaaatcctc tgtacgcacc cacctcagaa catgtgaacg 2880
tcctactgac ccgcacggag gaccgcatcg tgtggaaaac actagccggc gacccatgga 2940

```
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
```

```
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gatgaggcct ggcctgccct cctacctgat catcctggcc gtgtgcctgt tcagccacct   7620
gctgtccagc agatacggcg ccgaggccgt gagcgagccc ctggacaagg ctttccacct   7680
```

gctgctgaac acctacggca gacccatccg gtttctgcgg gagaacacca cccagtgcac 7740
ctacaacagc agcctgcgga acagcaccgt cgtgagagag aacgccatca gcttcaactt 7800
tttccagagc tacaaccagt actacgtgtt ccacatgccc agatgcctgt ttgccggccc 7860
tctggccgag cagttcctga accaggtgga cctgaccgag acactggaaa gataccagca 7920
gcggctgaat acctacgccc tggtgtccaa ggacctggcc agctaccggt cctttagcca 7980
gcagctcaag gctcaggata gcctcggcga gcagcctacc accgtgcccc ctcccatcga 8040
cctgagcatc ccccacgtgt ggatgcctcc ccagaccacc cctcacggct ggaccgagag 8100
ccacaccacc tccggcctgc acagacccca cttcaaccag acctgcatcc tgttcgacgg 8160
ccacgacctg ctgtttagca ccgtgacccc ctgcctgcac cagggcttct acctgatcga 8220
cgagctgaga tacgtgaaga tcaccctgac cgaggatttc ttcgtggtca ccgtgtccat 8280
cgacgacgac acccccatgc tgctgatctt cggccacctg cccagagtgc tgttcaaggc 8340
cccctaccag cgggacaact tcatcctgcg gcagaccgag aagcacgagc tgctggtgct 8400
ggtcaagaag gaccagctga accggcactc ctacctgaag gaccccgact tcctggacgc 8460
cgccctggac ttcaactacc tggacctgag cgccctgctg agaaacagct tccacagata 8520
cgccgtggac gtgctgaagt ccggacggtg ccagatgctc gatcggcgga ccgtggagat 8580
ggccttcgcc tatgccctcg ccctgttcgc cgctgccaga caggaagagg ctggcgccca 8640
ggtgtcagtg cccagagccc tggatagaca ggccgccctg ctgcagatcc aggaattcat 8700
gatcacctgc ctgagccaga cccccccctag aaccaccctg ctgctgtacc ccacagccgt 8760
ggatctggcc aagagggccc tgtggacccc caaccagatc accgacatca caagcctcgt 8820
gcggctcgtg tacatcctga gcaagcagaa ccagcagcac ctgatccccc agtgggccct 8880
gagacagatc gccgacttcg ccctgaagct gcacaagacc catctggcca gctttctgag 8940
cgccttcgcc aggcaggaac tgtacctgat gggcagcctg gtccacagca tgctggtgca 9000
taccaccgag cggcgggaga tcttcatcgt ggagacaggc ctgtgtagcc tggccgagct 9060
gtcccacttt acccagctgc tggcccaccc tcaccacgag tacctgagcg acctgtacac 9120
cccctgcagc agcagcggca gacgggacca cagcctggaa cggctgacca gactgttccc 9180
cgatgccacc gtgcctgcta cagtgcctgc cgccctgtcc atcctgtcca ccatgcagcc 9240
cagcaccctg gaaaccttcc ccgacctgtt ctgcctgccc ctgggcgaga gctttagcgc 9300
cctgaccgtg tccgagcacg tgtcctacat cgtgaccaat cagtacctga tcaagggcat 9360
cagctacccc gtgtccacca cagtcgtggg ccagagcctg atcatcaccc agaccgacag 9420
ccagaccaag tgcgagctga cccggaacat gcacaccaca cacagcatca ccgtggccct 9480
gaacatcagc ctggaaaact gcgctttctg tcagtctgcc ctgctggaat acgacgatac 9540
ccagggcgtg atcaacatca tgtacatgca cgacagcgac gacgtgctgt tcgccctgga 9600
cccctacaac gaggtggtgg tgtccagccc ccggacccac tacctgatgc tgctgaagaa 9660
cggcaccgtg ctggaagtga ccgacgtggt ggtggacgcc accgacggca gcggatctgg 9720
gtcccaccat caccatcacc attgataatc tagaggcccc tataactctc tacggctaac 9780
ctgaatggac tacgacatag tctagtccgc caagatgtgc agaaggcccg actgcggctt 9840
cagcttcagc cctggacccg tgatcctgct gtggtgctgc ctgctgctgc ctatcgtgtc 9900
ctctgccgcc gtgtctgtgg cccctacagc cgccgagaag gtgccagccg agtgccccga 9960
gctgaccaga agatgcctgc tgggcgaggt gttcgagggc gacaagtacg agagctggct 10020

```
gcggcccctg gtcaacgtga ccggcagaga tggccccctg agccagctga tccggtacag  10080
acccgtgacc cccgaggccg ccaatagcgt gctgctggac gaggccttcc tggataccct  10140
ggccctgctg tacaacaacc ccgaccagct gagagccctg ctgaccctgc tgtccagcga  10200
caccgccccc agatggatga ccgtgatgcg gggctacagc gagtgtggag atggcagccc  10260
tgccgtgtac acctgcgtgg acgacctgtg cagaggctac gacctgacca gactgagcta  10320
cggccggtcc atcttcacag agcacgtgct gggcttcgag ctggtgcccc ccagcctgtt  10380
caacgtggtg gtggccatcc ggaacgaggc caccagaacc aacagagccg tgcggctgcc  10440
tgtgtctaca gccgctgcac ctgagggcat cacactgttc tacggcctgt acaacgccgt  10500
gaaagagttc tgcctccggc accagctgga tccccccctg ctgagacacc tggacaagta  10560
ctacgccggc ctgcccccag agctgaagca gaccagagtg aacctgcccg cccacagcag  10620
atatggccct caggccgtgg acgccagatg ataacgccgg cggcccctat aactctctac  10680
ggctaacctg aatggactac gacatagtct agtccgccaa gatgagcccc aaggacctga  10740
ccccttcct gacaaccctg tggctgctcc tgggccatag cagagtgcct agagtgcggg  10800
ccgaggaatg ctgcgagttc atcaacgtga accacccccc cgagcggtgc tacgacttca  10860
agatgtgcaa ccggttcacc gtggccctga gatgccccga cggcgaagtg tgctacagcc  10920
ccgagaaaac cgccgagatc cggggcatcg tgaccaccat gacccacagc ctgacccggc  10980
aggtggtgca caacaagctg accagctgca actacaaccc cctgtacctg gaagccgacg  11040
gccggatcag atgcggcaaa gtgaacgaca aggcccagta cctgctggga gccgccggaa  11100
gcgtgcccta ccggtggatc aacctggaat acgacaagat cacccggatc gtgggcctgg  11160
accagtacct ggaaagcgtg aagaagcaca agcggctgga cgtgtgcaga gccaagatgg  11220
gctacatgct gcagtgataa ggcgcgccaa cgttactggc cgaagccgct tggaataagg  11280
ccggtgtgcg tttgtctata tgttattttc caccatattg ccgtcttttg gcaatgtgag  11340
ggcccggaaa cctggccctg tcttcttgac gagcattcct aggggtcttt cccctctcgc  11400
caaaggaatg caaggtctgt tgaatgtcgt gaaggaagca gttcctctgg aagcttcttg  11460
aagacaaaca acgtctgtag cgaccctttg caggcagcgg aaccccccac ctggcgacag  11520
gtgcctctgc ggccaaaagc cacgtgtata agatacacct gcaaaggcgg cacaacccca  11580
gtgccacgtt gtgagttgga tagttgtgga aagagtcaaa tggctctcct caagcgtatt  11640
caacaagggg ctgaaggatg cccagaaggt accccattgt atgggatctg atctggggcc  11700
tcggtgcaca tgctttacat gtgtttagtc gaggttaaaa aaacgtctag gccccccgaa  11760
ccacggggac gtggttttcc tttgaaaaac acgataatat gctgcggctg ctgctgagac  11820
accacttcca ctgcctgctg ctgtgtgccg tgtgggccac cccttgtctg gccagccctt  11880
ggagcaccct gaccgccaac cagaacccta gcccccccttg gtccaagctg acctacagca  11940
agccccacga cgccgccacc ttctactgcc cctttctgta ccccagccct cccagaagcc  12000
ccctgcagtt cagcggcttc cagagagtgt ccaccggccc tgagtgccgg aacgagacac  12060
tgtacctgct gtacaaccgg gagggccaga cactggtgga gcggagcagc acctgggtga  12120
aaaaagtgat ctggtatctg agcggccgga accagaccat cctgcagcgg atgcccagaa  12180
ccgccagcaa gcccagcgac ggcaacgtgc agatcagcgt ggaggacgcc aaaatcttcg  12240
gagcccacat ggtgcccaag cagaccaagc tgctgagatt cgtggtcaac gacggcacca  12300
gatatcagat gtgcgtgatg aagctggaaa gctgggccca cgtgttccgg gactactccg  12360
tgagcttcca ggtccggctg accttcaccg aggccaacaa ccagacctac accttctgca  12420
```

```
cccaccccaa cctgatcgtg tgataagtac ctttgtacgc ctgttttata ccccctccct  12480
gatttgcaac ttagaagcaa cgcaaaccag atcaatagta ggtgtgacat accagtcgca  12540
tcttgatcaa gcacttctgt atccccggac cgagtatcaa tagactgtgc acacggttga  12600
aggagaaaac gtccgttacc cggctaacta cttcgagaag cctagtaacg ccattgaagt  12660
tgcagagtgt ttcgctcagc actccccccg tgtagatcag gtcgatgagt caccgcattc  12720
cccacgggcg accgtggcgg tggctgcgtt ggcggcctgc ctatggggta acccatagga  12780
cgctctaata cggacatggc gtgaagagtc tattgagcta gttagtagtc ctccggcccc  12840
tgaatgcggc taatcctaac tgcggagcac atacccttaa tccaaagggc agtgtgtcgt  12900
aacgggcaac tctgcagcgg aaccgactac tttgggtgtc cgtgtttctt tttattcttg  12960
tattggctgc ttatggtgac aattaaagaa ttgttaccat atagctattg gattggccat  13020
ccagtgtcaa acagagctat tgtatatctc tttgttggat tcacacctct cactcttgaa  13080
acgttacaca ccctcaatta cattatactg ctgaacacga agcgcatatg cggctgtgca  13140
gagtgtggct gtccgtgtgc ctgtgtgccg tggtgctggg ccagtgccag agagagacag  13200
ccgagaagaa cgactactac cgggtgcccc actactggga tgcctgcagc agagccctgc  13260
ccgaccagac ccggtacaaa tacgtggagc agctcgtgga cctgaccctg aactaccact  13320
acgacgccag ccacggcctg gacaacttcg acgtgctgaa gcggatcaac gtgaccgagg  13380
tgtccctgct gatcagcgac ttccggcggc agaacagaag aggcggcacc aacaagcgga  13440
ccaccttcaa cgccgctggc tctctggccc ctcacgccag atccctggaa ttcagcgtgc  13500
ggctgttcgc caactgataa cgttgcatcc tgcaggatac agcagcaatt ggcaagctgc  13560
ttacatagaa ctcgcggcga ttggcatgcc gccttaaaat ttttatttta tttttctttt  13620
cttttccgaa tcggattttg tttttaatat ttcaaaaaaa aaaaaaaaaa aaaaaaaaaa  13680
aaaaaaaagg gtcggcatgg catctccacc tcctcgcggt ccgacctggg catccgaagg  13740
aggacgcacg tccactcgga tggctaaggg agagccacgt ttaaacgcta gagcaagacg  13800
tttcccgttg aatatggctc ataacacccc ttgtattact gtttatgtaa gcagacagtt  13860
ttattgttca tgatgatata tttttatctt gtgcaatgta acatcagaga ttttgagaca  13920
caacgtggct ttgttgaata aatcgaactt ttgctgagtt gaaggatcag atcacgcatc  13980
ttcccgacaa cgcagaccgt tccgtggcaa agcaaaagtt caaaatcacc aactggtcca  14040
cctacaacaa agctctcatc aaccgtggct ccctcacttt ctggctggat gatggggcga  14100
ttcaggcctg gtatgagtca gcaacacctt cttcacgagg cagacctcag cgctagcgga  14160
gtgtatactg gcttactatg ttggcactga tgagggtgtc agtgaagtgc ttcatgtggc  14220
aggagaaaaa aggctgcacc ggtgcgtcag cagaatatgt gatacaggat atattccgct  14280
tcctcgctca ctgactcgct acgctcggtc gttcgactgc ggcgagcgga aatggcttac  14340
gaacggggcg gagatttcct ggaagatgcc aggaagatac ttaacaggga agtgagaggg  14400
ccgcggcaaa gccgtttttc cataggctcc gcccccctga caagcatcac gaaatctgac  14460
gctcaaatca gtggtggcga aacccgacag gactataaag ataccaggcg tttccccctgg  14520
cggctccctc gtgcgctctc ctgttcctgc ctttcggttt accggtgtca ttccgctgtt  14580
atggccgcgt ttgtctcatt ccacgcctga cactcagttc cgggtaggca gttcgctcca  14640
agctggactg tatgcacgaa ccccccgttc agtccgaccg ctgcgcctta tccggtaact  14700
atcgtcttga gtccaacccg gaaagacatg caaaagcacc actggcagca gccactggta  14760
```

-continued

```
attgatttag aggagttagt cttgaagtca tgcgccggtt aaggctaaac tgaaaggaca  14820

agttttggtg actgcgctcc tccaagccag ttacctcggt tcaaagagtt ggtagctcag  14880

agaaccttcg aaaaaccgcc ctgcaaggcg gttttttcgt tttcagagca agagattacg  14940

cgcagaccaa aacgatctca agaagatcat cttattaagg ggtctgacgc tcagtggaac  15000

gaaaactcac gttaagggat tttggtcatg agattatcaa aaaggatctt cacctagatc  15060

cttttaaatt aaaaatgaag ttttaaatca atctaaagta tatatgagta aacttggtct  15120

gacagttatt agaaaaattc atccagcaga cgataaaacg caatacgctg gctatccggt  15180

gccgcaatgc catacagcac cagaaaacga tccgcccatt cgccgcccag ttcttccgca  15240

atatcacggg tggccagcgc aatatcctga taacgatccg ccacgcccag acggccgcaa  15300

tcaataaagc cgctaaaacg gccattttcc accataatgt tcggcaggca cgcatcacca  15360

tgggtcacca ccagatcttc gccatccggc atgctcgctt tcagacgcgc aaacagctct  15420

gccggtgcca ggccctgatg ttcttcatcc agatcatcct gatccaccag gcccgcttcc  15480

atacgggtac gcgcacgttc aatacgatgt ttcgcctgat gatcaaacgg acaggtcgcc  15540

gggtccaggg tatgcagacg acgcatggca tccgccataa tgctcacttt ttctgccggc  15600

gccagatggc tagacagcag atcctgaccc ggcacttcgc ccagcagcag ccaatcacgg  15660

cccgcttcgg tcaccacatc cagcaccgcc gcacacggaa caccggtggt ggccagccag  15720

ctcagacgcg ccgcttcatc ctgcagctcg ttcagcgcac cgctcagatc ggttttcaca  15780

aacagcaccg gacgaccctg cgcgctcaga cgaaacaccg ccgcatcaga gcagccaatg  15840

gtctgctgcg cccaatcata gccaaacaga cgttccaccc acgctgccgg gctacccgca  15900

tgcaggccat cctgttcaat catactcttc ctttttcaat attattgaag catttatcag  15960

ggttattgtc tcatgagcgg atacatattt gaatgtattt agaaaaataa acaaataggg  16020

gttccgcgca catttccccg aaaagtgcca cctaaattgt aagcgttaat attttgttaa  16080

aattcgcgtt aaatttttgt taaatcagct cattttttaa ccaataggcc gaaatcggca  16140

aaatccctta taaatcaaaa gaatagaccg agatagggtt gagtggccgc tacagggcgc  16200

tcccattcgc cattcaggct gcgcaactgt tgggaagggc gtttcggtgc gggcctcttc  16260

gctattacgc cagctggcga aagggggatg tgctgcaagg cgattaagtt gggtaacgcc  16320

agggttttcc cagtcacacg cgtaatacga ctcactatag                        16360
```

```
<210> SEQ ID NO 16
<211> LENGTH: 868
<212> TYPE: PRT
<213> ORGANISM: Varicella zoster virus

<400> SEQUENCE: 16

Met Phe Val Thr Ala Val Val Ser Val Ser Pro Ser Ser Phe Tyr Glu
1               5                   10                  15

Ser Leu Gln Val Glu Pro Thr Gln Ser Glu Asp Ile Thr Arg Ser Ala
            20                  25                  30

His Leu Gly Asp Gly Asp Glu Ile Arg Glu Ala Ile His Lys Ser Gln
        35                  40                  45

Asp Ala Glu Thr Lys Pro Thr Phe Tyr Val Cys Pro Pro Pro Thr Gly
    50                  55                  60

Ser Thr Ile Val Arg Leu Glu Pro Pro Arg Thr Cys Pro Asp Tyr His
65                  70                  75                  80

Leu Gly Lys Asn Phe Thr Glu Gly Ile Ala Val Val Tyr Lys Glu Asn
                85                  90                  95
```

```
Ile Ala Ala Tyr Lys Phe Lys Ala Thr Val Tyr Tyr Lys Asp Val Ile
            100                 105                 110

Val Ser Thr Ala Trp Ala Gly Ser Ser Tyr Thr Gln Ile Thr Asn Arg
        115                 120                 125

Tyr Ala Asp Arg Val Pro Ile Pro Val Ser Glu Ile Thr Asp Thr Ile
    130                 135                 140

Asp Lys Phe Gly Lys Cys Ser Ser Lys Ala Thr Tyr Val Arg Asn Asn
145                 150                 155                 160

His Lys Val Glu Ala Phe Asn Glu Asp Lys Asn Pro Gln Asp Met Pro
                165                 170                 175

Leu Ile Ala Ser Lys Tyr Asn Ser Val Gly Ser Lys Ala Trp His Thr
            180                 185                 190

Thr Asn Asp Thr Tyr Met Val Ala Gly Thr Pro Gly Thr Tyr Arg Thr
        195                 200                 205

Gly Thr Ser Val Asn Cys Ile Ile Glu Glu Val Glu Ala Arg Ser Ile
    210                 215                 220

Phe Pro Tyr Asp Ser Phe Gly Leu Ser Thr Gly Asp Ile Ile Tyr Met
225                 230                 235                 240

Ser Pro Phe Phe Gly Leu Arg Asp Gly Ala Tyr Arg Glu His Ser Asn
                245                 250                 255

Tyr Ala Met Asp Arg Phe His Gln Phe Glu Gly Tyr Arg Gln Arg Asp
            260                 265                 270

Leu Asp Thr Arg Ala Leu Leu Glu Pro Ala Ala Arg Asn Phe Leu Val
        275                 280                 285

Thr Pro His Leu Thr Val Gly Trp Asn Trp Lys Pro Lys Arg Thr Glu
    290                 295                 300

Val Cys Ser Leu Val Lys Trp Arg Glu Val Glu Asp Val Val Arg Asp
305                 310                 315                 320

Glu Tyr Ala His Asn Phe Arg Phe Thr Met Lys Thr Leu Ser Thr Thr
                325                 330                 335

Phe Ile Ser Glu Thr Asn Glu Phe Asn Leu Asn Gln Ile His Leu Ser
            340                 345                 350

Gln Cys Val Lys Glu Glu Ala Arg Ala Ile Ile Asn Arg Ile Tyr Thr
        355                 360                 365

Thr Arg Tyr Asn Ser Ser His Val Arg Thr Gly Asp Ile Gln Thr Tyr
    370                 375                 380

Leu Ala Arg Gly Gly Phe Val Val Val Phe Gln Pro Leu Leu Ser Asn
385                 390                 395                 400

Ser Leu Ala Arg Leu Tyr Leu Gln Glu Leu Val Arg Glu Asn Thr Asn
                405                 410                 415

His Ser Pro Gln Lys His Pro Thr Arg Asn Thr Arg Ser Arg Arg Ser
            420                 425                 430

Val Pro Val Glu Leu Arg Ala Asn Arg Thr Ile Thr Thr Thr Ser Ser
        435                 440                 445

Val Glu Phe Ala Met Leu Gln Phe Thr Tyr Asp His Ile Gln Glu His
    450                 455                 460

Val Asn Glu Met Leu Ala Arg Ile Ser Ser Ser Trp Cys Gln Leu Gln
465                 470                 475                 480

Asn Arg Glu Arg Ala Leu Trp Ser Gly Leu Phe Pro Ile Asn Pro Ser
                485                 490                 495

Ala Leu Ala Ser Thr Ile Leu Asp Gln Arg Val Lys Ala Arg Ile Leu
            500                 505                 510
```

```
Gly Asp Val Ile Ser Val Ser Asn Cys Pro Glu Leu Gly Ser Asp Thr
        515                 520                 525

Arg Ile Ile Leu Gln Asn Ser Met Arg Val Ser Gly Ser Thr Thr Arg
    530                 535                 540

Cys Tyr Ser Arg Pro Leu Ile Ser Ile Val Ser Leu Asn Gly Ser Gly
545                 550                 555                 560

Thr Val Glu Gly Gln Leu Gly Thr Asp Asn Glu Leu Ile Met Ser Arg
                565                 570                 575

Asp Leu Leu Glu Pro Cys Val Ala Asn His Lys Arg Tyr Phe Leu Phe
            580                 585                 590

Gly His His Tyr Val Tyr Tyr Glu Asp Tyr Arg Tyr Val Arg Glu Ile
        595                 600                 605

Ala Val His Asp Val Gly Met Ile Ser Thr Tyr Val Asp Leu Asn Leu
    610                 615                 620

Thr Leu Leu Lys Asp Arg Glu Phe Met Pro Leu Gln Val Tyr Thr Arg
625                 630                 635                 640

Asp Glu Leu Arg Asp Thr Gly Leu Leu Asp Tyr Ser Glu Ile Gln Arg
                645                 650                 655

Arg Asn Gln Met His Ser Leu Arg Phe Tyr Asp Ile Asp Lys Val Val
            660                 665                 670

Gln Tyr Asp Ser Gly Thr Ala Ile Met Gln Gly Met Ala Gln Phe Phe
        675                 680                 685

Gln Gly Leu Gly Thr Ala Gly Gln Ala Val Gly His Val Val Leu Gly
    690                 695                 700

Ala Thr Gly Ala Leu Leu Ser Thr Val His Gly Phe Thr Thr Phe Leu
705                 710                 715                 720

Ser Asn Pro Phe Gly Ala Leu Ala Val Gly Leu Leu Val Leu Ala Gly
                725                 730                 735

Leu Val Ala Ala Phe Phe Ala Tyr Arg Tyr Val Leu Lys Leu Lys Thr
            740                 745                 750

Ser Pro Met Lys Ala Leu Tyr Pro Leu Thr Thr Lys Gly Leu Lys Gln
        755                 760                 765

Leu Pro Glu Gly Met Asp Pro Phe Ala Glu Lys Pro Asn Ala Thr Asp
    770                 775                 780

Thr Pro Ile Glu Glu Ile Gly Asp Ser Gln Asn Thr Glu Pro Ser Val
785                 790                 795                 800

Asn Ser Gly Phe Asp Pro Asp Lys Phe Arg Glu Ala Gln Glu Met Ile
                805                 810                 815

Lys Tyr Met Thr Leu Val Ser Ala Ala Glu Arg Gln Glu Ser Lys Ala
            820                 825                 830

Arg Lys Lys Asn Lys Thr Ser Ala Leu Leu Thr Ser Arg Leu Thr Gly
        835                 840                 845

Leu Ala Leu Arg Asn Arg Arg Gly Tyr Ser Arg Val Arg Thr Glu Asn
    850                 855                 860

Val Thr Gly Val
865


<210> SEQ ID NO 17
<211> LENGTH: 841
<212> TYPE: PRT
<213> ORGANISM: Varicella zoster virus

<400> SEQUENCE: 17

Met Phe Ala Leu Val Leu Ala Val Val Ile Leu Pro Leu Trp Thr Thr
1               5                   10                  15
```

```
Ala Asn Lys Ser Tyr Val Thr Pro Thr Pro Ala Thr Arg Ser Ile Gly
            20                  25                  30

His Met Ser Ala Leu Leu Arg Glu Tyr Ser Asp Arg Asn Met Ser Leu
        35                  40                  45

Lys Leu Glu Ala Phe Tyr Pro Thr Gly Phe Asp Glu Glu Leu Ile Lys
    50                  55                  60

Ser Leu His Trp Gly Asn Asp Arg Lys His Val Phe Leu Val Ile Val
65                  70                  75                  80

Lys Val Asn Pro Thr Thr His Glu Gly Asp Val Gly Leu Val Ile Phe
                85                  90                  95

Pro Lys Tyr Leu Leu Ser Pro Tyr His Phe Lys Ala Glu His Arg Ala
            100                 105                 110

Pro Phe Pro Ala Gly Arg Phe Gly Phe Leu Ser His Pro Val Thr Pro
        115                 120                 125

Asp Val Ser Phe Phe Asp Ser Ser Phe Ala Pro Tyr Leu Thr Thr Gln
    130                 135                 140

His Leu Val Ala Phe Thr Thr Phe Pro Pro Asn Pro Leu Val Trp His
145                 150                 155                 160

Leu Glu Arg Ala Glu Thr Ala Ala Thr Ala Glu Arg Pro Phe Gly Val
                165                 170                 175

Ser Leu Leu Pro Ala Arg Pro Thr Val Pro Lys Asn Thr Ile Leu Glu
            180                 185                 190

His Lys Ala His Phe Ala Thr Trp Asp Ala Leu Ala Arg His Thr Phe
        195                 200                 205

Phe Ser Ala Glu Ala Ile Ile Thr Asn Ser Thr Leu Arg Ile His Val
    210                 215                 220

Pro Leu Phe Gly Ser Val Trp Pro Ile Arg Tyr Trp Ala Thr Gly Ser
225                 230                 235                 240

Val Leu Leu Thr Ser Asp Ser Gly Arg Val Glu Val Asn Ile Gly Val
                245                 250                 255

Gly Phe Met Ser Ser Leu Ile Ser Leu Ser Ser Gly Leu Pro Ile Glu
            260                 265                 270

Leu Ile Val Val Pro His Thr Val Lys Leu Asn Ala Val Thr Ser Asp
        275                 280                 285

Thr Thr Trp Phe Gln Leu Asn Pro Pro Gly Pro Asp Pro Gly Pro Ser
    290                 295                 300

Tyr Arg Val Tyr Leu Leu Gly Arg Gly Leu Asp Met Asn Phe Ser Lys
305                 310                 315                 320

His Ala Thr Val Asp Ile Cys Ala Tyr Pro Glu Glu Ser Leu Asp Tyr
                325                 330                 335

Arg Tyr His Leu Ser Met Ala His Thr Glu Ala Leu Arg Met Thr Thr
            340                 345                 350

Lys Ala Asp Gln His Asp Ile Asn Glu Glu Ser Tyr Tyr His Ile Ala
        355                 360                 365

Ala Arg Ile Ala Thr Ser Ile Phe Ala Leu Ser Glu Met Gly Arg Thr
    370                 375                 380

Thr Glu Tyr Phe Leu Leu Asp Glu Ile Val Asp Val Gln Tyr Gln Leu
385                 390                 395                 400

Lys Phe Leu Asn Tyr Ile Leu Met Arg Ile Gly Ala Gly Ala His Pro
                405                 410                 415

Asn Thr Ile Ser Gly Thr Ser Asp Leu Ile Phe Ala Asp Pro Ser Gln
            420                 425                 430
```

```
Leu His Asp Glu Leu Ser Leu Leu Phe Gly Gln Val Lys Pro Ala Asn
        435                 440                 445

Val Asp Tyr Phe Ile Ser Tyr Asp Glu Ala Arg Asp Gln Leu Lys Thr
    450                 455                 460

Ala Tyr Ala Leu Ser Arg Gly Gln Asp His Val Asn Ala Leu Ser Leu
465                 470                 475                 480

Ala Arg Arg Val Ile Met Ser Ile Tyr Lys Gly Leu Leu Val Lys Gln
                485                 490                 495

Asn Leu Asn Ala Thr Glu Arg Gln Ala Leu Phe Phe Ala Ser Met Ile
            500                 505                 510

Leu Leu Asn Phe Arg Glu Gly Leu Glu Asn Ser Ser Arg Val Leu Asp
        515                 520                 525

Gly Arg Thr Thr Leu Leu Leu Met Thr Ser Met Cys Thr Ala Ala His
    530                 535                 540

Ala Thr Gln Ala Ala Leu Asn Ile Gln Glu Gly Leu Ala Tyr Leu Asn
545                 550                 555                 560

Pro Ser Lys His Met Phe Thr Ile Pro Asn Val Tyr Ser Pro Cys Met
                565                 570                 575

Gly Ser Leu Arg Thr Asp Leu Thr Glu Glu Ile His Val Met Asn Leu
            580                 585                 590

Leu Ser Ala Ile Pro Thr Arg Pro Gly Leu Asn Glu Val Leu His Thr
        595                 600                 605

Gln Leu Asp Glu Ser Glu Ile Phe Asp Ala Ala Phe Lys Thr Met Met
    610                 615                 620

Ile Phe Thr Thr Trp Thr Ala Lys Asp Leu His Ile Leu His Thr His
625                 630                 635                 640

Val Pro Glu Val Phe Thr Cys Gln Asp Ala Ala Ala Arg Asn Gly Glu
                645                 650                 655

Tyr Val Leu Ile Leu Pro Ala Val Gln Gly His Ser Tyr Val Ile Thr
            660                 665                 670

Arg Asn Lys Pro Gln Arg Gly Leu Val Tyr Ser Leu Ala Asp Val Asp
        675                 680                 685

Val Tyr Asn Pro Ile Ser Val Val Tyr Leu Ser Lys Asp Thr Cys Val
    690                 695                 700

Ser Glu His Gly Val Ile Glu Thr Val Ala Leu Pro His Pro Asp Asn
705                 710                 715                 720

Leu Lys Glu Cys Leu Tyr Cys Gly Ser Val Phe Leu Arg Tyr Leu Thr
                725                 730                 735

Thr Gly Ala Ile Met Asp Ile Ile Ile Ile Asp Ser Lys Asp Thr Glu
            740                 745                 750

Arg Gln Leu Ala Ala Met Gly Asn Ser Thr Ile Pro Pro Phe Asn Pro
        755                 760                 765

Asp Met His Gly Asp Asp Ser Lys Ala Val Leu Leu Phe Pro Asn Gly
    770                 775                 780

Thr Val Val Thr Leu Leu Gly Phe Glu Arg Arg Gln Ala Ile Arg Met
785                 790                 795                 800

Ser Gly Gln Tyr Leu Gly Ala Ser Leu Gly Gly Ala Phe Leu Ala Val
                805                 810                 815

Val Gly Phe Gly Ile Ile Gly Trp Met Leu Cys Gly Asn Ser Arg Leu
            820                 825                 830

Arg Glu Tyr Asn Lys Ile Pro Leu Thr
        835                 840
```

<210> SEQ ID NO 18
<211> LENGTH: 160
<212> TYPE: PRT
<213> ORGANISM: Varicella zoster virus

<400> SEQUENCE: 18

```
Met Ala Ser His Lys Trp Leu Leu Gln Met Ile Val Phe Leu Lys Thr
1               5                   10                  15

Ile Thr Ile Ala Tyr Cys Leu His Leu Gln Asp Asp Thr Pro Leu Phe
            20                  25                  30

Phe Gly Ala Lys Pro Leu Ser Asp Val Ser Leu Ile Ile Thr Glu Pro
        35                  40                  45

Cys Val Ser Ser Val Tyr Glu Ala Trp Asp Tyr Ala Ala Pro Pro Val
    50                  55                  60

Ser Asn Leu Ser Glu Ala Leu Ser Gly Ile Val Val Lys Thr Lys Cys
65                  70                  75                  80

Pro Val Pro Glu Val Ile Leu Trp Phe Lys Asp Lys Gln Met Ala Tyr
                85                  90                  95

Trp Thr Asn Pro Tyr Val Thr Leu Lys Gly Leu Thr Gln Ser Val Gly
            100                 105                 110

Glu Glu His Lys Ser Gly Asp Ile Arg Asp Ala Leu Leu Asp Ala Leu
        115                 120                 125

Ser Gly Val Trp Val Asp Ser Thr Pro Ser Ser Thr Asn Ile Pro Glu
    130                 135                 140

Asn Gly Cys Val Trp Gly Ala Asp Arg Leu Phe Gln Arg Val Cys Gln
145                 150                 155                 160
```

<210> SEQ ID NO 19
<211> LENGTH: 354
<212> TYPE: PRT
<213> ORGANISM: Varicella zoster virus

<400> SEQUENCE: 19

```
Met Phe Leu Ile Gln Cys Leu Ile Ser Ala Val Ile Phe Tyr Ile Gln
1               5                   10                  15

Val Thr Asn Ala Leu Ile Phe Lys Gly Asp His Val Ser Leu Gln Val
            20                  25                  30

Asn Ser Ser Leu Thr Ser Ile Leu Ile Pro Met Gln Asn Asp Asn Tyr
        35                  40                  45

Thr Glu Ile Lys Gly Gln Leu Val Phe Ile Gly Glu Gln Leu Pro Thr
    50                  55                  60

Gly Thr Asn Tyr Ser Gly Thr Leu Glu Leu Leu Tyr Ala Asp Thr Val
65                  70                  75                  80

Ala Phe Cys Phe Arg Ser Val Gln Val Ile Arg Tyr Asp Gly Cys Pro
                85                  90                  95

Arg Ile Arg Thr Ser Ala Phe Ile Ser Cys Arg Tyr Lys His Ser Trp
            100                 105                 110

His Tyr Gly Asn Ser Thr Asp Arg Ile Ser Thr Glu Pro Asp Ala Gly
        115                 120                 125

Val Met Leu Lys Ile Thr Lys Pro Gly Ile Asn Asp Ala Gly Val Tyr
    130                 135                 140

Val Leu Leu Val Arg Leu Asp His Ser Arg Ser Thr Asp Gly Phe Ile
145                 150                 155                 160

Leu Gly Val Asn Val Tyr Thr Ala Gly Ser His His Asn Ile His Gly
                165                 170                 175

Val Ile Tyr Thr Ser Pro Ser Leu Gln Asn Gly Tyr Ser Thr Arg Ala
```

```
            180                 185                 190

Leu Phe Gln Gln Ala Arg Leu Cys Asp Leu Pro Ala Thr Pro Lys Gly
        195                 200                 205

Ser Gly Thr Ser Leu Phe Gln His Met Leu Asp Leu Arg Ala Gly Lys
    210                 215                 220

Ser Leu Glu Asp Asn Pro Trp Leu His Glu Asp Val Val Thr Thr Glu
225                 230                 235                 240

Thr Lys Ser Val Val Lys Glu Gly Ile Glu Asn His Val Tyr Pro Thr
                245                 250                 255

Asp Met Ser Thr Leu Pro Glu Lys Ser Leu Asn Asp Pro Pro Glu Asn
            260                 265                 270

Leu Leu Ile Ile Ile Pro Ile Val Ala Ser Val Met Ile Leu Thr Ala
        275                 280                 285

Met Val Ile Val Ile Val Ile Ser Val Lys Arg Arg Arg Ile Lys Lys
    290                 295                 300

His Pro Ile Tyr Arg Pro Asn Thr Lys Thr Arg Arg Gly Ile Gln Asn
305                 310                 315                 320

Ala Thr Pro Glu Ser Asp Val Met Leu Glu Ala Ala Ile Ala Gln Leu
                325                 330                 335

Ala Thr Ile Arg Glu Glu Ser Pro Pro His Ser Val Val Asn Pro Phe
            340                 345                 350

Val Lys


<210> SEQ ID NO 20
<211> LENGTH: 623
<212> TYPE: PRT
<213> ORGANISM: Varicella zoster virus

<400> SEQUENCE: 20

Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Ile Asp Glu Asp Lys Leu Asp Thr Asn
        35                  40                  45

Ser Val Tyr Glu Pro Tyr Tyr His Ser Asp His Ala Glu Ser Ser Trp
    50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
        115                 120                 125

Asp Thr Gly Ile His Val Ile Pro Thr Leu Asn Gly Asp Asp Arg His
    130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
```

```
        195                 200                 205

Thr Gly Asp Ala Ala Pro Ala Ile Gln His Ile Cys Leu Lys His Thr
    210                 215                 220

Thr Cys Phe Gln Asp Val Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
            260                 265                 270

Glu Leu Glu Leu Asp Pro Pro Glu Ile Glu Pro Gly Val Leu Lys Val
        275                 280                 285

Leu Arg Thr Glu Lys Gln Tyr Leu Gly Val Tyr Ile Trp Asn Met Arg
    290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
            340                 345                 350

Val Gly Asp Thr Phe Ser Leu Ala Met His Leu Gln Tyr Lys Ile His
        355                 360                 365

Glu Ala Pro Phe Asp Leu Leu Leu Glu Trp Leu Tyr Val Pro Ile Asp
    370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
        435                 440                 445

Glu Pro Ser Phe Gly Leu Ile Leu His Asp Gly Gly Thr Thr Leu Lys
    450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr Lys Pro Lys Glu Ile Thr Pro Val
        515                 520                 525

Asn Pro Gly Thr Ser Pro Leu Leu Arg Tyr Ala Ala Trp Thr Gly Gly
    530                 535                 540

Leu Ala Ala Val Val Leu Leu Cys Leu Val Ile Phe Leu Ile Cys Thr
545                 550                 555                 560

Ala Lys Arg Met Arg Val Lys Ala Tyr Arg Val Asp Lys Ser Pro Tyr
                565                 570                 575

Asn Gln Ser Met Tyr Tyr Ala Gly Leu Pro Val Asp Asp Phe Glu Asp
            580                 585                 590

Ser Glu Ser Thr Asp Thr Glu Glu Glu Phe Gly Asn Ala Ile Gly Gly
        595                 600                 605

Ser His Gly Gly Ser Ser Tyr Thr Val Tyr Ile Asp Lys Thr Arg
    610                 615                 620
```

<210> SEQ ID NO 21
<211> LENGTH: 13339
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 21

```
ataggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagct cgccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tagacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
```

gagcgctgaa cactgatgaa gaatattaca aaactgtcaa gcccagcgag cacgacggcg 2040
aatacctgta cgacatcgac aggaaacagt gcgtcaagaa agaactagtc actgggctag 2100
ggctcacagg cgagctggtg gatcctccct tccatgaatt cgcctacgag agtctgagaa 2160
cacgaccagc cgctccttac caagtaccaa ccatagggggt gtatggcgtg ccaggatcag 2220
gcaagtctgg catcattaaa agcgcagtca ccaaaaaaga tctagtggtg agcgccaaga 2280
aagaaaactg tgcagaaatt ataagggacg tcaagaaaat gaaagggctg gacgtcaatg 2340
ccagaactgt ggactcagtg ctcttgaatg gatgcaaaca ccccgtagag accctgtata 2400
ttgacgaagc ttttgcttgt catgcaggta ctctcagagc gctcatagcc attataagac 2460
ctaaaaaggc agtgctctgc ggggatccca aacagtgcgg tttttttaac atgatgtgcc 2520
tgaaagtgca ttttaaccac gagatttgca cacaagtctt ccacaaaagc atctctcgcc 2580
gttgcactaa atctgtgact tcggtcgtct caaccttgtt ttacgacaaa aaaatgagaa 2640
cgacgaatcc gaaagagact aagattgtga ttgacactac cggcagtacc aaacctaagc 2700
aggacgatct cattctcact tgtttcagag ggtgggtgaa gcagttgcaa atagattaca 2760
aaggcaacga aataatgacg gcagctgcct ctcaagggct gacccgtaaa ggtgtgtatg 2820
ccgttcggta caaggtgaat gaaaatcctc tgtacgcacc cacctcagaa catgtgaacg 2880
tcctactgac ccgcacggag gaccgcatcg tgtggaaaac actagccggc gacccatgga 2940
taaaaacact gactgccaag taccctggga atttcactgc cacgatagag gagtggcaag 3000
cagagcatga tgccatcatg aggcacatct tggagagacc ggaccctacc gacgtcttcc 3060
agaataaggc aaacgtgtgt tgggccaagg ctttagtgcc ggtgctgaag accgctggca 3120
tagacatgac cactgaacaa tggaacactg tggattattt tgaaacggac aaagctcact 3180
cagcagagat agtattgaac caactatgcg tgaggttctt tggactcgat ctggactccg 3240
gtctattttc tgcacccact gttccgttat ccattaggaa taatcactgg gataactccc 3300
cgtcgcctaa catgtacggg ctgaataaag aagtggtccg tcagctctct cgcaggtacc 3360
cacaactgcc tcgggcagtt gccactggaa gagtctatga catgaacact ggtacactgc 3420
gcaattatga tccgcgcata aacctagtac ctgtaaacag aagactgcct catgctttag 3480
tcctccacca taatgaacac ccacagagtg acttttcttc attcgtcagc aaattgaagg 3540
gcagaactgt cctggtggtc ggggaaaagt tgtccgtccc aggcaaaatg gttgactggt 3600
tgtcagaccg gcctgaggct accttcagag ctcggctgga tttaggcatc ccaggtgatg 3660
tgcccaaata tgacataata tttgttaatg tgaggacccc atataaatac catcactatc 3720
agcagtgtga agaccatgcc attaagctta gcatgttgac caagaaagct tgtctgcatc 3780
tgaatcccgg cggaacctgt gtcagcatag gttatggtta cgctgacagg gccagcgaaa 3840
gcatcattgg tgctatagcg cggcagttca agttttcccg ggtatgcaaa ccgaaatcct 3900
cacttgaaga gacggaagtt ctgtttgtat tcattgggta cgatcgcaag gcccgtacgc 3960
acaatcctta caagctttca tcaaccttga ccaacattta tacaggttcc agactccacg 4020
aagccggatg tgcaccctca tatcatgtgg tgcgagggga tattgccacg gccaccgaag 4080
gagtgattat aaatgctgct aacagcaaag gacaacctgg cggaggggtg tgcggagcgc 4140
tgtataagaa attcccggaa agcttcgatt tacagccgat cgaagtagga aaagcgcgac 4200
tggtcaaagg tgcagctaaa catatcattc atgccgtagg accaaacttc aacaaagttt 4260
cggaggttga aggtgacaaa cagttggcag aggcttatga gtccatcgct aagattgtca 4320
acgataacaa ttacaagtca gtagcgattc cactgttgtc caccggcatc ttttccggga 4380

```
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
```

-continued

```
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtcgagtct   7560
agtcgacgcc accatgttcg tgaccgccgt ggtgtccgtg tcccccagca gcttttacga   7620
gagcctgcag gtcgagccca cccagagcga ggacatcaca agatctgccc acctgggcga   7680
cggcgacgag atcagagagg ccatccacaa gagccaggac gccgagacaa agcccacctt   7740
ctacgtgtgc cccccaccta ccggctctac aattgtgcgg ctggaacccc ccagaacctg   7800
ccctgattac cacctgggca agaacttcac cgagggaatt gccgtggtgt acaaagagaa   7860
tatcgccgcc tacaagttca aggccaccgt gtactacaag gacgtgatcg tgtccaccgc   7920
ctgggccggc agcagctaca cccagatcac caacagatac gccgaccggg tgcccatccc   7980
cgtgtctgag atcaccgaca ccatcgacaa gttcggcaag tgcagcagca aggccaccta   8040
cgtgcggaac aaccacaagg tggaagcctt caacgaggac aagaaccccc aggacatgcc   8100
cctgatcgcc agcaagtaca acagcgtggg ctccaaggcc tggcacacca ccaacgacac   8160
ctacatggtg gccggcaccc ccggcacata cagaacaggc accagcgtga actgcatcat   8220
cgaggaagtg gaagcccggt ccatcttccc atacgacagc ttcggcctga gcaccggcga   8280
cattatctac atgagccctt tcttcggcct gcgggacggc gcctacagag agcacagcaa   8340
ctacgccatg gaccggttcc accagttcga gggctacaga cagcgggacc tggacacaag   8400
agccctgctg gaacctgccg ccagaaactt cctggtcacc cctcacctga ccgtgggctg   8460
gaactggaag cccaagcgga ccgaagtgtg cagcctggtc aagtggcgcg aggtggaaga   8520
tgtcgtgcgg gatgagtacg cccacaactt ccggttcacc atgaagaccc tgagcaccac   8580
cttcatcagc gagacaaacg agttcaacct gaaccagatc cacctgagcc agtgcgtgaa   8640
agaggaagcc agagccatca tcaaccggat ctacaccacc cggtacaaca gcagccacgt   8700
gcggaccggc gatatccaga cctatctggc tagaggcggc ttcgtggtgg tgtttcagcc   8760
cctgctgagc aacagcctgg ctagactgta cctgcaggaa ctcgtcagag agaacaccaa   8820
ccacagcccc cagaagcacc ccacccggaa taccagatcc agacgcagcg tgcccgtgga   8880
actgagagcc aaccggacca tcaccaccac cagcagcgtg gaattcgcca tgctgcagtt   8940
cacctacgac cacatccagg aacacgtgaa cgagatgctg gcccggatca gcagcagttg   9000
gtgccagctg cagaatcggg aaagggccct gtggtccggc ctgttcccca tcaatccaag   9060
cgccctggcc agcaccatcc tggaccagag agtgaaggcc agaatcctgg gggacgtgat   9120
```

```
cagcgtgtcc aactgtcctg agctgggcag cgacacccgg atcatcctgc agaacagcat   9180
gcgggtgtcc ggcagcacca ccagatgcta cagcagaccc ctgatcagca tcgtgtccct   9240
gaacggcagc ggcacagtgg aaggccagct gggcaccgat aacgagctga tcatgagccg   9300
ggacctgctc gaaccctgcg tggccaatca caagcggtac tttctgttcg gccaccacta   9360
cgtgtactat gaggactaca gatacgtgcg cgagatcgcc gtgcacgacg tgggcatgat   9420
cagcacctac gtggacctga acctgaccct gctgaaggac cgcgagttca tgccactgca   9480
ggtctacacc cgggacgagc tgagagatac cggcctgctg gactacagcg agatccagcg   9540
gcggaaccag atgcactccc tgcggttcta cgacatcgac aaggtggtgc agtacgacag   9600
cggcaccgcc atcatgcagg gcatggccca gttctttcag ggcctgggaa cagccggaca   9660
ggccgtggga catgtggtgc tgggagctac aggcgccctg ctgtctaccg tgcacggctt   9720
caccaccttt ctgagcaacc ccttcggagc cctggctgtg ggactgctgg tcctggctgg   9780
actggtggcc gccttctttg cctaccgcta cgtgctgaag ctgaaaacca gccccatgaa   9840
ggccctgtac cccctgacca ccaagggcct gaagcagctg cctgagggca tggacccctt   9900
cgccgagaag cccaatgcca ccgacacccc catcgaggaa atcggcgaca gccagaacac   9960
cgagccctcc gtgaacagcg gcttcgaccc cgacaagttt cgcgaggccc aggaaatgat  10020
caagtacatg accctggtgt ctgctgccga gcggcaggaa agcaaggccc ggaagaagaa  10080
caagacctcc gccctgctga ccagcagact gacaggactg gccctgcgga acagacgggg  10140
ctatagcaga gtgcggaccg agaatgtgac cggcgtgtaa tctagacgcg gccgcataca  10200
gcagcaattg gcaagctgct tacatagaac tcgcggcgat tggcatgccg ccttaaaatt  10260
tttattttat ttttcttttc ttttccgaat cggattttgt ttttaatatt tcaaaaaaaa  10320
aaaaaaaaaa aaaaaaaaaa aaaaaaaggg tcggcatggc atctccacct cctcgcggtc  10380
cgacctgggc atccgaagga ggacgcacgt ccactcggat ggctaaggga gagccacgtt  10440
taaaccagct ccaattcgcc ctatagtgag tcgtattacg cgcgctcact ggccgtcgtt  10500
ttacaacgtc gtgactggga aaaccctggc gttacccaac ttaatcgcct tgcagcacat  10560
ccccctttcg ccagctggcg taatagcgaa gaggcccgca ccgatcgccc ttcccaacag  10620
ttgcgcagcc tgaatggcga atgggacgcg ccctgtagcg gcgcattaag cgcggcgggt  10680
gtggtggtta cgcgcagcgt gaccgctaca cttgccagcg ccctagcgcc cgctcctttc  10740
gctttcttcc cttcctttct cgccacgttc gccggctttc cccgtcaagc tctaaatcgg  10800
gggctccctt tagggttccg atttagtgct ttacggcacc tcgaccccaa aaaacttgat  10860
tagggtgatg gttcacgtag tgggccatcg ccctgataga cggtttttcg ccctttgacg  10920
ttggagtcca cgttctttaa tagtggactc ttgttccaaa ctggaacaac actcaaccct  10980
atctcggtct attcttttga tttataaggg attttgccga tttcggccta ttggttaaaa  11040
aatgagctga tttaacaaaa atttaacgcg aattttaaca aaatattaac gcttacaatt  11100
taggtggcac ttttcgggga aatgtgcgcg gaacccctat ttgtttattt ttctaaatac  11160
attcaaatat gtatccgctc atgagacaat aaccctgata aatgcttcaa taatattgaa  11220
aaaggaagag tatgagtatt caacatttcc gtgtcgccct tattcccttt tttgcggcat  11280
tttgccttcc tgtttttgct cacccagaaa cgctggtgaa agtaaaagat gctgaagatc  11340
agttgggtgc acgagtgggt tacatcgaac tggatctcaa cagcggtaag atccttgaga  11400
gttttcgccc cgaagaacgt tttccaatga tgagcacttt taaagttctg ctatgtggcg  11460
```

cggtattatc ccgtattgac gccgggcaag agcaactcgg tcgccgcata cactattctc 11520
agaatgactt ggttgagtac tcaccagtca cagaaaagca tcttacggat ggcatgacag 11580
taagagaatt atgcagtgct gccataacca tgagtgataa cactgcggcc aacttacttc 11640
tgacaacgat cggaggaccg aaggagctaa ccgctttttt gcacaacatg ggggatcatg 11700
taactcgcct tgatcgttgg gaaccggagc tgaatgaagc cataccaaac gacgagcgtg 11760
acaccacgat gcctgtagca atggcaacaa cgttgcgcaa actattaact ggcgaactac 11820
ttactctagc ttcccggcaa caattaatag actggatgga ggcggataaa gttgcaggac 11880
cacttctgcg ctcggccctt ccggctggct ggtttattgc tgataaatct ggagccggtg 11940
agcgtgggtc tcgcggtatc attgcagcac tggggccaga tggtaagccc tcccgtatcg 12000
tagttatcta cacgacgggg agtcaggcaa ctatggatga acgaaataga cagatcgctg 12060
agataggtgc ctcactgatt aagcattggt aactgtcaga ccaagtttac tcatatatac 12120
tttagattga tttaaaactt catttttaat ttaaaaggat ctaggtgaag atcctttttg 12180
ataatctcat gaccaaaatc ccttaacgtg agttttcgtt ccactgagcg tcagaccccg 12240
tagaaaagat caaaggatct tcttgagatc ctttttttct gcgcgtaatc tgctgcttgc 12300
aaacaaaaaa accaccgcta ccagcggtgg tttgtttgcc ggatcaagag ctaccaactc 12360
tttttccgaa ggtaactggc ttcagcagag cgcagatacc aaatactgtt cttctagtgt 12420
agccgtagtt aggccaccac ttcaagaact ctgtagcacc gcctacatac ctcgctctgc 12480
taatcctgtt accagtggct gctgccagtg gcgataagtc gtgtcttacc gggttggact 12540
caagacgata gttaccggat aaggcgcagc ggtcgggctg aacggggggt tcgtgcacac 12600
agcccagctt ggagcgaacg acctacaccg aactgagata cctacagcgt gagctatgag 12660
aaagcgccac gcttcccgaa gggagaaagg cggacaggta tccggtaagc ggcagggtcg 12720
gaacaggaga gcgcacgagg gagcttccag ggggaaacgc ctggtatctt tatagtcctg 12780
tcgggtttcg ccacctctga cttgagcgtc gatttttgtg atgctcgtca ggggggcgga 12840
gcctatggaa aaacgccagc aacgcggcct ttttacggtt cctggccttt tgctggcctt 12900
ttgctcacat gttctttcct gcgttatccc ctgattctgt ggataaccgt attaccgcct 12960
ttgagtgagc tgataccgct cgccgcagcc gaacgaccga gcgcagcgag tcagtgagcg 13020
aggaagcgga agagcgccca atacgcaaac cgcctctccc cgcgcgttgg ccgattcatt 13080
aatgcagctg gcacgacagg tttcccgact ggaaagcggg cagtgagcgc aacgcaatta 13140
atgtgagtta gctcactcat taggcacccc aggctttaca ctttatgctc ccggctcgta 13200
tgttgtgtgg aattgtgagc ggataacaat ttcacacagg aaacagctat gaccatgatt 13260
acgccaagcg cgcaattaac cctcactaaa gggaacaaaa gctgggtacc gggcccacgc 13320
gtaatacgac tcactatag 13339

<210> SEQ ID NO 22
<211> LENGTH: 13258
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 22
ataggcggcg catgagagaa gcccagacca attacctacc caaaatggag aaagttcacg 60
ttgacatcga ggaagacagc ccattcctca gagctttgca gcggagcttc ccgcagtttg 120

-continued

```
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagct cgccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa catagggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tagacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
```

```
ctaaaaaggc agtgctctgc ggggatccca aacagtgcgg ttttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgaggggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
```

```
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
```

```
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtcgagtct   7560
agtcgacgcc accatgttcg ccctggtgct ggccgtggtc atcctgcctc tgtggaccac   7620
cgccaacaag agctacgtga cccccacacc cgccaccaga tccatcggac acatgagcgc   7680
cctgctgaga gagtacagcg accggaacat gagcctgaag ctggaagcct tctaccccac   7740
cggcttcgac gaggaactga tcaagagcct gcactggggc aacgaccgga agcacgtgtt   7800
cctcgtgatc gtgaaagtga accccaccac ccacgagggc gacgtcggcc tggtcatctt   7860
ccccaagtac ctgctgagcc cctaccactt caaggccgag cacagagccc ccttccctgc   7920
tggccgcttt ggctttctga gccaccctgt gacccccgac gtgtcattct tcgacagcag   7980
cttcgccccc tacctgacca cacagcacct ggtggccttc accaccttcc cccccaatcc   8040
tctcgtgtgg cacctggaaa gagccgagac agccgccacc gccgaaagac cttttggcgt   8100
gtccctgctg cccgccagac ctaccgtgcc caagaacacc atcctggaac acaaggccca   8160
cttcgccacc tgggatgccc tggccagaca caccttcttt agcgccgagg ccatcatcac   8220
caacagcacc ctgagaatcc acgtgcccct gttcggcagc gtgtggccca tcagatactg   8280
ggccacaggc agcgtgctgc tgaccagcga tagcggcaga gtggaagtga acatcggcgt   8340
gggcttcatg agcagcctga tcagcctgag cagcggcctg cccatcgagc tgattgtggt   8400
gccccacacc gtgaagctga acgccgtgac cagcgacacc acctggttcc agctgaaccc   8460
ccctggccct gatcctggcc ctagttacag agtgtacctg ctgggcagag gcctggacat   8520
gaacttcagc aagcacgcca ccgtggacat ctgcgcctac cctgaggaaa gcctggacta   8580
cagataccac ctgagcatgg cccacaccga ggccctgaga atgaccacca aggccgacca   8640
gcacgacatc aacgaggaaa gctactacca cattgccgcc agaatcgcca ccagcatctt   8700
cgccctgagc gagatgggcc ggaccaccga gtactttctg ctggacgaga tcgtggacgt   8760
gcagtaccag ctgaagttcc tgaactacat cctgatgcgg atcggcgctg gcgcccaccc   8820
taataccatc agcggcacca gcgacctgat cttcgccgat cctagccagc tgcacgacga   8880
gctgagcctg ctgttcggcc aggtcaaacc cgccaacgtg gactacttca tcagctacga   8940
cgaggcccgg gaccagctga aaacagccta cgccctgtcc agaggccagg atcatgtgaa   9000
cgccctgtcc ctggccaggc gcgtgatcat gagcatctac aagggcctgc tggtcaagca   9060
gaacctgaac gccaccgagc ggcaggccct gttcttcgcc agcatgatcc tgctgaactt   9120
cagagagggc ctggaaaaca gcagccgggt gctggatggc agaaccaccc tgctgctgat   9180
gaccagcatg tgcacagccg cccatgccac acaggccgcc ctgaatatcc aggaaggcct   9240
ggcttacctg aaccccagca agcacatgtt caccatcccc aacgtgtaca gcccctgcat   9300
gggcagcctg agaaccgacc tgaccgaaga gatccacgtg atgaacctgc tgtccgccat   9360
ccccaccaga cccggactga atgaggtgct gcacacccag ctggacgagt ccgagatctt   9420
cgacgccgcc ttcaagacca tgatgatctt taccacctgg accgccaagg acctgcacat   9480
cctgcacaca cacgtgcccg aggtgttcac atgccaagat gccgccgctc ggaacggcga   9540
gtatgtgctg attctgcctg ccgtgcaggg ccacagctac gtgatcaccc ggaacaagcc   9600
```

```
ccagcggggc ctggtgtata gcctggctga cgtggacgtg tacaacccca tcagcgtggt   9660
gtacctgagc aaggatacct gcgtgtccga gcacggcgtg atcgaaacag tggccctgcc   9720
ccaccccgac aacctgaaag agtgcctgta ctgcggctcc gtgttcctgc ggtatctgac   9780
caccggcgcc atcatggaca tcatcatcat cgacagcaag gacaccgaga gacagctggc   9840
cgccatgggc aacagcacca tcccccccctt caaccccgac atgcacggcg acgatagcaa   9900
ggccgtgctg ctgttcccca acggcaccgt ggtcacactg ctgggcttcg agcggagaca   9960
ggccatcaga atgagcggcc agtacctggg cgcctctctg ggtggtgcct ttctggccgt  10020
cgtgggcttt ggcatcatcg gctggatgct gtgcggcaac agcagactgc gcgagtacaa  10080
caagatcccc ctgacctaat ctagacgcgg ccgcatacag cagcaattgg caagctgctt  10140
acatagaact cgcggcgatt ggcatgccgc cttaaaattt ttattttatt tttctttttct  10200
tttccgaatc ggattttgtt tttaatattt caaaaaaaaa aaaaaaaaaa aaaaaaaaaa  10260
aaaaaagggt cggcatggca tctccacctc ctcgcggtcc gacctgggca tccgaaggag  10320
gacgcacgtc cactcggatg gctaagggag agccacgttt aaaccagctc caattcgccc  10380
tatagtgagt cgtattacgc gcgctcactg gccgtcgttt tacaacgtcg tgactgggaa  10440
aaccctggcg ttacccaact taatcgcctt gcagcacatc ccccctttcgc cagctggcgt  10500
aatagcgaag aggcccgcac cgatcgccct tcccaacagt tgcgcagcct gaatggcgaa  10560
tgggacgcgc cctgtagcgg cgcattaagc gcggcgggtg tggtggttac gcgcagcgtg  10620
accgctacac ttgccagcgc cctagcgccc gctcctttcg ctttcttccc ttcctttctc  10680
gccacgttcg ccggctttcc ccgtcaagct ctaaatcggg ggctcccttt agggttccga  10740
tttagtgctt tacggcacct cgaccccaaa aaacttgatt agggtgatgg ttcacgtagt  10800
gggccatcgc cctgatagac ggtttttcgc cctttgacgt tggagtccac gttctttaat  10860
agtggactct tgttccaaac tggaacaaca ctcaacccta tctcggtcta ttcttttgat  10920
ttataaggga ttttgccgat ttcggcctat tggttaaaaa atgagctgat ttaacaaaaa  10980
tttaacgcga attttaacaa aatattaacg cttacaattt aggtggcact tttcggggaa  11040
atgtgcgcgg aacccctatt tgtttatttt tctaaataca ttcaaatatg tatccgctca  11100
tgagacaata accctgataa atgcttcaat aatattgaaa aaggaagagt atgagtattc  11160
aacatttccg tgtcgccctt attccctttt ttgcggcatt ttgccttcct gtttttgctc  11220
acccagaaac gctggtgaaa gtaaaagatg ctgaagatca gttgggtgca cgagtgggtt  11280
acatcgaact ggatctcaac agcggtaaga tccttgagag ttttcgcccc gaagaacgtt  11340
ttccaatgat gagcactttt aaagttctgc tatgtggcgc ggtattatcc cgtattgacg  11400
ccgggcaaga gcaactcggt cgccgcatac actattctca gaatgacttg gttgagtact  11460
caccagtcac agaaaagcat cttacggatg gcatgacagt aagagaatta tgcagtgctg  11520
ccataaccat gagtgataac actgcggcca acttacttct gacaacgatc ggaggaccga  11580
aggagctaac cgcttttttg cacaacatgg gggatcatgt aactcgcctt gatcgttggg  11640
aaccggagct gaatgaagcc ataccaaacg acgagcgtga caccacgatg cctgtagcaa  11700
tggcaacaac gttgcgcaaa ctattaactg gcgaactact tactctagct tcccggcaac  11760
aattaataga ctggatggag gcggataaag ttgcaggacc acttctgcgc tcggcccttc  11820
cggctggctg gtttattgct gataaatctg gagccggtga gcgtgggtct cgcggtatca  11880
ttgcagcact ggggccagat ggtaagccct cccgtatcgt agttatctac acgacgggga  11940
```

```
gtcaggcaac tatggatgaa cgaaatagac agatcgctga gataggtgcc tcactgatta  12000

agcattggta actgtcagac caagtttact catatatact ttagattgat ttaaaacttc  12060

atttttaatt taaaaggatc taggtgaaga tcctttttga taatctcatg accaaaatcc  12120

cttaacgtga gttttcgttc cactgagcgt cagaccccgt agaaaagatc aaaggatctt  12180

cttgagatcc tttttttctg cgcgtaatct gctgcttgca aacaaaaaaa ccaccgctac  12240

cagcggtggt ttgtttgccg gatcaagagc taccaactct ttttccgaag gtaactggct  12300

tcagcagagc gcagatacca aatactgttc ttctagtgta gccgtagtta ggccaccact  12360

tcaagaactc tgtagcaccg cctacatacc tcgctctgct aatcctgtta ccagtggctg  12420

ctgccagtgg cgataagtcg tgtcttaccg ggttggactc aagacgatag ttaccggata  12480

aggcgcagcg gtcgggctga acggggggtt cgtgcacaca gcccagcttg gagcgaacga  12540

cctacaccga actgagatac ctacagcgtg agctatgaga aagcgccacg cttcccgaag  12600

ggagaaaggc ggacaggtat ccggtaagcg gcagggtcgg aacaggagag cgcacgaggg  12660

agcttccagg gggaaacgcc tggtatcttt atagtcctgt cgggtttcgc cacctctgac  12720

ttgagcgtcg atttttgtga tgctcgtcag gggggcggag cctatggaaa aacgccagca  12780

acgcggcctt tttacggttc ctggcctttt gctggccttt tgctcacatg ttctttcctg  12840

cgttatcccc tgattctgtg gataaccgta ttaccgcctt tgagtgagct gataccgctc  12900

gccgcagccg aacgaccgag cgcagcgagt cagtgagcga ggaagcggaa gagcgcccaa  12960

tacgcaaacc gcctctcccc gcgcgttggc cgattcatta atgcagctgg cacgacaggt  13020

ttcccgactg gaaagcgggc agtgagcgca acgcaattaa tgtgagttag ctcactcatt  13080

aggcacccca ggctttacac tttatgctcc cggctcgtat gttgtgtgga attgtgagcg  13140

gataacaatt tcacacagga aacagctatg accatgatta cgccaagcgc gcaattaacc  13200

ctcactaaag ggaacaaaag ctgggtaccg ggcccacgcg taatacgact cactatag    13258
```

```
<210> SEQ ID NO 23
<211> LENGTH: 11215
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 23

ataggcggcg catgagagaa gcccagacca attacctacc caaaatggag aaagttcacg     60

ttgacatcga ggaagacagc ccattcctca gagctttgca gcggagcttc ccgcagtttg    120

aggtagaagc caagcaggtc actgataatg accatgctaa tgccagagcg ttttcgcatc    180

tggcttcaaa actgatcgaa acggaggtgg acccatccga cacgatcctt gacattggaa    240

gtgcgcccgc ccgcagaatg tattctaagc acaagtatca ttgtatctgt ccgatgagat    300

gtgcggaaga tccggacaga ttgtataagt atgcaactaa gctgaagaaa aactgtaagg    360

aaataactga taaggaattg gacaagaaaa tgaaggagct cgccgccgtc atgagcgacc    420

ctgacctgga aactgagact atgtgcctcc acgacgacga gtcgtgtcgc tacgaagggc    480

aagtcgctgt ttaccaggat gtatacgcgg ttgacggacc gacaagtctc tatcaccaag    540

ccaataaggg agttagagtc gcctactgga taggctttga caccacccct tttatgttta    600

agaacttggc tggagcatat ccatcatact ctaccaactg ggccgacgaa accgtgttaa    660

cggctcgtaa cataggccta tgcagctctg acgttatgga gcggtcacgt agagggatgt    720
```

```
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tagacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataaggacg tcaagaaaat gaaagggctg gacgtcaatg    2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttaac atgatgtgcc    2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
```

```
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgaggggga tattgccacg gccaccgaag   4080
gagtgattat aaatgctgct aacagcaaag gacaacctgg cggagggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
```

```
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtcgagtct   7560
agtcgacgcc accatggcca gccacaagtg gctgctgcag atgatcgtgt tcctgaaaac   7620
catcacaatc gcctactgcc tgcatctgca ggacgacacc cctctgttct tcggcgccaa   7680
gcctctgagc gacgtgtccc tgatcatcac cgagccttgc gtgtccagcg tgtacgaggc   7740
ctgggattat gccgcccctc ccgtgtccaa tctgagcgaa gccctgagcg gcatcgtggt   7800
```

```
caagaccaag tgccccgtgc ccgaagtgat cctgtggttc aaggacaagc agatggccta   7860
ctggaccaac ccttacgtga ccctgaaggg cctgacccag agcgtgggcg aggaacacaa   7920
gagcggcgac atcagagatg ccctgctgga tgccctgtcc ggtgtctggg tggacagcac   7980
accctccagc accaacatcc ccgagaacgg ctgtgtgtgg ggagccgacc ggctgttcca   8040
gagagtgtgt cagtaatcta gacgcggccg catacagcag caattggcaa gctgcttaca   8100
tagaactcgc ggcgattggc atgccgcctt aaaattttta ttttattttt cttttctttt   8160
ccgaatcgga ttttgttttt aatatttcaa aaaaaaaaaa aaaaaaaaaa aaaaaaaaaa   8220
aaagggtcgg catggcatct ccacctcctc gcggtccgac ctgggcatcc gaaggaggac   8280
gcacgtccac tcggatggct aagggagagc cacgtttaaa ccagctccaa ttcgccctat   8340
agtgagtcgt attacgcgcg ctcactggcc gtcgttttac aacgtcgtga ctgggaaaac   8400
cctggcgtta cccaacttaa tcgccttgca gcacatcccc ctttcgccag ctggcgtaat   8460
agcgaagagg cccgcaccga tcgcccttcc caacagttgc gcagcctgaa tggcgaatgg   8520
gacgcgccct gtagcggcgc attaagcgcg gcgggtgtgg tggttacgcg cagcgtgacc   8580
gctacacttg ccagcgccct agcgcccgct cctttcgctt tcttcccttc ctttctcgcc   8640
acgttcgccg gctttccccg tcaagctcta aatcgggggc tccctttagg gttccgattt   8700
agtgctttac ggcacctcga ccccaaaaaa cttgattagg gtgatggttc acgtagtggg   8760
ccatcgccct gatagacggt ttttcgccct ttgacgttgg agtccacgtt ctttaatagt   8820
ggactcttgt tccaaactgg aacaacactc aaccctatct cggtctattc ttttgattta   8880
taagggattt tgccgatttc ggcctattgg ttaaaaaatg agctgattta acaaaaattt   8940
aacgcgaatt ttaacaaaat attaacgctt acaatttagg tggcactttt cggggaaatg   9000
tgcgcggaac ccctatttgt ttatttttct aaatacattc aaatatgtat ccgctcatga   9060
gacaataacc ctgataaatg cttcaataat attgaaaaag gaagagtatg agtattcaac   9120
atttccgtgt cgcccttatt cccttttttg cggcattttg ccttcctgtt tttgctcacc   9180
cagaaacgct ggtgaaagta aaagatgctg aagatcagtt gggtgcacga gtgggttaca   9240
tcgaactgga tctcaacagc ggtaagatcc ttgagagttt tcgccccgaa gaacgttttc   9300
caatgatgag cacttttaaa gttctgctat gtggcgcggt attatcccgt attgacgccg   9360
ggcaagagca actcggtcgc cgcatacact attctcagaa tgacttggtt gagtactcac   9420
cagtcacaga aaagcatctt acggatggca tgacagtaag agaattatgc agtgctgcca   9480
taaccatgag tgataacact gcggccaact tacttctgac aacgatcgga ggaccgaagg   9540
agctaaccgc ttttttgcac aacatggggg atcatgtaac tcgccttgat cgttgggaac   9600
cggagctgaa tgaagccata ccaaacgacg agcgtgacac cacgatgcct gtagcaatgg   9660
caacaacgtt gcgcaaacta ttaactggcg aactacttac tctagcttcc cggcaacaat   9720
taatagactg gatggaggcg gataaagttg caggaccact tctgcgctcg gcccttccgg   9780
ctggctggtt tattgctgat aaatctggag ccggtgagcg tgggtctcgc ggtatcattg   9840
cagcactggg gccagatggt aagccctccc gtatcgtagt tatctacacg acggggagtc   9900
aggcaactat ggatgaacga aatagacaga tcgctgagat aggtgcctca ctgattaagc   9960
attggtaact gtcagaccaa gtttactcat atatacttta gattgattta aaacttcatt  10020
tttaatttaa aaggatctag gtgaagatcc tttttgataa tctcatgacc aaaatccctt  10080
aacgtgagtt ttcgttccac tgagcgtcag accccgtaga aaagatcaaa ggatcttctt  10140
gagatccttt ttttctgcgc gtaatctgct gcttgcaaac aaaaaaacca ccgctaccag  10200
```

```
cggtggtttg tttgccggat caagagctac caactctttt tccgaaggta actggcttca  10260

gcagagcgca gataccaaat actgttcttc tagtgtagcc gtagttaggc caccacttca  10320

agaactctgt agcaccgcct acatacctcg ctctgctaat cctgttacca gtggctgctg  10380

ccagtggcga taagtcgtgt cttaccgggt tggactcaag acgatagtta ccggataagg  10440

cgcagcggtc gggctgaacg gggggttcgt gcacacagcc cagcttggag cgaacgacct  10500

acaccgaact gagataccta cagcgtgagc tatgagaaag cgccacgctt cccgaaggga  10560

gaaaggcgga caggtatccg gtaagcggca gggtcggaac aggagagcgc acgagggagc  10620

ttccaggggg aaacgcctgg tatctttata gtcctgtcgg gtttcgccac ctctgacttg  10680

agcgtcgatt tttgtgatgc tcgtcagggg ggcggagcct atggaaaaac gccagcaacg  10740

cggccttttt acggttcctg gccttttgct ggccttttgc tcacatgttc tttcctgcgt  10800

tatcccctga ttctgtggat aaccgtatta ccgcctttga gtgagctgat accgctcgcc  10860

gcagccgaac gaccgagcgc agcgagtcag tgagcgagga agcggaagag cgcccaatac  10920

gcaaaccgcc tctccccgcg cgttggccga ttcattaatg cagctggcac gacaggtttc  10980

ccgactggaa agcgggcagt gagcgcaacg caattaatgt gagttagctc actcattagg  11040

caccccaggc tttacacttt atgctcccgg ctcgtatgtt gtgtggaatt gtgagcggat  11100

aacaatttca cacaggaaac agctatgacc atgattacgc caagcgcgca attaaccctc  11160

actaaaggga acaaaagctg ggtaccgggc ccacgcgtaa tacgactcac tatag       11215
```

```
<210> SEQ ID NO 24
<211> LENGTH: 13827
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 24
```

```
ataggcggcg catgagagaa gcccagacca attacctacc caaaatggag aaagttcacg     60

ttgacatcga ggaagacagc ccattcctca gagctttgca gcggagcttc ccgcagtttg    120

aggtagaagc caagcaggtc actgataatg accatgctaa tgccagagcg ttttcgcatc    180

tggcttcaaa actgatcgaa acggaggtgg acccatccga cacgatcctt gacattggaa    240

gtgcgcccgc ccgcagaatg tattctaagc acaagtatca ttgtatctgt ccgatgagat    300

gtgcggaaga tccggacaga ttgtataagt atgcaactaa gctgaagaaa aactgtaagg    360

aaataactga taaggaattg gacaagaaaa tgaaggagct cgccgccgtc atgagcgacc    420

ctgacctgga aactgagact atgtgcctcc acgacgacga gtcgtgtcgc tacgaagggc    480

aagtcgctgt ttaccaggat gtatacgcgg ttgacggacc gacaagtctc tatcaccaag    540

ccaataaggg agttagagtc gcctactgga taggctttga caccacccct tttatgttta    600

agaacttggc tggagcatat ccatcatact ctaccaactg ggccgacgaa accgtgttaa    660

cggctcgtaa cataggccta tgcagctctg acgttatgga gcggtcacgt agagggatgt    720

ccattcttag aaagaagtat ttgaaaccat ccaacaatgt tctattctct gttggctcga    780

ccatctacca cgagaagagg gacttactga ggagctggca cctgccgtct gtatttcact    840

tacgtggcaa gcaaaattac acatgtcggt gtgagactat agttagttgc gacgggtacg    900

tcgttaaaag aatagctatc agtccaggcc tgtatgggaa gccttcaggc tatgctgcta    960
```

-continued

```
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tagacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
```

```
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
```

```
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtcgagtct   7560
agtcgacgcc accatgttcg ccctggtgct ggccgtggtc atcctgcctc tgtggaccac   7620
cgccaacaag agctacgtga cccccacacc cgccaccaga tccatcggac acatgagcgc   7680
cctgctgaga gagtacagcg accggaacat gagcctgaag ctggaagcct tctaccccac   7740
cggcttcgac gaggaactga tcaagagcct gcactggggc aacgaccgga agcacgtgtt   7800
cctcgtgatc gtgaaagtga accccaccac ccacgagggc gacgtcggcc tggtcatctt   7860
ccccaagtac ctgctgagcc cctaccactt caaggccgag cacagagccc ccttccctgc   7920
tggccgcttt ggctttctga gccaccctgt gacccccgac gtgtcattct tcgacagcag   7980
cttcgccccc tacctgacca cacagcacct ggtggccttc accaccttcc cccccaatcc   8040
tctcgtgtgg cacctggaaa gagccgagac agccgccacc gccgaaagac cttttggcgt   8100
```

```
gtccctgctg cccgccagac ctaccgtgcc caagaacacc atcctggaac acaaggccca   8160
cttcgccacc tgggatgccc tggccagaca caccttcttt agcgccgagg ccatcatcac   8220
caacagcacc ctgagaatcc acgtgcccct gttcggcagc gtgtggccca tcagatactg   8280
ggccacaggc agcgtgctgc tgaccagcga tagcggcaga gtggaagtga acatcggcgt   8340
gggcttcatg agcagcctga tcagcctgag cagcggcctg cccatcgagc tgattgtggt   8400
gccccacacc gtgaagctga acgccgtgac cagcgacacc acctggttcc agctgaaccc   8460
ccctggccct gatcctggcc ctagttacag agtgtacctg ctgggcagag gcctggacat   8520
gaacttcagc aagcacgcca ccgtggacat ctgcgcctac cctgaggaaa gcctggacta   8580
cagataccac ctgagcatgg cccacaccga ggccctgaga atgaccacca aggccgacca   8640
gcacgacatc aacgaggaaa gctactacca cattgccgcc agaatcgcca ccagcatctt   8700
cgccctgagc gagatgggcc ggaccaccga gtactttctg ctggacgaga tcgtggacgt   8760
gcagtaccag ctgaagttcc tgaactacat cctgatgcgg atcggcgctg gcgcccaccc   8820
taataccatc agcggcacca gcgacctgat cttcgccgat cctagccagc tgcacgacga   8880
gctgagcctg ctgttcggcc aggtcaaacc cgccaacgtg gactacttca tcagctacga   8940
cgaggcccgg gaccagctga aaacagccta cgccctgtcc agaggccagg atcatgtgaa   9000
cgccctgtcc ctggccaggc gcgtgatcat gagcatctac aagggcctgc tggtcaagca   9060
gaacctgaac gccaccgagc ggcaggccct gttcttcgcc agcatgatcc tgctgaactt   9120
cagagagggc ctggaaaaca gcagccgggt gctggatggc agaaccaccc tgctgctgat   9180
gaccagcatg tgcacagccg cccatgccac acaggccgcc ctgaatatcc aggaaggcct   9240
ggcttacctg aaccccagca agcacatgtt caccatcccc aacgtgtaca gcccctgcat   9300
gggcagcctg agaaccgacc tgaccgaaga gatccacgtg atgaacctgc tgtccgccat   9360
ccccaccaga cccggactga atgaggtgct gcacacccag ctggacgagt ccgagatctt   9420
cgacgccgcc ttcaagacca tgatgatctt taccacctgg accgccaagg acctgcacat   9480
cctgcacaca cacgtgcccg aggtgttcac atgccaagat gccgccgctc ggaacggcga   9540
gtatgtgctg attctgcctg ccgtgcaggg ccacagctac gtgatcaccc ggaacaagcc   9600
ccagcggggc ctggtgtata gcctggctga cgtggacgtg tacaacccca tcagcgtggt   9660
gtacctgagc aaggatacct gcgtgtccga gcacggcgtg atcgaaacag tggccctgcc   9720
ccaccccgac aacctgaaag agtgcctgta ctgcggctcc gtgttcctgc ggtatctgac   9780
caccggcgcc atcatggaca tcatcatcat cgacagcaag gacaccgaga gacagctggc   9840
cgccatgggc aacagcacca tcccccccctt caaccccgac atgcacggcg acgatagcaa   9900
ggccgtgctg ctgttcccca acggcaccgt ggtcacactg ctgggcttcg agcggagaca   9960
ggccatcaga atgagcggcc agtacctggg cgcctctctg ggtggtgcct ttctggccgt  10020
cgtgggcttt ggcatcatcg gctggatgct gtgcggcaac agcagactgc gcgagtacaa  10080
caagatcccc ctgacctaat ctagacgtcg cgaccaccca ggatccgcct ataactctct  10140
acggctaacc tgaatggact acgacatagt ctagtcgacg ccaccatggc cagccacaag  10200
tggctgctgc agatgatcgt gttcctgaaa accatcacaa tcgcctactg cctgcatctg  10260
caggacgaca cccctctgtt cttcggcgcc aagcctctga gcgacgtgtc cctgatcatc  10320
accgagcctt gcgtgtccag cgtgtacgag gcctgggatt atgccgcccc tcccgtgtcc  10380
aatctgagcg aagccctgag cggcatcgtg gtcaagacca agtgccccgt gcccgaagtg  10440
```

```
atcctgtggt tcaaggacaa gcagatggcc tactggacca acccttacgt gaccctgaag  10500
ggcctgaccc agagcgtggg cgaggaacac aagagcggcg acatcagaga tgccctgctg  10560
gatgccctgt ccggtgtctg ggtggacagc acaccctcca gcaccaacat ccccgagaac  10620
ggctgtgtgt ggggagccga ccggctgttc cagagagtgt gtcagtaatc tagacgcggc  10680
cgcatacagc agcaattggc aagctgctta catagaactc gcggcgattg gcatgccgcc  10740
ttaaaatttt tattttattt ttcttttctt ttccgaatcg gattttgttt ttaatatttc  10800
aaaaaaaaaa aaaaaaaaaa aaaaaaaaaa aaaaagggtc ggcatggcat ctccacctcc  10860
tcgcggtccg acctgggcat ccgaaggagg acgcacgtcc actcggatgg ctaagggaga  10920
gccacgttta aaccagctcc aattcgccct atagtgagtc gtattacgcg cgctcactgg  10980
ccgtcgtttt acaacgtcgt gactgggaaa accctggcgt tacccaactt aatcgccttg  11040
cagcacatcc ccctttcgcc agctggcgta atagcgaaga ggcccgcacc gatcgccctt  11100
cccaacagtt gcgcagcctg aatggcgaat gggacgcgcc ctgtagcggc gcattaagcg  11160
cggcgggtgt ggtggttacg cgcagcgtga ccgctacact tgccagcgcc ctagcgcccg  11220
ctcctttcgc tttcttccct tcctttctcg ccacgttcgc cggctttccc cgtcaagctc  11280
taaatcgggg gctcccttta gggttccgat ttagtgcttt acggcacctc gaccccaaaa  11340
aacttgatta gggtgatggt tcacgtagtg ggccatcgcc ctgatagacg gtttttcgcc  11400
ctttgacgtt ggagtccacg ttctttaata gtggactctt gttccaaact ggaacaacac  11460
tcaaccctat ctcggtctat tcttttgatt tataagggat tttgccgatt tcggcctatt  11520
ggttaaaaaa tgagctgatt taacaaaaat ttaacgcgaa ttttaacaaa atattaacgc  11580
ttacaattta ggtggcactt ttcggggaaa tgtgcgcgga acccctattt gtttattttt  11640
ctaaatacat tcaaatatgt atccgctcat gagacaataa ccctgataaa tgcttcaata  11700
atattgaaaa aggaagagta tgagtattca acatttccgt gtcgccctta ttcccttttt  11760
tgcggcattt tgccttcctg tttttgctca cccagaaacg ctggtgaaag taaaagatgc  11820
tgaagatcag ttgggtgcac gagtgggtta catcgaactg gatctcaaca gcggtaagat  11880
ccttgagagt tttcgccccg aagaacgttt tccaatgatg agcactttta aagttctgct  11940
atgtggcgcg gtattatccc gtattgacgc cgggcaagag caactcggtc gccgcataca  12000
ctattctcag aatgacttgg ttgagtactc accagtcaca gaaaagcatc ttacggatgg  12060
catgacagta agagaattat gcagtgctgc cataaccatg agtgataaca ctgcggccaa  12120
cttacttctg acaacgatcg gaggaccgaa ggagctaacc gcttttttgc acaacatggg  12180
ggatcatgta actcgccttg atcgttggga accggagctg aatgaagcca taccaaacga  12240
cgagcgtgac accacgatgc ctgtagcaat ggcaacaacg ttgcgcaaac tattaactgg  12300
cgaactactt actctagctt cccggcaaca attaatagac tggatggagg cggataaagt  12360
tgcaggacca cttctgcgct cggcccttcc ggctggctgg tttattgctg ataaatctgg  12420
agccggtgag cgtgggtctc gcggtatcat tgcagcactg gggccagatg gtaagccctc  12480
ccgtatcgta gttatctaca cgacggggag tcaggcaact atggatgaac gaaatagaca  12540
gatcgctgag ataggtgcct cactgattaa gcattggtaa ctgtcagacc aagtttactc  12600
atatatactt tagattgatt taaaacttca tttttaattt aaaaggatct aggtgaagat  12660
cctttttgat aatctcatga ccaaaatccc ttaacgtgag ttttcgttcc actgagcgtc  12720
agaccccgta gaaaagatca aaggatcttc ttgagatcct ttttttctgc gcgtaatctg  12780
ctgcttgcaa acaaaaaaac caccgctacc agcggtggtt tgtttgccgg atcaagagct  12840
```

```
accaactctt tttccgaagg taactggctt cagcagagcg cagataccaa atactgttct  12900

tctagtgtag ccgtagttag gccaccactt caagaactct gtagcaccgc ctacatacct  12960

cgctctgcta atcctgttac cagtggctgc tgccagtggc gataagtcgt gtcttaccgg  13020

gttggactca agacgatagt taccggataa ggcgcagcgg tcgggctgaa cggggggttc  13080

gtgcacacag cccagcttgg agcgaacgac ctacaccgaa ctgagatacc tacagcgtga  13140

gctatgagaa agcgccacgc ttcccgaagg gagaaaggcg gacaggtatc cggtaagcgg  13200

cagggtcgga acaggagagc gcacgaggga gcttccaggg ggaaacgcct ggtatcttta  13260

tagtcctgtc gggtttcgcc acctctgact tgagcgtcga tttttgtgat gctcgtcagg  13320

ggggcggagc ctatggaaaa acgccagcaa cgcggccttt ttacggttcc tggccttttg  13380

ctggcctttt gctcacatgt tctttcctgc gttatcccct gattctgtgg ataaccgtat  13440

taccgccttt gagtgagctg ataccgctcg ccgcagccga acgaccgagc gcagcgagtc  13500

agtgagcgag gaagcggaag agcgcccaat acgcaaaccg cctctccccg cgcgttggcc  13560

gattcattaa tgcagctggc acgacaggtt tcccgactgg aaagcgggca gtgagcgcaa  13620

cgcaattaat gtgagttagc tcactcatta ggcaccccag gctttacact ttatgctccc  13680

ggctcgtatg ttgtgtggaa ttgtgagcgg ataacaattt cacacaggaa acagctatga  13740

ccatgattac gccaagcgcg caattaaccc tcactaaagg gaacaaaagc tgggtaccgg  13800

gcccacgcgt aatacgactc actatag                                     13827
```

<210> SEQ ID NO 25
<211> LENGTH: 12604
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 25

```
ataggcggcg catgagagaa gcccagacca attacctacc caaaatggag aaagttcacg     60

ttgacatcga ggaagacagc ccattcctca gagctttgca gcggagcttc ccgcagtttg    120

aggtagaagc caagcaggtc actgataatg accatgctaa tgccagagcg ttttcgcatc    180

tggcttcaaa actgatcgaa acggaggtgg acccatccga cacgatcctt gacattggaa    240

gtgcgcccgc ccgcagaatg tattctaagc acaagtatca ttgtatctgt ccgatgagat    300

gtgcggaaga tccggacaga ttgtataagt atgcaactaa gctgaagaaa aactgtaagg    360

aaataactga taaggaattg gacaagaaaa tgaaggagct cgccgccgtc atgagcgacc    420

ctgacctgga aactgagact atgtgcctcc acgacgacga gtcgtgtcgc tacgaagggc    480

aagtcgctgt ttaccaggat gtatacgcgg ttgacggacc gacaagtctc tatcaccaag    540

ccaataaggg agttagagtc gcctactgga taggctttga caccacccct tttatgttta    600

agaacttggc tggagcatat ccatcatact ctaccaactg ggccgacgaa accgtgttaa    660

cggctcgtaa cataggccta tgcagctctg acgttatgga gcggtcacgt agagggatgt    720

ccattcttag aaagaagtat ttgaaaccat ccaacaatgt tctattctct gttggctcga    780

ccatctacca cgagaagagg gacttactga ggagctggca cctgccgtct gtatttcact    840

tacgtggcaa gcaaaattac acatgtcggt gtgagactat agttagttgc gacgggtacg    900

tcgttaaaag aatagctatc agtccaggcc tgtatgggaa gccttcaggc tatgctgcta    960
```

```
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tagacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
```

```
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggagggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
```

```
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
ggcccctat aactctctac ggctaacctg aatggactac gacatagtct agtcgagtct   7560
agtcgacgcc accatgggca ccgtgaacaa gcctgtcgtg ggcgtgctga tgggcttcgg   7620
catcatcacc ggcaccctga gaatcaccaa ccctgtgcgg gccagcgtgc tgagatacga   7680
cgacttccac atcgacgagg acaagctgga caccaacagc gtgtacgagc cctactacca   7740
cagcgaccac gccgagagca gctgggtcaa cagaggcgag agcagccgga aggcctacga   7800
ccacaacagc ccctacatct ggccccggaa cgactacgac ggcttcctgg aaaacgccca   7860
cgagcaccac ggcgtgtaca atcagggcag aggcatcgac agcggcgaga gactgatgca   7920
gcccacacag atgagcgccc aggaagatct gggcgacgac acaggcatcc acgtgatccc   7980
caccctgaac ggcgacgacc ggcacaagat cgtgaacgtg gaccagcggc agtacggcga   8040
cgtgttcaag ggcgacctga accctaagcc ccagggccag agactgatcg aggtgtccgt   8100
```

```
ggaagagaac caccccttca ccctgagagc ccccatccag agaatctacg gcgtgcggta   8160
taccgagact tggagcttcc tgcccagcct gacctgtaca ggcgacgccg ctcctgccat   8220
ccagcacatc tgcctgaagc acaccacctg tttccaggac gtggtggtgg acgtggactg   8280
cgccgagaac accaaagagg accagctggc cgagatcagc taccggttcc agggcaagaa   8340
agaggccgac cagccctgga tcgtggtcaa taccagcacc ctgttcgacg agctggaact   8400
ggaccccccc gagattgaac ccggcgtgct gaaggtgctg cggaccgaga agcagtacct   8460
gggcgtgtac atctggaaca tgcggggctc cgacggcacc tctacctacg ccaccttcct   8520
ggtcacatgg aagggcgacg agaaaacccg gaaccctacc cctgccgtga cccctcagcc   8580
tagaggcgcc gagttccata tgtggaatta ccactcccac gtgttcagcg tgggcgacac   8640
cttcagcctg gccatgcatc tgcagtacaa gatccacgag gccccccttcg acctgctgct  8700
ggaatggctg tacgtgccca tcgaccctac ctgccagccc atgcggctgt acagcacctg   8760
tctgtaccac cccaacgccc ctcagtgcct gagccacatg aacagcggct gcaccttcac   8820
cagccctcac ctggctcaga gggtggccag caccgtgtac cagaattgcg agcacgccga   8880
caactacacc gcctactgcc tgggcatcag ccacatggaa cccagcttcg gcctgatcct   8940
gcacgatggc ggcaccaccc tgaagttcgt ggacacaccc gagagcctga gcggcctgta   9000
cgtgttcgtg gtgtacttca acggccacgt ggaagccgtg gcctacaccg tggtgtccac   9060
cgtggaccac ttcgtgaacg ccatcgagga aagaggcttc ccacccacag ccggacagcc   9120
tccagccacc accaagccca aagaaatcac ccccgtgaac cccggcacca gcccccctgct  9180
gagatatgct gcttggacag gcggactggc cgctgtggtg ctgctgtgcc tggtcatctt   9240
cctgatctgc accgccaagc ggatgagagt gaaggcctac cgggtggaca agtcccccta   9300
caaccagagc atgtactacg ccggcctgcc cgtggacgat ttcgaggata gcgagagcac   9360
cgacaccgag gaagagttcg gcaacgccat cggcggatct cacggcggca gcagctacac   9420
cgtgtacatc gacaagacca gataatctag acgcggccgc atacagcagc aattggcaag   9480
ctgcttacat agaactcgcg gcgattggca tgccgcctta aaatttttat tttatttttc   9540
ttttcttttc cgaatcggat tttgttttta atatttcaaa aaaaaaaaaa aaaaaaaaaa   9600
aaaaaaaaaa aagggtcggc atggcatctc cacctcctcg cggtccgacc tgggcatccg   9660
aaggaggacg cacgtccact cggatggcta agggagagcc acgtttaaac cagctccaat   9720
tcgccctata gtgagtcgta ttacgcgcgc tcactggccg tcgttttaca acgtcgtgac   9780
tgggaaaacc ctggcgttac ccaacttaat cgccttgcag cacatccccc tttcgccagc   9840
tggcgtaata gcgaagaggc ccgcaccgat cgcccttccc aacagttgcg cagcctgaat   9900
ggcgaatggg acgcgccctg tagcggcgca ttaagcgcgg cgggtgtggt ggttacgcgc   9960
agcgtgaccg ctacacttgc cagcgcccta gcgcccgctc ctttcgcttt cttcccttcc   10020
tttctcgcca cgttcgccgg ctttccccgt caagctctaa atcgggggct ccctttaggg   10080
ttccgattta gtgctttacg gcacctcgac cccaaaaaac ttgattaggg tgatggttca   10140
cgtagtgggc catcgccctg atagacggtt tttcgccctt tgacgttgga gtccacgttc   10200
tttaatagtg gactcttgtt ccaaactgga acaacactca accctatctc ggtctattct   10260
tttgatttat aagggatttt gccgatttcg gcctattggt taaaaaatga gctgatttaa   10320
caaaaattta acgcgaattt taacaaaata ttaacgctta caatttaggt ggcacttttc   10380
ggggaaatgt gcgcggaacc cctatttgtt tatttttcta aatacattca aatatgtatc   10440
```

```
cgctcatgag acaataaccc tgataaatgc ttcaataata ttgaaaaagg aagagtatga  10500

gtattcaaca tttccgtgtc gcccttattc ccttttttgc ggcattttgc cttcctgttt  10560

ttgctcaccc agaaacgctg gtgaaagtaa aagatgctga agatcagttg ggtgcacgag  10620

tgggttacat cgaactggat ctcaacagcg gtaagatcct tgagagtttt cgccccgaag  10680

aacgttttcc aatgatgagc acttttaaag ttctgctatg tggcgcggta ttatcccgta  10740

ttgacgccgg gcaagagcaa ctcggtcgcc gcatacacta ttctcagaat gacttggttg  10800

agtactcacc agtcacagaa aagcatctta cggatggcat gacagtaaga gaattatgca  10860

gtgctgccat aaccatgagt gataacactg cggccaactt acttctgaca acgatcggag  10920

gaccgaagga gctaaccgct tttttgcaca acatggggga tcatgtaact cgccttgatc  10980

gttgggaacc ggagctgaat gaagccatac caaacgacga gcgtgacacc acgatgcctg  11040

tagcaatggc aacaacgttg cgcaaactat taactggcga actacttact ctagcttccc  11100

ggcaacaatt aatagactgg atggaggcgg ataaagttgc aggaccactt ctgcgctcgg  11160

cccttccggc tggctggttt attgctgata aatctggagc cggtgagcgt gggtctcgcg  11220

gtatcattgc agcactgggg ccagatggta agccctcccg tatcgtagtt atctacacga  11280

cggggagtca ggcaactatg gatgaacgaa atagacagat cgctgagata ggtgcctcac  11340

tgattaagca ttggtaactg tcagaccaag tttactcata tatactttag attgatttaa  11400

aacttcattt ttaatttaaa aggatctagg tgaagatcct ttttgataat ctcatgacca  11460

aaatccctta acgtgagttt tcgttccact gagcgtcaga ccccgtagaa aagatcaaag  11520

gatcttcttg agatcctttt tttctgcgcg taatctgctg cttgcaaaca aaaaaaccac  11580

cgctaccagc ggtggtttgt ttgccggatc aagagctacc aactcttttt ccgaaggtaa  11640

ctggcttcag cagagcgcag ataccaaata ctgttcttct agtgtagccg tagttaggcc  11700

accacttcaa gaactctgta gcaccgccta catacctcgc tctgctaatc ctgttaccag  11760

tggctgctgc cagtggcgat aagtcgtgtc ttaccgggtt ggactcaaga cgatagttac  11820

cggataaggc gcagcggtcg ggctgaacgg ggggttcgtg cacacagccc agcttggagc  11880

gaacgaccta caccgaactg agatacctac agcgtgagct atgagaaagc gccacgcttc  11940

ccgaagggag aaaggcggac aggtatccgg taagcggcag ggtcggaaca ggagagcgca  12000

cgagggagct tccaggggga aacgcctggt atctttatag tcctgtcggg tttcgccacc  12060

tctgacttga gcgtcgattt ttgtgatgct cgtcaggggg gcggagccta tggaaaaacg  12120

ccagcaacgc ggccttttta cggttcctgg ccttttgctg gccttttgct cacatgttct  12180

ttcctgcgtt atcccctgat tctgtggata accgtattac cgcctttgag tgagctgata  12240

ccgctcgccg cagccgaacg accgagcgca gcgagtcagt gagcgaggaa gcggaagagc  12300

gcccaatacg caaaccgcct ctccccgcgc gttggccgat tcattaatgc agctggcacg  12360

acaggtttcc cgactggaaa gcgggcagtg agcgcaacgc aattaatgtg agttagctca  12420

ctcattaggc accccaggct ttacacttta tgctcccggc tcgtatgttg tgtggaattg  12480

tgagcggata acaatttcac acaggaaaca gctatgacca tgattacgcc aagcgcgcaa  12540

ttaaccctca ctaaagggaa caaaagctgg gtaccgggcc cacgcgtaat acgactcact  12600

atag                                                               12604
```

<210> SEQ ID NO 26
<211> LENGTH: 11797
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 26

```
ataggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagct cgccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tagacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
```

```
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
```

```
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
```

-continued

```
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtcgagtct   7560
agtcgacgcc accatgtttc tgatccagtg cctgatcagc gccgtgatct tctatattca   7620
agtcacaaac gccctgatct ttaagggcga ccacgtgtca ctgcaggtca acagcagcct   7680
gaccagcatc ctgatcccca tgcagaacga caattacacc gagatcaagg gccagctggt   7740
gttcatcggc gagcagctgc ccaccggcac caattacagc ggcaccctgg aactgctgta   7800
cgccgatacc gtggccttct gcttcagaag cgtgcaggtc atcagatacg acggctgccc   7860
ccggatcaga accagcgcct tcatcagctg ccggtacaag cacagctggc actacggcaa   7920
cagcaccgac cggatcagca ccgaacctga tgccggcgtg atgctgaaga tcaccaagcc   7980
cggcatcaac gacgccggcg tgtacgtgct gctcgtgcgg ctggatcaca gcagaagcac   8040
cgacggcttc atcctgggcg tgaacgtgta caccgccggc agccaccaca acatccacgg   8100
cgtgatctac accagcccca gcctgcagaa cggctacagc accagagccc tgttccagca   8160
ggccagactg tgcgatctgc ccgccacacc taagggcagc ggcacaagcc tgtttcagca   8220
catgctggac ctgagagccg gcaagagcct ggaagataac ccctggctgc acgaggacgt   8280
ggtcaccacc gagacaaaga gcgtggtcaa agagggcatc gagaaccacg tgtaccccac   8340
cgacatgagc accctgcccg agaagtccct gaacgacccc cctgagaacc tgctgatcat   8400
catccccatc gtggccagcg tgatgatcct gaccgccatg gtcatcgtga tcgtgatcag   8460
cgtgaagcgg cggagaatca agaagcaccc catctaccgg cccaacacca agaccagacg   8520
gggcatccag aacgccaccc ctgagtccga cgtgatgctg gaagccgcca ttgcccagct   8580
ggccaccatc agagaggaaa gcccccctca cagcgtcgtg aacccccttcg tgaagtaatc   8640
tagacgcggc cgcatacagc agcaattggc aagctgctta catagaactc gcggcgattg   8700
gcatgccgcc ttaaaatttt tattttattt ttcttttctt ttccgaatcg gattttgttt   8760
ttaatatttc aaaaaaaaaa aaaaaaaaaa aaaaaaaaaa aaaaagggtc ggcatggcat   8820
ctccacctcc tcgcggtccg acctgggcat ccgaaggagg acgcacgtcc actcggatgg   8880
ctaagggaga gccacgttta aaccagctcc aattcgccct atagtgagtc gtattacgcg   8940
cgctcactgg ccgtcgtttt acaacgtcgt gactgggaaa accctggcgt tacccaactt   9000
aatcgccttg cagcacatcc ccctttcgcc agctggcgta atagcgaaga ggcccgcacc   9060
gatcgccctt cccaacagtt gcgcagcctg aatggcgaat gggacgcgcc ctgtagcggc   9120
gcattaagcg cggcgggtgt ggtggttacg cgcagcgtga ccgctacact tgccagcgcc   9180
ctagcgcccg ctcctttcgc tttcttccct tcctttctcg ccacgttcgc cggctttccc   9240
cgtcaagctc taaatcgggg gctcccttta gggttccgat ttagtgcttt acggcacctc   9300
```

```
gaccccaaaa aacttgatta gggtgatggt tcacgtagtg ggccatcgcc ctgatagacg   9360
gtttttcgcc ctttgacgtt ggagtccacg ttctttaata gtggactctt gttccaaact   9420
ggaacaacac tcaaccctat ctcggtctat tcttttgatt tataagggat tttgccgatt   9480
tcggcctatt ggttaaaaaa tgagctgatt taacaaaaat ttaacgcgaa ttttaacaaa   9540
atattaacgc ttacaattta ggtggcactt ttcggggaaa tgtgcgcgga acccctattt   9600
gtttattttt ctaaatacat tcaaatatgt atccgctcat gagacaataa ccctgataaa   9660
tgcttcaata atattgaaaa aggaagagta tgagtattca acatttccgt gtcgccctta   9720
ttcccttttt tgcggcattt tgccttcctg tttttgctca cccagaaacg ctggtgaaag   9780
taaaagatgc tgaagatcag ttgggtgcac gagtgggtta catcgaactg gatctcaaca   9840
gcggtaagat ccttgagagt tttcgccccg aagaacgttt tccaatgatg agcactttta   9900
aagttctgct atgtggcgcg gtattatccc gtattgacgc cgggcaagag caactcggtc   9960
gccgcataca ctattctcag aatgacttgg ttgagtactc accagtcaca gaaaagcatc  10020
ttacggatgg catgacagta agagaattat gcagtgctgc cataaccatg agtgataaca  10080
ctgcggccaa cttacttctg acaacgatcg gaggaccgaa ggagctaacc gcttttttgc  10140
acaacatggg ggatcatgta actcgccttg atcgttggga accggagctg aatgaagcca  10200
taccaaacga cgagcgtgac accacgatgc ctgtagcaat ggcaacaacg ttgcgcaaac  10260
tattaactgg cgaactactt actctagctt cccggcaaca attaatagac tggatggagg  10320
cggataaagt tgcaggacca cttctgcgct cggcccttcc ggctggctgg tttattgctg  10380
ataaatctgg agccggtgag cgtgggtctc gcggtatcat tgcagcactg gggccagatg  10440
gtaagccctc ccgtatcgta gttatctaca cgacggggag tcaggcaact atggatgaac  10500
gaaatagaca gatcgctgag ataggtgcct cactgattaa gcattggtaa ctgtcagacc  10560
aagtttactc atatatactt tagattgatt taaaacttca tttttaattt aaaaggatct  10620
aggtgaagat cctttttgat aatctcatga ccaaaatccc ttaacgtgag ttttcgttcc  10680
actgagcgtc agaccccgta gaaaagatca aaggatcttc ttgagatcct ttttttctgc  10740
gcgtaatctg ctgcttgcaa acaaaaaaac caccgctacc agcggtggtt tgtttgccgg  10800
atcaagagct accaactctt tttccgaagg taactggctt cagcagagcg cagataccaa  10860
atactgttct tctagtgtag ccgtagttag gccaccactt caagaactct gtagcaccgc  10920
ctacatacct cgctctgcta atcctgttac cagtggctgc tgccagtggc gataagtcgt  10980
gtcttaccgg gttggactca agacgatagt taccggataa ggcgcagcgg tcgggctgaa  11040
cggggggttc gtgcacacag cccagcttgg agcgaacgac ctacaccgaa ctgagatacc  11100
tacagcgtga gctatgagaa agcgccacgc ttcccgaagg gagaaaggcg gacaggtatc  11160
cggtaagcgg cagggtcgga acaggagagc gcacgaggga gcttccaggg ggaaacgcct  11220
ggtatcttta tagtcctgtc gggtttcgcc acctctgact tgagcgtcga tttttgtgat  11280
gctcgtcagg ggggcggagc ctatggaaaa acgccagcaa cgcggccttt ttacggttcc  11340
tggccttttg ctggcctttt gctcacatgt tctttcctgc gttatcccct gattctgtgg  11400
ataaccgtat taccgccttt gagtgagctg ataccgctcg ccgcagccga acgaccgagc  11460
gcagcgagtc agtgagcgag gaagcggaag agcgcccaat acgcaaaccg cctctccccg  11520
cgcgttggcc gattcattaa tgcagctggc acgacaggtt tcccgactgg aaagcgggca  11580
gtgagcgcaa cgcaattaat gtgagttagc tcactcatta ggcaccccag gctttacact  11640
```

```
ttatgctccc ggctcgtatg ttgtgtggaa ttgtgagcgg ataacaattt cacacaggaa  11700

acagctatga ccatgattac gccaagcgcg caattaaccc tcactaaagg gaacaaaagc  11760

tgggtaccgg gcccacgcgt aatacgactc actatag                           11797


<210> SEQ ID NO 27
<211> LENGTH: 13755
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 27

ataggcggcg catgagagaa gcccagacca attacctacc caaaatggag aaagttcacg     60

ttgacatcga ggaagacagc ccattcctca gagctttgca gcggagcttc ccgcagtttg    120

aggtagaagc caagcaggtc actgataatg accatgctaa tgccagagcg ttttcgcatc    180

tggcttcaaa actgatcgaa acggaggtgg acccatccga cacgatcctt gacattggaa    240

gtgcgcccgc ccgcagaatg tattctaagc acaagtatca ttgtatctgt ccgatgagat    300

gtgcggaaga tccggacaga ttgtataagt atgcaactaa gctgaagaaa aactgtaagg    360

aaataactga taaggaattg gacaagaaaa tgaaggagct cgccgccgtc atgagcgacc    420

ctgacctgga aactgagact atgtgcctcc acgacgacga gtcgtgtcgc tacgaagggc    480

aagtcgctgt ttaccaggat gtatacgcgg ttgacggacc gacaagtctc tatcaccaag    540

ccaataaggg agttagagtc gcctactgga taggctttga caccacccct tttatgttta    600

agaacttggc tggagcatat ccatcatact ctaccaactg ggccgacgaa accgtgttaa    660

cggctcgtaa cataggccta tgcagctctg acgttatgga gcggtcacgt agagggatgt    720

ccattcttag aaagaagtat ttgaaaccat ccaacaatgt tctattctct gttggctcga    780

ccatctacca cgagaagagg gacttactga ggagctggca cctgccgtct gtatttcact    840

tacgtggcaa gcaaaattac acatgtcggt gtgagactat agttagttgc gacgggtacg    900

tcgttaaaag aatagctatc agtccaggcc tgtatgggaa gccttcaggc tatgctgcta    960

cgatgcaccg cgagggattc ttgtgctgca aagtgacaga cacattgaac ggggagaggg   1020

tctcttttcc cgtgtgcacg tatgtgccag ctacattgtg tgaccaaatg actggcatac   1080

tggcaacaga tgtcagtgcg gacgacgcgc aaaaactgct ggttgggctc aaccagcgta   1140

tagtcgtcaa cggtcgcacc cagagaaaca ccaataccat gaaaaattac cttttgcccg   1200

tagtggccca ggcatttgct aggtgggcaa aggaatataa ggaagatcaa gaagatgaaa   1260

ggccactagg actacgagat agacagttag tcatggggtg ttgttgggct tttagaaggc   1320

acaagataac atctatttat aagcgcccgg atacccaaac catcatcaaa gtgaacagcg   1380

atttccactc attcgtgctg cccaggatag gcagtaacac attggagatc gggctgagaa   1440

caagaatcag gaaaatgtta gaggagcaca aggagccgtc acctctcatt accgccgagg   1500

acgtacaaga agctaagtgc gcagccgatg aggctaagga ggtgcgtgaa gccgaggagt   1560

tgcgcgcagc tctaccacct ttggcagctg atgttgagga gcccactctg gaagccgatg   1620

tagacttgat gttacaagag gctggggccg gctcagtgga gacacctcgt ggcttgataa   1680

aggttaccag ctacgatggc gaggacaaga tcggctctta cgctgtgctt tctccgcagg   1740

ctgtactcaa gagtgaaaaa ttatcttgca tccaccctct cgctgaacaa gtcatagtga   1800

taacacactc tggccgaaaa gggcgttatg ccgtggaacc ataccatggt aaagtagtgg   1860
```

```
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggagggggtg tgcggagcgc   4140
tgtataagaa attcccggaa agcttcgatt tacagccgat cgaagtagga aaagcgcgac   4200
```

```
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
```

aacatactga agaacggccc aaggtacagg tgatccaggc tgccgatccg ctagcaacag 6660
cgtatctgtg cggaatccac cgagagctgg ttaggagatt aaatgcggtc ctgcttccga 6720
acattcatac actgtttgat atgtcggctg aagactttga cgctattata gccgagcact 6780
tccagcctgg ggattgtgtt ctggaaactg acatcgcgtc gtttgataaa agtgaggacg 6840
acgccatggc tctgaccgcg ttaatgattc tggaagactt aggtgtggac gcagagctgt 6900
tgacgctgat tgaggcggct ttcggcgaaa tttcatcaat acatttgccc actaaaacta 6960
aatttaaatt cggagccatg atgaaatctg gaatgttcct cacactgttt gtgaacacag 7020
tcattaacat tgtaatcgca agcagagtgt tgagagaacg gctaaccgga tcaccatgtg 7080
cagcattcat tggagatgac aatatcgtga aaggagtcaa atcggacaaa ttaatggcag 7140
acaggtgcgc cacctggttg aatatggaag tcaagattat agatgctgtg gtgggcgaga 7200
aagcgcctta tttctgtgga gggtttattt tgtgtgactc cgtgaccggc acagcgtgcc 7260
gtgtggcaga ccccctaaaa aggctgttta agcttggcaa acctctggca gcagacgatg 7320
aacatgatga tgacaggaga agggcattgc atgaagagtc aacacgctgg aaccgagtgg 7380
gtattctttc agagctgtgc aaggcagtag aatcaaggta tgaaaccgta ggaacttcca 7440
tcatagttat ggccatgact actctagcta gcagtgttaa atcattcagc tacctgagag 7500
gggcccctat aactctctac ggctaacctg aatggactac gacatagtct agtcgagtct 7560
agtcgacgcc accatgggca ccgtgaacaa gcctgtcgtg ggcgtgctga tgggcttcgg 7620
catcatcacc ggcaccctga gaatcaccaa ccctgtgcgg gccagcgtgc tgagatacga 7680
cgacttccac atcgacgagg acaagctgga caccaacagc gtgtacgagc cctactacca 7740
cagcgaccac gccgagagca gctgggtcaa cagaggcgag agcagccgga aggcctacga 7800
ccacaacagc ccctacatct ggccccggaa cgactacgac ggcttcctgg aaaacgccca 7860
cgagcaccac ggcgtgtaca atcagggcag aggcatcgac agcggcgaga gactgatgca 7920
gcccacacag atgagcgccc aggaagatct gggcgacgac acaggcatcc acgtgatccc 7980
caccctgaac ggcgacgacc ggcacaagat cgtgaacgtg gaccagcggc agtacggcga 8040
cgtgttcaag ggcgacctga accctaagcc ccagggccag agactgatcg aggtgtccgt 8100
ggaagagaac caccccttca ccctgagagc ccccatccag agaatctacg gcgtgcggta 8160
taccgagact tggagcttcc tgcccagcct gacctgtaca ggcgacgccg ctcctgccat 8220
ccagcacatc tgcctgaagc acaccacctg tttccaggac gtggtggtgg acgtggactg 8280
cgccgagaac accaaagagg accagctggc cgagatcagc taccggttcc agggcaagaa 8340
agaggccgac cagccctgga tcgtggtcaa taccagcacc ctgttcgacg agctggaact 8400 ggacccccccc gagattgaac ccggcgtgct gaaggtgctg cggaccgaga agcagtacct 8460
gggcgtgtac atctggaaca tgcggggctc cgacggcacc tctacctacg ccaccttcct 8520
ggtcacatgg aagggcgacg agaaaacccg gaaccctacc cctgccgtga cccctcagcc 8580
tagaggcgcc gagttccata tgtggaatta ccactcccac gtgttcagcg tgggcgacac 8640
cttcagcctg gccatgcatc tgcagtacaa gatccacgag gcccccttcg acctgctgct 8700
ggaatggctg tacgtgccca tcgaccctac ctgccagccc atgcggctgt acagcacctg 8760
tctgtaccac cccaacgccc ctcagtgcct gagccacatg aacagcggct gcaccttcac 8820
cagccctcac ctggctcaga gggtggccag caccgtgtac cagaattgcg agcacgccga 8880
caactacacc gcctactgcc tgggcatcag ccacatggaa cccagcttcg gcctgatcct 8940

```
gcacgatggc ggcaccaccc tgaagttcgt ggacacaccc gagagcctga gcggcctgta   9000
cgtgttcgtg gtgtacttca acggccacgt ggaagccgtg gcctacaccg tggtgtccac   9060
cgtggaccac ttcgtgaacg ccatcgagga aagaggcttc ccacccacag ccggacagcc   9120
tccagccacc accaagccca aagaaatcac ccccgtgaac cccggcacca gcccccctgct  9180
gagatatgct gcttggacag gcggactggc cgctgtggtg ctgctgtgcc tggtcatctt   9240
cctgatctgc accgccaagc ggatgagagt gaaggcctac cgggtggaca agtcccccta   9300
caaccagagc atgtactacg ccggcctgcc cgtggacgat ttcgaggata gcgagagcac   9360
cgacaccgag gaagagttcg gcaacgccat cggcggatct cacggcggca gcagctacac   9420
cgtgtacatc gacaagacca gataatctag acgtcgcgac cacccaggat ccgcctataa   9480
ctctctacgg ctaacctgaa tggactacga catagtctag tcgacgccac catgtttctg   9540
atccagtgcc tgatcagcgc cgtgatcttc tatattcaag tcacaaacgc cctgatcttt   9600
aagggcgacc acgtgtcact gcaggtcaac agcagcctga ccagcatcct gatccccatg   9660
cagaacgaca attacaccga gatcaagggc cagctggtgt tcatcggcga gcagctgccc   9720
accggcacca attacagcgg caccctggaa ctgctgtacg ccgataccgt ggccttctgc   9780
ttcagaagcg tgcaggtcat cagatacgac ggctgccccc ggatcagaac cagcgccttc   9840
atcagctgcc ggtacaagca cagctggcac tacggcaaca gcaccgaccg gatcagcacc   9900
gaacctgatg ccggcgtgat gctgaagatc accaagcccg gcatcaacga cgccggcgtg   9960
tacgtgctgc tcgtgcggct ggatcacagc agaagcaccg acggcttcat cctgggcgtg   10020
aacgtgtaca ccgccggcag ccaccacaac atccacggcg tgatctacac cagccccagc   10080
ctgcagaacg gctacagcac cagagccctg ttccagcagg ccagactgtg cgatctgccc   10140
gccacaccta agggcagcgg cacaagcctg tttcagcaca tgctggacct gagagccggc   10200
aagagcctgg aagataaccc ctggctgcac gaggacgtgg tcaccaccga gacaaagagc   10260
gtggtcaaag agggcatcga gaaccacgtg taccccaccg acatgagcac cctgcccgag   10320
aagtccctga acgacccccc tgagaacctg ctgatcatca tccccatcgt ggccagcgtg   10380
atgatcctga ccgccatggt catcgtgatc gtgatcagcg tgaagcggcg gagaatcaag   10440
aagcacccca tctaccggcc caacaccaag accagacggg gcatccagaa cgccacccct   10500
gagtccgacg tgatgctgga agccgccatt gcccagctgg ccaccatcag agaggaaagc   10560
ccccctcaca gcgtcgtgaa ccccttcgtg aagtaatcta gacgcggccg catacagcag   10620
caattggcaa gctgcttaca tagaactcgc ggcgattggc atgccgcctt aaaattttta   10680
ttttattttt cttttctttt ccgaatcgga ttttgttttt aatatttcaa aaaaaaaaaa   10740
aaaaaaaaaa aaaaaaaaaa aaagggtcgg catggcatct ccacctcctc gcggtccgac   10800
ctgggcatcc gaaggaggac gcacgtccac tcggatggct aagggagagc cacgtttaaa   10860
ccagctccaa ttcgccctat agtgagtcgt attacgcgcg ctcactggcc gtcgttttac   10920
aacgtcgtga ctgggaaaac cctggcgtta cccaacttaa tcgccttgca gcacatcccc   10980
ctttcgccag ctggcgtaat agcgaagagg cccgcaccga tcgcccttcc caacagttgc   11040
gcagcctgaa tggcgaatgg gacgcgccct gtagcggcgc attaagcgcg gcgggtgtgg   11100
tggttacgcg cagcgtgacc gctacacttg ccagcgccct agcgcccgct cctttcgctt   11160
tcttcccttc ctttctcgcc acgttcgccg gctttccccg tcaagctcta aatcgggggc   11220
tccctttagg gttccgattt agtgctttac ggcacctcga ccccaaaaaa cttgattagg   11280
gtgatggttc acgtagtggg ccatcgccct gatagacggt tttcgccct ttgacgttgg   11340
```

agtccacgtt ctttaatagt ggactcttgt tccaaactgg aacaacactc aaccctatct 11400
cggtctattc ttttgattta taagggattt tgccgatttc ggcctattgg ttaaaaaatg 11460
agctgattta acaaaaattt aacgcgaatt ttaacaaaat attaacgctt acaatttagg 11520
tggcactttt cggggaaatg tgcgcggaac ccctatttgt ttatttttct aaatacattc 11580
aaatatgtat ccgctcatga gacaataacc ctgataaatg cttcaataat attgaaaaag 11640
gaagagtatg agtattcaac atttccgtgt cgcccttatt cccttttttg cggcattttg 11700
ccttcctgtt tttgctcacc cagaaacgct ggtgaaagta aaagatgctg aagatcagtt 11760
gggtgcacga gtgggttaca tcgaactgga tctcaacagc ggtaagatcc ttgagagttt 11820
tcgccccgaa gaacgttttc caatgatgag cacttttaaa gttctgctat gtggcgcggt 11880
attatcccgt attgacgccg ggcaagagca actcggtcgc cgcatacact attctcagaa 11940
tgacttggtt gagtactcac cagtcacaga aaagcatctt acggatggca tgacagtaag 12000
agaattatgc agtgctgcca taaccatgag tgataacact gcggccaact tacttctgac 12060
aacgatcgga ggaccgaagg agctaaccgc ttttttgcac aacatggggg atcatgtaac 12120
tcgccttgat cgttgggaac cggagctgaa tgaagccata ccaaacgacg agcgtgacac 12180
cacgatgcct gtagcaatgg caacaacgtt gcgcaaacta ttaactggcg aactacttac 12240
tctagcttcc cggcaacaat taatagactg gatggaggcg gataaagttg caggaccact 12300
tctgcgctcg gcccttccgg ctggctggtt tattgctgat aaatctggag ccggtgagcg 12360
tgggtctcgc ggtatcattg cagcactggg gccagatggt aagccctccc gtatcgtagt 12420
tatctacacg acggggagtc aggcaactat ggatgaacga aatagacaga tcgctgagat 12480
aggtgcctca ctgattaagc attggtaact gtcagaccaa gtttactcat atatacttta 12540
gattgattta aaacttcatt tttaatttaa aaggatctag gtgaagatcc tttttgataa 12600
tctcatgacc aaaatccctt aacgtgagtt ttcgttccac tgagcgtcag accccgtaga 12660
aaagatcaaa ggatcttctt gagatccttt ttttctgcgc gtaatctgct gcttgcaaac 12720
aaaaaaacca ccgctaccag cggtggtttg tttgccggat caagagctac caactctttt 12780
tccgaaggta actggcttca gcagagcgca gataccaaat actgttcttc tagtgtagcc 12840
gtagttaggc caccacttca agaactctgt agcaccgcct acatacctcg ctctgctaat 12900
cctgttacca gtggctgctg ccagtggcga taagtcgtgt cttaccgggt tggactcaag 12960
acgatagtta ccggataagg cgcagcggtc gggctgaacg gggggttcgt gcacacagcc 13020
cagcttggag cgaacgacct acaccgaact gagataccta cagcgtgagc tatgagaaag 13080
cgccacgctt cccgaaggga gaaaggcgga caggtatccg gtaagcggca gggtcggaac 13140
aggagagcgc acgagggagc ttccaggggg aaacgcctgg tatctttata gtcctgtcgg 13200
gtttcgccac ctctgacttg agcgtcgatt tttgtgatgc tcgtcagggg ggcggagcct 13260
atggaaaaac gccagcaacg cggccttttt acggttcctg gccttttgct ggccttttgc 13320
tcacatgttc tttcctgcgt tatcccctga ttctgtggat aaccgtatta ccgcctttga 13380
gtgagctgat accgctcgcc gcagccgaac gaccgagcgc agcgagtcag tgagcgagga 13440
agcggaagag cgcccaatac gcaaaccgcc tctccccgcg cgttggccga ttcattaatg 13500
cagctggcac gacaggtttc ccgactggaa agcgggcagt gagcgcaacg caattaatgt 13560
gagttagctc actcattagg caccccaggc tttacacttt atgctcccgg ctcgtatgtt 13620
gtgtggaatt gtgagcggat aacaatttca cacaggaaac agctatgacc atgattacgc 13680

-continued

```
caagcgcgca attaaccctc actaaaggga acaaaagctg ggtaccgggc ccacgcgtaa  13740

tacgactcac tatag                                                   13755


<210> SEQ ID NO 28
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28

aaaaaaaaaa aaaaaaaaaa aaaaaaaaaa                                      30
```

CATIONIC OIL-IN-WATER EMULSIONS

RELATED APPLICATIONS

This application is a continuation of U.S. patent application Ser. No. 15/467,660, which is a divisional of U.S. patent application Ser. No. 14/130,886, filed Apr. 14, 2014, which is the U.S. National Stage of International Application No. PCT/US2012/045845, filed Jul. 6, 2012 and published in English, which claims the benefit of U.S. Provisional Application No. 61/505,109, filed Jul. 6, 2011, U.S. Provisional Application No. 61/545,936, filed Oct. 11, 2011, and U.S. Provisional Application No. 61/585,641, filed Jan. 11, 2012; the entire contents of each of the foregoing patent applications is incorporated herein by reference.

SEQUENCE LISTING

The instant application contains a Sequence Listing which has been submitted in ASCII format via EFS-Web and is hereby incorporated by reference in its entirety. Said ASCII copy, created on Dec. 5, 2018, is named VN54691D1_US_Sequence_listing.txt and is 424,354 bytes in size.

BACKGROUND OF THE INVENTION

Nucleic acid therapeutics have promise for treating diseases ranging from inherited disorders to acquired conditions such as cancer, infectious disorders (AIDS), heart disease, arthritis, and neurodegenerative disorders (e.g., Parkinson's and Alzheimer's). Not only can functional genes be delivered to repair a genetic deficiency or induce expression of exogenous gene products, but nucleic acid can also be delivered to inhibit endogenous gene expression to provide a therapeutic effect. Inhibition of gene expression can be mediated by, e.g., antisense oligonucleotides, double-stranded RNAs (e.g., siRNAs, miRNAs), or ribozymes.

A key step for such therapy is to deliver nucleic acid molecules into cells in vivo. However, in vivo delivery of nucleic acid molecules, in particular RNA molecules, faces a number of technical hurdles. First, due to cellular and serum nucleases, the half life of RNA injected in vivo is only about 70 seconds (see, e.g., Kurreck, Eur. J. Bioch. 270: 1628-44 (2003)). Efforts have been made to increase stability of injected RNA by the use of chemical modifications; however, there are several instances where chemical alterations led to increased cytotoxic effects or loss of or decreased function. In one specific example, cells were intolerant to doses of an RNAi duplex in which every second phosphate was replaced by phosphorothioate (Harborth, et al, Antisense Nucleic Acid Drug Rev. 13(2): 83-105 (2003)). As such, there is a need to develop delivery systems that can deliver sufficient amounts of nucleic acid molecules (in particular RNA molecules) in vivo to elicit a therapeutic response, but that are not toxic to the host.

Nucleic acid based vaccines are an attractive approach to vaccination. For example, intramuscular (IM) immunization of plasmid DNA encoding for antigen can induce cellular and humoral immune responses and protect against challenge. DNA vaccines offer certain advantages over traditional vaccines using protein antigens, or attenuated pathogens. For example, as compared to protein vaccines, DNA vaccines can be more effective in producing a properly folded antigen in its native conformation, and in generating a cellular immune response. DNA vaccines also do not have some of the safety problems associated with killed or attenuated pathogens. For example, a killed viral preparation may contain residual live viruses, and an attenuated virus may mutate and revert to a pathogenic phenotype.

One limitation of nucleic acid based vaccines is that large doses of nucleic acid are generally required to obtain potent immune responses in non-human primates and humans. Therefore, delivery systems and adjuvants are required to enhance the potency of nucleic acid based vaccines. Various methods have been developed for introducing nucleic acid molecules into cells, such as calcium phosphate transfection, polyprene transfection, protoplast fusion, electroporation, microinjection and lipofection.

Cationic lipids have been formulated as liposomes to deliver genes into cells. In addition, cationic lipid emulsions have been developed to deliver DNA molecules into cells. See, e.g., Kim, et al., International Journal of Pharmaceutics, 295, 35-45 (2005).

Ott et al. (Journal of Controlled Release, volume 79, pages 1-5, 2002) describes an approach involving a cationic sub-micron emulsion as a delivery system/adjuvant for DNA. The sub-micron emulsion approach is based on MF59, a potent squalene in water adjuvant that is a component of commercially approved product Fluad®. 1,2-dioleoyl-3-trimethylammonium-propane (DOTAP) was used to facilitate intracellular delivery of plasmid DNA.

Yi et al. (Pharmaceutical Research, 17, 314-320 (2000)) discloses cationic oil-in-water emulsions that used soybean oil and DOTAP as the cationic lipid. Cholesterol, DOPE, and polymeric lipids were also included in some of the emulsions. The emulsions were shown to enhance the efficiency of in vitro transfection of DNA in the presence of up to 90% serum. The average size of the emulsion particles ranged from 181 nm to 344 nm, and the particle size increased after the emulsions were diluted in PBS buffer.

Kim et al. (Pharmaceutical Research, vol. 18, pages 54-60, 2001) and Chung et al. (Journal of Controlled Release, volume 71, pages 339-350, 2001) disclose various oil-in-water emulsions that were used to enhance in vitro and in vivo transfection efficiency of DNA molecules. Among the cationic lipids tested, DOTAP formed the most stable and efficient emulsion for DNA delivery. Among the oils tested, squalene, light mineral oil, and jojoba bean oil formed stable emulsions with small particles. The efficiencies of in vitro transfection were shown to correlate to the stability of the emulsions (e.g., the emulsion formulated by squalene at 100 mg/mL and DOTAP at 24 mg/mL showed high in vitro transfection efficiency). The emulsions were prepared by first mixing the cationic lipid with water to form a liposome suspension (by sonication). Liposomes were then added to the oil (such as squalene) and the mixture was sonicated to form an oil-in-water emulsion.

RNA molecules encoding an antigen or a derivative thereof may also be used as vaccines. RNA vaccines offer certain advantages as compared to DNA vaccines. However, compared with DNA-based vaccines, relatively minor attention has been given to RNA-based vaccines. RNAs are highly susceptible to degradation by nucleases when administered as a therapeutic or vaccine. Additionally, RNAs are not actively transported into cells. See, e.g., Vajdy, M., et al., *Mucosal adjuvants and delivery systems for protein-, DNA- and RNA-based vaccines*, Immunol Cell Biol, 2004. 82(6): p. 617-27.

Therefore, there is a need to provide delivery systems for nucleic acid molecules or other negatively charged molecules. The delivery systems are useful for nucleic acid-based vaccines, in particular RNA-based vaccines.

SUMMARY OF THE INVENTION

The invention relates to cationic oil-in-water emulsions that contain high concentrations of cationic lipids and have a defined oil:lipid ratio. The oil and cationic lipid are separate components of the emulsions, and preferably the oil is not ionic. The cationic lipid can interact with the negatively charged molecule thereby anchoring the molecule to the emulsion particles. The cationic emulsions described herein are useful for delivering negatively charged molecules, such as nucleic acid molecules (e.g., an RNA molecule encoding an antigen), to cells, and for formulating nucleic acid-based vaccines.

In one aspect, the invention provides an oil-in-water emulsion comprising particles that are dispersed in an aqueous continuous phase, wherein the emulsion is characterized by: (a) the average diameter of said particles is from about 80 nm to 180 nm in diameter; (b) the emulsion comprises an oil and a cationic lipid, wherein (i) the ratio of oil:cationic lipid (mole:mole) is at least about 8:1 (mole:mole), (ii) the concentration of cationic lipid in said emulsion is at least about 2.5 mM, and (iii) with the proviso that the cationic lipid is not DC-Cholesterol. Preferably, the oil-in-water emulsion is stable. In some embodiments, the ratio of oil:lipid (mole:mole) is from about 10:1 (mole:mole) to about 43:1 (mole:mole). The oil in water emulsion can contain from about 0.2% to about 8% (w/v) oil. In some embodiments, the oil is squalene or squalane.

In another aspect, the invention provides an oil-in-water emulsion comprising particles that are dispersed in an aqueous continuous phase, wherein the emulsion is characterized by: (a) the average diameter of said particles is from about 80 nm to 180 nm in diameter; (b) the emulsion comprises an oil and a cationic lipid, wherein (i) the ratio of oil:cationic lipid (mole:mole) is at least about 4:1 (mole:mole), (ii) the concentration of cationic lipid in said emulsion is at least about 2.5 mM, (iii) the oil is present from about 0.2% to about 8% (w/v); and (iv) with the proviso that the cationic lipid is not DC-Cholesterol. Preferably, the oil-in-water emulsion is stable. In some embodiments, the ratio of oil:lipid (mole:mole) is from about 4:1 (mole:mole) to about 43:1 (mole:mole). In some embodiments, the oil is squalene or squalane. In some embodiments, the oil is present from 0.6% to 4% (w/v). In some embodiments, the oil is present from about 1% to about 3.2% (w/v).

The oil-in-water emulsion of this aspect can further comprise a surfactant, such as a nonionic surfactant. Preferably, the surfactant is not a Polyethylene Glycol (PEG)-lipid. The surfactant can be present in an amount from about 0.01% to about 2.5% (w/v). In some embodiments, the surfactant is SPAN85 (Sorbtian Trioleate), Tween 80 (polysorbate 80), or a combination thereof. In some embodiments, the oil-in-water emulsion contains equal amounts of SPAN85 (Sorbtian Trioleate) and Tween 80 (polysorbate 80), for example 0.5% (w/v) of each.

Preferably the head group of the cationic lipid comprises a quaternary amine. For example, in some embodiments the cationic lipid is selected from the group consisting of: 1,2-dioleoyloxy-3-(trimethylammonio)propane (DOTAP), 1,2-dioleoyl-sn-glycero-3-ethylphosphocholine (DOEPC), N,N-dioleoyl-N,N-dimethylammonium chloride (DODAC), and N-[1-(2, 3-dioleyloxy)propyl]-N,N,N-trimethylammonium chloride (DOTMA).

In some embodiments, the emulsion is characterized by: (a) the average diameter of the emulsion particles is from about 80 nm to 180 nm in diameter; (b) the emulsion comprises an oil and DOTAP, wherein (i) the ratio of oil:DOTAP (mole:mole) is at least about 8:1 (mole:mole), and (ii) the concentration of DOTAP in said emulsion is at least about 2.58 mM (1.8 mg/mL), or from about 2.58 mM (1.8 mg/mL) to about 7.16 mM (5 mg/mL). The oil can be squalene or squalane.

In some embodiments, the emulsion is characterized by: (a) the average diameter of the emulsion particles is from about 80 nm to 180 nm in diameter; (b) the emulsion comprises an oil and DOTAP, wherein (i) the ratio of oil:DOTAP (mole:mole) is at least about 4:1 (mole:mole), (ii) the concentration of DOTAP in said emulsion is at least about 2.58 mM (1.8 mg/mL), and (iii) the oil is present from about 0.2% to about 8% (w/v). In some embodiments, the oil is squalene or squalane. In some embodiments, the concentration of DOTAP from about 2.58 mM (1.8 mg/mL) to about 7.16 mM (5 mg/mL). In some embodiments, the oil is present from 0.6% to 4% (w/v). In some embodiments, the oil is present from about 1% to about 3.2% (w/v).

The invention also provides a method for preparing an oil-in-water emulsion comprising particles that are dispersed in an aqueous continuous phase, wherein the emulsion is characterized by: (a) the average diameter of said particles is from about 80 nm to 180 nm in diameter; (b) the emulsion comprises an oil and a cationic lipid, wherein (i) the ratio of oil:cationic lipid (mole:mole) is at least about 8:1 (mole: mole), (ii) the concentration of cationic lipid in said emulsion is at least about 2.5 mM, and (iii) with the proviso that the cationic lipid is not DC-Cholesterol, the method comprises (a) directly dissolving the cationic lipid in the oil to form an oil phase; (b) providing an aqueous phase of the emulsion; and (c) dispersing the oil phase in the aqueous phase by homogenization. The oil can be heated to a temperature between about 30° C. to about 65° C. to facilitate dissolution of the cationic lipid in the oil. Higher temperatures may also be used, as long as there is no significant degradation of oil or the cationic lipid.

The invention also provides a method for preparing an oil-in-water emulsion comprising particles that are dispersed in an aqueous continuous phase, wherein the emulsion is characterized by: (a) the average diameter of said particles is from about 80 nm to 180 nm in diameter; (b) the emulsion comprises an oil and a cationic lipid, wherein (i) the ratio of oil:cationic lipid (mole:mole) is at least about 4:1 (mole: mole), (ii) the concentration of cationic lipid in said emulsion is at least about 2.5 mM, (iii) the oil is present from about 0.2% to about 8% (w/v); and (iv) with the proviso that the cationic lipid is not DC-Cholesterol, the method comprises (a) directly dissolving the cationic lipid in the oil to form an oil phase; (b) providing an aqueous phase of the emulsion; and (c) dispersing the oil phase in the aqueous phase by homogenization. The oil can be heated to a temperature between about 30° C. to about 65° C. to facilitate dissolution of the cationic lipid in the oil. Higher temperatures may also be used, as long as there is no significant degradation of oil or the cationic lipid.

In another aspect, the invention provides a composition comprising a nucleic acid molecule (preferably an RNA molecule) complexed with a particle of a cationic oil-in-water emulsion, wherein the particle comprises an oil that is in liquid phase at 25° C., and a cationic lipid; and (i) the ratio of oil:lipid (mole:mole) is at least about 8:1 (mole:mole); (ii) the concentration of cationic lipid in said composition is at least about 1.25 mM; and (iii) with the proviso that the cationic lipid is not DC-Cholesterol. Preferably, the average diameter of the emulsion particles is from about 80 nm to 180 nm, or about 80 nm to 150 nm, or about 80 nm to about 130 nm, and the NIP ratio of the composition is at least about 4:1, or from about 4:1 to about 20:1, or from about 4:1 to about 15:1. In certain embodiments, the ratio of oil:lipid (mole:mole) is from about 10:1 (mole:mole) to about 43:1 (mole:mole). The oil in water emulsion can contain from about 0.1% to about 5% (w/v) oil. In some embodiments, the oil is squalene or squalane.

In another aspect, the invention provides a composition comprising a nucleic acid molecule (preferably an RNA molecule) complexed with a particle of a cationic oil-in-water emulsion, wherein the particle comprises an oil that is in liquid phase at 25° C., and a cationic lipid; and (i) the ratio of oil:lipid (mole:mole) is at least about 4:1 (mole:mole); (ii) the concentration of cationic lipid in said composition is at least about 1.25 mM; (iii) the oil is present from about 0.1% to about 4% (w/v); and (iv) with the proviso that the cationic lipid is not DC-Cholesterol. Preferably, the average diameter of the emulsion particles is from about 80 nm to 180 nm, or about 80 nm to 150 nm, or about 80 nm to about 130 nm, and the NIP ratio of the composition is at least about 4:1, or from about 4:1 to about 20:1, or from about 4:1 to about 15:1. In certain embodiments, the ratio of oil:lipid (mole:mole) is from about 4:1 (mole:mole) to about 43:1 (mole:mole). In some embodiments, the oil is squalene or squalane. In some embodiments, the oil is present from 0.6% to 4% (w/v). In some embodiments, the oil is present from about 1% to about 3.2% (w/v).

The oil-in-water emulsion of this aspect can further comprise a surfactant, such as a nonionic surfactant. Preferably, surfactant is not a Polyethylene Glycol (PEG)-lipid. The surfactant can be present in an amount from about 0.005% to about 1.25% (w/v). In some embodiments, the surfactant is SPAN85 (Sorbtian Trioleate), Tween 80 (polysorbate 80), or a combination thereof. In some embodiments, the oil-in-water emulsion contains equal amounts of SPAN85 (Sorbtian Trioleate) and Tween 80 (polysorbate 80), for example 0.25% or 0.5% (w/v) of each.

Preferably the head group of the cationic lipid comprises a quaternary amine. For example, in some embodiments the cationic lipid is selected from the group consisting of: 1,2-dioleoyloxy-3-(trimethylammonio)propane (DOTAP), 1,2-dioleoyl-sn-glycero-3-ethylphosphocholine (DOEPC), N,N-dioleoyl-N,N-dimethylammonium chloride (DODAC), and N-[1-(2, 3-dioleyloxy)propyl]-N,N,N-trimethylammonium chloride (DOTMA).

In some embodiments, the invention provides a composition comprising a nucleic acid molecule (preferably an RNA molecule) complexed with a particle of a cationic oil-in-water emulsion, wherein the particle comprises an oil that is in liquid phase at 25° C. and DOTAP; and (i) the ratio of oil:DOTAP (mole:mole) is at least about 8:1 (mole:mole); (ii) the concentration of DOTAP in said composition is at least about 1.29 mM, or from about 1.29 mM (0.9 mg/mL) to about 3.58 mM (2.5 mg/mL). The oil can be squalene or squalane. Optionally, the N/P ratio is at least 4:1.

In preferred embodiments, the composition is buffered (e.g., with a citrate buffer, succinate buffer, acetate buffer) and has a pH of about 6.0 to about 8.0, preferably about 6.2 to about 6.8. The composition can further comprise an inorganic salt, and the concentration of inorganic salt is preferably no greater than 30 mM. Optionally, the composition can further comprise a nonionic tonicifying agent, and preferably is isotonic.

The invention also provides a method for preparing a composition comprising a nucleic acid molecule (preferably an RNA molecule) complexed with a particle of a cationic oil-in-water emulsion, comprising: (i) providing an oil-in-water emulsion as described herein; (ii) providing an aqueous solution comprising the RNA molecule; and (iii) combining the oil-in-water emulsion of (i) and the aqueous solution of (ii), thereby preparing the composition. In some embodiments, the cationic oil-in-water emulsion and RNA solution are combined at about 1:1 (v/v) ratio. The aqueous solution comprising the RNA molecule is preferably buffered (e.g., with a citrate buffer, succinate buffer, acetate buffer), can contain a inorganic salt (e.g. NaCl), which is preferably present at about 20 mM or less. In one embodiment, the aqueous solution comprising the RNA molecule contains 2 mM citrate buffer and 20 mM NaCl. Optionally, the aqueous solution comprising the RNA molecule further comprises an nonionic tonicifying agent, and is isotonic. In one embodiment, the aqueous solution further comprises about 560 mM sucrose. Optionally, the aqueous solution comprising the RNA molecule further comprises a polymer or nonionic surfactant, such as Pluronic® F127, at from about 0.05% to about 20% (w/v).

In another aspect, the invention provides an oil-in-water emulsion comprising particles that are dispersed in an aqueous continuous phase, wherein the emulsion comprises an oil and a cationic lipid, the average diameter of said particles is from about 80 nm to 180 nm, the oil is present from 0.6% to 4% (w/v); and the concentration of cationic lipid in said emulsion is at least about 1.25 mM. Preferably, the oil-in-water emulsion is stable. In some embodiments, the concentration of cationic lipid in said emulsion is at least about 2.5 mM. In some embodiments, the oil is squalene or squalane.

The oil-in-water emulsion of this aspect can further comprise a surfactant, such as a nonionic surfactant. Preferably, surfactant is not a Polyethylene Glycol (PEG)-lipid. The surfactant can be present in an amount from about 0.01% to about 2.5% (w/v). In some embodiments, the surfactant is SPAN85 (Sorbtian Trioleate), Tween 80 (polysorbate 80), or a combination thereof. In some embodiments, the oil-in-water emulsion contains equal amounts of SPAN85 (Sorbtian Trioleate) and Tween 80 (polysorbate 80), for example 0.25% or 0.5% (w/v) of each.

Preferably the head group of the cationic lipid comprises a quaternary amine. For example, in some embodiments the cationic lipid is selected from the group consisting of: 1,2-dioleoyloxy-3-(trimethylammonio)propane (DOTAP), 1,2-dioleoyl-sn-glycero-3-ethylphosphocholine (DOEPC), N,N-dioleoyl-N,N-dimethylammonium chloride (DODAC), and N-[1-(2, 3-dioleyloxy)propyl]-N,N,N-trimethylammonium chloride (DOTMA).

The invention provides a composition comprising a nucleic acid molecule (preferably an RNA molecule) complexed with a particle of an oil-in-water emulsion that contains particles that are dispersed in an aqueous continuous phase, wherein the emulsion comprises an oil and a cationic lipid, the average diameter of said particles is from about 80 nm to 180 nm, the oil is present from 0.6% to 4% (w/v); and the concentration of cationic lipid in said emulsion is at least about 1.25 mM. Preferably, the oil-in-water emulsion is stable. In some embodiments, the concentration of cationic lipid in said emulsion is at least about 2.5 mM. In some embodiments, the oil s squalene or squalane. Preferably, the N/P ratio of the composition is at least about 4:1.

In preferred embodiments, the composition is buffered (e.g., with a citrate buffer, succinate buffer, acetate buffer) and has a pH of about 6.0 to about 8.0, preferably about 6.2 to about 6.8. The composition can further comprise an inorganic salt, and the concentration of inorganic salt is preferably no greater than 30 mM. Optionally, the composition can further comprise a nonionic tonicifying agent, and preferably is isotonic.

The invention also relates to a method of generating an immune response in a subject, comprising administering to a subject in need thereof the composition as described herein. Preferably the amount of the cationic lipid administered to the subject (as a component of the composition) in a single administration is no more than about 30 mg. In particular embodiments, the cationic lipid is DOTAP and the total amount of DOTAP administered to the subject in a single administration is no more than about 24 mg, or no more than about 4 mg.

BRIEF DESCRIPTION OF THE DRAWINGS

FIG. 4 is a graph showing anti-VZV protein antibody response in immune sera from mice immunized with monocistronic RNA replicons that encoded VZV proteins or bicistronic RNA replicons that encoded VZV gE and gI, or gH and gL. The mice were immunized with 7 μg RNA formulated with CMF32.

DETAILED DESCRIPTION OF THE INVENTION

1. Overview

Figure 1:
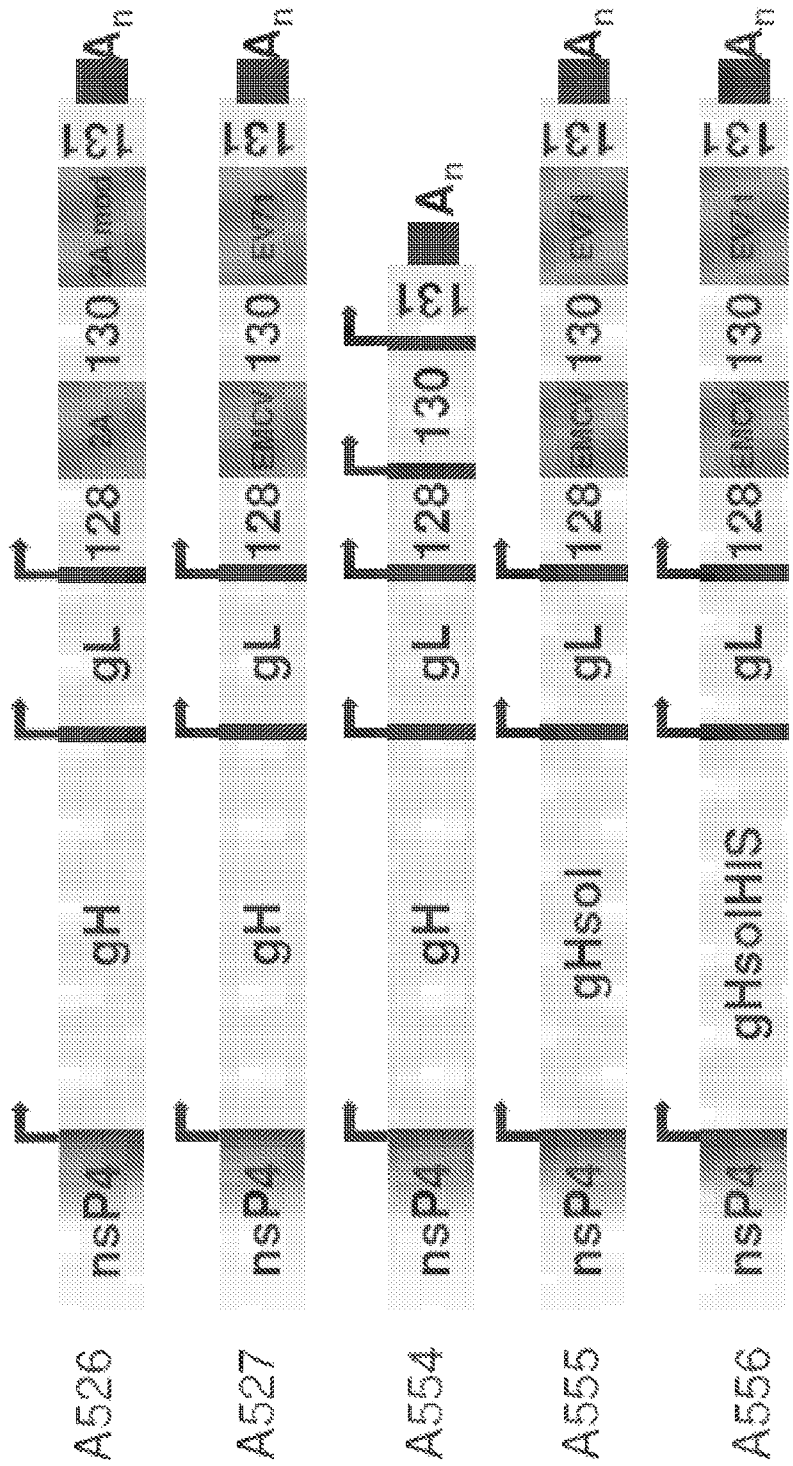
FIG. 1 is a schematic of pentacistronic RNA replicons, A526, A527, A554, A555 and A556, that encode five CMV proteins. Subgenomic promoters are shown by arrows, other control elements are labeled.

This invention generally relates to cationic oil-in-water emulsions that contain high concentrations of cationic lipids and have a defined oil:cationic lipid ratio. The oil and cationic lipid are separate components of the emulsions, and preferably the oil is not ionic. The cationic lipid can interact with a negatively charged molecule, such as a nucleic acid, thereby anchoring the negatively charged molecule to the emulsion particles. The cationic emulsions described herein are useful for delivering negatively charged molecules, such as nucleic acid molecules (e.g., an RNA molecule encoding a protein or peptide, small interfering RNA, self-replicating RNA, and the like), to cells in vivo, and for formulating nucleic acid-based vaccines.

In particular, the present invention is based on the discovery that stable cationic oil-in-water emulsions that contain high concentrations of cationic lipids and have a defined oil:cationic lipid ratio can be successfully made. Emulsions that contain high concentrations of cationic lipids allow more negatively charged molecules (such as RNA molecules) to be formulated with emulsion particles, thereby increasing the efficiency of delivery. In particular, for many therapeutics such as vaccines small volumes (e.g., 0.5 mL per dose) are preferred for administration. Emulsions that contain high concentrations of cationic lipids and have a defined oil:cationic lipid ratio, as described herein, will allow for the delivery of a higher dose of RNA within a specified volume.

In preferred embodiments, an RNA molecule is complexed with a particle of the oil-in-water emulsion. The complexed RNA molecule is stabilized and protected from RNase-mediated degradation, and is more efficiently taken up by cells relative to free ("naked") RNA.

In addition, when the RNA is delivered to induce expression of an encoded protein, such as in the context of an RNA vaccine, emulsions that contain high concentrations of cationic lipids can increase the amount of RNA molecules that are complexed with emulsion particles. As more RNA molecules are delivered to host cells, higher amount of the encoded protein antigen is produced, which in turn enhances the potency and immunogenicity of the RNA vaccine. Finally, the immunogenicity of the encoded protein can be enhanced due to adjuvant effects of the emulsion. Therefore, in addition to more efficient delivery of a negatively charged molecule (e.g., an RNA molecule that encodes an antigen), the cationic emulsions can also enhance the immune response through adjuvant activity. For example, as described and exemplified herein, formulations in which RNA molecules (encoding respiratory syncytial virus (RSV) F protein) were complexed with high-DOTAP emulsions generated higher immune responses in a mouse model and a cotton rat model of RSV, as compared to RNA molecules complexed with low-DOTAP emulsions.

Accordingly, in one aspect, the invention provides an oil-in-water emulsion comprising particles that are dispersed in an aqueous continuous phase, wherein the emulsion is characterized by: (a) the average diameter of said particles is from about 80 nm to 180 nm; (b) the emulsion comprises an oil and a cationic lipid, wherein (i) the ratio of oil:cationic lipid (mole:mole) is at least about 8:1 (mole:mole), (ii) the concentration of cationic lipid in said emulsion is at least about 2.5 mM, and (iii) the cationic lipid is not DC-Cholesterol.

In another aspect, the invention provides an oil-in-water emulsion comprising particles that are dispersed in an aqueous continuous phase, wherein the emulsion is characterized by: (a) the average diameter of said particles is from about 80 nm to 180 nm; (b) the emulsion comprises an oil and a cationic lipid, wherein (i) the ratio of oil:cationic lipid (mole:mole) is at least about 4:1 (mole:mole), (ii) the concentration of cationic lipid in said emulsion is at least about 2.5 mM, (iii) the oil is present from about 0.2% to about 8% (w/v); and (iv) with the proviso that the cationic lipid is not DC-Cholesterol.

The cationic emulsion may further comprise a surfactant (e.g., Tween 80, SPAN85, or a combination thereof).

In another aspect, the invention also provides several specific formulations of cationic oil-in-water emulsions that contain high concentrations of cationic lipids and can be used to deliver negatively charged molecules.

In another aspect, the invention provides a method of preparing an oil-in-water emulsion, comprising: (1) directly dissolving a cationic lipid in an oil to form an oil phase; (2) providing an aqueous phase of the emulsion; and (3) dispersing the oil phase in the aqueous phase (e.g., by homogenization). If desired, the oil may be heated to a temperature between about 30° C. to about 65° C. to facilitate the dissolving of the lipid in the oil. Preferably, the ratio of oil:cationic lipid (mole:mole) in the oil phase is at least about 8:1 (mole:mole), and alternatively or in addition, the average diameter of said particles is from about 80 nm to 180 nm, and/or the concentration of cationic lipid in the oil phase is at least about 5 mM.

In another aspect, the invention provides a method of preparing a composition that comprises a negatively charged molecule (such as an RNA molecule) complexed with a particle of a cationic oil-in-water emulsion, comprising: (i) providing an oil-in-water emulsion as described herein; (ii) providing an aqueous solution comprising the RNA molecule; and (iii) combining the aqueous solution of (ii) and the oil-in-water emulsion of (i), thereby preparing the composition. If desired, the aqueous solution comprising the RNA molecule may comprise a salt (e.g., NaCl), a buffer (e.g., a citrate buffer), a nonionic tonicifying agent (e.g., sucrose, trehalose, sorbitol, or dextrose), a polymer (e.g., Pluronic® F127), or any combination thereof.

The cationic emulsions of the invention can be used to deliver a negatively charge molecule, such as a nucleic acid (e.g., RNA). The compositions may be administered to a subject in need thereof to generate or potentiate an immune response. The compositions can also be co-delivered with another immunogenic molecule, immunogenic composition or vaccine to enhance the effectiveness of the induced immune response.

2. Definitions

The term "about", as used here, refers to +/−5% of a value.

An "antigen" refers to a molecule containing one or more epitopes (either linear, conformational or both).

A "buffer" refers to an aqueous solution that resists changes in the pH of the solution.

As used herein, "nucleotide analog" or "modified nucleotide" refers to a nucleotide that contains one or more chemical modifications (e.g., substitutions) in or on the nitrogenous base of the nucleoside (e.g., cytosine (C), thymine (T) or uracil (U)), adenine (A) or guanine (G)).

As used herein, an emulsion "particle" refers to a oil droplet suspended in the aqueous (continuous) phase of an oil-in-water emulsion. The particle further comprises a cationic liquid, and optionally additional components, such as a surfactant.

The term "polymer" refers to a molecule consisting of individual chemical moieties, which may be the same or different, that are joined together. As used herein, the term "polymer" refers to individual chemical moieties that are joined end-to-end to form a linear molecule, as well as individual chemical moieties joined together in the form of a branched (e.g., a "multi-arm" or "star-shaped") structure. Exemplary polymers include, e.g., poloxamers. Poloxamers are nonionic triblock copolymers having a central hydrophobic chain of polyoxypropylene (poly(propylene oxide)) flanked by two hydrophilic chains of polyoxyethylene (poly (ethylene oxide)).

As use herein, "saccharide" encompasses monosaccharides, oligosaccharides, or polysaccharides in straight chain or ring forms, or a combination thereof to form a saccharide chain. Oligosaccharides are saccharides having two or more monosaccharide residues. Examples of saccharides include glucose, maltose, maltotriose, maltotetraose, sucrose and trehalose.

An emulsion is "stable" when the emulsion particles remain separated without significant agglomeration or coalescence for at least one month, preferably at least two months, at 4° C. The average particle diameter (average number diameter) of a stable emulsion does not change by more than 10% when the emulsion is stored at 4° C. for one month, or preferably two months.

The term "surfactant" is a term of art and generally refers to any molecule having both a hydrophilic group (e.g., a polar group), which energetically prefers solvation by water, and a hydrophobic group which is not well solvated by water. The term "nonionic surfactant" is a known term in the art and generally refers to a surfactant molecule whose hydrophilic group (e.g., polar group) is not electrostatically charged.

The "Zeta potential" of an emulsion is determined by the electrophoretic mobility of the emulsion particles. The velocity of a particle in a unit electric field is referred to as its electrophoretic mobility. Zeta potential is related to the electrophoretic mobility by the Henry equation:

$$U_E = \frac{2\varepsilon z f(ka)}{3\eta}$$

where $U_E$=electrophoretic mobility, z=zeta potential, ε=dielectric constant, η=viscosity and f(ka)=Henry's function. Zeta potential is typically measured using an electrophoretic mobility apparatus, such as a Zetasizer Nano Z (Malvern Instruments Ltd, United Kingdom).

3. Cationic Oil-in-Water Emulsions

The cationic oil-in-water emulsions disclosed herein are generally described in the manner that is conventional in the art, by concentrations of components that are used to prepare the emulsions. It is understood in the art that during the process of producing emulsions, including sterilization and other downstream processes, small amounts of oil (e.g., squalene), cationic lipid (e.g., DOTAP), or other components may be lost, and the actual concentrations of these components in the final product (e.g., a packaged, sterilized emulsion that is ready for administration) might be slightly lower than starting amounts, sometimes by up to about 10%, by up to about 20%, by up to about 25%, or by up to about 35%.

This invention generally relates to cationic oil-in-water emulsions that contain high concentrations of cationic lipids and a defined oil:cationic lipid ratio. The emulsions are particularly suitable for delivering negatively charged molecules, such as an RNA molecule, to a cell. The cationic lipid can interact with the negatively charged molecule, for example through electrostatic forces and hydrophobic/hydrophilic interactions, thereby anchoring the molecule to the emulsion particles. The cationic emulsions described herein are useful for delivering a negatively charged molecule, such as an RNA molecule encoding an antigen or small interfering RNA to cells in vivo. For example, the cationic emulsions described herein provide advantages for delivering RNA molecules that encode one or more antigens, including self-replicating RNAs, as vaccines.

The discrete phase (or dispersed phase) of the emulsion comprises an oil and a cationic lipid, wherein the cationic lipid facilitates dispersing the oil in the aqueous (continuous) phase. One or more optional components may be present in the emulsion, such as surfactants (e.g., nonionic surfactants) as described below.

The particles of the oil-in-water emulsions have an average diameter (i.e., average number diameter) of 1 micrometer or less. It is particularly desirable that the average particle diameter of the cationic emulsions is about 180 nm or less, about 170 nm or less, about 160 nm or less, about 150 nm or less, about 140 nm or less, about 130 nm or less, about 120 nm or less, about 110 nm or less, or about 100 nm or less; for example, from about 80 nm to 180 nm, from about 80 nm to 170 nm, from about 80 nm to 160 nm, from about 80 nm to 150 nm, from about 80 nm to 140 nm, from about 80 nm to 130 nm, from about 80 nm to 120 nm; from about 80 nm to 110 nm, or from about 80 nm to 100 nm. Particularly preferred average particle diameter is about 100 nm, or from about 100 nm to about 130 nm.

The size (average diameter) of the emulsion particles can be varied by changing the ratio of surfactant to oil (increasing the ratio decreases particle size), operating pressure of homogenization (increasing operating pressure of homogenization typically reduces particle size), temperature (increasing temperature decreases particle size), changing the type of oil, inclusion of certain types of buffers in the aqueous phase, and other process parameters, as described in detail below. In some cases, the size of the emulsion particles may affect the immunogenicity of the RNA-emulsion complex, as exemplified herein.

The oil-in-water emulsions described herein are stable.

The particles of the emulsions described herein can be complexed with a negatively charged molecule. Prior to complexation with the negatively charged molecule, the overall net charge of the particles (typically measured as zeta-potential) should be positive (cationic). The overall net charge of the particles may vary, depending on the type of the cationic lipid and the amount of the cationic lipid in the emulsion, the amount of oil in the emulsion (e.g., higher percentage of oil typically results in less charge on the surface of the particles), and may also be affected by any additional component (e.g., surfactant(s)) that is present in the emulsion. Preferably, the zeta-potential of the pre-complexation particles are no more than about 50 mV, no more than about 45 mV, no more than about 40 mV, no more than about 35 mV, no more than about 30 mV, no more than about 25 mV, no more than about 20 mV; from about 5 mV to about 50 mV, from about 10 mV to about 50 mV, from about 10 mV to about 45 mV, from about 10 mV to about 40 mV, from about 10 mV to about 35 mV, from about 10 mV to about 30 mV, from about 10 mV to about 25 mV, or from about 10 mV to about 20 mV. Zeta potential can be affected by (i) pH of the emulsion, (ii) conductivity of the emulsion (e.g., salinity), and (iii) the concentration of the various components of the emulsion (polymer, non-ionic surfactants etc.). The Zeta potential of the cationic oil-in-water emulsions is measured using a Malvern Nanoseries Zetasizer (Westborough, Mass.). The sample is diluted 1:100 in water (viscosity: 0.8872cp, RI: 1.330, Dielectric constant: 78.5) and is added to a polystyrene latex capillary cell (Malvern, Westborough, Mass.). Zeta potential is measured at 25° C. with a 2 minute equilibration time and analyzed using the Smoluchowski model (F(Ka) value=1.5). Data is reported in mV.

An exemplary cationic emulsion of the invention is referred herein as "CMF32." The oil of CMF32 is squalene (at 4.3% w/v) and the cationic lipid is DOTAP (at 3.2 mg/mL). CMF32 also includes the surfactants SPAN85 (sorbitan trioleate at 0.5% v/v) and Tween 80 (polysorbate 80; polyoxyethuylenesorbitan monooleate; at 0.5% v/v). Thus, emulsion particles of CMF32 comprise squalene, SPAN85, Tween80, and DOTAP. RNA molecules were shown to complex with CMF32 particles efficiently at 4:1, 6:1, 8:1, 10:1, 12:1, and 14:1 N/P ratios. Other exemplary cationic emulsions include, e.g., the emulsions referred to herein as "CMF34" (4.3% w/v squalene, 0.5% Tween 80, 0.5% SPAN85, and 4.4 mg/mL DOTAP), "CMF35" (4.3% w/v squalene, 0.5% Tween 80, 0.5% SPAN85, 5.0 mg/mL DOTAP), and other emulsions described herein.

Certain exemplary cationic oil-in-water emulsions of the invention comprise DOTAP and squalene at concentrations of 2.1 mg/ml to 2.84 mg/ml (preferably 2.23 mg/ml to 2.71 mg/ml), and 30.92 mg/ml to 41.92 mg/ml (preferably 32.82 mg/ml to about 40.02 mg/ml), respectively, and further comprise equal amounts of SPAN85 and Tween80 (e.g., about 0.5% each). Other exemplary cationic oil-in-water emulsions of the invention comprise DOTAP and squalene at concentrations of 2.78 mg/ml to 3.76 mg/ml (preferably 2.94 mg/ml to 3.6 mg/ml), and 18.6 mg/ml to 25.16 mg/ml (preferably 19.69 mg/ml to about 24.07 mg/ml), respectively, and further comprise equal amounts of SPAN85 and Tween80 (e.g., about 0.5% each). Preferably, the particles of these emulsions have an average diameter from 80 nm to 180 nm.

The individual components of the oil-in-water emulsions of the present invention are known in the art, although such compositions have not been combined in the manner described herein. Accordingly, the individual components, although described below both generally and in some-detail for preferred embodiments, are well known in the art, and the terms used herein, such as oil, surfactant, etc., are sufficiently well known to one skilled in the art without further description. In addition, while preferred ranges of the amount of the individual components of the emulsions are provided, the actual ratios of the components of a particular emulsion may need to be adjusted so that emulsion particles of desired size and physical property are properly formed. For example, if a particular amount of oil is used (e.g. 5% v/v oil), then, the amount of surfactant should be at level that is sufficient to disperse the oil particle into the aqueous phase to form a stable emulsion. The actual amount of surfactant required to disperse the oil into the aqueous phase depends on the type of surfactant and the type of oil used for the emulsion; and the amount of oil may also vary according to the desired particle size (as this changes the surface area between the two phases). The actual amounts and the relative proportions of the components of a desired emulsion can be readily determined by a skilled artisan.

A. Oil

The particles of the cationic oil-in-water emulsions comprise an oil.

The oil preferably is in the liquid phase at 1° C. or above, and is immiscible to water.

Preferably, the oil is a metabolizable, non-toxic oil; more preferably one of about 6 to about 30 carbon atoms including, but not limited to, alkanes, alkenes, alkynes, and their corresponding acids and alcohols, the ethers and esters thereof, and mixtures thereof. The oil may be any vegetable oil, fish oil, animal oil or synthetically prepared oil that can be metabolized by the body of the subject to which the emulsion will be administered, and is not toxic to the subject. The subject may be an animal, typically a mammal, and preferably a human.

In certain embodiments, the oil is in liquid phase at 25° C. The oil is in liquid phase at 25° C., when it displays the properties of a fluid (as distinguished from solid and gas; and having a definite volume but no definite shape) when stored at 25° C. The emulsion, however, may be stored and used at any suitable temperature. Preferably, the oil is in liquid phase at 4° C.

The oil may be any long chain alkane, alkene or alkyne, or an acid or alcohol derivative thereof either as the free acid, its salt or an ester such as a mono-, or di- or triester, such as the triglycerides and esters of 1,2-propanediol or similar poly-hydroxy alcohols. Alcohols may be acylated employing a mono- or poly-functional acid, for example acetic acid, propanoic acid, citric acid or the like. Ethers derived from long chain alcohols which are oils and meet the other criteria set forth herein may also be used.

The individual alkane, alkene or alkyne moiety and its acid or alcohol derivatives will generally have from about 6 to about 30 carbon atoms. The moiety may have a straight or branched chain structure. It may be fully saturated or have one or more double or triple bonds. Where mono or poly ester- or ether-based oils are employed, the limitation of about 6 to about 30 carbons applies to the individual fatty acid or fatty alcohol moieties, not the total carbon count.

Any suitable oils from an animal, fish or vegetable source may be used. Sources for vegetable oils include nuts, seeds and grains, and suitable oils peanut oil, soybean oil, coconut oil, and olive oil and the like. Other suitable seed oils include safflower oil, cottonseed oil, sunflower seed oil, sesame seed oil and the like. In the grain group, corn oil, and the oil of other cereal grains such as wheat, oats, rye, rice, teff, triticale and the like may also be used. The technology for obtaining vegetable oils is well developed and well known. The compositions of these and other similar oils may be found in, for example, the Merck Index, and source materials on foods, nutrition and food technology.

About six to about ten carbon fatty acid esters of glycerol and 1,2-propanediol, while not occurring naturally in seed oils, may be prepared by hydrolysis, separation and esterification of the appropriate materials starting from the nut and seed oils. These products are commercially available under the name NEOBEES from PVO International, Inc., Chemical Specialties Division, 416 Division Street, Boongon, N.J. and others.

Animal oils and fats are often in solid phase at physiological temperatures due to the fact that they exist as triglycerides and have a higher degree of saturation than oils from fish or vegetables. However, fatty acids are obtainable from animal fats by partial or complete triglyceride saponification which provides the free fatty acids. Fats and oils from mammalian milk are metabolizable and may therefore be used in the practice of this invention. The procedures for separation, purification, saponification and other means necessary for obtaining pure oils from animal sources are well known in the art.

Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Squalene (2,6,10,15,19,23-hexamethyl-2,6,10,14,18,22-tetracosahexaene), a branched, unsaturated terpenoid, is particularly preferred herein. A major source of squalene is shark liver oil, although plant oils (primarily vegetable oils), including amaranth seed, rice bran, wheat germ, and olive oils, are also suitable sources. Squalene can also be obtained from yeast or other suitable microbes. In some embodiments, Squalene is preferably obtained from non-animal sources, such as from olives, olive oil or yeast. Squalane, the saturated analog to squalene, is also preferred. Fish oils, including squalene and squalane, are readily available from commercial sources or may be obtained by methods known in the art.

In certain embodiments, the oil comprises an oil that is selected from the group consisting of: Castor oil, Coconut oil, Corn oil, Cottonseed oil, Evening primrose oil, Fish oil, Jojoba oil, Lard oil, Linseed oil, Olive oil, Peanut oil, Safflower oil, Sesame oil, Soybean oil, Squalene, Squalane, Sunflower oil and Wheatgerm oil. In exemplary embodiments, the oil comprises Squalene or Squalane.

The oil component of the emulsion may be present in an amount from about 0.2% to about 10% (v/v). For example, the cationic oil-in-water emulsion may comprise from about 0.2% to about 10% (v/v) oil, from about 0.2% to about 9% (v/v) oil, from about 0.2% to about 8% (v/v) oil, from about 0.2% to about 7% (v/v) oil, from about 0.2% to about 6% (v/v) oil, from about 0.2% to about 5% (v/v) oil, from about 0.3% to about 10% (v/v) oil, from about 0.4% to about 10% (v/v) oil, from about 0.5% to about 10% (v/v) oil, from about 1% to about 10% (v/v) oil, from about 2% to about 10% (v/v) oil, from about 3% to about 10% (v/v) oil, from about 4% to about 10% (v/v) oil, from about 5% to about 10% (v/v) oil, from about 0.2% to about 10% (w/v) oil, from about 0.2% to about 9% (w/v) oil, from about 0.2% to about 8% (w/v) oil, from about 0.2% to about 7% (w/v) oil, from about 0.2% to about 6% (w/v) oil, from about 0.2% to about 5% (w/v) oil, from about 0.2% to about 4.3% (w/v) oil, from about 0.6% to about 4% (w/v) oil, from about 0.7% to about 4% (w/v) oil, from about 0.8% to about 4% (w/v) oil, from about 0.9% to about 4% (w/v) oil, from about 1.0% to about 4% (w/v) oil, from about 0.6% to about 3.5% (w/v) oil, from about 0.6% to about 3% (w/v) oil, about 0.5% (v/v) oil, about 0.6% (v/v) oil, about 0.7% (v/v) oil, about 0.8% (v/v) oil, about 0.9% (v/v) oil, about 1% (v/v) oil, about 1.5% (v/v) oil, about 2% (v/v) oil, about 2.5% (v/v) oil, about 3% (v/v) oil, about 3.5% (v/v) oil, about 4% (v/v) oil, about 5% (v/v) oil, about 10% (v/v) oil, about 0.5% (w/v) oil, about 1% (w/v) oil, about 1.5% (w/v) oil, about 2% (w/v) oil, about 2.5% (w/v) oil, about 3% (w/v) oil, about 3.5% (w/v) oil, about 4% (w/v) oil, about 4.3% (w/v) oil, about 5% (w/v) oil, about 5.5% (w/v) oil, about 6% (w/v) oil, about 6.5% (w/v) oil, about 7% (w/v) oil, about 7.5% (w/v) oil, or about 8% (w/v) oil.

The cationic oil-in-water emulsion may also comprise from about 0.2% to about 8% (v/v) oil, for example, from 0.6% (w/v) to 4% (w/v), from about 1% (w/v) to about 3.2% (w/v), about 1% (w/v), about 1.1% (w/v), about 1.2% (w/v), about 1.3% (w/v), about 1.4% (w/v), about 1.5% (w/v), about 1.6% (w/v), about 1.7% (w/v), about 1.8% (w/v), about 1.9% (w/v), about 2.0% (w/v), about 2.1% (w/v), about 2.15% (w/v), about 2.2% (w/v), about 2.3% (w/v), about 2.4% (w/v), about 2.5% (w/v), about 2.6% (w/v), about 2.7% (w/v), about 2.8% (w/v), about 2.9% (w/v), 3.0% (w/v), about 3.1% (w/v), about 3.2% (w/v), about 3.3% (w/v), about 3.4% (w/v), about 3.5% (w/v), about 3.6% (w/v), about 3.7% (w/v), about 3.8% (w/v), about 3.9% (w/v), or about 4.0% (w/v) oil.

In an exemplary embodiment, the cationic oil-in-water emulsion comprises about 5% (v/v) oil. In another exemplary embodiment, the cationic oil-in-water emulsion comprises about 4.3% (w/v) squalene. In other exemplary embodiments, the cationic oil-in-water emulsion comprises from 0.6% (w/v) to 4% (w/v) squalene, for example, from about 1% (w/v) to about 3.2% (w/v) squalene, such as 1.08% (w/v), 2.15% (w/v), or 3.23% (w/v) squalene, as shown in the Examples.

As noted above, the percentage of oil described above is determined based on the initial amount of the oil that is used to prepare the emulsions. It is understood in the art that the actual concentration of the oil in the final product (e.g., a packaged, sterilized emulsion that is ready for administration) might be slightly lower, sometimes by up to about 10%, by up to about 20%, by up to about 25%, or by up to about 35%.

B. Cationic Lipids

The emulsion particles described herein comprise a cationic lipid, which can interact with the negatively charged molecule thereby anchoring the molecule to the emulsion particles.

Any suitable cationic lipid may be used. Generally, the cationic lipid contains a nitrogen atom that is positively charged under physiological conditions. The head group of the cationic lipid can comprise a tertiary amine or, preferably, a quaternary amine Certain suitable cationic lipids comprise two saturated or unsaturated fatty acid chains (e.g., side chains having from about 10 to about 30 carbon atoms).

The cationic lipid can have a positive charge at about 12 pH, about 11 pH, about 10 pH, about 9 pH, about 8 pH, about 7 pH, or about 6 pH.

Suitable cationic lipids include, benzalkonium chloride (BAK), benzethonium chloride, cetrimide (which contains tetradecyltrimethylammonium bromide and possibly small amounts of dodecyltrimethylammonium bromide and hexadecyltrimethyl ammonium bromide), cetylpyridinium chloride (CPC), cetyl trimethylammonium chloride (CTAC), primary amines, secondary amines, tertiary amines, including but not limited to N,N',N'-polyoxyethylene (10)-N-tallow-1,3-diaminopropane, other quaternary amine salts, including but not limited to dodecyltrimethylammonium bromide, hexadecyltrimethyl-ammonium bromide, mixed alkyl-trimethyl-ammonium bromide, benzyldimethyldodecylammonium chloride, benzyldimethylhexadecyl-ammonium chloride, benzyltrimethylammonium methoxide, cetyldimethylethylammonium bromide, dimethyldioctadecyl ammonium bromide (DDAB), methylbenzethonium chloride, decamethonium chloride, methyl mixed trialkyl ammonium chloride, methyl trioctylammonium chloride), N,N-dimethyl-N-[2 (2-methyl-4-(1,1,3,3tetramethylbutyl)-phenoxyl-ethoxy)ethyl]-benzenemetha-naminium chloride (DEBDA), dialkyldimetylammonium salts, [1-(2,3-dioleyloxy)-propyl]-N,N,N,trimethylammonium chloride, 1,2-diacyl-3-(trimethylammonio) propane (acyl group= dimyristoyl, dipalmitoyl, distearoyl, dioleoyl), 1,2-diacyl-3 (dimethylammonio)propane (acyl group=dimyristoyl, dipalmitoyl, distearoyl, dioleoyl), 1,2-dioleoyl-3-(4'-trimethyl-ammonio)butanoyl-sn-glycerol, 1,2-dioleoyl 3-succinyl-sn-glycerol choline ester, cholesteryl (4'-trimethylammonio) butanoate), N-alkyl pyridinium salts (e.g. cetylpyridinium bromide and cetylpyridinium chloride), N-alkylpiperidinium salts, dicationic bolaform electrolytes ($C_{12}Me_6$; $C_{12}Bu_6$), dialkylglycetylphosphorylcholine, lysolecithin, L-α dioleoylphosphatidylethanolamine, cholesterol hemisuccinate choline ester, lipopolyamines, including but not limited to dioctadecylamidoglycylspermine (DOGS), dipalmitoyl phosphatidylethanol-amidospermine (DPPES), lipopoly-L (or D)-lysine (LPLL, LPDL), poly (L (or D)-lysine conjugated to N-glutarylphosphatidylethanolamine, didodecyl glutamate ester with pendant amino group ($C_{12}GluPhC_nN^+$), ditetradecyl glutamate ester with pendant amino group ($C_{14}GluC_nN^+$), cationic derivatives of cholesterol, including but not limited to cholesteryl-3β-oxysuccinamidoethylenetrimethylammonium salt, cholesteryl-3β-oxysuccinamidoethylenedimethylamine, cholesteryl-3β-carboxyamidoethylenetrimethylammonium salt, cholesteryl-3β-carboxyamidoethylenedimethylamine, and 3γ-[N—(N',N-dimethylaminoetanecarbomoyl]cholesterol) (DC-Cholesterol), 1,2-dioleoyloxy-3-(trimethylammonio) propane (DOTAP), dimethyldioctadecylammonium (DDA), 1,2-Dimyristoyl-3-TrimethylAmmoniumPropane (DMTAP), dipalmitoyl($C_{16:0}$)trimethyl ammonium propane (DPTAP), distearoyltrimethylammonium propane (DSTAP), N-[1-(2, 3-dioleyloxy)propyl]-N,N,N-trimethylammonium chloride (DOTMA), N,N-dioleoyl-N,N-dimethylammonium chloride (DODAC), 1,2-dioleoyl-sn-glycero-3-ethylphosphocholine (DOEPC), 1,2-dioleoyl-3-dimethylammonium-propane (DODAP), 1,2-dilinoleyloxy-3-dimethylaminopropane (DLinDMA), and combination thereof.

In preferred embodiments, the cationic lipid is selected from the group consisting of 1,2-dioleoyloxy-3-(trimethylammonio)propane (DOTAP), 1,2-dioleoyl-sn-glycero-3-ethylphosphocholine (DOEPC), N,N-dioleoyl-N,N-dimethylammonium chloride (DODAC), and N-[1-(2, 3-dioleyloxy)propyl]-N,N,N-trimethylammonium chloride (DOTMA). In certain embodiments, the cationic lipid is not DC-Cholesterol.

Preferably, the cationic lipid selected for the emulsion is soluble in the oil that is selected for the emulsion. This permits high cationic lipid concentrations to be achieved in the emulsion, by directly dissolving the lipid in the oil prior to dispersion in the mobile phase. It is within the knowledge in the art to determine whether a particular lipid is soluble in the oil and choose an appropriate oil and lipid combination accordingly. For example, solubility can be predicted based on the structures of the lipid and oil (e.g., the solubility of a lipid may be determined by the structure of its tail). For example, lipids having one or two unsaturated fatty acid chains (e.g., oleoyl tails, or linolyl tails), such as DOTAP, DOEPC, DODAC, DOTMA, are soluble in squalene or squalane. Alternatively, solubility can be determined according to the quantity of the lipid that dissolves in a given quantity of the oil to form a saturated solution. Such methods are known in the art. The solubility of exemplary saturated or unsaturated fatty acids in squalene is also provided in the Examples. Preferably, the saturation concentration of the lipid in the oil is at least about 1 mg/ml, at least about 5 mg/ml, at least about 10 mg/ml, at least about 25 mg/ml, at least about 50 mg/ml or at least about 100 mg/ml.

Preferably, the concentration of cationic lipid in the emulsion before the negatively charged molecule is complexed is at least about 1.25 mM, at least about 1.5 mM, at least about 1.75 mM, at least about 2.0 mM, at least about 2.25 mM, at least about 2.5 mM, at least about 2.75 mM, at least about 3.0 mM, at least about 3.25 mM, at least about 3.5 mM, at least about 3.75 mM, at least about 4.0 mM, at least about 4.25 mM, at least about 4.5 mM, at least about 4.75 mM, at least about 5.0 mM, at least about 5.25 mM, at least about 5.5 mM, at least about 5.75 mM, at least about 6 mM, at least about 6.25 mM, at least about 6.5 mM, at least about 6.75 mM, at least about 7 mM, at least about 7.25 mM, at least about 7.5 mM, at least about 7.75 mM, at least about 8 mM, at least about 8.25 mM, at least about 8.5 mM, at least about 8.75 mM, at least about 9 mM, at least about 9.25 mM, at least about 9.5 mM, at least about 9.75 mM, or at least about 10 mM.

In certain embodiments, the cationic lipid is DOTAP. The cationic oil-in-water emulsion may comprise from about 0.8 mg/ml to about 10 mg/ml DOTAP. For example, the cationic oil-in-water emulsion may comprise DOTAP at from about 1.7 mg/ml to about 10 mg/ml, from about 1.8 mg/ml to about 10 mg/ml, from about 2.0 mg/ml to about 10 mg/ml, from about 2.2 mg/ml to about 10 mg/ml, from about 2.4 mg/ml to about 10 mg/ml, from about 2.6 mg/ml to about 10 mg/ml, from about 2.8 mg/ml to about 10 mg/ml, from about 3.0 mg/ml to about 10 mg/ml, from about 3.2 mg/ml to about 10 mg/ml, from about 3.4 mg/ml to about 10 mg/ml, from about 3.6 mg/ml to about 10 mg/ml, from about 4.0 mg/ml to about 10 mg/ml, from about 4.4 mg/ml to about 10 mg/ml, from about 4.8 mg/ml to about 10 mg/ml, from about 5 mg/ml to about 10 mg/ml, from about 1.7 mg/ml to about 5 mg/ml, from about 1.8 mg/ml to about 5 mg/ml, from about 1.8 mg/ml to about 6 mg/ml, from about 1.8 mg/ml to about 7 mg/ml, from about 1.8 mg/ml to about 8 mg/ml, from about 1.8 mg/ml to about 9 mg/ml, about 1.7 mg/ml, about 1.8 mg/ml, about 2.0 mg/ml, about 2.2 mg/ml, about 2.4 mg/ml, about 2.6 mg/ml, about 2.8 mg/ml, about 3.0 mg/ml, about 3.2 mg/ml, about 3.4 mg/ml, about 3.6 mg/ml, about 3.8 mg/ml, about 4.0 mg/ml, about 4.2 mg/ml, about 4.4 mg/ml, about 4.6 mg/ml, about 4.8 mg/ml, about 5.0 mg/ml, about 5.2 mg/ml, about 5.5 mg/ml, about 6.0 mg/ml, at least about 0.8 mg/ml, at least about 0.85 mg/ml, at least about 0.9 mg/ml, at least about 1.0 mg/ml, at least about 1.1 mg/ml, at least about 1.2 mg/ml, at least about 1.3 mg/ml, at least about 1.4 mg/ml, at least about 1.5 mg/ml, at least about 1.6 mg/ml, at least about 1.7 mg/ml, etc.

In an exemplary embodiment, the cationic oil-in-water emulsion comprises from about 1.8 mg/ml to about 5.0 mg/ml DOTAP.

In certain embodiments, the cationic lipid is DOEPC. The cationic oil-in-water emulsion may comprise from about 0.8 mg/ml to about 10 mg/ml DOEPC. For example, the cationic oil-in-water emulsion may comprise DOEPC at from about 1.7 mg/ml to about 10 mg/ml, from about 1.8 mg/ml to about 10 mg/ml, from about 2.0 mg/ml to about 10 mg/ml, from about 2.2 mg/ml to about 10 mg/ml, from about 2.4 mg/ml to about 10 mg/ml, from about 2.6 mg/ml to about 10 mg/ml, from about 2.8 mg/ml to about 10 mg/ml, from about 3.0 mg/ml to about 10 mg/ml, from about 3.2 mg/ml to about 10 mg/ml, from about 3.4 mg/ml to about 10 mg/ml, from about 3.6 mg/ml to about 10 mg/ml, from about 4.0 mg/ml to about 10 mg/ml, from about 4.4 mg/ml to about 10 mg/ml, from about 4.8 mg/ml to about 10 mg/ml, from about 5 mg/ml to about 10 mg/ml, from about 1.7 mg/ml to about 5 mg/ml, from about 1.8 mg/ml to about 5 mg/ml, from about 1.8 mg/ml to about 6 mg/ml, from about 1.8 mg/ml to about 7 mg/ml, from about 1.8 mg/ml to about 8 mg/ml, from about 1.8 mg/ml to about 9 mg/ml, about 1.7 mg/ml, about 1.8 mg/ml, about 2.0 mg/ml, about 2.2 mg/ml, about 2.4 mg/ml, about 2.6 mg/ml, about 2.8 mg/ml, about 3.0 mg/ml, about 3.2 mg/ml, about 3.4 mg/ml, about 3.6 mg/ml, about 3.8 mg/ml, about 4.0 mg/ml, about 4.2 mg/ml, about 4.4 mg/ml, about 4.6 mg/ml, about 4.8 mg/ml, about 5.0 mg/ml, about 5.2 mg/ml, about 5.5 mg/ml, about 6.0 mg/ml, at least about 0.8 mg/ml, at least about 0.85 mg/ml, at least about 0.9 mg/ml, at least about 1.0 mg/ml, at least about 1.1 mg/ml, at least about 1.2 mg/ml, at least about 1.3 mg/ml, at least about 1.4 mg/ml, at least about 1.5 mg/ml, at least about 1.6 mg/ml, at least about 1.7 mg/ml, etc.

In certain embodiments, the cationic lipid is DODAC. The cationic oil-in-water emulsion may comprise from about 0.8 mg/ml to about 10 mg/ml DODAC. For example, the cationic oil-in-water emulsion may comprise DODAC at from about 1.7 mg/ml to about 10 mg/ml, from about 1.8 mg/ml to about 10 mg/ml, from about 2.0 mg/ml to about 10 mg/ml, from about 2.2 mg/ml to about 10 mg/ml, from about 2.4 mg/ml to about 10 mg/ml, from about 2.6 mg/ml to about 10 mg/ml, from about 2.8 mg/ml to about 10 mg/ml, from about 3.0 mg/ml to about 10 mg/ml, from about 3.2 mg/ml to about 10 mg/ml, from about 3.4 mg/ml to about 10 mg/ml, from about 3.6 mg/ml to about 10 mg/ml, from about 4.0 mg/ml to about 10 mg/ml, from about 4.4 mg/ml to about 10 mg/ml, from about 4.8 mg/ml to about 10 mg/ml, from about 5 mg/ml to about 10 mg/ml, from about 1.7 mg/ml to about 5 mg/ml, from about 1.8 mg/ml to about 5 mg/ml, from about 1.8 mg/ml to about 6 mg/ml, from about 1.8 mg/ml to about 7 mg/ml, from about 1.8 mg/ml to about 8 mg/ml, from about 1.8 mg/ml to about 9 mg/ml, about 1.7 mg/ml, about 1.8 mg/ml, about 2.0 mg/ml, about 2.2 mg/ml, about 2.4 mg/ml, about 2.6 mg/ml, about 2.8 mg/ml, about 3.0 mg/ml, about 3.2 mg/ml, about 3.4 mg/ml, about 3.6 mg/ml, about 3.8 mg/ml, about 4.0 mg/ml, about 4.2 mg/ml, about 4.4 mg/ml, about 4.6 mg/ml, about 4.8 mg/ml, about 5.0 mg/ml, about 5.2 mg/ml, about 5.5 mg/ml, about 6.0 mg/ml, at least about 0.8 mg/ml, at least about 0.85 mg/ml, at least about 0.9 mg/ml, at least about 1.0 mg/ml, at least about 1.1 mg/ml, at least about 1.2 mg/ml, at least about 1.3 mg/ml, at least about 1.4 mg/ml, at least about 1.5 mg/ml, at least about 1.6 mg/ml, at least about 1.7 mg/ml, etc.

In certain embodiments, the cationic lipid is DOTMA. The cationic oil-in-water emulsion may comprise from about 0.8 mg/ml to about 10 mg/ml DOTMA. For example, the cationic oil-in-water emulsion may comprise DOTMA at from about 1.7 mg/ml to about 10 mg/ml, from about 1.8 mg/ml to about 10 mg/ml, from about 2.0 mg/ml to about 10 mg/ml, from about 2.2 mg/ml to about 10 mg/ml, from about 2.4 mg/ml to about 10 mg/ml, from about 2.6 mg/ml to about 10 mg/ml, from about 2.8 mg/ml to about 10 mg/ml, from about 3.0 mg/ml to about 10 mg/ml, from about 3.2 mg/ml to about 10 mg/ml, from about 3.4 mg/ml to about 10 mg/ml, from about 3.6 mg/ml to about 10 mg/ml, from about 4.0 mg/ml to about 10 mg/ml, from about 4.4 mg/ml to about 10 mg/ml, from about 4.8 mg/ml to about 10 mg/ml, from about 5 mg/ml to about 10 mg/ml, from about 1.7 mg/ml to about 5 mg/ml, from about 1.8 mg/ml to about 5 mg/ml, from about 1.8 mg/ml to about 6 mg/ml, from about 1.8 mg/ml to about 7 mg/ml, from about 1.8 mg/ml to about 8 mg/ml, from about 1.8 mg/ml to about 9 mg/ml, about 1.7 mg/ml, about 1.8 mg/ml, about 2.0 mg/ml, about 2.2 mg/ml, about 2.4 mg/ml, about 2.6 mg/ml, about 2.8 mg/ml, about 3.0 mg/ml, about 3.2 mg/ml, about 3.4 mg/ml, about 3.6 mg/ml, about 3.8 mg/ml, about 4.0 mg/ml, about 4.2 mg/ml, about 4.4 mg/ml, about 4.6 mg/ml, about 4.8 mg/ml, about 5.0 mg/ml, about 5.2 mg/ml, about 5.5 mg/ml, about 6.0 mg/ml, at least about 0.8 mg/ml, at least about 0.85 mg/ml, at least about 0.9 mg/ml, at least about 1.0 mg/ml, at least about 1.1 mg/ml, at least about 1.2 mg/ml, at least about 1.3 mg/ml, at least about 1.4 mg/ml, at least about 1.5 mg/ml, at least about 1.6 mg/ml, at least about 1.7 mg/ml, etc.

As noted above, the concentration of a lipid described above is determined based on the initial amount of the lipid that is used to prepare the emulsions. It is understood in the art that the actual concentration of the oil in the final product (e.g., a packaged, sterilized emulsion that is ready for administration) might be slightly lower, sometimes by up to about 10%, by up to about 20%, by up to about 25%, or by up to about 35%.

C. Oil to Lipid Ratio

The cationic oil-in-water emulsions of the invention have a defined oil:lipid ratio. For example, the ratio of oil:lipid (mole:mole) of the emulsion may be at least about 8:1 (mole:mole), at least about 8.5:1 (mole:mole), at least about 9:1 (mole:mole), at least about 9.5:1 (mole:mole), at least about 10:1 (mole:mole), at least about 10.5:1 (mole:mole), at least about 11:1 (mole:mole), at least about 11.5:1 (mole:mole), at least about 12:1 (mole:mole), at least about 12.5:1 (mole:mole), at least about 13:1 (mole:mole), at least about 13.5:1 (mole:mole), at least about 14:1 (mole:mole), at least about 14.5:1 (mole:mole), at least about 15:1 (mole:mole), at least about 15.5:1 (mole:mole), at least about 16:1 (mole: mole), at least about 16.5:1 (mole:mole), at least about 17:1 (mole:mole), from about 8:1 (mole:mole) to about 50:1 (mole:mole), from about 9:1 (mole:mole) to about 50:1 (mole:mole), from about 10:1 (mole:mole) to about 50:1 (mole:mole), from about 8:1 (mole:mole) to about 49:1 (mole:mole), from about 8:1 (mole:mole) to about 48:1 (mole:mole), from about 8:1 (mole:mole) to about 47:1 (mole:mole), from about 8:1 (mole:mole) to about 46:1 (mole:mole), from about 8:1 (mole:mole) to about 45:1 (mole:mole), from about 8:1 (mole:mole) to about 44:1 (mole:mole), from about 8:1 (mole:mole) to about 43:1 (mole:mole), from about 8:1 (mole:mole) to about 42:1 (mole:mole), from about 8:1 (mole:mole) to about 41:1 (mole:mole), from about 9:1 (mole:mole) to about 43:1 (mole:mole), from about 10:1 (mole:mole) to about 43:1 (mole:mole), from about 11:1 (mole:mole) to about 43:1 (mole:mole), from about 12:1 (mole:mole) to about 43:1 (mole:mole), from about 13:1 (mole:mole) to about 43:1 (mole:mole), from about 14:1 (mole:mole) to about 43:1 (mole:mole), from about 15:1 (mole:mole) to about 43:1 (mole:mole), from about 16:1 (mole:mole) to about 43:1 (mole:mole), from about 17:1 (mole:mole) to about 43:1 (mole:mole), etc.

If desired, the ratio of oil:lipid (mole:mole) of the emulsion may be at least about 4:1 (mole:mole), at least about 4.2:1 (mole:mole), at least about 4.5:1 (mole:mole), at least about 5:1 (mole:mole), at least about 5.5:1 (mole:mole), at least about 6:1 (mole:mole), at least about 6.5:1 (mole: mole), 7:1 (mole:mole), at least about 7.5:1 (mole:mole), from about 4:1 (mole:mole) to about 50:1 (mole:mole), from about 5:1 (mole:mole) to about 50:1 (mole:mole), from about 6:1 (mole:mole) to about 50:1 (mole:mole), from about 7:1 (mole:mole) to about 50:1 (mole:mole), from about 4:1 (mole:mole) to about 49:1 (mole:mole), from about 4:1 (mole:mole) to about 48:1 (mole:mole), from about 4:1 (mole:mole) to about 47:1 (mole:mole), from about 4:1 (mole:mole) to about 46:1 (mole:mole), from about 4:1 (mole:mole) to about 45:1 (mole:mole), from about 4:1 (mole:mole) to about 44:1 (mole:mole), from about 4:1 (mole:mole) to about 43:1 (mole:mole), from about 4:1 (mole:mole) to about 42:1 (mole:mole), from about 4:1 (mole:mole) to about 41:1 (mole:mole), from about 5:1 (mole:mole) to about 43:1 (mole:mole), from about 6:1 (mole:mole) to about 43:1 (mole:mole), from about 7:1 (mole:mole) to about 43:1 (mole:mole), etc.

Sometimes, there may be a need to strike a balance between the desire to increase the concentration of a cationic lipid (thereby increasing the amount of nucleic acid molecules loaded to the emulsion particle), and toxicity or tolerability of the lipid when administered in vivo. For example, it has been reported that high doses of DOTAP can have toxic effects. See, e.g., Lappalainen et al., Pharm. Res., vol. 11(8):1127-31 (1994). The optimal range of lipid dose in a particular emulsion can be determined in accordance with the knowledge of a skilled clinician.

If the oil comprises a mixture of molecules, the molar concentration of the oil can be calculated based on the average molecular weight of the oil. For example, the average molecular weight of soybean oil (292.2) can be calculated according to the average fatty acid distribution (12% weight percentage of palmitic acid; 52% weight percentage of linolenic acid; etc), and the molecular weight of each component.

C. Additional Components

The cationic oil-in-water emulsions described herein may further comprise additional components. For example, the emulsions may comprise components that can promote particle formation, improve the complexation between the negatively charge molecules and the cationic particles, or increase the stability of the negatively charge molecule (e.g., to prevent degradation of an RNA molecule). If desired, the cationic oil-in-water emulsion can contain an antioxidant, such as citrate, ascorbate or salts thereof.

Surfactants

In certain embodiments, the cationic oil-in-water emulsion as described herein further comprises a surfactant.

A substantial number of surfactants have been used in the pharmaceutical sciences. These include naturally derived materials such as gums from trees, vegetable protein, sugar-based polymers such as alginates, and the like. Certain oxypolymers or polymers having a hydroxide or other hydrophilic substituent on the carbon backbone have surfactant activity, for example, povidone, polyvinyl alcohol, and glycol ether-based mono- and poly-functional compounds. Ionic or nonionic detergents and long chain fatty-acid-derived compounds can also be used in this invention.

Specific examples of suitable surfactants include the following:

1. Water-soluble soaps, such as the sodium, potassium, ammonium and alkanol-ammonium salts of higher fatty acids ($C_{10}$-$C_{22}$), in particular sodium and potassium tallow and coconut soaps.

2. Anionic synthetic non-soap surfactants, which can be represented by the water-soluble salts of organic sulfuric acid reaction products having in their molecular structure an alkyl radical containing from about 8 to 22 carbon atoms and a radical selected from the group consisting of sulfonic acid and sulfuric acid ester radicals. Examples of these are the sodium or potassium alkyl sulfates, derived from tallow or coconut oil; sodium or potassium alkyl benzene sulfonates; sodium alkyl glyceryl ether sulfonates; sodium coconut oil fatty acid monoglyceride sulfonates and sulfates; sodium or potassium salts of sulfuric acid esters of the reaction product of one mole of a higher fatty alcohol and about 1 to 6 moles of ethylene oxide; sodium or potassium alkyl phenol ethylene oxide ether sulfonates, with 1 to 10 units of ethylene oxide per molecule and in which the alkyl radicals contain from 8 to 12 carbon atoms; the reaction product of fatty acids esterified with isethionic acid and neutralized with sodium hydroxide; sodium or potassium salts of fatty acid amide of a methyl tauride; and sodium and potassium salts of $SO_3$-sulfonated $C_{10}$-$C_{24}\alpha$-olefins.

3. Nonionic synthetic surfactants made by the condensation of alkylene oxide groups with an organic hydrophobic compound. Typical hydrophobic groups include condensation products of propylene oxide with propylene glycol, alkyl phenols, condensation product of propylene oxide and ethylene diamine, aliphatic alcohols having 8 to 22 carbon atoms, and amides of fatty acids.

4. Nonionic surfactants, such as amine oxides, phosphine oxides and sulfoxides, having semipolar characteristics. Specific examples of long chain tertiary amine oxides include dimethyldodecylamine oxide and bis-(2-hydroxyethyl) dodecylamine Specific examples of phosphine oxides are found in U.S. Pat. No. 3,304,263, issued Feb. 14, 1967, and include dimethyldodecylphosphine oxide and dimethyl-(2hydroxydodecyl) phosphine oxide.

5. Long chain sulfoxides, including those corresponding to the formula $R^1$—SO—$R^2$ wherein $R^1$ and $R^2$ are substituted or unsubstituted alkyl radicals, the former containing from about 10 to about 28 carbon atoms, whereas $R^2$ contains from 1 to 3 carbon atoms. Specific examples of these sulfoxides include dodecyl methyl sulfoxide and 3-hydroxy tridecyl methyl sulfoxide.

6. Ampholytic synthetic surfactants, such as sodium 3-dodecylaminopropionate and sodium 3-dodecylaminopropane sulfonate.

7. Zwitterionic synthetic surfactants, such as 3-(N,N-dimethyl-N-hexadecylammonio)propane-1-sulfonate and 3-(N,N-dimethyl-N-hexadecylammonio)-2-hydroxy propane-1-sulfonate.

Additionally, all of the following types of surfactants can be used in a composition of the present invention: (a) soaps (i.e., alkali salts) of fatty acids, rosin acids, and tall oil; (b) alkyl arene sulfonates; (c) alkyl sulfates, including surfactants with both branched-chain and straight-chain hydrophobic groups, as well as primary and secondary sulfate groups; (d) sulfates and sulfonates containing an intermediate linkage between the hydrophobic and hydrophilic groups, such as the fatty acylated methyl taurides and the sulfated fatty monoglycerides; (e) long-chain acid esters of polyethylene glycol, especially the tall oil esters; (f) polyethylene glycol ethers of alkylphenols; (g) polyethylene glycol ethers of long-chain alcohols and mercaptans; and (h) fatty acyl diethanol amides. Since surfactants can be classified in more than one manner, a number of classes of surfactants set forth in this paragraph overlap with previously described surfactant classes.

There are a number of surfactants specifically designed for and commonly used in biological situations. Such surfactants are divided into four basic types: anionic, cationic, zwitterionic (amphoteric), and nonionic. Exemplary anionic surfactants include, e.g., perfluorooctanoate (PFOA or PFO), perfluorooctanesulfonate (PFOS), alkyl sulfate salts such as sodium dodecyl sulfate (SDS) or ammonium lauryl sulfate, sodium laureth sulfate (also known as sodium lauryl ether sulfate, SLES), alkyl benzene sulfonate, and fatty acid salts. Exemplary cationic surfactants include, e.g., alkyltrimethylammonium salts such as cetyl trimethylammonium bromide (CTAB, or hexadecyl trimethyl ammonium bromide), cetylpyridinium chloride (CPC), polyethoxylated tallow amine (POEA), benzalkonium chloride (BAC), benzethonium chloride (BZT). Exemplary zwitterionic (amphoteric) surfactants include, e.g., dodecyl betaine, cocamidopropyl betaine, and coco ampho glycinate. Exemplary nonionic surfactants include, e.g., alkyl poly(ethylene oxide), alkylphenol poly(ethylene oxide), copolymers of poly(ethylene oxide) and poly(propylene oxide) (commercially called poloxamers or poloxamines), Aayl polyglucosides (e.g., octyl glucoside or decyl maltoside), fatty alcohols (e.g., cetyl alcohol or oleyl alcohol), cocamide MEA, cocamide DEA, Pluronic® F-68 (polyoxyethylene-polyoxypropylene block copolymer), and polysorbates, such as Tween 20 (polysorbate 20), Tween 80 (polysorbate 80; polyoxyethuylenesorbitan monooleate), dodecyl dimethylamine oxide, and vitamin E tocopherol propylene glycol succinate (Vitamin E TPGS).

A particularly useful group of surfactants are the sorbitan-based non-ionic surfactants. These surfactants are prepared by dehydration of sorbitol to give 1,4-sorbitan which is then reacted with one or more equivalents of a fatty acid. The fatty-acid-substituted moiety may be further reacted with ethylene oxide to give a second group of surfactants.

The fatty-acid-substituted sorbitan surfactants are made by reacting 1,4-sorbitan with a fatty acid such as lauric acid, palmitic acid, stearic acid, oleic acid, or a similar long chain fatty acid to give the 1,4-sorbitan mono-ester, 1,4-sorbitan sesquiester or 1,4-sorbitan triester. The common names for these surfactants include, for example, sorbitan monolaurate, sorbitan monopalmitate, sorbitan monoestearate, sorbitan monooleate, sorbitan sesquioleate, and sorbitan trioleate. These surfactants are commercially available under the name SPAN® or ARLACEL®, usually with a letter or number designation which distinguishes between the various mono, di- and triester substituted sorbitans.

SPAN® and ARLACEL® surfactants are hydrophilic and are generally soluble or dispersible in oil. They are also soluble in most organic solvents. In water they are generally insoluble but dispersible. Generally these surfactants will have a hydrophilic-lipophilic balance (HLB) number between 1.8 to 8.6. Such surfactants can be readily made by means known in the art or are commercially available.

A related group of surfactants comprises olyoxyethylene sorbitan monoesters and olyoxyethylene sorbitan triesters. These materials are prepared by addition of ethylene oxide to a 1,4-sorbitan monester or triester. The addition of polyoxyethylene converts the lipophilic sorbitan mono- or triester surfactant to a hydrophilic surfactant generally soluble or dispersible in water and soluble to varying degrees in organic liquids.

These materials, commercially available under the mark TWEEN®, are useful for preparing oil-in-water emulsions and dispersions, or for the solubilization of oils and making anhydrous ointments water-soluble or washable. The TWEEN® surfactants may be combined with a related sorbitan monester or triester surfactants to promote emulsion stability. TWEEN® surfactants generally have a HLB value falling between 9.6 to 16.7. TWEEN® surfactants are commercially available.

A third group of non-ionic surfactants which could be used alone or in conjunction with SPANS, ARLACEL® and TWEEN® surfactants are the polyoxyethylene fatty acids made by the reaction of ethylene oxide with a long-chain fatty acid. The most commonly available surfactant of this type is solid under the name MYRJ® and is a polyoxyethylene derivative of stearic acid. MYRJ® surfactants are hydrophilic and soluble or dispersible in water like TWEEN® surfactants. The MYRJ® surfactants may be blended with TWEEN® surfactants or with TWEEN®/SPAN® or ARLACEL® surfactant mixtures for use in forming emulsions. MYRJ® surfactants can be made by methods known in the art or are available commercially.

A fourth group of polyoxyethylene based non-ionic surfactants are the polyoxyethylene fatty acid ethers derived from lauryl, acetyl, stearyl and oleyl alcohols. These materials are prepared as above by addition of ethylene oxide to a fatty alcohol. The commercial name for these surfactants is BRIJ®. BRIJ® surfactants may be hydrophilic or lipophilic depending on the size of the polyoxyethylene moiety in the surfactant. While the preparation of these compounds is available from the art, they are also readily available from commercial sources.

Other non-ionic surfactants which could potentially be used are, for example, polyoxyethylene, polyol fatty acid esters, polyoxyethylene ether, polyoxypropylene fatty ethers, bee's wax derivatives containing polyoxyethylene, polyoxyethylene lanolin derivative, polyoxyethylene fatty glycerides, glycerol fatty acid esters or other polyoxyethylene acid alcohol or ether derivatives of long-chain fatty acids of 12-22 carbon atoms.

As the emulsions and formulations of the invention are intended to be multi-phase systems, it is preferable to choose an emulsion-forming non-ionic surfactant which has an HLB value in the range of about 7 to 16. This value may be obtained through the use of a single non-ionic surfactant such as a TWEEN® surfactant or may be achieved by the use of a blend of surfactants such as with a sorbitan mono, di- or triester based surfactant; a sorbitan ester polyoxyethylene fatty acid; a sorbitan ester in combination with a polyoxyethylene lanolin derived surfactant; a sorbitan ester surfactant in combination with a high HLB polyoxyethylene fatty ether surfactant; or a polyethylene fatty ether surfactant or polyoxyethylene sorbitan fatty acid.

In certain embodiments, the emulsion comprises a single non-ionic surfactant, most particularly a TWEEN® surfactant, as the emulsion stabilizing non-ionic surfactant. In an exemplary embodiment, the emulsion comprises TWEEN® 80, otherwise known as polysorbate 80 or polyoxyethylene 20 sorbitan monooleate. In other embodiments, the emulsion comprises two or more non-ionic surfactants, in particular a TWEEN® surfactant and a SPAN® surfactant. In an exemplary embodiment, the emulsion comprises TWEEN® 80 and SPAN®85.

The oil-in-water emulsions can contain from about 0.01% to about 2.5% surfactant (w/v), about 0.01% to about 2% surfactant, 0.01% to about 1.5% surfactant, 0.01% to about 1% surfactant, 0.01% to about 0.5% surfactant, 0.05% to about 0.5% surfactant, 0.08% to about 0.5% surfactant, about 0.08% surfactant, about 0.1% surfactant, about 0.2% surfactant, about 0.3% surfactant, about 0.4% surfactant, about 0.5% surfactant, about 0.6% surfactant, about 0.7% surfactant, about 0.8% surfactant, about 0.9% surfactant, or about 1% surfactant.

Alternatively or in addition, the oil-in-water emulsions can contain 0.05% to about 1%, 0.05% to about 0.9%, 0.05% to about 0.8%, 0.05% to about 0.7%, 0.05% to about 0.6%, 0.05% to about 0.5%, about 0.08%, about 0.1%, about 0.2%, about 0.3%, about 0.4%, about 0.5%, about 0.6%, about 0.7%, about 0.8%, about 0.9%, or about 1% (w/v) Tween 80 (polysorbate 80; polyoxyethuylenesorbitan monooleate).

In an exemplary embodiment, the oil-in-water emulsion contains 0.08% (w/v) Tween 80 (polysorbate 80; polyoxyethuylenesorbitan monooleate).

Alternatively or in addition, the oil-in-water emulsions can contain 0.05% to about 1%, 0.05% to about 0.9%, 0.05% to about 0.8%, 0.05% to about 0.7%, 0.05% to about 0.6%, 0.05% to about 0.5%, about 0.08%, about 0.1%, about 0.2%, about 0.3%, about 0.4%, about 0.5%, about 0.6%, about 0.7%, about 0.8%, about 0.9%, or about 1% (w/v) SPAN85 (sorbitan trioleate).

The oil-in-water emulsions can contain a combination of surfactants described herein. For example, a combination of Tween 80 (polysorbate 80; polyoxyethuylenesorbitan monooleate) and SPAN85 (sorbitan trioleate) may be used. The emulsions may contain various amounts of Tween 80 and SPAN85 (e.g., those exemplified above) or equal amounts. For example, the oil-in-water emulsions can contain (w/v) about 0.05% Tween 80 and about 0.05% SPAN85, about 0.1% Tween 80 and about 0.1% SPAN85, about 0.2% Tween 80 and about 0.2% SPAN85, about 0.3% Tween 80 and about 0.3% SPAN85, about 0.4% Tween 80 and about 0.4% SPAN85, about 0.5% Tween 80 and about 0.5% SPAN85, about 0.6% Tween 80 and about 0.6% SPAN85, about 0.7% Tween 80 and about 0.7% SPAN85, about 0.8% Tween 80 and about 0.8% SPAN85, about 0.9% Tween 80 and about 0.9% SPAN85, or about 1% Tween 80 and about 1.0% SPAN85.

In certain embodiments, the surfactant is a Polyethylene Glycol (PEG)-lipid. In other embodiments, the emulsion does not comprise a PEG-lipid. PEG-lipids, such as PEG coupled to dialkyloxypropyls (PEG-DAA), PEG coupled to diacylglycerol (PEG-DAG), PEG coupled to phosphatidylethanolamine (PE) (PEG-PE) or some other phospholipids (PEG-phospholipids), PEG conjugated to ceramides (PEG-Cer), or a combination thereof, may also be used as surfactants (see, e.g., U.S. Pat. No. 5,885,613; U.S. patent application publication Nos. 2003/0077829, 2005/0175682 and 2006/0025366). Other suitable PEG-lipids include, e.g., PEG-dialkyloxypropyl (DAA) lipids or PEG-diacylglycerol (DAG) lipids. Exemplary PEG-DAG lipids include, e.g., PEG-dilauroylglycerol ($C_{12}$) lipids, PEG-dimyristoylglycerol ($C_{14}$) lipids, PEG-dipalmitoylglycerol ($C_{16}$) lipids, or PEG-distearoylglycerol ($C_{18}$) lipids. Exemplary PEG-DAA lipids include, e.g., PEG-dilauryloxypropyl ($C_{12}$) lipids, PEG-dimyristyloxypropyl ($C_{14}$) lipids, PEG-dipalmityloxypropyl ($C_{16}$) lipids, or PEG-distearyloxypropyl ($C_{18}$) lipids.

PEGs are classified by their molecular weights; for example, PEG 2000 has an average molecular weight of about 2,000 daltons, and PEG 5000 has an average molecular weight of about 5,000 daltons. PEGs are commercially available from Sigma Chemical Co. as well as other companies and include, for example, the following: monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-$NH_2$), monomethoxypolyethylene glycol-tresylate (MePEG-TRES), and monomethoxypolyethylene glycol-imidazolyl-carbonyl (MePEG-IM). In addition, monomethoxypolyethyleneglycol-acetic acid (MePEG-$CH_2COOH$), is particularly useful for preparing the PEG-lipid conjugates including, e.g., PEG-DAA conjugates.

D. Aqueous Phase (Continuous Phase)

The aqueous phase (continuous phase) of the oil-in-water emulsions is water, or an aqueous solution that can contain a salt (e.g., NaCl), a buffer (e.g., a citrate buffer), a nonionic tonicifying agent (e.g., a saccharide), a polymer, a surfactant, or any combination thereof. The aqueous phase of the pre-complexed emulsions (oil-in-water emulsions before the addition of the negatively charged molecules) can differ from the aqueous phase of the post-complexed emulsions (oil-in-water emulsions in which the negatively charged molecules are complexed with the emulsion particles). In general, the pre-complexed emulsions are prepared in an aqueous solvent that promotes the formation of particles with desired properties (e.g., average diameter, and the like). The pre-complexed emulsions are diluted with an aqueous solution that contains the negatively charged molecule, and other desired components, to produce the final cationic oil-in-water emulsion, which contains the final aqueous phase with desired osmolarity and tonicity. The aqueous phase can contain an antioxidant, such as citrate, ascorbate or salts thereof.

When the emulsions are formulated for in vivo administration, it is preferable to make up the final solution so that the tonicity and osmolarity of the emulsion are substantially the same as normal physiological fluids in order to prevent undesired post-administration consequences, such as swelling or rapid absorption of the composition. It is also preferable to buffer the aqueous phase in order to maintain a pH compatible with normal physiological conditions. Also, in certain instances, it may be desirable to maintain the pH at a particular level in order to insure the stability of certain components of the emulsion. For example, it may be desirable to prepare an emulsion that is isotonic and isosmotic. To control tonicity, the emulsion may comprise a physiological salt, such as a sodium salt. Sodium chloride (NaCl), for example, may be used at about 0.9% (w/v) (physiological saline). Other salts that may be present include potassium chloride, potassium dihydrogen phosphate, disodium phosphate, magnesium chloride, calcium chloride, etc. Non-ionic tonicifying agents can also be used to control tonicity. A number of non-ionic tonicity modifying agents ordinarily known to those in the art. These are typically carbohydrates of various classifications (see, for example, Voet and Voet (1990) Biochemistry (John Wiley & Sons, New York). Monosaccharides classified as aldoses such as glucose, mannose, arabinose, and ribose, as well as those classified as ketoses such as fructose, sorbose, and xylulose can be used as non-ionic tonicifying agents in the present invention. Disaccharides such a sucrose, maltose, trehalose, and lactose can also be used. In addition, alditols (acyclic polyhydroxy alcohols, also referred to as sugar alcohols) such as glycerol, mannitol, xylitol, and sorbitol are non-ionic tonicifying agents useful in the present invention. Non-ionic tonicity modifying agents can be present at a concentration of from about 0.1% to about 10% or about 1% to about 10%, depending upon the agent that is used.

The aqueous phase may be buffered. Any physiologically acceptable buffer may be used herein, such as water, citrate buffers, phosphate buffers, acetate buffers, tris buffers, bicarbonate buffers, carbonate buffers, succinate buffer, or the like. The pH of the aqueous component will preferably be between 6.0-8.0, more preferable about 6.2 to about 6.8. In an exemplary embodiment, the buffer is 10 mM citrate buffer with a pH at 6.5. In another exemplary embodiment, the aqueous phase is, or the buffer prepared using, RNase-free water or DEPC treated water. In some cases, high salt in the buffer might interfere with complexation of negatively charged molecule to the emulsion particle therefore is avoided. In other cases, certain amount of salt in the buffer may be included.

In an exemplary embodiment, the buffer is 10 mM citrate buffer with a pH at 6.5. If desired the aqueous phase is, or the buffer is prepared using, RNase-free water or DEPC treated water.

The aqueous phase may also comprise additional components such as molecules that change the osmolarity of the aqueous phase or molecules that stabilizes the negatively charged molecule after complexation. Preferably, the osmolarity of the aqueous phase is adjusted using a non-ionic tonicifying agent, such as a sugar (e.g., trehalose, sucrose, dextrose, fructose, reduced palatinose, etc.), a sugar alcohol (such as mannitol, sorbitol, xylitol, erythritol, lactitol, maltitol, glycerol, etc.). If desired a nonionic polymer polymer (e.g., a poly(alkyl glycol) such as polyethylene glycol, polypropylene glycol, or polybutlyene glycol) or nonionic surfactant can be used.

In certain embodiments, the aqueous phase of the cationic oil-in-water emulsion may comprise a polymer or a surfactant, or a combination thereof. In an exemplary embodiment, the oil-in-water emulsion contains a poloxamer Poloxamers are nonionic triblock copolymers having a central hydrophobic chain of polyoxypropylene (poly(propylene oxide)) flanked by two hydrophilic chains of polyoxyethylene (poly (ethylene oxide)). Poloxamers are also known by the trade name Pluronic® polymers. Poloxamer polymers may lead to greater stability and increased RNase resistance of the RNA molecule after RNA complexation.

Alternatively or in addition, the cationic oil-in-water emulsion may comprise from about 0.1% to about 20% (w/v) polymer, or from about 0.05% to about 10% (w/v) polymer. For example, the cationic oil-in-water emulsion may comprise a polymer (e.g., a poloxamer such as Pluronic® F127 ((Ethylene Oxide/Propylene Oxide Block Copolymer: $H(OCH_2CH_2)_x(OCH_3CH(CH_3))_y(OCH_2CH_2)_zOH$)) at from about 0.1% to about 20% (w/v), from about 0.1% to about 10% (w/v), from about 0.05% to about 10% (w/v), or from about 0.05% to about 5% (w/v).

In an exemplary embodiment, the oil-in-water emulsion comprises about 4% (w/v), or about 8% (w/v) Pluronic® F127.

The quantity of the aqueous component employed in these compositions will be that amount necessary to bring the value of the composition to unity. That is, a quantity of aqueous component sufficient to make 100% will be mixed, with the other components listed above in order to bring the compositions to volume.

4. Negatively Charged Molecules

When a negatively charged molecule is to be delivered, it can be complexed with the particles of the cationic oil-in-water emulsions. The negatively charged molecule is complexed with the emulsion particles by, for example, interactions between the negatively charged molecule and the cationic lipid on the surface of the particles, as well as hydrophobic/hydrophilic interactions between the negatively charged molecule and the surface of the particles. Although not wishing to be bound by any particular theory, it is believed that the negatively charged molecules interact with the cationic lipid through non-covalent, ionic charge interactions (electrostatic forces), and the strength of the complex as well as the amount of negatively charged compound that can be complexed to a particle are related to the amount of cationic lipid in the particle. Additionally, hydrophobic/hydrophilic interactions between the negatively charged molecule and the surface of the particles may also play a role.

Examples of negatively charged molecules include negatively charged peptides, polypeptides or proteins, nucleic acid molecules (e.g., single or double stranded RNA or DNA), small molecules (e.g., small molecule immune potentiators (SMIPs), phosphonate, fluorophosphonate, etc.) and the like. In preferred aspects, the negatively charged molecule is an RNA molecule, such as an RNA that encodes a peptide, polypeptide or protein, including self-replicating RNA molecules, or a small interfering RNA.

The complex can be formed by using techniques known in the art, examples of which are described herein. For example, a nucleic acid-particle complex can be formed by mixing a cationic emulsion with the nucleic acid molecule, for example by vortexing. The amount of the negatively charged molecule and cationic lipid in the emulsions may be adjusted or optimized to provide desired strength of binding and binding capacity. For example, as described and exampled herein, exemplary RNA-particle complexes were produced by varying the RNA: cationic lipid ratios (as measured by the "N/P ratio"). The term N/P ratio refers to the amount (moles) of protonatable nitrogen atoms in the cationic lipid divided by the amount (moles) of phosphates on the RNA.

Preferred N/P ratios are from about 1:1 to about 20:1, from about 2:1 to about 18:1, from about 3:1 to 16:1, from about 4:1 to about 14:1, from about 6:1 to about 12:1, about 3:1, about 4:1, about 5:1, about 6:1, about 7:1, about 8:1, about 9:1, about 10:1, about 11:1, about 12:1, about 13:1, about 14:1, about 15:1, or about 16:1. Alternatively, preferred N/P ratios are at least about 3:1, at least about 4:1, at least about 5:1, at least about 6:1, at least about 7:1, at least about 8:1, at least about 9:1, at least about 10:1, at least about 11:1, at least about 12:1, at least about 13:1, at least about 14:1, at least about 15:1, or at least about 16:1. A more preferred N/P ratio is about 4:1 or higher.

Each emulsion may have its own optimal or preferred N/P ratio to produce desired effects (e.g., desired level of expression of the complexed RNA), which can be determined experimentally (e.g., using the assays as described herein or other techniques known in the art, such as measuring expression level of a protein that is encoded by the RNA, or measuring the percentage of the RNA molecules being released from the complex in the presence of heparin). Generally, the N/P ratio should be at a value that at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% of the RNA molecules are released from the RNA-particle complexes when the RNA-particle complexes are taken up by cells. In some embodiments, the N/P ratio is a value that provides for release of at least 0.5% or at least 1% of the RNA molecules are released from the RNA-particle complexes when the RNA-particle complexes are taken up by cells.

The expression level of an antigen encoded by the RNA molecule may not necessarily correlate with the immunogenicity of the antigen. In such cases, optimal or preferred N/P ratio fore immunogenicity may be determined by, e.g., measuring specific antibody titers.

The cationic oil-in-water emulsions described herein are particularly suitable for formulating nucleic acid-based vaccines (e.g., DNA vaccines, RNA vaccines). The formation of a nucleic acid-emulsion particle complex facilitates the uptake of the nucleic acid into host cells, and protects the nucleic acid molecule from nuclease degradation. Transfected cells can then express the antigen encoded by the nucleic acid molecule, which can produce an immune response to the antigen. Like live or attenuated viruses, nucleic acid-based vaccines can effectively engage both MHC-I and MHC-II pathways allowing for the induction of $CD8^+$ and $CD4^+$ T cell responses, whereas antigen present in soluble form, such as recombinant protein, generally induces only antibody responses.

In certain embodiments, the negatively charged molecule described herein is an RNA molecule. In certain embodiments, the RNA molecule encodes an antigen (peptide, polypeptide or protein) and the cationic oil in water emulsion is suitable for use as an RNA-based vaccine. The composition can contain more than one species of RNA molecule encoding an antigen, e.g., two, three, five, or ten different species of RNA molecules that are complexed to the emulsion particles. That is, the composition can contain one or more different species of RNA molecules, each encoding a different antigen. Alternatively or in addition, one RNA molecule may also encode more than one antigen, e.g., a bicistronic, or tricistronic RNA molecule that encodes different or identical antigens. Accordingly, the cationic oil in water emulsion is suitable for use as an RNA-based vaccine, that is monovalent or multivalent. If desired, the RNA molecule can be polycistronic.

The sequence of the RNA molecule may be codon optimized or deoptimized for expression in a desired host, such as a human cell.

The sequence of the RNA molecule may be modified if desired, for example to increase the efficacy of expression or replication of the RNA, or to provide additional stability or resistance to degradation. For example, the RNA sequence can be modified with respect to its codon usage, for example, to increase translation efficacy and half-life of the RNA. A poly A tail (e.g., of about 30 adenosine residues or more) (SEQ ID NO: 28) may be attached to the 3' end of the RNA to increase its half-life. The 5' end of the RNA may be capped with a modified ribonucleotide with the structure m7G (5') ppp (5') N (cap 0 structure) or a derivative thereof, which can be incorporated during RNA synthesis or can be enzymatically engineered after RNA transcription (e.g., by using Vaccinia Virus Capping Enzyme (VCE) consisting of mRNA triphosphatase, guanylyl-transferase and guanine-7-methytransferase, which catalyzes the construction of N7-monomethylated cap 0 structures). Cap 0 structure plays an important role in maintaining the stability and translational efficacy of the RNA molecule. The 5' cap of the RNA molecule may be further modified by a 2'-O-Methyltransferase which results in the generation of a cap 1 structure (m7Gppp [m2'-O] N), which may further increases translation efficacy.

If desired, the RNA molecule can comprise one or more modified nucleotides in addition to any 5' cap structure. There are more than 96 naturally occurring nucleoside modifications found on mammalian RNA. See, e.g., Limbach et al., *Nucleic Acids Research,* 22(12):2183-2196 (1994). The preparation of nucleotides and modified nucleotides and nucleosides are well-known in the art, e.g. from U.S. Pat. Nos. 4,373,071, 4,458,066, 4,500,707, 4,668,777, 4,973,679, 5,047,524, 5,132,418, 5,153,319, 5,262,530, 5,700,642 all of which are incorporated by reference in their entirety herein, and many modified nucleosides and modified nucleotides are commercially available.

Modified nucleobases which can be incorporated into modified nucleosides and nucleotides and be present in the RNA molecules include: m5C (5-methylcytidine), m5U (5-methyluridine), m6A (N6-methyladenosine), s2U (2-thiouridine), Um (2'-O-methyluridine), m1A (1-methyladenosine); m2A (2-methyladenosine); Am (2-1-O-methyladenosine); ms2m6A (2-methylthio-N6-methyladenosine); i6A (N6-isopentenyladenosine); ms2i6A (2-methylthio-N6isopentenyladenosine); io6A (N6-(cis-hydroxyisopentenyl)adenosine); ms2io6A (2-methylthio-N6-(cis-hydroxyisopentenyl) adenosine); g6A (N6-glycinylcarbamoyladenosine); t6A (N6-threonyl carbamoyladenosine); ms2t6A (2-methylthio-N6-threonyl carbamoyladenosine); m6t6A (N6-methyl-N6-threonylcarbamoyladenosine); hn6A(N6-hydroxynorvalylcarbamoyl adenosine); ms2hn6A (2-methylthio-N6-hydroxynorvalyl carbamoyladenosine); Ar(p) (2'-O-ribosyladenosine (phosphate)); I (inosine); m1I (1-methylinosine); m'Im (1,2'-O-dimethylinosine); m3C (3-methylcytidine); Cm (2T-O-methylcytidine); s2C (2-thiocytidine); ac4C (N4-acetylcytidine); f5C (5-fonnylcytidine); m5Cm (5,2-O-dimethy1cytidine); ac4Cm (N4acetyl2TOmethylcytidine); k2C (lysidine); m1G (1-methylguanosine); m2G (N2-methylguanosine); m7G (7-methylguanosine); Gm (2'-O-methylguanosine); m22G (N2,N2-dimethylguanosine); m2Gm (N2,2'-O-dimethylguanosine); m22Gm (N2,N2,2'-O-trimethylguanosine); Gr(p) (2'-O-ribosylguanosine (phosphate)); yW (wybutosine); o2yW (peroxywybutosine); OHyW (hydroxywybutosine); OHyW* (undermodified hydroxywybutosine); imG (wyosine); mimG (methylguanosine); Q (queuosine); oQ (epoxyqueuosine); galQ (galtactosyl-queuosine); manQ (mannosyl-queuosine); preQo (7-cyano-7-deazaguanosine); preQi (7-aminomethyl-7-deazaguanosine); G* (archaeosine); D (dihydrouridine); m5Um (5,2'-O-dimethyluridine); s4U (4-thiouridine); m5s2U (5-methyl-2-thiouridine); s2Um (2-thio-2'-O-methyluridine); acp3U (3-(3-amino-3-carboxypropyl)uridine); hoSU (5-hydroxyuridine); moSU (5-methoxyuridine);

cmo5U (uridine 5-oxyacetic acid); mcmo5U (uridine 5-oxyacetic acid methyl ester); chm5U (5-(carboxyhydroxymethyl)uridine)); mchm5U (5-(carboxyhydroxymethyl)uridine methyl ester); mcm5U (5-methoxycarbonyl methyluridine); mcm5Um (S-methoxycarbonylmethyl-2-O-methyluridine); mcm5s2U (5-methoxycarbonylmethyl-2-thiouridine); nm5s2U (5-aminomethyl-2-thiouridine); mnm5U (5-methylaminomethyluridine); mnm5s2U (5-methylaminomethyl-2-thiouridine); mnm5se2U (5-methylaminomethyl-2-selenouridine); ncm5U (5-carbamoylmethyl uridine); ncm5Um (5-carbamoylmethyl-2'-O-methyluridine); cmnm5U (5-carboxymethylaminomethyluridine); cnmm5Um (5-carboxymethylaminomethyl-2-L-Omethy1uridine); cmnm5s2U (5-carboxymethylaminomethyl-2-thiouridine); m62A (N6,N6-dimethyladenosine); Tm (2'-O-methylinosine); m4C (N4-methylcytidine); m4Cm (N4,2-O-dimethylcytidine); hm5C (5-hydroxymethylcytidine); m3U (3-methyluridine); cm5U (5-carboxymethyluridine); m6Am (N6,T-O-dimethyladenosine); rn62Am (N6,N6,O-2-trimethyladenosine); m2'7G (N2,7-dimethylguanosine); m2'2'7G (N2,N2,7-trimethylguanosine); m3Um (3,2T-O-dimethyluridine); m5D (5-methyldihydrouridine); f5Cm (5-formyl-2'-O-methylcytidine); m1Gm (1,2'-O-dimethylguanosine); m'Am (1,2-O-dimethyl adenosine) irinomethyluridine); tm5s2U (S-taurinomethyl-2-thiouridine)); imG-14 (4-demethyl guanosine); imG2 (isoguanosine); ac6A (N6-acetyladenosine), hypoxanthine, inosine, 8-oxo-adenine, 7-substituted derivatives thereof, dihydrouracil, pseudouracil, 2-thiouracil, 4-thiouracil, 5-aminouracil, 5-methyluracil, 5-($C_2$-$C_6$)-alkenyluracil, 5-($C_2$-$C_6$)-alkynyluracil, 5-(hydroxymethyl)uracil, 5-chlorouracil, 5-fluorouracil, 5-bromouracil, 5-hydroxycytosine, 5-($C_1$-$C_6$)-alkylcytosine, 5-methylcytosine, 5-($C_2$-$C_6$)-alkenylcytosine, 5-($C_2$-$C_6$)-alkynylcytosine, 5-chlorocytosine, 5-fluorocytosine, 5-bromocytosine, $N^2$-dimethylguanine, 7-deazaguanine, 8-azaguanine, 7-deaza-7-substituted guanine, 7-deaza-7-(C2-C6)alkynylguanine, 7-deaza-8-substituted guanine, 8-hydroxyguanine, 6-thioguanine, 8-oxoguanine, 2-aminopurine, 2-amino-6-chloropurine, 2,4-diaminopurine, 2,6-diaminopurine, 8-azapurine, substituted 7-deazapurine, 7-deaza-7-substituted purine, 7-deaza-8-substituted purine, hydrogen (abasic residue), m5C, m5U, m6A, s2U, W, or 2'-O-methyl-U. Many of these modified nucleobases and their corresponding ribonucleosides are available from commercial suppliers. See, e.g., WO 2011/005799 which is incorporated herein by reference.

If desired, the RNA molecule can contain phosphoramidate, phosphorothioate, and/or methylphosphonate linkages.

In some embodiments, the RNA molecule does not include modified nucleotides, e.g., does not include modified nucleobases, and all of the nucleotides in the RNA molecule are conventional standard ribonucleotides A, U, G and C, with the exception of an optional 5' cap that may include, for example, 7-methylguanosine. In other embodiments, the RNA may include a 5' cap comprising a 7'-methylguanosine, and the first 1, 2 or 3 5' ribonucleotides may be methylated at the 2' position of the ribose.

A. Self-Replicating RNA

In some aspects, the cationic oil in water emulsion contains a self-replicating RNA molecule. In certain embodiments, the self-replicating RNA molecule is derived from or based on an alphavirus.

Self-replicating RNA molecules are well known in the art and can be produced by using replication elements derived from, e.g., alphaviruses, and substituting the structural viral proteins with a nucleotide sequence encoding a protein of interest. Cells transfected with self-replicating RNA briefly produce antigen before undergoing apoptotic death. This death is a likely result of requisite double-stranded (ds) RNA intermediates, which also have been shown to super-activate Dendritic Cells. Thus, the enhanced immunogenicity of self-replicating RNA may be a result of the production of pro-inflammatory dsRNA, which mimics an RNA-virus infection of host cells.

Advantageously, the cell's machinery is used by self-replicating RNA molecules to generate an exponential increase of encoded gene products, such as proteins or antigens, which can accumulate in the cells or be secreted from the cells. Overexpression of proteins or antigens by self-replicating RNA molecules takes advantage of the immunostimulatory adjuvant effects, including stimulation of toll-like receptors (TLR) 3, 7 and 8 and non TLR pathways (e.g, RIG-1, MD-5) by the products of RNA replication and amplification, and translation which induces apoptosis of the transfected cell.

The self-replicating RNA generally contains at least one or more genes selected from the group consisting of viral replicases, viral proteases, viral helicases and other non-structural viral proteins, and also comprise 5'- and 3'-end cis-active replication sequences, and if desired, a heterologous sequences that encode a desired amino acid sequences (e.g., an antigen of interest). A subgenomic promoter that directs expression of the heterologous sequence can be included in the self-replicating RNA. If desired, the heterologous sequence (e.g., an antigen of interest) may be fused in frame to other coding regions in the self-replicating RNA and/or may be under the control of an internal ribosome entry site (IRES).

In certain embodiments, the self-replicating RNA molecule is not encapsulated in a virus-like particle. Self-replicating RNA molecules of the invention can be designed so that the self-replicating RNA molecule cannot induce production of infectious viral particles. This can be achieved, for example, by omitting one or more viral genes encoding structural proteins that are necessary for the production of viral particles in the self-replicating RNA. For example, when the self-replicating RNA molecule is based on an alpha virus, such as Sinebis virus (SIN), Semliki forest virus and Venezuelan equine encephalitis virus (VEE), one or more genes encoding viral structural proteins, such as capsid and/or envelope glycoproteins, can be omitted.

If desired, self-replicating RNA molecules of the invention can also be designed to induce production of infectious viral particles that are attenuated or virulent, or to produce viral particles that are capable of a single round of subsequent infection.

When delivered to a vertebrate cell, a self-replicating RNA molecule can lead to the production of multiple daughter RNAs by transcription from itself (or from an antisense copy of itself). The self-replicating RNA can be directly translated after delivery to a cell, and this translation provides a RNA-dependent RNA polymerase which then produces transcripts from the delivered RNA. Thus the delivered RNA leads to the production of multiple daughter RNAs. These transcripts are antisense relative to the delivered RNA and may be translated themselves to provide in situ expression of a gene product, or may be transcribed to provide further transcripts with the same sense as the delivered RNA which are translated to provide in situ expression of the gene product.

One suitable system for achieving self-replication is to use an alphavirus-based RNA replicon. Alphaviruses comprise a set of genetically, structurally, and serologically related arthropod-borne viruses of the Togaviridae family Twenty-six known viruses and virus subtypes have been classified within the alphavirus genus, including, Sindbis virus, Semliki Forest virus, Ross River virus, and Venezuelan equine encephalitis virus. As such, the self-replicating RNA of the invention may incorporate a RNA replicase derived from semliki forest virus (SFV), sindbis virus (SIN), Venezuelan equine encephalitis virus (VEE), Ross-River virus (RRV), or other viruses belonging to the alphavirus family.

An alphavirus-based "replicon" expression vectors can be used in the invention. Replicon vectors may be utilized in several formats, including DNA, RNA, and recombinant replicon particles. Such replicon vectors have been derived from alphaviruses that include, for example, Sindbis virus (Xiong et al. (1989) Science 243:1188-1191; Dubensky et al., (1996) J. Virol. 70:508-519; Hariharan et al. (1998) J. Virol. 72:950-958; Polo et al. (1999) PNAS 96:4598-4603), Semliki Forest virus (Liljestrom (1991) Bio/Technology 9:1356-1361; Berglund et al. (1998) Nat. Biotech. 16:562-565), and Venezuelan equine encephalitis virus (Pushko et al. (1997) Virology 239:389-401). Alphaviruses-derived replicons are generally quite similar in overall characteristics (e.g., structure, replication), individual alphaviruses may exhibit some particular property (e.g., receptor binding, interferon sensitivity, and disease profile) that is unique. Therefore, chimeric alphavirus replicons made from divergent virus families may also be useful.

Alphavirus-based replicons are (+)-stranded replicons that can be translated after delivery to a cell to give of a replicase (or replicase-transcriptase). The replicase is translated as a polyprotein which auto-cleaves to provide a replication complex which creates genomic (−)-strand copies of the +-strand delivered RNA. These (−)-strand transcripts can themselves be transcribed to give further copies of the (+)-stranded parent RNA and also to give a subgenomic transcript which encodes the desired gene product. Translation of the subgenomic transcript thus leads to in situ expression of the desired gene product by the infected cell. Suitable alphavirus replicons can use a replicase from a sindbis virus, a semliki forest virus, an eastern equine encephalitis virus, a venezuelan equine encephalitis virus, etc.

A preferred self-replicating RNA molecule thus encodes (i) a RNA-dependent RNA polymerase which can transcribe RNA from the self-replicating RNA molecule and (ii) a polypeptide antigen. The polymerase can be an alphavirus replicase e.g. comprising alphavirus protein nsP4.

Whereas natural alphavirus genomes encode structural virion proteins in addition to the non-structural replicase, it is preferred that an alphavirus based self-replicating RNA molecule of the invention does not encode alphavirus structural proteins. Thus the self-replicating RNA can lead to the production of genomic RNA copies of itself in a cell, but not to the production of RNA-containing alphavirus virions. The inability to produce these virions means that, unlike a wild-type alphavirus, the self-replicating RNA molecule cannot perpetuate itself in infectious form. The alphavirus structural proteins which are necessary for perpetuation in wild-type viruses are absent from self-replicating RNAs of the invention and their place is taken by gene(s) encoding the desired gene product, such that the subgenomic transcript encodes the desired gene product rather than the structural alphavirus virion proteins.

Thus a self-replicating RNA molecule useful with the invention may have two open reading frames. The first (5') open reading frame encodes a replicase; the second (3') open reading frame encodes a polypeptide antigen. In some embodiments the RNA may have additional (downstream) open reading frames e.g. that encode another desired gene products. A self-replicating RNA molecule can have a 5' sequence which is compatible with the encoded replicase.

In other aspects, the self-replicating RNA molecule is derived from or based on a virus other than an alphavirus, preferably, a positive-stranded RNA virus, and more preferably a picornavirus, flavivirus, rubivirus, pestivirus, hepacivirus, calicivirus, or coronavirus. Suitable wild-type alphavirus sequences are well-known and are available from sequence depositories, such as the American Type Culture Collection, Rockville, Md. Representative examples of suitable alphaviruses include Aura (ATCC VR-368), Bebaru virus (ATCC VR-600, ATCC VR-1240), Cabassou (ATCC VR-922), Chikungunya virus (ATCC VR-64, ATCC VR-1241), Eastern equine encephalomyelitis virus (ATCC VR-65, ATCC VR-1242), Fort Morgan (ATCC VR-924), Getah virus (ATCC VR-369, ATCC VR-1243), Kyzylagach (ATCC VR-927), Mayaro (ATCC VR-66), Mayaro virus (ATCC VR-1277), Middleburg (ATCC VR-370), Mucambo virus (ATCC VR-580, ATCC VR-1244), Ndumu (ATCC VR-371), Pixuna virus (ATCC VR-372, ATCC VR-1245), Ross River virus (ATCC VR-373, ATCC VR-1246), Semliki Forest (ATCC VR-67, ATCC VR-1247), Sindbis virus (ATCC VR-68, ATCC VR-1248), Tonate (ATCC VR-925), Triniti (ATCC VR-469), Una (ATCC VR-374), Venezuelan equine encephalomyelitis (ATCC VR-69, ATCC VR-923, ATCC VR-1250 ATCC VR-1249, ATCC VR-532), Western equine encephalomyelitis (ATCC VR-70, ATCC VR-1251, ATCC VR-622, ATCC VR-1252), Whataroa (ATCC VR-926), and Y-62-33 (ATCC VR-375).

The self-replicating RNA molecules of the invention are larger than other types of RNA (e.g. mRNA). Typically, the self-replicating RNA molecules of the invention contain at least about 4 kb. For example, the self-replicating RNA can contain at least about 5 kb, at least about 6 kb, at least about 7 kb, at least about 8 kb, at least about 9 kb, at least about 10 kb, at least about 11 kb, at least about 12 kb or more than 12 kb. In certain examples, the self-replicating RNA is about 4 kb to about 12 kb, about 5 kb to about 12 kb, about 6 kb to about 12 kb, about 7 kb to about 12 kb, about 8 kb to about 12 kb, about 9 kb to about 12 kb, about 10 kb to about 12 kb, about 11 kb to about 12 kb, about 5 kb to about 11 kb, about 5 kb to about 10 kb, about 5 kb to about 9 kb, about 5 kb to about 8 kb, about 5 kb to about 7 kb, about 5 kb to about 6 kb, about 6 kb to about 12 kb, about 6 kb to about 11 kb, about 6 kb to about 10 kb, about 6 kb to about 9 kb, about 6 kb to about 8 kb, about 6 kb to about 7 kb, about 7 kb to about 11 kb, about 7 kb to about 10 kb, about 7 kb to about 9 kb, about 7 kb to about 8 kb, about 8 kb to about 11 kb, about 8 kb to about 10 kb, about 8 kb to about 9 kb, about 9 kb to about 11 kb, about 9 kb to about 10 kb, or about 10 kb to about 11 kb.

The self-replicating RNA molecules of the invention may comprise one or more modified nucleotides (e.g., pseudouridine, N6-methyladenosine, 5-methylcytidine, 5-methyluridine).

The self-replicating RNA molecule may encode a single polypeptide antigen or, optionally, two or more of polypeptide antigens linked together in a way that each of the sequences retains its identity (e.g., linked in series) when expressed as an amino acid sequence. The polypeptides generated from the self-replicating RNA may then be produced as a fusion polypeptide or engineered in such a manner to result in separate polypeptide or peptide sequences.

The self-replicating RNA of the invention may encode one or more polypeptide antigens that contain a range of epitopes. Preferably epitopes capable of eliciting either a helper T-cell response or a cytotoxic T-cell response or both.

The self-replicating RNA molecules described herein may be engineered to express multiple nucleotide sequences, from two or more open reading frames, thereby allowing co-expression of proteins, such as a two or more antigens together with cytokines or other immunomodulators, which can enhance the generation of an immune response. Such a self-replicating RNA molecule might be particularly useful, for example, in the production of various gene products (e.g., proteins) at the same time, for example, as a bivalent or multivalent vaccine.

The self-replicating RNA molecules of the invention can be prepared using any suitable method. Several suitable methods are known in the art for producing RNA molecules that contain modified nucleotides. For example, a self-replicating RNA molecule that contains modified nucleotides can be prepared by transcribing (e.g., in vitro transcription) a DNA that encodes the self-replicating RNA molecule using a suitable DNA-dependent RNA polymerase, such as T7 phage RNA polymerase, SP6 phage RNA polymerase, T3 phage RNA polymerase, and the like, or mutants of these polymerases which allow efficient incorporation of modified nucleotides into RNA molecules. The transcription reaction will contain nucleotides and modified nucleotides, and other components that support the activity of the selected polymerase, such as a suitable buffer, and suitable salts. The incorporation of nucleotide analogs into a self-replicating RNA may be engineered, for example, to alter the stability of such RNA molecules, to increase resistance against RNases, to establish replication after introduction into appropriate host cells ("infectivity" of the RNA), and/or to induce or reduce innate and adaptive immune responses.

Suitable synthetic methods can be used alone, or in combination with one or more other methods (e.g., recombinant DNA or RNA technology), to produce a self-replicating RNA molecule of the invention. Suitable methods for de novo synthesis are well-known in the art and can be adapted for particular applications. Exemplary methods include, for example, chemical synthesis using suitable protecting groups such as CEM (Masuda et al., (2007) *Nucleic Acids Symposium Series* 51:3-4), the β-cyanoethyl phosphoramidite method (Beaucage S L et al. (1981) *Tetrahedron Lett* 22:1859); nucleoside H-phosphonate method (Garegg Petal. (1986) *Tetrahedron Lett* 27:4051-4; Froehler B C et al. (1986) *Nucl Acid Res* 14:5399-407; Garegg Petal. (1986) *Tetrahedron Lett* 27:4055-8; Gaffney B L et al. (1988) *Tetrahedron Lett* 29:2619-22). These chemistries can be performed or adapted for use with automated nucleic acid synthesizers that are commercially available. Additional suitable synthetic methods are disclosed in Uhlmann et al. (1990) *Chem Rev* 90:544-84, and Goodchild J (1990) *Bioconjugate Chem* 1: 165. Nucleic acid synthesis can also be performed using suitable recombinant methods that are well-known and conventional in the art, including cloning, processing, and/or expression of polynucleotides and gene products encoded by such polynucleotides. DNA shuffling by random fragmentation and PCR reassembly of gene fragments and synthetic polynucleotides are examples of known techniques that can be used to design and engineer polynucleotide sequences. Site-directed mutagenesis can be used to alter nucleic acids and the encoded proteins, for example, to insert new restriction sites, alter glycosylation patterns, change codon preference, produce splice variants, introduce mutations and the like. Suitable methods for transcription, translation and expression of nucleic acid sequences are known and conventional in the art. (See generally, Current Protocols in Molecular Biology, Vol. 2, Ed. Ausubel, et al., Greene Publish. Assoc. & Wiley Interscience, Ch. 13, 1988; Glover, DNA Cloning, Vol. II, IRL Press, Wash., D.C., Ch. 3, 1986; Bitter, et al., in Methods in Enzymology 153:516-544 (1987); The Molecular Biology of the Yeast *Saccharomyces*, Eds. Strathern et al., Cold Spring Harbor Press, Vols. I and II, 1982; and Sambrook et al., Molecular Cloning: A Laboratory Manual, Cold Spring Harbor Press, 1989.)

The presence and/or quantity of one or more modified nucleotides in a self-replicating RNA molecule can be determined using any suitable method. For example, a self-replicating RNA can be digested to monophosphates (e.g., using nuclease P1) and dephosphorylated (e.g., using a suitable phosphatase such as CIAP), and the resulting nucleosides analyzed by reversed phase HPLC (e.g., usings a YMC Pack ODS-AQ column (5 micron, 4.6×250 mm) and elute using a gradient, 30% B (0-5 min) to 100% B (5-13 min) and at 100% B (13-40) min, flow Rate (0.7 ml/min), UV detection (wavelength: 260 nm), column temperature (30° C.). Buffer A (20 mM acetic acid—ammonium acetate pH 3.5), buffer B (20 mM acetic acid—ammonium acetate pH 3.5/methanol [90/10])).

Optionally, the self-replicating RNA molecules of the invention may include one or more modified nucleotides so that the self-replicating RNA molecule will have less immunomodulatory activity upon introduction or entry into a host cell (e.g., a human cell) in comparison to the corresponding self-replicating RNA molecule that does not contain modified nucleotides.

If desired, the self-replicating RNA molecules can be screened or analyzed to confirm their therapeutic and prophylactic properties using various in vitro or in vivo testing methods that are known to those of skill in the art. For example, vaccines comprising self-replicating RNA molecule can be tested for their effect on induction of proliferation or effector function of the particular lymphocyte type of interest, e.g., B cells, T cells, T cell lines, and T cell clones. For example, spleen cells from immunized mice can be isolated and the capacity of cytotoxic T lymphocytes to lyse autologous target cells that contain a self replicating RNA molecule that encodes a polypeptide antigen. In addition, T helper cell differentiation can be analyzed by measuring proliferation or production of TH1 (IL-2 and IFN-γ) and/or TH2 (IL-4 and IL-5) cytokines by ELISA or directly in CD4+ T cells by cytoplasmic cytokine staining and flow cytometry.

Self-replicating RNA molecules that encode a polypeptide antigen can also be tested for ability to induce humoral immune responses, as evidenced, for example, by induction of B cell production of antibodies specific for an antigen of interest. These assays can be conducted using, for example, peripheral B lymphocytes from immunized individuals. Such assay methods are known to those of skill in the art. Other assays that can be used to characterize the self-replicating RNA molecules of the invention can involve detecting expression of the encoded antigen by the target cells. For example, FACS can be used to detect antigen expression on the cell surface or intracellularly. Another advantage of FACS selection is that one can sort for different levels of expression; sometimes-lower expression may be desired. Other suitable method for identifying cells which express a particular antigen involve panning using monoclonal antibodies on a plate or capture using magnetic beads coated with monoclonal antibodies.

B. Antigens

In certain embodiments, the negatively charged molecule described herein is a nucleic acid molecule (e.g., an RNA molecule) that encodes an antigen. Suitable antigens include, but are not limited to, a bacterial antigen, a viral antigen, a fungal antigen, a protozoan antigen, a plant antigen, a cancer antigen, or a combination thereof.

Suitable antigens include proteins and peptides from a pathogen such as a virus, bacteria, fungus, protozoan, plant or from a tumor. Viral antigens and immunogens that can be encoded by the self-replicating RNA molecule include, but are not limited to, proteins and peptides from a Orthomyxoviruses, such as Influenza A, B and C; Paramyxoviridae viruses, such as Pneumoviruses (RSV), Paramyxoviruses (PIV), Metapneumovirus and Morbilliviruses (e.g., measles); Pneumoviruses, such as Respiratory syncytial virus (RSV), Bovine respiratory syncytial virus, Pneumonia virus of mice, and Turkey rhinotracheitis virus; Paramyxoviruses, such as Parainfluenza virus types 1-4 (PIV), Mumps virus, Sendai viruses, Simian virus 5, Bovine parainfluenza virus, Nipahvirus, Henipavirus and Newcastle disease virus; Poxviridae, including a Orthopoxvirus such as Variola vera (including but not limited to, Variola major and Variola minor); Metapneumoviruses, such as human metapneumovirus (hMPV) and avian metapneumoviruses (aMPV); Morbilliviruses, such as Measles; Picornaviruses, such as Enteroviruses, Rhinoviruses, Heparnavirus, Parechovirus, Cardioviruses and Aphthoviruses; Enteroviruseses, such as Poliovirus types 1, 2 or 3, Coxsackie A virus types 1 to 22 and 24, Coxsackie B virus types 1 to 6, Echovirus (ECHO) virus types 1 to 9, 11 to 27 and 29 to 34 and Enterovirus 68 to 71, Bunyaviruses, including a Orthobunyavirus such as California encephalitis virus; a Phlebovirus, such as Rift Valley Fever virus; a Nairovirus, such as Crimean-Congo hemorrhagic fever virus; Heparnaviruses, such as, Hepatitis A virus (HAV); Togaviruses (Rubella), such as a Rubivirus, an Alphavirus, or an Arterivirus; Flaviviruses, such as Tick-borne encephalitis (TBE) virus, Dengue (types 1, 2, 3 or 4) virus, Yellow Fever virus, Japanese encephalitis virus, Kyasanur Forest Virus, West Nile encephalitis virus, St. Louis encephalitis virus, Russian spring-summer encephalitis virus, Powassan encephalitis virus; Pestiviruses, such as Bovine viral diarrhea (BVDV), Classical swine fever (CSFV) or Border disease (BDV); Hepadnaviruses, such as Hepatitis B virus, Hepatitis C virus; Rhabdoviruses, such as a Lyssavirus (Rabies virus) and Vesiculovirus (VSV), Caliciviridae, such as Norwalk virus, and Norwalk-like Viruses, such as Hawaii Virus and Snow Mountain Virus; Coronaviruses, such as SARS, Human respiratory coronavirus, Avian infectious bronchitis (IBV), Mouse hepatitis virus (MHV), and Porcine transmissible gastroenteritis virus (TGEV); Retroviruses such as an Oncovirus, a Lentivirus or a Spumavirus; Reoviruses, as an Orthoreovirus, a Rotavirus, an Orbivirus, or a Coltivirus; Parvoviruses, such as Parvovirus B19; Delta hepatitis virus (HDV); Hepatitis E virus (HEV); Hepatitis G virus (HGV); Human Herpesviruses, such as, by way Herpes Simplex Viruses (HSV), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8); Papovaviruses, such as Papillomaviruses and Polyomaviruses, Adenoviruess and Arenaviruses.

In some embodiments, the antigen elicits an immune response against a virus which infects fish, such as: infectious salmon anemia virus (ISAV), salmon pancreatic disease virus (SPDV), infectious pancreatic necrosis virus (IPNV), channel catfish virus (CCV), fish lymphocystis disease virus (FLDV), infectious hematopoietic necrosis virus (IHNV), koi herpesvirus, salmon picorna-like virus (also known as picorna-like virus of atlantic salmon), land-locked salmon virus (LSV), atlantic salmon rotavirus (ASR), trout strawberry disease virus (TSD), coho salmon tumor virus (CSTV), or viral hemorrhagic septicemia virus (VHSV).

In some embodiments the antigen elicits an immune response against a parasite from the *Plasmodium* genus, such as *P. falciparum, P. vivax, P. malariae* or *P. ovale*. Thus the invention may be used for immunizing against malaria. In some embodiments the antigen elicits an immune response against a parasite from the Caligidae family, particularly those from the *Lepeophtheirus* and *Caligus* genera e.g. sea lice such as *Lepeophtheirus salmonis* or *Caligus rogercresseyi.*

Bacterial antigens and immunogens that can be encoded by the self-replicating RNA molecule include, but are not limited to, proteins and peptides from *Neisseria meningitides, Streptococcus pneumoniae, Streptococcus pyogenes, Moraxella catarrhalis, Bordetella pertussis, Burkholderia* sp. (e.g., *Burkholderia mallei, Burkholderia pseudomallei* and *Burkholderia cepacia*), *Staphylococcus aureus, Staphylococcus epidermis, Haemophilus influenzae, Clostridium tetani* (Tetanus), *Clostridium perfringens, Clostridium botulinums* (Botulism), *Cornynebacterium diphtherias* (Diphtheria), *Pseudomonas aeruginosa, Legionella pneumophila, Coxiella burnetii, Brucella* sp. (e.g., *B. abortus, B. canis, B. melitensis, B. neotomae, B. ovis, B. suis* and *B. pinnipediae*), *Francisella* sp. (e.g., *F. novicida, F. philomiragia* and *F. tularensis*), *Streptococcus agalactiae, Neiserria gonorrhoeae, Chlamydia trachomatis, Treponema pallidum* (Syphilis), *Haemophilus ducreyi, Enterococcus faecalis, Enterococcus faecium, Helicobacter pylori, Staphylococcus saprophyticus, Yersinia enterocolitica, E. coli* (such as enterotoxigenic *E. coli* (ETEC), enteroaggregative *E. coli* (EAggEC), diffusely adhering *E. coli* (DAEC), enteropathogenic *E. coli* (EPEC), extraintestinal pathogenic *E. coli* (ExPEC; such as uropathogenic *E. coli* (UPEC) and meningitis/sepsis-associated *E. coli* (MNEC)), and/or enterohemorrhagic *E. coli* (EHEC), *Bacillus anthracis* (anthrax), *Yersinia pestis* (plague), *Mycobacterium tuberculosis, Rickettsia, Listeria monocytogenes, Chlamydia pneumoniae, Vibrio cholerae, Salmonella typhi* (typhoid fever), *Borrelia burgdorfer, Porphyromonas gingivalis, Klebsiella, Mycoplasma pneumoniae*, etc.

Fungal antigens and immunogens that can be encoded by the self-replicating RNA molecule include, but are not limited to, proteins and peptides from Dermatophytres, including: *Epidermophyton floccusum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T verrucosum* var. album, var. *discoides*, var. *ochraceum, Trichophyton violaceum*, and/or *Trichophyton faviforme*; or from *Aspergillus fumigatus, Aspergillus flavus, Aspergillus niger, Aspergillus nidulans, Aspergillus terreus, Aspergillus sydowii, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea,*

*Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae, Microsporidia, Encephalitozoon* spp., *Septata intestinalis* and *Enterocytozoon bieneusi*; the less common are *Brachiola* spp, *Microsporidium* spp., *Nosema* spp., *Pleistophora* spp., *Trachipleistophora* spp., *Vittaforma* spp *Paracoccidioides brasiliensis, Pneumocystis carinii, Pythiumn insidiosum, Pityrosporum ovale, Sacharomyces cerevisae, Saccharomyces boulardii, Saccharomyces pombe, Scedosporium apiosperum, Sporothrix schenckii, Trichosporon beigelii, Toxoplasma gondii, Penicillium mameffei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, *Saksenaea* spp., *Alternaria* spp, *Curvularia* spp, *Helminthosporium* spp, *Fusarium* spp, *Aspergillus* spp, *Penicillium* spp, *Monolinia* spp, *Rhizoctonia* spp, *Paecilomyces* spp, *Pithomyces* spp, and *Cladosporium* spp.

Protazoan antigens and immunogens that can be encoded by the self-replicating RNA molecule include, but are not limited to, proteins and peptides from *Entamoeba histolytica, Giardia lambli, Cryptosporidium parvum, Cyclospora cayatanensis* and *Toxoplasma.*

Plant antigens and immunogens that can be encoded by the self-replicating RNA molecule include, but are not limited to, proteins and peptides from *Ricinus communis.*

Suitable antigens include proteins and peptides from a virus such as, for example, human immunodeficiency virus (HIV), hepatitis A virus (HAV), hepatitis B virus (HBV), hepatitis C virus (HCV), herpes simplex virus (HSV), cytomegalovirus (CMV), influenza virus (flu), respiratory syncytial virus (RSV), parvovorus, norovirus, human papilloma virus (HPV), rhinovirus, yellow fever virus, rabies virus, Dengue fever virus, measles virus, mumps virus, rubella virus, varicella zoster virus, enterovirus (e.g., enterovirus 71), ebola virus, and bovine diarrhea virus. Preferably, the antigenic substance is selected from the group consisting of HSV glycoprotein gD, HIV glycoprotein gp120, HIV glycoprotein gp 40, HIV p55 gag, and polypeptides from the pol and tat regions. In other preferred embodiments of the invention, the antigen is a protein or peptide derived from a bacterium such as, for example, *Helicobacter pylori, Haemophilus influenza, Vibrio cholerae* (cholera), *C. diphtherias* (diphtheria), *C. tetani* (tetanus), *Neisseria meningitidis, B. pertussis, Mycobacterium tuberculosis*, and the like.

HIV antigens that can be encoded by the self-replicating RNA molecules of the invention are described in U.S. application Ser. No. 490,858, filed Mar. 9, 1990, and published European application number 181150 (May 14, 1986), as well as U.S. application Ser. Nos. 60/168,471; 09/475,515; 09/475,504; and Ser. No. 09/610,313, the disclosures of which are incorporated herein by reference in their entirety.

Cytomegalovirus antigens that can be encoded by the self-replicating RNA molecules of the invention are described in U.S. Pat. No. 4,689,225, U.S. application Ser. No. 367,363, filed Jun. 16, 1989 and PCT Publication WO 89/07143, the disclosures of which are incorporated herein by reference in their entirety.

Hepatitis C antigens that can be encoded by the self-replicating RNA molecules of the invention are described in PCT/US88/04125, published European application number 318216 (May 31, 1989), published Japanese application number 1-500565 filed Nov. 18, 1988, Canadian application 583,561, and EPO 388,232, disclosures of which are incorporated herein by reference in their entirety. A different set of HCV antigens is described in European patent application 90/302866.0, filed Mar. 16, 1990, and U.S. application Ser. No. 456,637, filed Dec. 21, 1989, and PCT/US90/01348, the disclosures of which are incorporated herein by reference in their entirety.

In some embodiments, the antigen is derived from an allergen, such as pollen allergens (tree-, herb, weed-, and grass pollen allergens); insect or arachnid allergens (inhalant, saliva and venom allergens, e.g. mite allergens, cockroach and midges allergens, hymenopthera venom allergens); animal hair and dandruff allergens (from e.g. dog, cat, horse, rat, mouse, etc.); and food allergens (e.g. a gliadin). Important pollen allergens from trees, grasses and herbs are such originating from the taxonomic orders of Fagales, Oleales, Pinales and platanaceae including, but not limited to, birch (*Betula*), alder (*Alnus*), hazel (*Corylus*), hornbeam (*Carpinus*) and olive (*Olea*), cedar (*Cryptomeria* and *Juniperus*), plane tree (*Platanus*), the order of Poales including grasses of the genera *Lolium, Phleum, Poa, Cynodon, Dactylis, Holcus, Phalaris, Secale*, and *Sorghum*, the orders of Asterales and Urticales including herbs of the genera *Ambrosia, Artemisia*, and *Parietaria*. Other important inhalation allergens are those from house dust mites of the genus *Dermatophagoides* and *Euroglyphus*, storage mite e.g. *Lepidoglyphys, Glycyphagus* and *Tyrophagus*, those from cockroaches, midges and fleas e.g. *Blatella, Periplaneta, Chironomus* and *Ctenocepphalides*, and those from mammals such as cat, dog and horse, venom allergens including such originating from stinging or biting insects such as those from the taxonomic order of Hymenoptera including bees (Apidae), wasps (Vespidea), and ants (Formicoidae).

In certain embodiments, a tumor immunogen or antigen, or cancer immunogen or antigen, can be encoded by the self-replicating RNA molecule. In certain embodiments, the tumor immunogens and antigens are peptide-containing tumor antigens, such as a polypeptide tumor antigen or glycoprotein tumor antigens.

Tumor immunogens and antigens appropriate for the use herein encompass a wide variety of molecules, such as (a) polypeptide-containing tumor antigens, including polypeptides (which can range, for example, from 8-20 amino acids in length, although lengths outside this range are also common), lipopolypeptides and glycoproteins.

In certain embodiments, tumor immunogens are, for example, (a) full length molecules associated with cancer cells, (b) homologs and modified forms of the same, including molecules with deleted, added and/or substituted portions, and (c) fragments of the same. Tumor immunogens include, for example, class I-restricted antigens recognized by CD8+ lymphocytes or class II-restricted antigens recognized by CD4+ lymphocytes.

In certain embodiments, tumor immunogens include, but are not limited to, (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors), (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLR-FUT, (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer), (d) shared antigens, for example, melanoma-melanocyte differentiation antigens such as MART-1/Melan A, gp100, MC1R, melanocyte-stimulating hormone receptor, tyrosinase, tyrosinase related protein-1/TRP1 and tyrosinase related protein-2/TRP2 (associated with, e.g., melanoma), (e) prostate associated antigens such as PAP, PSA, PSMA, PSH-P1, PSM-P1, PSM-P2, associated with e.g., prostate cancer, (f) immunoglobulin idiotypes (associated with myeloma and B cell lymphomas, for example).

In certain embodiments, tumor immunogens include, but are not limited to, p15, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein\cyclophilin C-associated protein), TAAL6, TAG72, TLP, TPS, and the like.

C. Formulations for the Negatively Charged Molecule

The negatively charged molecule (such as RNA) is generally provided in the form of an aqueous solution, or a form that can be readily dissolved in an aqueous solution (e.g., lyophilized). The aqueous solution can be water, or an aqueous solution that comprises a salt (e.g., NaCl), a buffer (e.g., a citrate buffer), a nonionic tonicifying agent (e.g., a saccharide), a polymer, a surfactant, or a combination thereof. If the formulation is intended for in vivo administration, it is preferable that the aqueous solution is a physiologically acceptable buffer that maintains a pH that is compatible with normal physiological conditions. Also, in certain instances, it may be desirable to maintain the pH at a particular level in order to insure the stability of certain components of the formulation.

For example, it may be desirable to prepare an aqueous solution that is isotonic and/or isosmotic. Hypertonic and hypotonic solutions sometimes could cause complications and undesirable effects when injected, such as post-administration swelling or rapid absorption of the composition because of differential ion concentrations between the composition and physiological fluids. To control tonicity, the emulsion may comprise a physiological salt, such as a sodium salt. Sodium chloride (NaCl), for example, may be used at about 0.9% (w/v) (physiological saline). Other salts that may be present include potassium chloride, potassium dihydrogen phosphate, disodium phosphate dehydrate, magnesium chloride, calcium chloride, etc. In an exemplary embodiment, the aqueous solution comprises 10 mM NaCl and other salts or non-ionic tonicifying agents. As described herein, non-ionic tonicifying agents can also be used to control tonicity.

The aqueous solution may be buffered. Any physiologically acceptable buffer may be used herein, such as citrate buffers, phosphate buffers, acetate buffers, succinate buffer, tris buffers, bicarbonate buffers, carbonate buffers, or the like. The pH of the aqueous solution will preferably be between 6.0-8.0, more preferably about 6.2 to about 6.8. In some cases, certain amount of salt may be included in the buffer. In other cases, salt in the buffer might interfere with complexation of negatively charged molecule to the emulsion particle, and therefore is avoided.

The aqueous solution may also comprise additional components such as molecules that change the osmolarity of the aqueous solution or molecules that stabilizes the negatively charged molecule after complexation. For example, the osmolality can be adjusted using a non-ionic tonicifying agent, which are generally carbohydrates but can also be polymers. (See, e.g., Voet and Voet (1990) Biochemistry (John Wiley & Sons, New York.) Examples of suitable non-ionic tonicifying agents include sugars (e.g., a monosaccharide, a disaccharide, or a polysaccharide, such as trehalose, sucrose, dextrose, fructose), sugar alcohols (e.g., mannitol, sorbitol, xylitol, erythritol, lactitol, maltitol, glycerol, reduced palatinose), and combinations thereof. If desired, a nonionic polymer (e.g., a poly(alkyl glycol), such as polyethylene glycol, polypropylene glycol, or polybutlyene glycol), or nonionic surfactant can be used. These types of agents, in particular sugar and sugar alcohols, are also cryoprotectants that can protect RNA, and other negatively charged molecules, when lyophilized. In exemplary embodiments, the buffer comprises from about 560 nM to 600 mM of trehalose, sucrose, sorbitol, or dextrose. In other exemplary embodiments, the buffer comprises from about 500 nM to 600 mM of trehalose, sucrose, sorbitol, or dextrose.

In some case, it may be preferable to prepare an aqueous solution comprising the negatively charged molecule as a hypertonic solution, and to prepare the cationic emulsion using unadulterated water or a hypotonic buffer. When the emulsion and the negatively charged molecule are combined, the mixture becomes isotonic. For example, an aqueous solution comprising RNA can be a 2× hypertonic solution, and the cationic emulsion can be prepared using 10 mM Citrate buffer. When the RNA solution and the emulsion are mixed at 1:1 (v/v) ratio, the composition becomes isotonic. Based on desired relative amounts of the emulsion to the aqueous solution that comprises the negatively charged molecule (e.g., 1:1 (v/v) mix, 2:1 (v/v) mix, 1:2 (v/v) mix, etc.), one can readily determine the tonicity of the aqueous solution that is required in order to achieve an isotonic mixture.

Similarly, compositions that have physiological osmolality may be desirable for in vivo administration. Physiological osmolality is from about 255 mOsm/kg water to about 315 mOsm/kg water. Sometimes, it may be preferable to prepare an aqueous solution comprising the negatively charged molecule as a hyperosmolar solution, and to prepare the cationic emulsion using unadulterated water or a hypoosmolar buffer. When the emulsion and the negatively charged molecule are combined, physiological osmolality is achieved. Based on desired relative amounts of the emulsion to the aqueous solution that comprises the negatively charged molecule (e.g., 1:1 (v/v) mix, 2:1 (v/v) mix, 1:2 (v/v) mix, etc.), one can readily determine the osmolality of the aqueous solution that is required in order to achieve an iso-osmolar mixture.

In certain embodiments, the aqueous solution comprising the negatively charged molecule may further comprise a polymer or a surfactant, or a combination thereof. In an exemplary embodiment, the oil-in-water emulsion contains a poloxamer. In particular, the inventors have observed that adding Pluronic® F127 to the RNA aqueous solution prior to complexation to cationic emulsion particles led to greater stability and increased RNase resistance of the RNA molecule. Addition of pluronic F127 to RNA aqueous solution was also found to decrease the particle size of the RNA/CNE complex. Poloxamer polymers may also facilitate appropriate decomplexation/release of the RNA molecule, prevent aggregation of the emulsion particles, and have immune modulatory effect. Other polymers that may be used include, e.g., Pluronic® F68 or PEG300.

Alternatively or in addition, the aqueous solution comprising the negatively charged molecule may comprise from about 0.05% to about 20% (w/v) polymer. For example, the cationic oil-in-water emulsion may comprise a polymer (e.g., a poloxamer such as Pluronic® F127, Pluronic® F68, or PEG300) at from about 0.05% to about 10% (w/v), such as 0.05%, 0.5%, 1%, or 5%.

The buffer system may comprise any combination of two or more molecules described above (salt, buffer, saccharide, polymer, etc). In an preferred embodiment, the buffer comprises 560 mM sucrose, 20 mM NaCl, and 2 mM Citrate, which can be mixed with a cationic oil in water emulsion described herein to produce a final aqueous phase that comprises 280 mM sucrose, 10 mM NaCl and 1 mM citrate.

5. Methods of Preparation

In another aspect, the invention provides a method of preparing the oil-in-water emulsions as described herein, comprising: (1) combining the oil and the cationic lipid to form the oil phase of the emulsion; (2) providing an aqueous solution to form the aqueous phase of the emulsion; and (3) dispersing the oil phase in the aqueous phase, for example, by homogenization. Homogenization may be achieved in any suitable way, for example, using a commercial homogenizer (e.g., IKA T25 homogenizer, available at VWR International (West Chester, Pa.).

In certain embodiments, the oil-in-water emulsions are prepared by (1) directly dissolving the cationic lipid in the oil to form an oil phase; (2) providing the aqueous phase of the emulsion; and (3) dispersing the oil phase in the aqueous phase by homogenization. The method does not use an organic solvent (such as chloroform ($CHCl_3$), dichloromethane (DCM), ethanol, acetone, Tetrahydrofuran (THF), 2,2,2 trifluoroethanol, acetonitrile, ethyl acetate, hexane, Dimethylformamide (DMF), Dimethyl sulfoxide (DMSO), etc.) to solubilize the cationic lipid first before adding the lipid to the oil.

It may be desirable to heat the oil to a temperature between about 37° C. to about 65° C. to facilitate the dissolving of the lipid. Desired amount of the cationic lipid (e.g., DOTAP) can be measured and added directly to the oil to reach a desired final concentration.

If the emulsion comprises one or more surfactants, the surfactant(s) may be included in the oil phase or the aqueous phase according to the conventional practice in the art. For example, SPAN85 can be dissolved in the oil phase (e.g., squalene), and Tween 80 may be dissolved in the aqueous phase (e.g., in a citrate buffer).

In another aspect, the invention provides a method of preparing a composition that comprises a negatively charged molecule (such as RNA) complexed with a particle of a cationic oil-in-water emulsion, comprising: (i) providing a cationic oil-in-water emulsion as described herein; (ii) providing a aqueous solution comprising the negatively charged molecule (such as RNA); and (iii) combining the oil-in-water emulsion of (i) and the aqueous solution of (iii), so that the negatively charged molecule complexes with the particle of the emulsion.

For example, a cationic oil-in-water emulsion may be combined with an aqueous RNA solution in any desired relative amounts, e.g., about 1:1 (v/v), about 1.5:1 (v/v), about 2:1 (v/v), about 2.5:1 (v/v), about 3:1 (v/v), about 3.5:1 (v/v), about 4:1 (v/v), about 5:1 (v/v), about 10:1 (v/v), about 1:1.5 (v/v), about 1:2 (v/v), about 1:2.5 (v/v), about 1:3 (v/v), about 1:3.5 (v/v), about 1:4 (v/v), about 1:1.5 (v/v), or about 1:1.10 (v/v), etc.

Additional optional steps to promote particle formation, to improve the complexation between the negatively charge molecules and the cationic particles, to increase the stability of the negatively charge molecule (e.g., to prevent degradation of an RNA molecule), to facilitate appropriate decomplexation/release of the negatively charged molecules (such as an RNA molecule), or to prevent aggregation of the emulsion particles may be included. For example, a polymer (e.g., Pluronic® F127) or a surfactant may be added to the aqueous solution that comprises the negatively charged molecule (such as RNA).

The size of the emulsion particles can be varied by changing the ratio of surfactant to oil (increasing the ratio decreases particle size), operating pressure (increasing operating pressure reduces particle size), temperature (increasing temperature decreases particle size), and other process parameters. Actual particle size will also vary with the particular surfactant, oil, and cationic lipid used, and with the particular operating conditions selected. Emulsion particle size can be verified by use of sizing instruments, such as the commercial Sub-Micron Particle Analyzer (Model N4MD) manufactured by the Coulter Corporation, and the parameters can be varied using the guidelines set forth above until the average diameter of the particles is less than less than about 200 nm, less than about 150 nm, or less than about 100 nm. Preferably, the particles have an average diameter of about 180 nm or less, about 150 nm or less, about 140 nm or less, or about 130 nm or less, about 120 nm or less, or about 100 nm or less, from about 50 nm to 200 nm, from about 80 nm to 200 nm, from about 50 nm to 180 nm, from about 60 nm to 180 nm, from about 70 to 180 nm, or from about 80 nm to 180 nm, from about 80 nm to about 170 nm, from about 80 nm to about 160 nm, from about 80 nm to about 150 nm, from about 80 nm to about 140 nm, from about 80 nm to about 130 nm, from about 80 nm to about 120 nm, from about 80 nm to about 110 nm, or from about 80 nm to about 100 nm. Emulsions wherein the mean particle size is about 200 nm or less allow for sterile filtration.

Optional processes for preparing the cationic oil-in-water emulsion (pre-complexation emulsion), or the negatively charged molecule-emulsion complex, include, e.g., sterilization, particle size selection (e.g., removing large particles), filling, packaging, and labeling, etc. For example, if the pre-complexation emulsion, or the negatively charged molecule-emulsion complex, is formulated for in vivo administration, it may be sterilized. For example, the formulation can be sterilized by filtering through a sterilizing grade filter (e.g., through a 0.22 micron filter). Other sterilization techniques include a thermal process, or a radiation sterilization process, or using pulsed light to produce a sterile composition.

The cationic oil-in-water emulsion described herein can be used to manufacture vaccines. Sterile and/or clinical grade cationic oil-in-water emulsions can be prepared using similar methods as described for MF59. See, e.g., Ott et al., Methods in Molecular Medicine, 2000, Volume 42, 211-228, in VACCINE ADJUVANTS (O'Hagan ed.), Humana Press. For example, similar to the manufacturing process of MF59, the oil phase and the aqueous phase of the emulsion can be combined and processed in a rotor stator homogenizer, or an inline homogenizer, to yield a coarse emulsion. The coarse emulsion can then be fed into a microfluidizer, where it can be further processed to obtain a stable submicron emulsion. The coarse emulsion can be passed through the interaction chamber of the microfluidizer repeatedly until the desired particle size is obtained. The bulk emulsion can then be filtered (e.g., though a 0.22-μm filter under nitrogen) to remove large particles, yielding emulsion bulk that can be filled into suitable containers (e.g., glass bottles). For vaccine antigens that have demonstrated long-term stability in the presence of oil-in-water emulsion for self storage, the antigen and emulsion may be combined and sterile-filtered (e.g., though a 0.22-μm filter membrane). The combined single vial vaccine can be filled into single-dose containers. For vaccine antigens where long-term stability has not been demonstrated, the emulsion can be supplied as a separate vial. In such cases, the emulsion bulk can be filtered-sterilized (e.g., though a 0.22-μm filter membrane), filled, and packaged in final single-dose vials.

Quality control may be optionally performed on a small sample of the emulsion bulk or admixed vaccine, and the bulk or admixed vaccine will be packaged into doses only if the sample passes the quality control test.

6. Kits, Pharmaceutical Compositions and Administration

In another aspect, the invention provides a pharmaceutical composition comprising a negatively charged molecule (such as RNA) complexed with a particle of a cationic oil-in-water emulsion, as described herein, and may further comprise one or more pharmaceutically acceptable carriers, diluents, or excipients. In preferred embodiments, the pharmaceutical composition is an immunogenic composition, which can be used as a vaccine.

Alternatively, the compositions described herein may be used to deliver a negatively charged molecule to cells. For example, nucleic acid molecules (e.g., DNA or RNA) can be delivered to cells for a variety of purposes, such as to induce production of a desired gene product (e.g., protein), to regulate expression of a gene, for gene therapy and the like. The compositions described herein may also be used to deliver a nucleic acid molecule (e.g., DNA or RNA) to cells for therapeutic purposes, such as to treat a disease such as cancers or proliferative disorders, metabolic diseases, cardiovascular diseases, infections, allergies, to induce an immune response and the like. For example, nucleic acid molecules may be delivered to cells to inhibit the expression of a target gene. Such nucleic acid molecules include, e.g., antisense oligonucleotides, double-stranded RNAs, such as small interfering RNAs and the like. Double-stranded RNA molecules, such as small interfering RNAs, can trigger RNA interference, which specifically silences the corresponding target gene (gene knock down). Antisense oligonucleotides are single strands of DNA or RNA that are complementary to a chosen sequence. Generally, antisense RNA can prevent protein translation of certain messenger RNA strands by binding to them. Antisense DNA can be used to target a specific, complementary (coding or non-coding) RNA. Therefore, the cationic emulsions described herein are useful for delivering antisense oligonucleotides or double-stranded RNAs for treatment of, for example, cancer by inhibiting production of an oncology target.

The invention also provides kits, wherein the negatively charged molecule (such as RNA) and the cationic oil-in-water emulsion are in separate containers. For example, the kit can contain a first container comprising a composition comprising the negatively charged molecule (such as RNA), and a second container comprising cationic oil-in-water emulsion. The two components may be mixed prior to administration, e.g., within about 72 hours, about 48 hours, about 24 hours, about 12 hours, about 10 hours, about 9 hours, about 8 hours, about 7 hours, about 6 hours, about 5 hours, about 4 hours, about 3 hours, about 2 hours, about 1 hour, about 45 minutes, about 30 minutes, about 15 minutes, about 10 minutes, about 5 minutes prior to administration. The two components may also be mixed about 1 minute or immediately prior to administration.

The negatively charged molecule (e.g., RNA) may be in liquid form or can be in solid form (e.g., lyophilized). If in solid form, the kit may comprise a third container comprising a suitable aqueous solution to rehydrate the negatively charged molecule. Suitable aqueous solutions include pharmaceutically-acceptable buffers such as phosphate-buffered saline, Ringer's solution, dextrose solution, or any one of the aqueous solutions described above. In certain embodiments, sterile water may be used as the aqueous solution for rehydration, in particular in cases where additional components, such as tonicifying agents and/or osmolality adjusting agents are lyophilized along with the negatively charged molecule (e.g., RNA). Alternatively, the lyophilized negatively charged molecule (e.g., RNA) may be mixed directly with the cationic emulsion.

If the composition (e.g., a vaccine) comprises a negatively charged molecule (e.g., RNA) and an additional component, such as a protein immunogen, both components can be frozen and lyophilized (either separately, or as a mixture), and reconstituted and mixed with the cationic emulsion prior to administration.

The kit can further comprise other materials useful to the end-user, including other pharmaceutically acceptable formulating solutions such as buffers, diluents, filters, needles, and syringes or other delivery device. For example, the kit may include a dual chamber syringe that contain water or the emulsion in one chamber, and the negatively charged molecule (e.g., RNA) is provided in solid (e.g. lyophilized) form in the other chamber.

The kit may further include another container comprising an adjuvant (such as an aluminum containing adjuvant or MF59). In general, aluminum containing adjuvants are not preferred because they may interfere with the complexation of the negatively charged molecule with the cationic emulsion.

Suitable containers for the compositions include, for example, bottles, vials, syringes, and test tubes. Containers can be formed from a variety of materials, including glass or plastic. A container may have a sterile access port (for example, the container may be an intravenous solution bag or a vial having a stopper pierceable by a hypodermic injection needle). Dual-chamber syringe may also be used, wherein the negatively charged molecule (e.g., RNA) is lyophilized, and either reconstituted with water in the syringe, or reconstituted directly with a cationic emulsion described herein.

The kit can also comprise a package insert containing written instructions for methods of inducing immunity or for treating infections. The package insert can be an unapproved draft package insert or can be a package insert approved by the Food and Drug Administration (FDA) or other regulatory body.

The invention also provides a delivery device pre-filled with the compositions described above.

The pharmaceutical compositions provided herein may be administered singly or in combination with one or more additional therapeutic agents. The method of administration include, but are not limited to, oral administration, rectal administration, parenteral administration, subcutaneous administration, intravenous administration, intravitreal administration, intramuscular administration, inhalation, intranasal administration, topical administration, ophthalmic administration, or otic administration.

A therapeutically effective amount of the compositions described herein will vary depending on, among others, the disease indicated, the severity of the disease, the age and relative health of the subject, the potency of the compound administered, the mode of administration and the treatment desired.

In other embodiments, the pharmaceutical compositions described herein can be administered in combination with one or more additional therapeutic agents. The additional therapeutic agents may include, but are not limited to antibiotics or antibacterial agents, antiemetic agents, antifungal agents, anti-inflammatory agents, antiviral agents, immunomodulatory agents, cytokines, antidepressants, hormones, alkylating agents, antimetabolites, antitumour antibiotics, antimitotic agents, topoisomerase inhibitors, cytostatic agents, anti-invasion agents, antiangiogenic agents, inhibitors of growth factor function inhibitors of viral replication, viral enzyme inhibitors, anticancer agents, α-interferons, β-interferons, ribavirin, hormones, and other toll-like receptor modulators, immunoglobulins (Igs), and antibodies modulating Ig function (such as anti-IgE (omalizumab)).

In certain embodiments, the pharmaceutical compositions provided herein are used in the treatment of infectious diseases including, but not limited to, disease cased by the pathogens disclosed herein, including viral diseases such as genital warts, common warts, plantar warts, rabies, respiratory syncytial virus (RSV), hepatitis B, hepatitis C, Dengue virus, yellow fever, herpes simplex virus (by way of example only, HSV-I, HSV-II, CMV, or VZV), molluscum contagiosum, vaccinia, variola, lentivirus, human immunodeficiency virus (HIV), human papilloma virus (HPV), hepatitis virus (hepatitis C virus, hepatitis B virus, hepatitis A virus), cytomegalovirus (CMV), varicella zoster virus (VZV), rhinovirus, enterovirus (e.g. EV71), adenovirus, coronavirus (e.g., SARS), influenza, para-influenza, mumps virus, measles virus, rubella virus, papovavirus, hepadnavirus, flavivirus, retrovirus, arenavirus (by way of example only, LCM, Junin virus, Machupo virus, Guanarito virus and Lassa Fever) and filovirus (by way of example only, ebola virus or marburg virus).

In certain embodiments, the pharmaceutical compositions provided herein are used in the treatment of bacterial, fungal, and protozoal infections including, but not limited to, malaria, tuberculosis and *Mycobacterium avium*, leprosy; *pneumocystis carnii*, cryptosporidiosis, histoplasmosis, toxoplasmosis, trypanosome infection, leishmaniasis, infections caused by bacteria of the genus *Escherichia, Enterobacter, Salmonella, Staphylococcus, Klebsiella, Proteus, Pseudomonas, Streptococcus*, and *Chlamydia*, and fungal infections such as candidiasis, aspergillosis, histoplasmosis, and cryptococcal meningitis.

In certain embodiments, the pharmaceutical compositions provided herein are used in the treatment of respiratory diseases and/or disorders, dermatological disorders, ocular diseases and/or disorders, genitourinary diseases and/or disorders including, allograft rejection, auto-immune and allergic, cancer, or damaged or ageing skin such as scarring and wrinkles.

In another aspect, the invention provides a method for generating or potentiating an immune response in a subject in need thereof, such as a mammal, comprising administering an effective amount of a composition as disclosed herein. The immune response is preferably protective and preferably involves antibodies and/or cell-mediated immunity. The method may be used to induce a primary immune response and/or to boost an immune response.

In certain embodiments, the compositions disclosed herein may be used as a medicament, e.g., for use in raising or enhancing an immune response in a subject in need thereof, such as a mammal.

In certain embodiments, the compositions disclosed herein may be used in the manufacture of a medicament for generating or potentiating an immune response in a subject in need thereof, such as a mammal.

The mammal is preferably a human, but may be, e.g., a cow, a pig, a chicken, a cat or a dog, as the pathogens covered herein may be problematic across a wide range of species. Where the vaccine is for prophylactic use, the human is preferably a child (e.g., a toddler or infant), a teenager, or an adult; where the vaccine is for therapeutic use, the human is preferably a teenager or an adult. A vaccine intended for children may also be administered to adults, e.g., to assess safety, dosage, immunogenicity, etc.

One way of checking efficacy of therapeutic treatment involves monitoring pathogen infection after administration of the compositions or vaccines disclosed herein. One way of checking efficacy of prophylactic treatment involves monitoring immune responses, systemically (such as monitoring the level of IgG1 and IgG2a production) and/or mucosally (such as monitoring the level of IgA production), against the antigen. Typically, antigen-specific serum antibody responses are determined post-immunization but pre-challenge whereas antigen-specific mucosal antibody responses are determined post-immunization and post-challenge.

Another way of assessing the immunogenicity of the compositions or vaccines disclosed herein where the nucleic acid molecule (e.g., the RNA) encodes a protein antigen is to express the protein antigen recombinantly for screening patient sera or mucosal secretions by immunoblot and/or microarrays. A positive reaction between the protein and the patient sample indicates that the patient has mounted an immune response to the protein in question. This method may also be used to identify immunodominant antigens and/or epitopes within protein antigens.

The efficacy of the compositions can also be determined in vivo by challenging appropriate animal models of the pathogen of interest infection.

Dosage can be by a single dose schedule or a multiple dose schedule. Multiple doses may be used in a primary immunization schedule and/or in a booster immunization schedule. In a multiple dose schedule the various doses may be given by the same or different routes, e.g., a parenteral prime and mucosal boost, a mucosal prime and parenteral boost, etc. Multiple doses will typically be administered at least 1 week apart (e.g., about 2 weeks, about 3 weeks, about 4 weeks, about 6 weeks, about 8 weeks, about 10 weeks, about 12 weeks, about 16 weeks, etc.).

In certain embodiments, the total amount of cationic lipid, such as DOTAP, that is administered to the subject in a single administration is no more than about 30 mg, or no more than about 24 mg.

In certain embodiments, the total amount of cationic lipid, such as DOTAP, that is administered to the subject in a single administration is no more than 4 mg.

The compositions disclosed herein that include one or more antigens or are used in conjunction with one or more antigens may be used to treat both children and adults. Thus a human subject may be less than 1 year old, 1-5 years old, 5-15 years old, 15-55 years old, or at least 55 years old. Preferred subjects for receiving the compositions are the elderly (e.g., >50 years old, >60 years old, and preferably >65 years), the young (e.g., <5 years old), hospitalized patients, healthcare workers, armed service and military personnel, pregnant women, the chronically ill, or immunodeficient patients. The compositions are not suitable solely for these groups, however, and may be used more generally in a population.

The compositions disclosed herein that include one or more antigens or are used in conjunction with one or more antigens may be administered to patients at substantially the same time as (e.g., during the same medical consultation or visit to a healthcare professional or vaccination centre) other vaccines, e.g., at substantially the same time as a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine, a hepatitis B virus vaccine, a meningococcal conjugate vaccine (such as a tetravalent A C W135 Y vaccine), a respiratory syncytial virus vaccine, etc.

In certain embodiments, the compositions provided herein include or optionally include one or more immunoregulatory agents such as adjuvants. Exemplary adjuvants include, but are not limited to, a TH1 adjuvant and/or a TH2 adjuvant, further discussed below. In certain embodiments, the adjuvants used in the immunogenic compositions provide herein include, but are not limited to:

1. Mineral-Containing Compositions;
2. Oil Emulsions;
3. Saponin Formulations;
4. Virosomes and Virus-Like Particles;
5. Bacterial or Microbial Derivatives;
6. Bioadhesives and Mucoadhesives;
7. Liposomes;
8. Polyoxyethylene Ether and Polyoxyethylene Ester Formulations;
9. Polyphosphazene (PCPP);
10. Muramyl Peptides;
11. Imidazoquinolone Compounds;
12. Thiosemicarbazone Compounds;
13. Tryptanthrin Compounds;
14. Human Immunomodulators;
15. Lipopeptides;
16. Benzonaphthyridines;
17. Microparticles
18. Immunostimulatory polynucleotide (such as RNA or DNA; e.g., CpG-containing oligonucleotides)

EXEMPLIFICATION

The invention now being generally described, it will be more readily understood by reference to the following examples, which are included merely for purposes of illustration of certain aspects and embodiments of the present invention, and are not intended to limit the invention.

Example 1: Development of Cationic Oil-in-Water Emulsions

In this Example, cationic nanoemulsions (referred herein as "CNEs") that contain high concentrations of cationic lipid (DOTAP) were developed for the delivery of self replicating RNA.

The CNE formulations are summarized in Table 1 below, and were modified based on CNE01. CNE01, CMF40, CNE16, CNE02, and CNE17 were used as reference samples for comparative studies.

TABLE 1

| | CNE | Cationic Lipid mg/mL | Surfactant | Squalene | oil:Lipid ratio (mole:mole) | Aqueous phase |
|---|---|---|---|---|---|---|
| Ref. 1 | CNE01 | DOTAP (in $CHCl_3$) 0.8 | 0.5% SPAN 85 0.5% Tween 80 | 4.3% | 91.7:1 | 10 mM citrate buffer pH 6.5 |
| Ref. 2 | CMF40 | DOTAP (no organic solvent) 1.0 | 0.5% SPAN 85 0.5% Tween 80 | 4.3% | 73.3:1 | 10 mM citrate buffer pH 6.5 |
| Ref. 3 | CNE16 | DOTAP (no organic solvent) 1.2 | 0.5% SPAN 85 0.5% Tween 80 | 4.3% | 61.1:1 | 10 mM citrate buffer pH 6.5 |
| Ref. 4 | CNE02 | DOTAP (no organic solvent) 1.6 | 0.5% SPAN 85 0.5% Tween 80 | 4.3% | 45.8:1 | 10 mM citrate buffer pH 6.5 |
| Ref. 5 | CNE17 | DOTAP (in DCM) 1.4 | 0.5% SPAN 85 0.5% Tween 80 | 4.3% | 52.4:1 | 10 mM citrate buffer pH 6.5 |

TABLE 1-continued

|  | CNE | Cationic Lipid mg/mL | Surfactant | Squalene | oil:Lipid ratio (mole:mole) | Aqueous phase |
|---|---|---|---|---|---|---|
| Example 1 | CMF41 | DOTAP (no organic solvent) 1.8 | 0.5% SPAN 85 0.5% Tween 80 | 4.3% | 40.7:1 | 10 mM citrate buffer pH 6.5 |
| Example 2 | CMF30 | DOTAP (no organic solvent) 2.0 | 0.5% SPAN 85 0.5% Tween 80 | 4.3% | 36.7:1 | 10 mM citrate buffer pH 6.5 |
| Example 3 | CMF31 | DOTAP (no organic solvent) 2.6 | 0.5% SPAN 85 0.5% Tween 80 | 4.3% | 28.2:1 | 10 mM citrate buffer pH 6.5 |
| Example 4 | CMF32 | DOTAP (no organic solvent) 3.2 | 0.5% SPAN 85 0.5% Tween 80 | 4.3% | 22.9:1 | 10 mM citrate buffer pH 6.5 |
| Example 5 | CMF33 | DOTAP (no organic solvent) 3.8 | 0.5% SPAN 85 0.5% Tween 80 | 4.3% | 19.3:1 | 10 mM citrate buffer pH 6.5 |
| Example 6 | CMF34 | DOTAP (no organic solvent) 4.4 | 0.5% SPAN 85 0.5% Tween 80 | 4.3% | 16.7:1 | 10 mM citrate buffer pH 6.5 |
| Example 7 | CMF35 | DOTAP (no organic solvent) 5.0 | 0.5% SPAN 85 0.5% Tween 80 | 4.3% | 14.7:1 | 10 mM citrate buffer pH 6.5 |
| Example 8 | CMF44 | DOTAP (no organic solvent) 4.4 | 0.5% SPAN 85 0.5% Tween 80 | 3.23% | 12.5:1 | 10 mM citrate buffer pH 6.5 |
| Example 9 | CMF45 | DOTAP (no organic solvent) 4.4 | 0.5% SPAN 85 0.5% Tween 80 | 2.15% | 8.4:1 | 10 mM citrate buffer pH 6.5 |
| Example 10 | CMF46 | DOTAP (no organic solvent) 4.4 | 0.5% SPAN 85 0.5% Tween 80 | 1.08% | 4.2:1 | 10 mM citrate buffer pH 6.5 |

CNEs were prepared similar to charged MF59 as previously described (Ott et al., Journal of Controlled Release, volume 79, pages 1-5, 2002), with one major modification. DOTAP was dissolved in the squalene directly, and no organic solvent was used. It was discovered that inclusion of a solvent in emulsions that contained greater than 1.6 mg/ml DOTAP produced a foamy feedstock that could not be microfluidized to produce an emulsion. Heating squalene to 37° C. allowed DOTAP to be directly dissolved in squalene, and then the oil phase could be successfully dispersed in the aqueous phase (e.g., by homogenization) to produce an emulsion. DOTAP is soluble in squalene and higher concentrations of DOTAP in squalene than those listed in Table 1 may be achieved. However, it has been reported that high dose of DOTAP can have toxic effects. See, e.g., Lappalainen et al., Pharm. Res., vol. 11(8):1127-31 (1994).

Briefly, squalene was heated to 37° C., and DOTAP was dissolved directly in squalene in the presence of SPAN 85. The resulting oil phase was then combined with the aqueous phase (Tween 80 in citrate buffer) and immediately homogenized for 2 min using an IKA T25 homogenizer at 24K RPM to produce a homogeneous feedstock (primary emulsions). The primary emulsions were passed three to five times through a M-110S Microfluidizer or a M-110P Microfluidizer (Microfluidics, Newton, Mass.) with an ice bath cooling coil at a homogenization pressure of approximately 15K-20K PSI. The 20 ml batch samples were removed from the unit and stored at 4° C.

It should be noted that the concentrations of the components of the CNEs, as describes in Table 1, are concentrations calculated according the initial amounts of these components that were used to prepare the emulsions. It is understood that during the process of producing emulsions, or during the filter sterilization process, small amounts of squalene, DOTAP, or other components may be lost, and the actual concentrations of these components in the final product (e.g., a packaged, sterilized emulsion that is ready for administration) might be slightly lower, typically by up to about 20%, sometimes by up to about 25%, or up to about 35%. However, the conventional practice in the art is to describe the concentration of a particular component based on the initial amount that is used to prepare the emulsion, instead of the actual concentration in the final product.

Table 2 below shows the difference between the "theoretical" concentrations of squalene and DOTAP (calculated according the initial amounts of squalene and DOTAP that were used to prepare the emulsions), and the actual concentrations of squalene and DOTAP as measured in the final product.

TABLE 2

| CNE | Theoretical DOTAP (mg/mL) | Actual DOTAP (mg/mL) | % of Theoretical DOTAP Yield | Theoretical Squalene (mg/mL) | Actual Squalene (mg/mL) | % of Theoretical Squalene Yield |
|---|---|---|---|---|---|---|
| CMF32 Batch 1 | 3.2 | 2.20 | 68.76 | 43 | 19.33 | 44.95 |
| CMF32 Batch 2 | 3.2 | 2.57 | 80.32 | 43 | 34.45 | 80.12 |
| CMF32 Batch 3 | 3.2 | 2.37 | 73.95 | 43 | 38.38 | 89.25 |
| CMF34 Batch 1 | 4.4 | 2.75 | 62.44 | 43 | 30.46 | 70.84 |
| CMF34 Batch 2 | 4.4 | 3.21 | 73.00 | 43 | 33.98 | 79.02 |
| CMF34 Batch 3 | 4.4 | 3.08 | 70.08 | 43 | 32.71 | 76.07 |
| CMF34 Batch 4 | 4.4 | 3.52 | 79.93 | 43 | 28.95 | 67.34 |

Example 2: Preparation RNA-Particle Complexes

1. RNA Synthesis

Plasmid DNA encoding an alphavirus replicon (self-replicating RNA) was used as a template for synthesis of RNA in vitro. Each replicon contains the genetic elements required for RNA replication but lacks sequences encoding gene products that are necessary for particle assembly. The structural genes of the alphavirus genome were replaced by sequences encoding a heterologous protein (whose expression is driven by the alphavirus subgenomic promoter). Upon delivery of the replicons to eukaryotic cells, the positive-stranded RNA is translated to produce four non-structural proteins, which together replicate the genomic RNA and transcribe abundant subgenomic mRNAs encoding the heterologous protein. Due to the lack of expression of the alphavirus structural proteins, replicons are incapable of generating infectious particles. A bacteriophage T7 promoter is located upstream of the alphavirus cDNA to facilitate the synthesis of the replicon RNA in vitro, and the hepatitis delta virus (HDV) ribozyme located immediately downstream of the poly(A)-tail generates the correct 3'-end through its self-cleaving activity.

Following linearization of the plasmid DNA downstream of the HDV ribozyme with a suitable restriction endonuclease, run-off transcripts were synthesized in vitro using T7 or SP6 bacteriophage derived DNA-dependent RNA polymerase. Transcriptions were performed for 2 hours at 37° C. in the presence of 7.5 mM (T7 RNA polymerase) or 5 mM (SP6 RNA polymerase) final concentration of each of the nucleoside triphosphates (ATP, CTP, GTP and UTP) following the instructions provided by the manufacturer (Ambion, Austin, Tex.). Following transcription, the template DNA was digested with TURBO DNase (Ambion, Austin, Tex.). The replicon RNA was precipitated with LiCl and reconstituted in nuclease-free water. Uncapped RNA was capped post-transcriptionally with Vaccinia Capping Enzyme (VCE) using the ScriptCap $m^7G$ Capping System (Epicentre Biotechnologies, Madison, Wis.) as outlined in the user manual. Post-transcriptionally capped RNA was precipitated with LiCl and reconstituted in nuclease-free water. Alternatively, replicons may be capped by supplementing the transcription reactions with 6 mM (for T7 RNA polymerase) or 4 mM (for SP6 RNA polymerase) $m^7G(5')ppp(5')G$, a non-reversible cap structure analog (New England Biolabs, Beverly, Mass.) and lowering the concentration of guanosine triphosphate to 1.5 mM (for T7 RNA polymerase) or 1 mM (for SP6 RNA polymerase). The transcripts may be then purified by TURBO DNase (Ambion, Austin, Tex.) digestion followed by LiCL precipitation and a wash in 75% ethanol.

The concentration of the RNA samples was determined by measuring the optical density at 260 nm. Integrity of the in vitro transcripts was confirmed by denaturing agarose gel electrophoresis for the presence of the full length construct.

2. RNA Complexation

The term N/P ratio refers to the amount of nitrogen in the cationic lipid in relation to the amount of phosphates on the RNA. The nitrogen is the charge bearing element within the cationic lipids tested. The phosphate can be found on the RNA backbone. An N/P charge ratio of 10/1 indicates that there are 10 positively charged nitrogen from the cationic lipid present for each negatively charged phosphate on the RNA.

The number of nitrogens in solution was calculated from the cationic lipid concentration, DOTAP for example has one nitrogen that can be protonated per molecule. The RNA concentration was used to calculate the amount of phosphate in solution using an estimate of 3 nmols of phosphate per microgram of RNA. By varying the amount of RNA: Lipid, the N/P ratio can be modified. RNA was complexed to the CNEs in a range of nitrogen/phosphate ratios (N/P). Calculation of the N/P ratio was done by calculating the number of moles of protonatable nitrogens in the emulsion per milliliter. To calculate the number of phosphates, a constant of 3 nmols of phosphate per microgram of RNA was used. After the values were determined, the appropriate ratio of the emulsion was added to the RNA. Using these values, the RNA was diluted to the appropriate concentration and added directly into an equal volume of emulsion while vortexing lightly. The solution was allowed to sit at room temperature for approximately 2 hours. Once complexed the resulting solution was diluted to the appropriate concentration and used within 1 hour.

3. Particle Size Assay

Particle size of the emulsion was measured using a Zetasizer Nano ZS (Malvern Instruments, Worcestershire, UK) according to the manufacturer's instructions. Particle sizes are reported as the Z-Average (ZAve) with the polydispersity index (pdi). All samples were diluted in water prior to measurements. Additionally, particle size of the emulsion was measured using Horiba LA-930 particle sizer (Horiba Scientific, USA). Samples were diluted in water prior to measurements. Zeta potential was measured using Zetasizer Nano ZS using diluted samples according to the manufacturer's instructions.

4. Viral Replicon Particles (VRP)

To compare RNA vaccines to traditional RNA-vectored approaches for achieving in vivo expression of reporter genes or antigens, we utilized viral replicon particles (VRPs) produced in BHK cells by the methods described by Perri et al., *J. Virol,* 77:10394-10403 (2003). In this system, the antigen (or reporter gene) replicons consisted of alphavirus chimeric replicons (VCR) derived from the genome of Venezuelan equine encephalitis virus (VEEV) engineered to contain the 3' terminal sequences (3' UTR) of Sindbis virus and a Sindbis virus packaging signal (PS) (see FIG. 2 of Perri S., et al., *J Virol* 77: 10394-10403 (2003)). These replicons were packaged into VRPs by co-electroporating them into baby hamster kidney (BHK) cells along with defective helper RNAs encoding the Sindbis virus capsid and glycoprotein genes (see FIG. 2 of Perri et al). The VRPs were then harvested and titrated by standard methods and inoculated into animals in culture fluid or other isotonic buffers.

Example 3: The Effect of DOTAP Concentration on Immunogenicity

This Example shows that cationic oil-in-water emulsions made with high concentrations of DOTAP increased the immunogenicity of an RNA replicon that encodes the RSV-F antigen in a mouse model.

1. Materials and Methods

Heparin Binding Assay

RNA was complexed as described above. The RNA/CNE complex was incubated with various concentrations of heparin sulfate (Alfa Aesar, Ward Hill Mass.) for 30 minutes at Room Temperature. The resulting solutions were then placed on an Airfuge high speed centrifuge (Beckman Coulter, Brea, Calif.) for 15 minutes. The centrifuge tubes were punctured with a tuberculin syringe and the subnatant was removed. The solution was then assayed for RNA concentration using the Ribogreen assay (Invitrogen, Carlsbad Calif.) according to the manufactures directions. The samples were analyzed on a Biotek Synergy 4 (Winooski, Vt.) fluorescent plate reader. Free RNA values were calculated using a standard curve.

2. The Effect of DOTAP Concentration on RNA-Particle Interactions

Table 3 shows the effect of DOTAP concentration on RNA-particle interactions (as determined by Heparin binding assay, which measured the tightness of the RNA-particle interactions) and immunogenicity.

TABLE 3

| | | Heparin Binding Assay | |
|---|---|---|---|
| CNE | DOTAP concentration (mg/mL) | N/P ratio | % of RNA release in 8X heparin Sulfate |
| CNE01 | 0.8 | 2:1 | nt |
| | | 4:1 | nt |
| | | 6:1 | 62.82 |
| | | 8:1 | 54.18 |
| | | 10:1 | nt |
| | | 12:1 | 116.6 |
| | | 14:1 | 62.79 |
| CMF41 | 1.0 | 2:1 | nt |
| | | 4:1 | 4.61 |
| | | 6:1 | 33.41 |
| | | 8:1 | 70.68 |
| | | 10:1 | 54.92 |
| | | 12:1 | 52.93 |
| CNE16 | 1.2 | 2:1 | nt |
| | | 4:1 | 1.83 |
| | | 6:1 | nt |
| | | 8:1 | 33.79 |
| | | 10:1 | 58.86 |
| | | 12:1 | 68.02 |
| | | 14:1 | 55.07 |
| CNE17 | 1.4 | 2:1 | nt |
| | | 4:1 | nt |
| | | 6:1 | 3.91 |
| | | 8:1 | 44.00 |
| | | 10:1 | 69.65 |
| | | 12:1 | 61.53 |
| | | 14:1 | 57.26 |
| CNE02 | 1.6 | 2:1 | nt |
| | | 4:1 | nt |
| | | 6:1 | 2.01 |
| | | 8:1 | 2.87 |
| | | 10:1 | 7.38 |
| | | 12:1 | 19.37 |
| | | 14:1 | 21.44 |
| CMF41 | 1.8 | 2:1 | nt |
| | | 4:1 | 0.76 |
| | | 6:1 | 1.33 |
| | | 8:1 | 1.10 |
| | | 10:1 | 2.69 |
| | | 12:1 | 2.59 |
| | | 14:1 | 3.67 |
| CMF30 | 2.0 | 2:1 | nt |
| | | 4:1 | 0.7 |
| | | 6:1 | 0.81 |
| | | 8:1 | 1.17 |
| | | 10:1 | 2.35 |
| | | 12:1 | 5.15 |
| | | 14:1 | 9.44 |
| CMF30 | 2.6 | 2:1 | nt |
| | | 4:1 | nt |
| | | 6:1 | 0.83 |
| | | 8:1 | 1.18 |
| | | 10:1 | 1.00 |
| | | 12:1 | 0.96 |
| | | 14:1 | 1.10 |

nt = not tested.

As shown in Table 3, RNA molecules bound strongly to emulsion particles that were made with high concentrations of DOTAP (1.8 mg/mL or higher).

3. The Effect of DOTAP Concentration on RNA Loading

Table 4 shows the effect of DOTAP concentration on RNA loading. Increasing the concentration of DOTAP resulted in higher amount of RNA molecules being formulated into RNA-particle complexes.

TABLE 4

| | CNE | | | | | | | |
|---|---|---|---|---|---|---|---|---|
| | CNE17 | CMF41 | CMF30 | CMF31 | CMF32 | CMF33 | CMF34 | CMF35 |
| | DOTAP (in 0.5 ml emulsion) | | | | | | | |
| | 0.35 mg | 0.45 mg | 0.5 mg | 0.65 mg | 0.8 mg | 0.95 mg | 1.1 mg | 1.25 mg |
| N/P ratio | Amount of RNA (μg) | | | | | | | |
| 4 to 1 | 41.8 | 53.7 | 59.6 | 77.5 | 95.4 | 113.3 | 131.2 | 149.1 |
| 6 to 1 | 27.8 | 35.8 | 39.8 | 51.7 | 63.6 | 75.6 | 87.5 | 99.4 |
| 8 to 1 | 20.9 | 26.8 | 29.8 | 38.8 | 47.7 | 56.7 | 65.6 | 74.6 |
| 10 to 1 | 16.7 | 21.5 | 23.9 | 31 | 38.2 | 45.3 | 52.5 | 59.6 |
| 12 to 1 | 13.9 | 17.9 | 19.9 | 25.8 | 31.8 | 37.8 | 43.7 | 49.7 |
| 14 to 1 | 11.9 | 15.3 | 17 | 22.2 | 27.3 | 32.4 | 37.5 | 42.6 |

4. The Effect of DOTAP Concentration on Immunogenicity

Table 5 shows the effect of DOTAP concentration on the immunogenicity of the RSV F antigen in an in vivo mouse model.

The vA317 replicon that expresses the surface fusion glycoprotein of RSV (RSV-F) was used for this study. BALB/c mice, aged 8-10 weeks and weighing about 20 g, 10 animals per group, were given bilateral intramuscular vaccinations. All animals were injected in the quadriceps in the two hind legs each getting an equivalent volume (50 μL per leg) on days 0 and 21 with naked self-replicating RNA expressing RSV-F (vA317, 1 μg), 1 μg of A317 formulated in a liposome that contained 40% DlinDMA, 10% DSPC, 48% Chol, 2% PEG DMG 2000 (RV01(15)), or self-replicating RNA formulated in the indicated CNEs (1 vA317). For each administration, the formulations were freshly prepared. Serum was collected for antibody analysis on days 14 (2wp1) and 35 (2wp2).

TABLE 5

| CNE ([ ] DOTAP) | RNA (μg/0.5 mL) | N/P ratio | DOTAP (mg/0.5 mL) | 2wp1 GMT (Pooled) | 2wp2 GMT | 2wp2/2wp1 ratio |
|---|---|---|---|---|---|---|
| 1 μg vA317 | — | — | — | 764 | 344 | 0.5 |
| 1 μg RV01(15) | — | — | — | 3898 | 66348 | 17.0 |
| CNE01 (0.8 mg/mL) | 9.55 | 10:1 | 0.20 | 163 | 993 | 6.1 |
| CMF40 (1.0 mg/mL) | 11.93 | 10:1 | 0.25 | 505 | 3350 | 6.6 |
| CNE16 (1.2 mg/mL) | 14.32 | 10:1 | 0.30 | 465 | 3851 | 8.3 |
| CNE17 (1.4 mg/mL) | 16.70 | 10:1 | 0.35 | 843 | 3638 | 4.3 |
| CNE02 (1.6 mg/mL) | 19.09 | 10:1 | 0.40 | 1253 | 5507 | 4.4 |
| CMF41 (1.8 mg/mL) | 21.48 | 10:1 | 0.45 | 961 | 5132 | 5.3 |
| CMF30 (2.0 mg/mL) | 23.86 | 10:1 | 0.50 | 2021 | 10068 | 5.0 |
| CMF31 (2.6 mg/mL) | 31.02 | 10:1 | 0.65 | 1557 | 11940 | 7.7 |
| CMF32 (3.2 mg/mL) | 38.18 | 10:1 | 0.80 | 1124 | 6941 | 6.2 |

As shown in Table 5, increasing DOTAP concentration resulted in higher amount of RNA being loaded to the emulsion particles, which in turn increased the host immune response. A 3-fold increase in antibody titer (at 2wp2) for CMF31 was observed as compared to CNE17. In this model, a plateau in immunogenicity was observed at 2.6 mg/mL DOTAP (CMF31).

When the amounts of RNA and DOTAP administered to each mouse were held constant (meaning for emulsions with higher concentrations of DOTAP, smaller volumes of emulsion were used to prepare the RNA/emulsion complex; then, prior to immunization, the RNA/emulsion formulations were diluted such that the volumes of the RNA/emulsion formulations injected to the mice were the same), F-specific total IgG titers were comparable with different CNE formulations (Table 6). vA317 replicon was used for all CNE formulations. RNAs were made with Ambion kit. The GMT data reflect the geometric mean titer of individual mice in each group (8 mice/group). The result shows that smaller amount of the formulations were needed for emulsions with higher concentrations of DOTAP.

TABLE 6

| Formulation | RNA (μg/dose) | N/P ratio | DOTAP (μg/dose) | Squalene (mg/dose) | 2wp1 GMT | 2wp2 GMT | 2wp2/2wp1 (boost) | % of max geo mean titer, 2wp2 |
|---|---|---|---|---|---|---|---|---|
| Naked RNA | 1 | — | — | — | 764 | 334 | 0 | 0 |
| RV01 particles | 1 | — | — | — | 3898 | 66348 | 17 | — |
| CNE17 | 1 | 10:1 | 21 | 0.65 | 673 | 5314 | 8 | 41 |
| CMF41 | 1 | 10:1 | 21 | 0.50 | 784 | 7083 | 9 | 55 |
| CMF30 | 1 | 10:1 | 21 | 0.45 | 492 | 8543 | 17 | 66 |
| CMF31 | 1 | 10:1 | 21 | 0.35 | 1123 | 6972 | 6 | 54 |
| CMF32 | 1 | 10:1 | 21 | 0.28 | 1665 | 10498 | 6 | 82 |
| CMF33 | 1 | 10:1 | 21 | 0.24 | 1351 | 12279 | 9 | 96 |
| CMF34 | 1 | 10:1 | 21 | 0.20 | 936 | 12851 | 14 | 100 |
| CMF35 | 1 | 10:1 | 21 | 0.18 | 628 | 7766 | 12 | 60 |

Titers from pre-immunization serum contained undetectable titers.

When the amount of squalene and N/P ratio (DOTAP: RNA) administered to each mouse were held constant, F-specific total IgG titers increased as the amount of RNA and DOTAP in the formulations increased (Table 7). The vA317 replicon was used for all CNE formulations. RNAs were made with Ambion kit. The GMT data reflect the geometric mean titer of individual mice in each group (8 mice/group). The result shows that increasing DOTAP concentration resulted in higher amount of RNA being loaded to the emulsion particles, which in turn increased the host immune response.

TABLE 7

| Formulation | RNA (μg/dose) | N/P ratio | DOTAP (μg/dose) | Squalene (mg/dose) | 2wp1 GMT | 2wp2 GMT | 2wp2/2wp1 (boost) | % of max geo mean titer, 2wp2 |
|---|---|---|---|---|---|---|---|---|
| Naked | 11.9 | — | — | — | 14 | 682 | 49 | 2 |
| RV01 particles | 3.3 | — | — | — | 3767 | 64889 | 17 | — |
| RV01 particles | 11.9 | — | — | — | 6562 | 102359 | 16 | — |
| CNE17 | 0 | — | 70 | 2.15 | 5 | 5 | 1 | 1 |
| CMF35 | 0 | — | 250 | 2.15 | 10 | 5 | 1 | 1 |
| CNE17 | 3.3 | 10:1 | 70 | 2.15 | 223 | 8567 | 38 | 25 |
| CMF41 | 4.3 | 10:1 | 90 | 2.15 | 974 | 7020 | 7 | 21 |
| CMF30 | 4.8 | 10:1 | 100 | 2.15 | 1212 | 10999 | 9 | 33 |
| CMF31 | 6.2 | 10:1 | 130 | 2.15 | 874 | 15142 | 17 | 45 |
| CMF32 | 7.6 | 10:1 | 160 | 2.15 | 1816 | 22239 | 12 | 66 |
| CMF33 | 9.1 | 10:1 | 190 | 2.15 | 1862 | 17445 | 9 | 52 |
| CMF34 | 10.5 | 10:1 | 220 | 2.15 | 1302 | 33634 | 26 | 100 |
| CMF35 | 11.9 | 10:1 | 250 | 2.15 | 1554 | 24971 | 16 | 74 |
| Naïve | — | — | — | — | 5 | 5 | 1 | 0 |

CMF32 and CMF34 were further studied using different N/P ratios. Table 8 shows the F-specific total IgG titers of the formulations. Theoretical N/P ratios reflect the N/P ratios calculated according to the initial amounts of DOTAP and RNA that were used to prepare the formulations. Actual N/P ratios were slightly lower than theoretical N/P ratios because small amounts of DOTAP were lost during preparation of the emulsions. The vA317 was used for all CNE and CMF formulations. The GMT data reflect the mean $\log_{10}$ titer of individual mice in each group (8 mice/group). All formulations were adjusted to 300 mOsm/kg with sucrose. There were no obvious tolerability issues observed (e.g., body weight, early serum cytokines) with either CMF32 or CMF34 formulations.

Actual N/P ratios were determined by quantifying DOTAP content in CNE or CMF batches using HPLC with a charged aerosol detector (Corona Ultra, Chelmsford, Mass.). The CNE and CMF samples were diluted in isopropanol and injected onto a XTera C18 4.6×150 mm 3.5 um column (Waters, Milford, Mass.). The area under the curve was taken from the DOTAP peak in the chromatogram and the concentration was interpolated off a DOTAP standard curve. Using the actual DOTAP concentration, an actual N/P ratio was be calculated.

TABLE 8

| Formulation | RNA (µg/dose) | Theoretical N/P ratio | Actual N/P ratio | 2wp1 GMT | 2wp1 GMT | 2wp2/2wp1 (boost) |
|---|---|---|---|---|---|---|
| Naked | 1 | — | — | 68 | 1019 | 15 |
| RV01 | 1 | — | — | 9883 | 68116 | 7 |
| CNE17 | 1 | 10:1 | — | 1496 | 6422 | 4 |
| CMF32 | 1 | 12:1 | 9.4:1 | 2617 | 14246 | 5 |
| | 1 | 10:1 (batch 1) | 6.0:1 | 1537 | 10575 | 7 |
| | 1 | 10:1 (batch 2) | 8.0:1 | 2047 | 16244 | 8 |
| | 1 | 8:1 | 6.3:1 | 2669 | 7656 | 3 |
| | 1 | 6:1 | 4.7:1 | 1713 | 4715 | 3 |
| | 1 | 4:1 | 3.1:1 | 872 | 3773 | 4 |
| CMF34 | 1 | 12:1 | 7.4:1 | 3141 | 10134 | 3 |
| | 1 | 10:1 (batch 1) | 6.1:1 | 1906 | 11081 | 6 |
| | 1 | 10:1 (batch 2) | 7.0:1 | 2388 | 9857 | 4 |
| | 1 | 8:1 | 5:1 | 1913 | 8180 | 4 |
| | 1 | 6:1 | 3.7:1 | 1764 | 6209 | 4 |
| | 1 | 4:1 | 2.5:1 | 1148 | 4936 | 4 |

Example 4: The Effect of DOTAP Concentration on Immunogenicity

This Example shows that cationic oil-in-water emulsions made with high concentrations of DOTAP increased the immunogenicity of an RNA replicon that encodes the RSV-F antigen in a cotton rat model.

1. Materials and Methods

RNA Replicon.

The sequence of the RNA replicon, vA142 RSV-F-delFP-full ribozyme

Vaccination of Cotton Rats.

Female cotton rats (*Sigmodon hispidis*) were obtained from Harlan Laboratories. All studies were approved and performed according to Novartis Animal Care and Use Committee. Groups of animals were immunized intramuscularly (i.m., 100 µl) with the indicated vaccines on day 0. Serum samples were collected 3 weeks after each immunization Immunized or unvaccinated control animals were challenged intranasally (i.n.) with $1\times10^5$ PFU RSV 4 weeks after the final immunization.

RSV-F Trimer Subunit Vaccine.

The RSV F trimer is a recombinant protein comprising the ectodomain of RSV F with a deletion of the fusion peptide region preventing association with other trimers. The resulting construct forms a homogeneous trimer, as observed by size exclusion chromatography, and has an expected phenotype consistent with a postfusion F conformation as observed by electron microscopy. The protein was expressed in insect cells or CHO cells and purified by virtue of a HIS-tagged in fusion with the construct's C-terminus followed by size exclusion chromatography using conventional techniques. The resulting protein sample exhibits greater than 95% purity. For the in vivo evaluation of the F-subunit vaccine, 100 µg/mL trimer protein was adsorbed on 2 mg/mL alum using 10 mM Histidine buffer, pH 6.3 and isotonicity adjusted with sodium chloride to 150 mM. F-subunit protein was adsorbed on alum overnight with gentle stirring at 2-8° C.

RSV F-Specific ELISA.

Individual serum samples were assayed for the presence of RSV F-specific IgG by enzyme-linked immunosorbent assay (ELISA). ELISA plates (MaxiSorp 96-well, Nunc) were coated overnight at 4° C. with 1 µg/ml purified RSV F (delp23-furdel-trunc uncleaved) in PBS. After washing (PBS with 0.1% Tween-20), plates were blocked with Superblock Blocking Buffer in PBS (Thermo Scientific) for at least 1.5 hr at 37° C. The plates were then washed, serial dilutions of serum in assay diluent (PBS with 0.1% Tween-20 and 5% goat serum) from experimental or control cotton rats were added, and plates were incubated for 2 hr at 37° C. After washing, plates were incubated with horse radish peroxidase (HRP)-conjugated chicken anti-cotton rat IgG (Immunology Consultants Laboratory, Inc, diluted 1:5,000 in assay diluent) for 1 hr at 37° C. Finally, plates were washed and 100 µl of TMB peroxidase substrate solution (Kirkegaard & Perry Laboratories, Inc) was added to each well. Reactions were stopped by addition of 100 µl of 1M $H_3PO_4$, and absorbance was read at 450 nm using a plate reader. For each serum sample, a plot of optical density (OD) versus logarithm of the reciprocal serum dilution was generated by nonlinear regression (GraphPad Prism). Titers were defined as the reciprocal serum dilution at an OD of approximately 0.5 (normalized to a standard, pooled sera from RSV-infected cotton rats with a defined titer of 1:2500, that was included on every plate).

Micro Neutralization Assay.

Serum samples were tested for the presence of neutralizing antibodies by a plaque reduction neutralization test (PRNT). Two-fold serial dilutions of HI-serum (in PBS with 5% HI-FBS) were added to an equal volume of RSV Long previously titered to give approximately 115 PFU/25 µl. Serum/virus mixtures were incubated for 2 hours at 37° C. and 5% CO2, to allow virus neutralization to occur, and then 25 µl of this mixture (containing approximately 115 PFU) was inoculated on duplicate wells of HEp-2 cells in 96 well plates. After 2 hr at 37° C. and 5% CO2, the cells were overlayed with 0.75% Methyl Cellulose/EMEM 5% HI-FBS and incubated for 42 hours. The number of infectious virus particles was determined by detection of syncytia formation by immunostaining followed by automated counting. The neutralization titer is defined as the reciprocal of the serum dilution producing at least a 60% reduction in number of synctia per well, relative to controls (no serum).

2. The Effect of DOTAP Concentration on Immunogenicity

Table 9 shows the effect of DOTAP concentration on the immunogenicity of the RSV F antigen in an in vivo cotton rat model. The first two vaccination used the RNA/CNE formulations as shown in Table 9. For the third vaccination, 3 µg of RSV F subunit protein (in alum) were used for all animals except the naïve group.

TABLE 9

| Formulation | RNA (μg/dose) | 3wp1 F-specific total IgG titers | 3wp2 F-specific total IgG titers | 3wp3 F-specific total IgG titers | 3wp1 F-specific Neutralizing IgG titers | 3wp2 F-specific Neutralizing IgG titers | 3wp3 F-specific Neutralizing IgG titers |
|---|---|---|---|---|---|---|---|
| 6 ug F-trimer + Alum | — | 16,373 | 64,928 | 84,133 | 327 | 3,565 | 3979 |
| 1E6 IU/ 200 ul VRP | — | 2819 | 2,478 | 15,473 | 135 | 299 | 1791 |
| CNE17 | 0.01 | 112 | 771 | 23,939 | 28 | 66 | 689 |
| (Ambion | 0.1 | 351 | 1,505 | 19,495 | 41 | 173 | 1060 |
| MegaScript | 1 | 722 | 2,379 | 22,075 | 82 | 249 | 2550 |
| RNA) | | | | | | | |
| CMF31 | 0.01 | 184 | 1,015 | 31,082 | 31 | 67 | 1301 |
| (Ambion | 0.1 | 375 | 1,250 | 16,597 | 51 | 99 | 2393 |
| MegaScript | 1 | 1013 | 2,736 | 20,861 | 199 | 341 | 2783 |
| RNA) | 10 | 4556 | 6,867 | 27,299 | 253 | 672 | 3593 |
| CMF34 | 0.01 | 214 | 690 | 25,470 | 35 | 38 | 1440 |
| (Ambion | 0.1 | 411 | 1,574 | 19,030 | 45 | 129 | 1835 |
| MegaScript | 1 | 953 | 2,248 | 18,894 | 75 | 353 | 3224 |
| RNA) | 10 | 4,804 | 5,122 | 16,566 | 282 | 521 | 3738 |
| CNE17 (In house synthesized RNA) | 1 | 1,042 | 2,944 | 23,097 | 128 | 288 | 2086 |
| Naïve | 5 | 5 | 5 | 5 | 0 | 10 | 10 |

Ambion MegaScript RNA and in house synthesized RNA were prepared using different processes.

Data from Table 9 show that all CNE-RNA formulations induced dose-dependent immune responses in the hosts (total IgG titers as well as neutralizing antibody titers). Administering CMF31-RNA and CMF34-RNA formulations produced similar F-specific total IgG titers, and each was greater than that of CNE17 at each of the indicated RNA dose. In addition, all CNE-RNA formulations induced good neutralizing antibody titers at 10 μg RNA. Neutralizing antibody titers for the CMF31-RNA, CMF34-RNA, and CNE17-RNA groups were similar, except for surprisingly high titer for the 1 μg RNA/CMF31 group.

Example 5: Assessing the Effects of Buffer Compositions on Immunogenicity

In this example, various emulsions based on CMF34 but with different buffer components were prepared.

Table 10 summarizes the results of murine immunogenicity studies when CMF34-formulated RNAs were prepared using different buffer systems.

TABLE 10

| Group # | Description: RNA | Description: Emulsion | Description: N/P ratio | 2wp1 | 2wp2 | 2wp2/2wp1 ratio |
|---|---|---|---|---|---|---|
| 1 | 1 μg RSV-F* | PBS | — | 100 | 2269 | 23 |
| 2 | RV01 (15) | PBS | — | 8388 | 105949 | 13 |
| 3 | 1 μg | CNE17 with 280 mM Sucrose | 10:1 | 898 | 9384 | 10 |
| 4 | RSV-F* | CMF34 with 280 mM Sucrose | 10:1 | 1835 | 10853 | 6 |
| 5 | | CMF34 with 280 mM Sucrose and 1 mM citrate | 10:1 | 1751 | 15589 | 9 |
| 6 | | CMF34 with 280 mM Sucrose and 10 mM citrate | 10:1 | 1699 | 17078 | 10 |
| 7 | | CMF34 with 280 mM Sucrose, 1 mM citrate, and 2 mM NaCl | 10:1 | 1342 | 16400 | 12 |
| 8 | | CMF34 with 280 mM Sucrose, 10 mM citrate, and 2 mM NaCl | 10:1 | 1318 | 10467 | 8 |
| 9 | | CMF34 with 280 mM Sucrose, 1 mM citrate, and 10 mM NaCl | 10:1 | 1735 | 12457 | 7 |
| 10 | | CMF34 with 280 mM Sucrose, 10 mM citrate, and 10 mM NaCl | 10:1 | 1365 | 14414 | 11 |

*vA375 replicon.

Example 6: Stability of the Emulsions

Stability of CMF34 was assessed by measuring the average diameter of the emulsion particles and polydispersity after the emulsion was produced (T=0) and after 1 month at 4° C. (T=1 month) and after 2 months at 4° C. (T=1 month). Stability was also assessed after 3, 6 and 12 months at 4° C. The results presented in Table 11 show that the emulsion was stabile for at least 12 months.

TABLE 11

| | T = 0 | T = 1 month | T = 2 months | T = 3 months | T = 6 months | T = 12 months |
|---|---|---|---|---|---|---|
| NanoZS (nm) | 101.4 | 100.6 | 99.76 | 99.23 | 101.0 | 101.0 |
| Polydispersity | 0.109 | 0.102 | 0.096 | 0.103 | 0.080 | 0.094 |

Example 7 Immunogenicity of Replicons Encoding Herpes Virus Proteins

A. CMV Proteins

Figure 2:
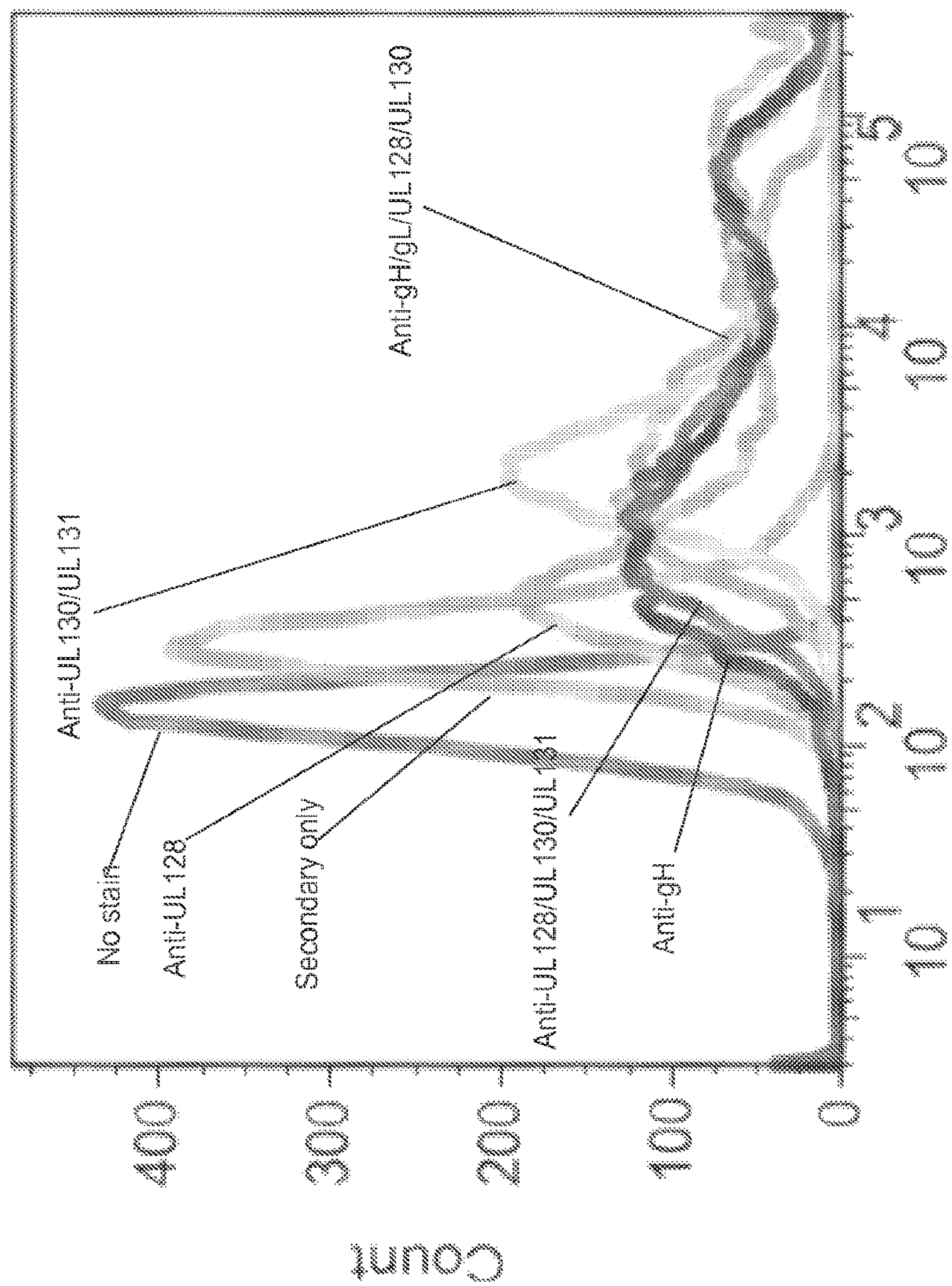
FIG. 2 is a fluorescence histogram showing that BHKV cells transfected with the A527 RNA replicon express the gH/gL/UL128/UL130/UL131 pentameric complex. Cell stain was performed using an antibody that binds a conformational epitope present on the pentameric complex.
Figure 3:
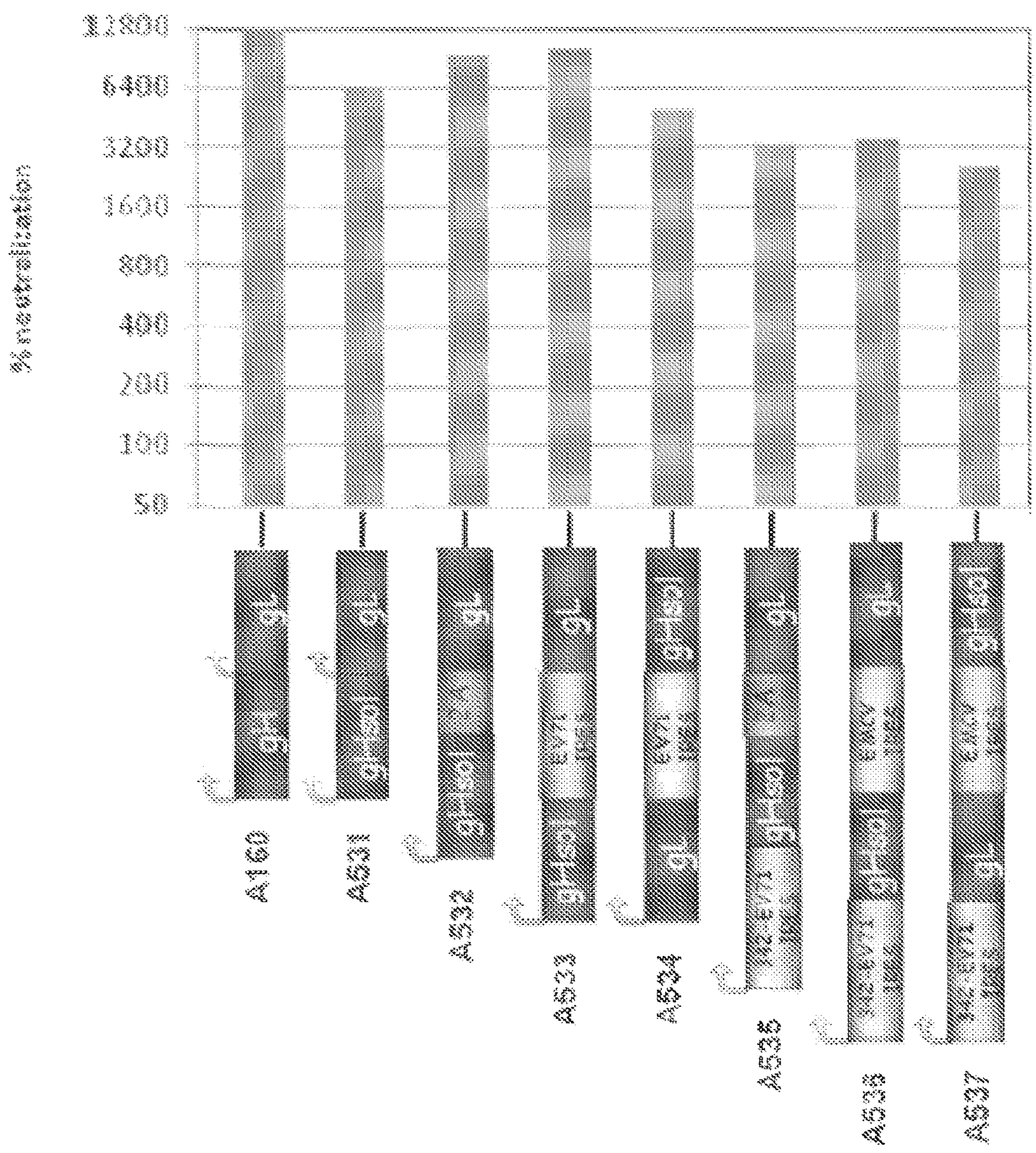
FIG. 3 is a schematic and graph. The schematic shows bicistronic RNA replicons, A160 and A531-A537, that encode CMV gH and gL. The graph shows neutralizing activity of immune sera from mice immunized with VRPs that contained the replicons.

Bicistronic and pentacistronic alphavirus replicons that express glycoprotein complexes from human cytomegalovirus (HCMV) were prepared, and are shown schematically in FIGS. 1 and 3. The alphavirus replicons were based on venezuelan equine encephalitis virus (VEE). The replicons were packaged into viral replicon particles (VRPs), encapsulated in lipid nanoparticles (LNP), or formulated with CMF34. Expression of the encoded HCMV proteins and protein complexes from each of the replicons was confirmed by immunoblot, co-immunoprecipitation, and flow cytometry. Flow cytometry was used to verify expression of the pentameric gH/gL/UL128/UL130/UL131 complex from pentameric replicons encoding the protein components of the complex, using human monoclonal antibodies specific to conformational epitopes present on the pentameric complex (Macagno et al (2010), *J. Virol.* 84(2):1005-13). FIG. 2 shows that these antibodies bind to BHKV cells transfected with replicon RNA expressing the HCMV gH/gL/UL128/UL130/UL131 pentameric complex (A527). Similar results were obtained when cells were infected with VRPs made from the same replicon construct. This shows that replicons designed to express the pentameric complex do indeed express the desired antigen and not the potential byproduct gH/gL.

The VRPs, RNA encapsulated in LNPs, and RNA formulated with CMF34 were used to immunize Balb/c mice by intramuscular injections in the rear quadriceps. The mice were immunized three times, three weeks apart, and serum samples were collected prior to each immunization as well as three weeks after the third and final immunization. The sera were evaluated in microneutralization assays and to measure the potency of the neutralizing antibody response that was elicited by the vaccinations. The titers are expressed as 50% neutralizing titer.

The immunogenicity of a number of different configurations of a bicistronic expression cassette for a soluble HCMV gH/gL complex in VRPs was assessed. FIG. 3 shows that VRPs expressing the membrane-anchored, full-length gH/gL complex elicited potent neutralizing antibodies at slightly higher titers than the soluble complex (gHsol/gL) expressed from a similar bicistronic expression cassette. Changing the order of the genes encoding gHsol and gL or replacing one of the subgenomic promoters with an IRES or an FMDV 2A site did not substantially improve immunogenicity.

To see if bicistronic and pentacistronic replicons expressing the gH/gL and pentameric complexes would elicit neutralizing antibodies in different formulations, cotton rats were immunized with bicistronic or pentacistronic replicons mixed with CMF34. Table 12 shows that replicons in CMF34 elicited comparable neutralizing antibody titers to the same replicons encapsulated in LNPs.

TABLE 12

Neutralizing antibody titers. The sera were collected three weeks after the second immunization.

| Replicon | 50% Neutralizing Titer |
|---|---|
| A160 gH FL/gL VRP $10^6$ IU | 594 |
| A160 gH FL/gL 1 μg LNP | 141 |
| A527 Pentameric IRES 1 μg LNP | 4,416 |
| A160 gH FL/gL 1 μg CMF34 | 413 |
| A527 Pentameric IRES 1 μg CMF34 | 4,411 |

B. VZV Proteins

Nucleic acids encoding VZV proteins were cloned into a VEE replicon vector to produce monocystronic replicons that encode gB, gH, gL, gE, and gI, and to produce bicistronic replicons that encode gH/gL or gE/gI. In the bicistronic replicons, expression of each VZV open reading frame was driven by a separate subgenomic promoter.

To prepare replicon RNA, plasmid encoding the replicon was linearized by digestion with PmeI, and the linearized plasmid was extracted with phenol/chloroform/isoamylalchohol, precipitated in sodium acetate/ethanol and resuspended in 20 μl of RNase-free water.

RNA was prepared by In vitro transcription of 1 μg of linearized DNA using the MEGAscript T7 kit (AMBION#AM1333). A 20 μl reaction was set up according to the manufacturer's instruction without cap analog and incubated for 2 hours at 32° C. TURBO DNase (1 μl) was added and the mixture was incubate for 30 min. at 32° C. RNase-free water (30 μl) and ammonium acetate solution (30 μl) were added. The solution was mixed and chilled for at least 30 min at −20° C. Then the solution was centrifuged at maximum speed for 25 min. at 4° C. The supernatant was discarded, and the pellet was rinsed with 70% ethanol, and again centrifuged at maximum speed for 10 min. at 4° C. The pellet was air dried and resuspended in 50 μl of RNase-free water. The concentration of RNA was measured and quality was check on a denaturing gel.

The RNA was capped using the ScriptCap m7G Capping System (Epicentre #SCCE0625). The reaction was scaled by combining the RNA and RNase-free water. The RNA was then denatured for 5-10 min. at 65° C. The denatured RNA was transferred quickly to ice and the following reagents were added in the following order: ScriptCap Capping Buffer, 10 mM GTP, 2 mM SAM fresh prepared, ScriptGuard RNase inhibitor, and ScriptCap Capping Enzyme. The mixture was incubated for 60 min. at 37° C. The reaction was stopped by adding RNase-free water and 7.5 M LiCl, mixing well and storing the mixture for at least 30 min at −20° C. Then, the mixture was centrifuged at maximum speed for 25 min. at 4° C., the pellet was rinsed with 70% ethanol, again centrifuged at maximum speed for 10 min. at 4° C. and the pellet was air dried. The pellet was resuspended in RNase-free water. The concentration of RNA was measured and quality was checked on a denaturing gel.

RNA Transfection

Cells (BHK-V cells) were seeded on 6-well plates brought to 90-95% confluence at the time of transfection. For each transfection 3 μg of RNA was diluted in 50 mL OPTIMEM media in a first tube. Lipofectamine 2000 was added to a second tube contained 50 mL OPTIMEM media. The first and second tubes were combined and kept for 20 min. at room temperature. The culture media in the 6-well plates were replaced with fresh media, and the RNA-Lipofectamine complex was placed onto the cells, and mixed by gently rocking the plate. The plates were incubated for 24 hours at 37° C. in a $CO_2$ incubator.

For immunofluorescence, transfected cells were harvested and seeded in 96 well plate, and intracellular staining was performed using commercially available mouse mAbs (dilution range 1:100 1:400). Cell pellets were fixed and permeabilized with Citofix-Citoperm solutions. A secondary reagent, Alexa488 labelled goat anti-mouse $F(ab')_2$ (1:400 final dilution), was used.

Expression of VZV proteins gE and gI was detected in cells transfected with monocistronic constructs (gE or gI), and expression of both gE and gI was detected in cells transfected with a bicistronic gE/gI construct in western blots using commercially available mouse antibodies, 13B1 for gE and 8C4 for gI. Expression of VZV protein gB was detected in cells transfected with a monocistronic construct encoding gB, by immunofluorescence using commercially available antibody 10G6. Expression of the VZV protein complex gH/gL, was detected by immunofluorescence in cells transfected with monocistronic gH and monocistronic gL, or with a bicistronic gH/gL construct. The gH/gL complex was detected using commercially available antibody SG3.

Murine Immunogenicity Studies

Groups of 8 female BALB/c mice aged 6-8 weeks and weighing about 20 g were immunized intramuscularly with 7.0 or 1.0 μg of replicon RNA formulated with CMF32 or LNP (RV01) at day 0, 21 and 42. Blood samples were taken from the immunized animals 3 weeks after the 2nd immunization and 3 weeks after the 3rd immunization. The groups are shown in Table 13.

TABLE 13

| Group | Antigen | Dose (micrograms) | Formulation |
|---|---|---|---|
| 1 | YFP | 7 | CMF32 |
| 2 | YFP | 1 | CMF32 |
| 3 | gB | 7 | CMF32 |
| 4 | gB | 1 | CMF32 |
| 5 | gE | 7 | CMF32 |
| 6 | gE | 1 | CMF32 |
| 7 | gH | 7 | CMF32 |
| 8 | gH | 1 | CMF32 |
| 9 | gI | 7 | CMF32 |
| 10 | gI | 1 | CMF32 |

TABLE 13-continued

| Group | Antigen | Dose (micrograms) | Formulation |
|---|---|---|---|
| 11 | gL | 7 | CMF32 |
| 12 | gL | 1 | CMF32 |
| 13 | gE/gI | 7 | CMF32 |
| 14 | gE/gI | 1 | CMF32 |
| 15 | gH/gL | 7 | CMF32 |
| 16 | gH/gL | 1 | CMF32 |

Immune response to VZV antigens

Serum samples were tested for the presence of antibodies to gB, by intracellular staining of VZV-replicon transfected MRC-5 cells. MRC-5 cells were maintained in Dulbecco Modified Eagle's Medium with 10% fetal bovine serum. VZV Oka strain inoculum (obtained from ATCC) was used to infect MRC-5 cell culture and infected whole cells were used for subpassage of virus. The ratio between infected and un-infected cells was 1:10. 30 hrs post infection cells were trypsin-dispersed for seeding in a 96 well plate to perform an intracellular staining with pools of mice sera (dilution range 1:200 to 1:800) obtained after immunization. Commercial mAbs were used as controls to quantify the infection level. Cell pellets ware fixed and permeabilized with Citofix-Citoperm solutions. A secondary reagent, Alexa488 labelled goat anti-mouse $F(ab')_2$ was used (1:400 final dilution).

Figure 4:
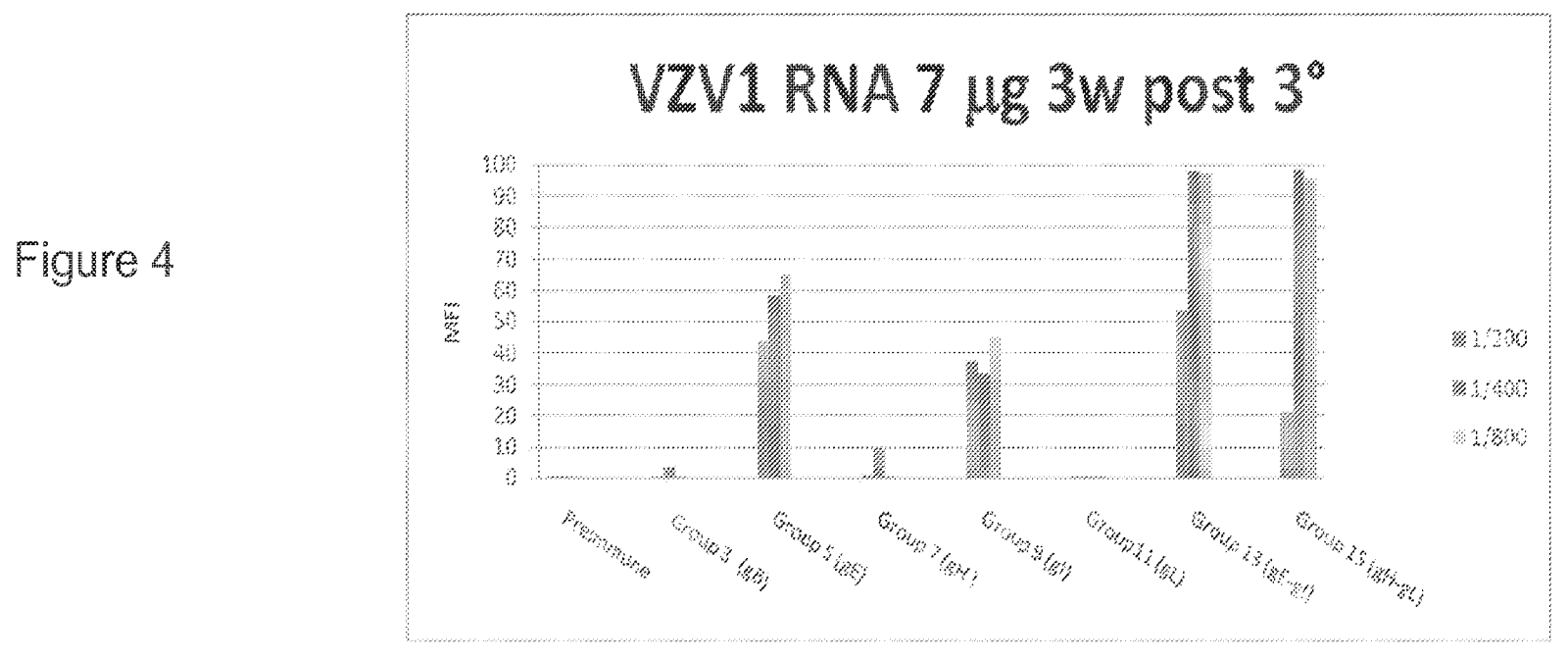

Commercial antibodies to gB (10G6), gH (SG3), and gE (13B1 (SBA) and 8612 (Millipore)) were used as positive controls, and each intracellularly stained infected MRC-5 cells Immune sera obtained 3 weeks after the third immunization with either 1 or 7 μg of RNA formulated with CMF32 were diluted 1/200, 1/400 and 1/800 and used to intracellularly stain infected MRC-5 cells. The results are shown in FIG. 4 (Study 1, groups 1, 5, 7, 9, 11, 13 and 15, CMF32 formulation).

Neutralizing Assay

Each immunized mouse serum was serially diluted by two fold increments starting at 1:20 in standard culture medium, and added to the equal volume of VZV suspension in the presence of guinea pig complement. After incubation for 1 hour at 37° C., the human epithelial cell line A549, was added. Infected cells can be measured after one week of culture by counting plaques formed in the culture under microscope. From the plaque number the % inhibition at each serum dilution was calculated. A chart for each serum sample was made by plotting the value of % inhibition against the logarithmic scale the dilution factor. Subsequently an approximate line of relationship between dilution factor and % inhibition was drawn. Then the 50% neutralization titer was determined as the dilution factor where the line crossed at the value of 50% inhibition.

Table 14 shows that sera obtained from mice immunized with monocistronic gE, bicistrnic gE/gI, and bicistronic gH/gL contained robust neutralizing antibody titers.

TABLE 14

| Neutralization titers of pooled sera from mice immunized with 7 μg RNA in CMF32 | | | | | | | | |
|---|---|---|---|---|---|---|---|---|
| Mouse ID | Control (YFP) | gB | gE | gI | gE/gI | gH | gL | gH/gL |
| 1 | <20 | <20 | 1111 | <20 | 440 | <20 | <20 | 1070 |
| 2 | <20 | <20 | 413 | 51 | >2560 | <20 | <20 | >2560 |
| 3 | <20 | <20 | >2560 | <20 | 1031 | <20 | <20 | >2560 |
| 4 | <20 | 20 | 2128 | <20 | 1538 | <20 | <20 | >2560 |
| 5 | <20 | 20 | 861 | <20 | 636 | 20 | <20 | >2560 |
| 6 | <20 | <20 | 1390 | <20 | 2339 | <20 | <20 | >2560 |
| 7 | <20 | <20 | 969 | <20 | 1903 | <20 | <20 | 900 |
| 8 | <20 | <20 | 1011 | 20 | 1969 | 20 | <20 | >2560 |
| 9 | <20* | <20* | <20* | <20* | <20* | <20* | <20* | <20* |

*pre-immune pooled sera

Example 8: The Solubility of Fatty Acids in Squalene

In this Example, the solubility of various fatty acids in squalene was examined, and shown in Table 15. Fatty acids at indicated amounts (40, 20, 10, or 5 mg/mL) were mixed with squalene at 60° C. In Table 15, (I) means that the fatty acid was soluble in squalene at the specified concentration; "x" means that the fatty acid was not soluble in squalene at the specified concentration; and "–" means that the solubility of the fatty acid at the specified concentration was not tested (because the fatty acid was soluble at a higher concentration). After the fatty acids were dissolved in squalene, the solutions were left at 4° C. overnight. The column labeled 4° C. overnight shows the solubility of the solutions in which each fatty acid was at its top concentration. For example oleic acid was soluble in squalene at 40 mg/ml and remained soluble in squalene at 4° C. overnight.

TABLE 15

| | Fatty acid | 40 mg/mL | 20 mg/mL | 10 mg/mL | 5 mg/mL | 4° C. (overnight) |
|---|---|---|---|---|---|---|
| Saturated Fatty Acids (Odd Carbon Chains) | Undecanoic Acid | ✓ | — | — | — | ✓ |
| | Tridecanoic Acid | ✓ | — | — | — | x |
| | Pentadecanoic Acid | ✓ | — | — | — | x |
| | Heptadecanoic Acid | x | x | x | ✓ | x |
| | Nonadecanoic Acid | x | x | x | x | x |
| | Heneicosanoic Acid | x | x | x | x | x |
| | Tricosanoic Acid | x | x | x | x | x |
| Saturated Fatty Acids (Even Carbon Chains) | Capric acid (10:0) | ✓ | — | — | — | ✓ |
| | Lauric acid (12:0) | ✓ | — | — | — | x |
| | Myristic Acid (14:0) | x | ✓ | — | — | x |
| | Palmitic Acid (16:0) | x | x | x | ✓ | x |
| | Stearic Acid (18:0) | x | x | x | ✓ | x |
| | Arachidic Acid (20:0) | x | x | x | ✓ | x |
| | Behenic Acid (22:0) | x | x | x | x | x |
| | Lignoceric Acid (24:0) | x | x | x | x | x |
| Unsaturated fatty acids | Docosahexaenoic Acid (22:6) | ✓ | — | — | — | ✓ |
| | Elaidic Acid (18:l)-trans | ✓ | — | — | — | x |
| | Erucic Acid (22:1) | ✓ | — | — | — | ✓ |
| | Linoleic Acid (18:2) | ✓ | — | — | — | ✓ |
| | Linolenic Acid (18:3) | ✓ | — | — | — | ✓ |
| | Nervonic Acid (24:1) | ✓ | — | — | — | x |
| | Oleic Acid (18:l)-cis | ✓ | — | — | — | ✓ |
| | Palmitoleic Acid (16:1) | ✓ | — | — | — | ✓ |
| | Petroselinic Acid (18:1) | ✓ | — | — | — | ✓ |

Sequences

The nucleotide sequence of a DNA encoding the vA317 RNA, which encodes the RSV-F antigen (SEQ ID NO: 1).

The nucleotide sequence of a DNA encoding the vA142 RNA (SEQ ID NO: 2).

The nucleotide sequence of a DNA encoding the vA375 RNA (SEQ ID NO: 3).

A526 Vector: SGP-gH-SGP-gL-SGP-UL128-2A-UL130-2Amod-UL131 (SEQ ID NO: 4).

A527 Vector: SGP-gH-SGP-gL-SGP-UL128-EMCV-UL130-EV71-UL131 (SEQ ID NO: 5).

A531 Vector: SGP-gHsol-SGP-gL (SEQ ID NO: 6).

A532 Vector: SGP-gHsol-2A-gL (SEQ ID NO: 7).

A533 Vector: SGP-gHsol-EV71-gL (SEQ ID NO: 8).

A534 Vector: SGP-gL-EV71-gH (SEQ ID NO: 9).

A535 Vector: SGP-342-EV71-gHsol-2A-gL (SEQ ID NO: 10).

A536 Vector: SGP-342-EV71-gHsol-EMCV-gL (SEQ ID NO: 11).

A537 Vector: SGP-342-EV71-gL-EMCV-gHsol (SEQ ID NO: 12).

A554 Vector: SGP-gH-SGP-gL-SGP-UL128-SGP-UL130-SGP-UL131 (SEQ ID NO: 13).

A555 Vector: SGP-gHsol-SGP-gL-SGP-UL128-SGP-UL130-SGP-UL131 (SEQ ID NO: 14).

A556 Vector: SGP-gHsol6His-SGP-gL-SGP-UL128-SGP-UL130-SGP-UL131 (SEQ ID NO: 15).

VZV gB (SEQ ID NO: 16).

VZV gH (SEQ ID NO: 17).

VZV gL (SEQ ID NO: 18).

VZV gI (SEQ ID NO: 19).

VZV gE (SEQ ID NO: 20).

VZV VEERep.SGPgB (SEQ ID NO: 21).

VZV VEERep.SGPgH (SEQ ID NO: 22).

VZV VEERep.SGPgL (SEQ ID NO: 23).

VZV VEERep.SGPgH-SGPgL (SEQ ID NO: 24).

VZV VEERep.SGPgE (SEQ ID NO: 25).
VZV VEERep.SGPgI (SEQ ID NO: 26).
VZV VEErep.SGPgE-SGPgI (SEQ ID NO: 27).

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications and patents cited in this disclosure are incorporated by reference in their entirety. To the extent the material incorporated by reference contradicts or is inconsistent with this specification, the specification will supersede any such material. The citation of any references herein is not an admission that such references are prior art to the present invention.

Those skilled in the art will recognize, or be able to ascertain using no more than routine experimentation, many equivalents to the specific embodiments of the invention described herein. Such equivalents are intended to be encompassed by the following embodiments.

The invention claimed is:

1. A method for preparing a composition comprising an RNA molecule complexed with a particle of a cationic oil-in-water emulsion, comprising:

(i) providing an oil-in-water emulsion comprising particles that are dispersed in an aqueous continuous phase, wherein the average diameter of said particles is from about 80 nm to about 150 nm; wherein the average diameter does not change by more than 10% when the emulsion is stored at 4° C. for one month; wherein the emulsion comprises an oil and a cationic lipid, and wherein;
  a. the ratio of oil:lipid (mole:mole) in the oil-in-water emulsion is at least about 8:1 (mole:mole),
  b. the concentration of cationic lipid in said composition is at least about 1.25 mM, and
  c. the cationic lipid is not DC-Cholesterol;

(ii) providing an aqueous solution comprising the RNA molecule; and (iii) combining the oil-in-water emulsion of (i) and the aqueous solution of (ii), thereby preparing the composition.

2. The method of claim 1, wherein the cationic oil-in-water emulsion of (i) and RNA solution of (ii) are combined at about 1:1 (v/v) ratio.

3. The method of claim 1, wherein the aqueous solution comprising the RNA molecule comprises a salt.

4. The method of claim 3, wherein the salt is NaCl.

5. The method of claim 4, wherein the aqueous solution comprises about 20 mM NaCl.

6. The method of claim 1, wherein the aqueous solution comprising the RNA molecule is a buffer.

7. The method of claim 6, wherein the buffer is a citrate buffer.

8. The method of claim 7, wherein the buffer comprises about 2 mM citrate.

9. The method of claim 1, wherein the aqueous solution comprising the RNA molecule comprises a nonionic tonicifying agent.

10. The method of claim 9, wherein the nonionic tonicifying agent is a sugar or sugar alcohol.

11. The method of claim 10, wherein the nonionic tonicifying agent is selected from the group consisting of sucrose, trehalose, sorbitol, dextrose and combination thereof.

12. The method of claim 9, wherein the nonionic tonicifying agent is sucrose.

13. The method of claim 12, wherein the aqueous solution comprises about 560 mM sucrose.

14. The method of claim 1, wherein the aqueous solution comprising the RNA molecule comprises a polymer.

15. The method of claim 1, wherein the oil is squalene or squalane.

16. The method of claim 1, wherein the particle further comprises a surfactant.

17. The method of claim 1, wherein said cationic lipid is DOTAP.

18. The method of claim 1, wherein the RNA molecule is a self-replicating RNA molecule that encodes an antigen.

19. The method of claim 18, wherein the self-replicating RNA is an alphavirus-derived RNA replicon.

20. The method of claim 1, wherein the average diameter of said particles is from about 80 nm to about 130 nm.

* * * * *